(12) United States Patent
Anderberg et al.

(10) Patent No.: US 11,143,658 B2
(45) Date of Patent: Oct. 12, 2021

(54) METHODS AND COMPOSITIONS FOR DIAGNOSIS AND PROGNOSIS OF RENAL INJURY AND RENAL FAILURE

(71) Applicant: ASTUTE MEDICAL, INC., San Diego, CA (US)

(72) Inventors: Joseph Anderberg, Encinitas, CA (US); Paul McPherson, Encinitas, CA (US); Jeff Gray, Solana Beach, CA (US); Kevin Nakamura, Cardiff by the Sea, CA (US); James Patrick Kampf, San Diego, CA (US); Thomas Kwan, San Diego, CA (US)

(73) Assignee: Astute Medical, Inc., San Diego, CA (US)

( * ) Notice: Subject to any disclaimer, the term of this patent is extended or adjusted under 35 U.S.C. 154(b) by 0 days.

(21) Appl. No.: 15/573,441

(22) PCT Filed: May 12, 2016

(86) PCT No.: PCT/US2016/032209
§ 371 (c)(1),
(2) Date: Nov. 10, 2017

(87) PCT Pub. No.: WO2016/183377
PCT Pub. Date: Nov. 17, 2016

(65) Prior Publication Data
US 2018/0095093 A1    Apr. 5, 2018

Related U.S. Application Data

(60) Provisional application No. 62/160,523, filed on May 12, 2015, provisional application No. 62/160,526, filed on May 12, 2015, provisional application No. 62/160,519, filed on May 12, 2015, provisional application No. 62/160,531, filed on May 12, 2015.

(51) Int. Cl.
*G01N 33/68* (2006.01)
(52) U.S. Cl.
CPC . *G01N 33/6893* (2013.01); *G01N 2333/4745* (2013.01); *G01N 2800/347* (2013.01); *G01N 2800/56* (2013.01)
(58) Field of Classification Search
CPC ......... G01N 2800/347; G01N 33/6893; G01N 2333/4745; G01N 2800/56; G01N 33/48
See application file for complete search history.

(56) References Cited

U.S. PATENT DOCUMENTS

2006/0134708 A1    6/2006  Yang
2012/0208717 A1    8/2012  Hu et al.
2013/0210041 A1*   8/2013  Anderberg ......... G01N 33/6893
                                                      435/7.94

FOREIGN PATENT DOCUMENTS

WO    WO 2011/025917      3/2011
WO    WO 2011/162819     12/2011
WO    WO 2011/162820     12/2011
WO       2013/096740 A1   6/2013

OTHER PUBLICATIONS

International Search Report and Written Opinion dated Sep. 16, 2016 in PCT/US2016/032209 (11 pages).
Ulinski et al., "Serum insulin-like growth factor binding protein (IGFBP)-4 and IGFBP-5 in children with chronic renal failure: relationship to growth and glomerular filtration rate", Pediatr Nephrol (2000) 14:589-597.
Fukuda et al., "Changes in serum insulin-like growth factor binding protein-2, -3, and -6 levels in patients with chronic renal failure following renal transplantation," Growth Hormone and IGF Res., Dec. 1, 1998, 8(6):481-486.
Jehle et al., "Insulin-like growth factor system components in hyperparathyroidism and renal osteodystrophy," Kidney International, Feb. 1, 2000, 57(2):423-436.
Extended European Search Report and Opinion dated Oct. 24, 2018, in European application (No. 16793563.4).
Official action dated May 24, 2019, in Chinese application (No. 201680038773.6).
Official action dated Jul. 9, 2019, in European application (No. 16793563.4).
Search Report dated May 16, 2019, in Chinese application (No. 201680038773.6).
Official action dated Apr. 16, 2020, in Chinese application (No. 201680038773.6).
Search Report dated Apr. 8, 2020, in Chinese application (No. 201680038773.6).
Official action dated Mar. 4, 2020, in European application (No. 16793563.4).
Official action dated Mar. 3, 2020, in Japanese application (No. 2017-559461).
Chawla et al., "Acute kidney disease and renal recovery: consensus report of the Acute Disease Quality Initiative (ADQI) 16 Workgroup," Nat Rev Nephrol, Apr. 2017, 13(4):241-257.

\* cited by examiner

*Primary Examiner* — Vanessa L. Ford
*Assistant Examiner* — Sandra E Dillahunt
(74) *Attorney, Agent, or Firm* — Womble Bond Dickinson (US) LLP

(57) ABSTRACT

The present invention relates to methods and compositions for monitoring, diagnosis, prognosis, and determination of treatment regimens in subjects suffering from or suspected of having a renal injury. In particular, the invention relates to using assays that detect one or more of Insulin-like growth factor-binding protein 2, Insulin-like growth factor-binding protein 3, Insulinlike growth factor-binding protein 4, and Insulin like growth factor-binding protein 6 as diagnostic and prognostic biomarker assays in renal injuries.

16 Claims, No Drawings
Specification includes a Sequence Listing.

METHODS AND COMPOSITIONS FOR DIAGNOSIS AND PROGNOSIS OF RENAL INJURY AND RENAL FAILURE

The present invention is filed under 35 U.S.C. § 371 as the U.S. national phase of International Patent Application No. PCT/US2016/032209, filed May 12, 2016, which designated the United States and claims priority from U.S. Provisional Patent Application No. 62/160,519 filed May 12, 2015; from U.S. Provisional Patent Application No. 62/160,523 filed May 12, 2015; from U.S. Provisional Patent Application No. 62/160,526 filed May 12, 2015; and from U.S. Provisional Patent Application No. 62/160,531 filed May 12, 2015, each of which is hereby incorporated in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on Nov. 10, 2017, is named AST_8153_US_SeqListing.txt and is 11 kilobytes in size.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, $17^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, $47^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, $17^{th}$ ed., Chapter 222, and which is hereby incorporated by reference in their entirety:

| Type | Risk Factors |
|---|---|
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |

| Type | Risk Factors |
|---|---|
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, *Curr Opin Nephrol Hypertens* 14:265-270, 2005 and Chertow et al, *J Am Soc Nephrol* 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, *J Am Soc Nephrol* 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit Care.* 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production <0.5 ml/kg/hr for 12 h;

"Failure": serum creatinine increased 3.0 fold from baseline OR creatinine >355 μmol/l (with a rise of >44) or urine output below 0.3 ml/kg/hr for 24 h or anuria for at least 12 hours;
And included two clinical outcomes:
"Loss": persistent need for renal replacement therapy for more than four weeks.
"ESRD": end stage renal disease—the need for dialysis for more than 3 months.
These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:
"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;
"Stage II": increase in serum creatinine to more than 200% (>2-fold) from baseline OR urine output less than 0.5 mL/kg per hour for more than 12 hours;
"Stage III": increase in serum creatinine to more than 300% (>3-fold) from baseline OR serum creatinine ≥354 μmol/L accompanied by an acute increase of at least 44 μmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of one or more markers selected from the group consisting of Insulin-like growth factor-binding protein 2, Insulin-like growth factor-binding protein 3, Insulin-like growth factor-binding protein 4, and Insulin-like growth factor-binding protein 6 (collectively referred to herein as "kidney injury markers, and individually as a "kidney injury marker") can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury).

These kidney injury markers may be used, individually or in panels comprising a plurality of kidney injury markers, for risk stratification (that is, to identify subjects at risk for a future injury to renal function, for future progression to reduced renal function, for future progression to ARF, for future improvement in renal function, etc.); for diagnosis of existing disease (that is, to identify subjects who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a subject will require renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In a first aspect, the present invention relates to methods for evaluating renal status in a subject. These methods comprise performing an assay method that is configured to detect one or more kidney injury markers of the present invention in a body fluid sample obtained from the subject. The assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are then correlated to the renal status of the subject. This correlation to renal status may include correlating the assay result(s) to one or more of risk stratification, diagnosis, prognosis, staging, classifying and monitoring of the subject as described herein. Thus, the present invention utilizes one or more kidney injury markers of the present invention for the evaluation of renal injury.

In certain embodiments, the methods for evaluating renal status described herein are methods for risk stratification of the subject; that is, assigning a likelihood of one or more future changes in renal status to the subject. In these embodiments, the assay result(s) is/are correlated to one or more such future changes. The following are preferred risk stratification embodiments.

In preferred risk stratification embodiments, these methods comprise determining a subject's risk for a future injury to renal function, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to a likelihood of such a future injury to renal function. For example, the measured concentration(s) may each be compared to a threshold value. For a "positive going" kidney injury marker, an increased likelihood of suffering a future injury to renal function is assigned to the subject when the measured concentration is above the threshold, relative to a likelihood assigned when the measured concentration is below the threshold. For a "negative going" kidney injury marker, an increased likelihood of suffering a future injury to renal function is assigned to the subject when the measured concentration is below the threshold, relative to a likelihood assigned when the measured concentration is above the threshold.

In other preferred risk stratification embodiments, these methods comprise determining a subject's risk for future reduced renal function, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to a likelihood of such reduced renal function. For example, the measured concentrations may each be compared to a threshold value. For a "positive going" kidney injury marker, an increased likelihood of suffering a future reduced renal function is assigned to the subject when the measured concentration is above the threshold, relative to a likelihood assigned when the measured concentration is below the threshold. For a "negative going" kidney injury marker, an increased likelihood of future reduced renal function is assigned to the subject when the measured concentration is below the threshold, relative to a likelihood assigned when the measured concentration is above the threshold.

In still other preferred risk stratification embodiments, these methods comprise determining a subject's likelihood for a future improvement in renal function, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to a likelihood of such a future improvement in renal function. For example, the measured concentration(s) may each be compared to a threshold value. For a "positive going" kidney injury marker, an increased likelihood of a future improvement in renal function is assigned to the subject when the measured concentration is below the threshold, relative to a likelihood assigned when the measured concentration is above the threshold. For a "negative going" kidney injury marker, an increased likelihood of a future improvement in renal function is assigned to the subject when the measured concentration is above the threshold, relative to a likelihood assigned when the measured concentration is below the threshold.

In yet other preferred risk stratification embodiments, these methods comprise determining a subject's risk for progression to ARF, and the result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to a likelihood of such progression to ARF. For example, the measured concentration(s) may each be compared to a threshold value. For a "positive going" kidney injury marker, an increased likelihood of progression to ARF is assigned to the subject when the measured concentration is above the threshold, relative to a likelihood assigned when the measured concentration is below the threshold. For a "negative going" kidney injury marker, an increased likelihood of progression to ARF is assigned to the subject when the measured concentration is below the threshold, relative to a likelihood assigned when the measured concentration is above the threshold.

And in other preferred risk stratification embodiments, these methods comprise determining a subject's outcome risk, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to a likelihood of the occurrence of a clinical outcome related to a renal injury suffered by the subject. For example, the measured concentration(s) may each be compared to a threshold value. For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the subject. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the subject is equivalent to diagnosis of a current condition.

In preferred risk stratification embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF.

In other embodiments, the methods for evaluating renal status described herein are methods for diagnosing a renal injury in the subject; that is, assessing whether or not a subject has suffered from an injury to renal function, reduced renal function, or ARF. In these embodiments, the assay result(s) is/are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to the occurrence or nonoccurrence of such an injury. For example, each of the measured concentration(s) may be compared to a threshold value. For a positive going marker, an increased likelihood of the occurrence of an injury to renal function is assigned to the subject when the measured concentration is above the threshold (relative to the likelihood assigned when the measured concentration is below the threshold); alternatively, when the measured concentration is below the threshold, an increased likelihood of the nonoccurrence of an injury to renal function may be assigned to the subject (relative to the likelihood assigned when the measured concentration is above the threshold). For a negative going marker, an increased likelihood of the occurrence of an injury to renal function is assigned to the subject when the measured concentration is below the threshold (relative to the likelihood assigned when the measured concentration is above the threshold); alternatively, when the measured concentration is above the threshold, an increased likelihood of the nonoccurrence of an injury to renal function may be assigned to the subject (relative to the likelihood assigned when the measured concentration is below the threshold).

In other preferred diagnostic embodiments, these methods comprise diagnosing the occurrence or nonoccurrence of reduced renal function, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the subject when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the subject (relative to the likelihood assigned when the measured concentration is above the threshold). For a negative going marker, an increased likelihood of the occurrence of an injury causing reduced renal function is assigned to the subject when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the subject (relative to the likelihood assigned when the measured concentration is below the threshold).

In yet other preferred diagnostic embodiments, these methods comprise diagnosing the occurrence or nonoccurrence of ARF, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to the occurrence or nonoccurrence of an injury causing ARF. For example, each of the measured concentration(s) may be compared to a threshold value. For a positive going marker, an increased likelihood of the occurrence of ARF is assigned to the subject when the measured concentration is above the threshold (relative to the likelihood assigned when the measured concentration is below the threshold); alternatively, when the measured concentration is below the threshold, an increased likelihood of the nonoccurrence of ARF may be assigned to the subject (relative to the likelihood assigned when the measured concentration is above the threshold). For a negative going marker, an increased likelihood of the occurrence of ARF is assigned to the subject when the measured concentration is below the threshold (relative to the likelihood assigned when the measured concentration is above the threshold); alternatively, when the measured concentration is above the threshold, an increased likelihood of the nonoccurrence of ARF may be assigned to the subject (relative to the likelihood assigned when the measured concentration is below the threshold).

In still other preferred diagnostic embodiments, these methods comprise diagnosing a subject as being in need of renal replacement therapy, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to a need for renal replacement therapy. For example, each of the measured concentration(s) may be compared to a threshold value. For a positive going marker, an increased likelihood of the occurrence of an injury creating a need for renal replacement therapy is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the subject (relative to the likelihood assigned when the measured concentration is above the threshold). For a negative going marker, an increased likelihood of the occurrence of an injury creating a need for renal replacement therapy is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the subject (relative to the likelihood assigned when the measured concentration is below the threshold).

In still other preferred diagnostic embodiments, these methods comprise diagnosing a subject as being in need of renal transplantation, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to a need for renal transplantation. For example, each of the measured concentration(s) may be compared to a threshold value. For a positive going marker, an increased likelihood of the occurrence of an injury creating a need for renal transplantation is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the subject (relative to the likelihood assigned when the measured concentration is above the threshold). For a negative going marker, an increased likelihood of the occurrence of an injury creating a need for renal transplantation is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the subject (relative to the likelihood assigned when the measured concentration is below the threshold).

In still other embodiments, the methods for evaluating renal status described herein are methods for monitoring a renal injury in the subject; that is, assessing whether or not renal function is improving or worsening in a subject who has suffered from an injury to renal function, reduced renal function, or ARF. In these embodiments, the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to the occurrence or nonoccurrence of a change in renal status. The following are preferred monitoring embodiments.

In preferred monitoring embodiments, these methods comprise monitoring renal status in a subject suffering from an injury to renal function, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other preferred monitoring embodiments, these methods comprise monitoring renal status in a subject suffering from reduced renal function, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject suffering from acute renal failure, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other additional preferred monitoring embodiments, these methods comprise monitoring renal status in a subject at risk of an injury to renal function due to the pre-existence of one or more known risk factors for prerenal, intrinsic renal, or postrenal ARF, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject having, or at risk of, an injury to renal function for future persistence of acute kidney injury. "Future persistence" as used herein refers to an existing acute renal injury that will continue for a period selected from the group consisting of 21 days, 14 days, 7 days, 5 days, 96 hours, 72 hours, 48 hours, 36 hours, 24 hours, and 12 hours. In certain embodiments the subject has an acute kidney injury at the time the sample is obtained. This is not meant to imply that the subject must have an acute kidney injury at the time the sample is obtained, but rather that the subject, upon onset of an acute kidney injury, suffers from an acute kidney injury that will persist. In various embodiments, the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to the future persistence of the acute kidney injury in the subject. For example, the measured concentration(s) may be compared to a threshold value. For a positive going marker, when the measured concentration is above the threshold, a future persistence of acute kidney injury may be assigned to the subject; alternatively, when the measured concentration is below the threshold, a future improvement of renal function may be assigned to the subject. For a negative going marker, when the measured concentration is below the threshold, a future persistence of acute kidney injury may be assigned to the subject; alternatively, when the measured concentration is above the threshold, a future improvement of renal function may be assigned to the subject.

In still other embodiments, the methods for evaluating renal status described herein are methods for classifying a renal injury in the subject; that is, determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage. In these embodiments, the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to a particular class and/or subclass. The following are preferred classification embodiments.

In preferred classification embodiments, these methods comprise determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage, and the assay result(s), for example a measured concentration of one or more markers selected from the group consisting of Insulin-like growth factor-binding protein 2, Insulin-like growth factor-binding protein 3, Insulin-like growth factor-binding protein 4, and/or Insulin-like growth factor-binding protein 6, is/are correlated to the injury classification for the subject. For example, the measured concentration may be compared to a threshold value, and when the measured concentration is above the threshold, a particular classification is assigned; alternatively, when the measured concentration is below the threshold, a different classification may be assigned to the subject.

A variety of methods may be used by the skilled artisan to arrive at a desired threshold value for use in these methods. For example, the threshold value may be determined from a population of normal subjects by selecting a concentration representing the $75^{th}$, $85^{th}$, $90^{th}$, $95^{th}$, or $99^{th}$ percentile of a kidney injury marker measured in such normal subjects. Alternatively, the threshold value may be determined from a "diseased" population of subjects, e.g., those suffering from an injury or having a predisposition for an injury (e.g., progression to ARF or some other clinical outcome such as death, dialysis, renal transplantation, etc.), by selecting a concentration representing the $75^{th}$, $85^{th}$, $90^{th}$, $95^{th}$, or $99^{th}$ percentile of a kidney injury marker measured in such subjects. In another alternative, the threshold value may be determined from a prior measurement of a kidney injury marker in the same subject; that is, a temporal change in the level of a kidney injury marker in the subject may be used to assign risk to the subject.

The foregoing discussion is not meant to imply, however, that the kidney injury markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, $17^{th}$ Ed., McGraw Hill, New York, pages 1741-1830, and Current Medical Diagnosis & Treatment 2008, $47^{th}$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

DETAILED DESCRIPTION OF THE INVENTION

The present invention relates to methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers. In various embodiments, a measured concentration of one or more markers selected from the group consisting of Insulin-like growth factor-binding protein 2, Insulin-like growth factor-binding protein 3, Insulin-like growth factor-binding protein 4, and Insulin-like growth factor-binding protein 6 or one or more markers related thereto, and optionally one or more additional kidney injury markers known in the art, are correlated to the renal status of the subject.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL ($\geq 8.8$ μmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl ($\geq 26.4$ μmol/1), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting.

As used herein, the term "Insulin-like growth factor-binding protein 3" refers to one or more polypeptides present in a biological sample that are derived from a Insulin-like growth factor-binding protein 3 precursor (human precursor Swiss-Prot entry P17936 (SEQ ID NO: 1)):

```
        10         20         30         40
MQRARPTLWA AALTLLVLLR GPPVARAGAS SAGLGPVVRC 50         60         70         80
EPCDARALAQ CAPPPAVCAE LVREPGCGCC LTCALSEGQP 90        100        110        120
CGIYTERCGS GLRCQPSPDE ARPLQALLDG RGLCVNASAV 130        140        150        160
SRLRAYLLPA PPAPGNASES EEDRSAGSVE SPSVSSTHRV 170        180        190        200
SDPKFHPLHS KIIIIKKGHA KDSQRYKVDY ESQSTDTQNF 210        220        230        240
SSESKRETEY GPCRREMEDT LNHLKFLNVL SPRGVHIPNC 250        260        270        280
DKKGFYKKKQ CRPSKGRKRG FCWCVDKYGQ PLPGYTTKGK

290
EDVHCYSMQS K
```

The following domains have been identified in Insulin-like growth factor-binding protein 3:

| Residues | Length | Domain ID |
|---|---|---|
| 1-27 | 27 | signal sequence |
| 28-291 | 264 | Insulin-like growth factor-binding protein 3 |
| 135-135 | | G → GEPPAPG (SEQ ID NO: 2) in isoform 2 |

As used herein, the term "Insulin-like growth factor-binding protein 2" refers to one or more polypeptides present in a biological sample that are derived from a Insulin-like growth factor-binding protein 2 precursor (human precursor Swiss-Prot entry P18065) (SEQ ID NO: 3)):

```
            10         20         30         40
        MLPRVGCPAL PLPPPPLLPL LLLLLGASGG GGGARAEVLF 50         60         70         80
        RCPPCTPERL AACGPPPVAP PAAVAAVAGG ARMPCAELVR 90        100        110        120
        EPGCGCCSVC ARLEGEACGV YTPRCGQGLR CYPHPGSELP 130        140        150        160
        LQALVMGEGT CEKRRDAEYG ASPEQVADNG DDHSEGGLVE 170        180        190        200
        NHVDSTMNML GGGGSAGRKP LKSGMKELAV FREKVTEQHR 210        220        230        240
        QMGKGGKHHL GLEEPKKLRP PPARTPCQQE LDQVLERIST 250        260        270        280
        MRLPDERGPL EHLYSLHIPN CDKHGLYNLK QCKMSLNGQR 290        300        310        320
        GECWCVNPNT GKLIQGAPTI RGDPECHLFY NEQQEARGVH TQRMQ
```

The following domains have been identified in Insulin-like growth factor-binding protein 2:

| Residues | Length | Domain ID |
|---|---|---|
| 1-35 | 35 | signal sequence |
| 36-325 | 290 | Insulin-like growth factor-binding protein 2 |

As used herein, the term "Insulin-like growth factor-binding protein 4" refers to one or more polypeptides present in a biological sample that are derived from a Insulin-like growth factor-binding protein 4 precursor (human precursor Swiss-Prot entry P22692(SEQ ID NO: 4)):

```
            10         20         30         40
        MLPLCLVAAL LLAAGPGPSL GDEAIHCPPC SEEKLARCRP 50         60         70         80
        PVGCEELVRE PGCGCCATCA LGLGMPCGVY TPRCGSGLRC 90        100        110        120
        YPPRGVEKPL HTLMHGQGVC MELAEIEAIQ ESLQPSDKDE 130        140        150        160
        GDHPNNSFSP CSAHDRRCLQ KHFAKIRDRS TSGGKMKVNG 170        180        190        200
        APREDARPVP QGSCQSELHR ALERLAASQS RTHEDLYIIP 210        220        230        240
        IPNCDRNGNF HPKQCHPALD GQRGKCWCVD RKTGVKLPGG

250
        LEPKGELDCH QLADSFRE
```

The following domains have been identified in Insulin-like growth factor-binding protein 4:

| Residues | Length | Domain ID |
|---|---|---|
| 1-21 | 21 | signal sequence |
| 22-258 | 237 | Insulin-like growth factor-binding protein 4 |
| 1-100 | | missing in isoform 2 |

As used herein, the term "Insulin-like growth factor-binding protein 6" refers to one or more polypeptides present in a biological sample that are derived from a Insulin-like growth factor-binding protein 6 precursor (human precursor Swiss-Prot entry P24592 (SEQ ID NO: 5)):

```
            10         20         30         40
        MTPHRLLPPL LLLLALLLAA SPGGALARCP GCGQGVQAGC 50         60         70         80
        PGGCVEEEDG GSPAEGCAEA EGCLRREGQE CGVYTPNCAP 90        100        110        120
        GLQCHPPKDD EAPLRALLLG RGRCLPARAP AVAEENPKES 130        140        150        160
        KPQAGTARPQ DVNRRDQQRN PGTSTTPSQP NSAGVQDTEM 170        180        190        200
        GPCRRHLDSV LQQLQTEVYR GAQTLYVPNC DHRGFYRKRQ 210        220        230        240
        CRSSQGQRRG PCWCVDRMGK SLPGSPDGNG SSSCPTGSSG
```

The following domains have been identified in Insulin-like growth factor-binding protein 6:

| Residues | Length | Domain ID |
|---|---|---|
| 1-27 | 27 | signal sequence |
| 28-240 | 213 | Insulin-like growth factor-binding protein 6 |

As used herein, the term "relating a signal to the presence or amount" of an analyte reflects this understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay.

The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, FIGURES and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, FIGURES and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c = K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, FIGURES, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the $97.5^{th}$ percentile of the concentration seen in a normal population. Another method may be to look at serial samples from the same patient, where a prior "baseline" result is used to monitor for temporal changes in a biomarker level.

Population studies may also be used to select a decision threshold. Receiver Operating Characteristic ("ROC") arose from the field of signal detection therory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1—specificity, the ROC graph is sometimes called the sensitivity vs (1—specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Nidogen-1 (P07355); Beta-glucuronidase (P08236); B-2-microglobulin (P61769); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase 9 (Q16790); Casein Kinase 2 (P68400); Clusterin (P10909); Complement C3 (P01024); Cysteine-rich protein (CYR61, 000622); Cytochrome C (P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02792; heavy chain P02794); Fructose-1,6-biphosphatase (P09467); GRO-alpha (CXCL1, (P09341); Growth Hormone (P01241); Hepatocyte growth factor (P14210); Insulin-like growth factor I (P05019); Immunoglobulin G; Immunoglobulin Light Chains (Kappa and Lambda); Interferon gamma (P01308); Lysozyme (P61626); Interleukin-1alpha (P01583); Interleukin-2 (P60568); Interleukin-4 (P05112); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (095631); Neutral endopeptidase (P08473); Osteopontin (014788); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (000206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N (P15144); CalbindinD28k (P05937); Cystatin C (P01034); 8 subunit of FIFO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itm1, P46977); Interleukin-6 (P05231); Interleukin-8 (P10145); Interleukin-18 (Q14116); IP-10 (10 kDa interferon-gamma-induced protein, P02778); IRPR (IFRD1, 000458); Isovaleryl-CoA dehydrogenase (IVD, P26440); I-TAC/CXCL11 (014625); Keratin 19 (P08727); Kim-1 (Hepatitis A virus cellular receptor 1, 043656); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, 015244); Osteoprotegerin (014788); P8 protein (060356); Plasminogen activator inhibitor 1 (PAI-1, P05121); ProANP (1-98) (P01160); Protein phosphatase 1-beta (PPI-beta, P62140); Rab GDI-beta (P50395); Renal kallikrein (P06870); RT1.B-1 (alpha) chain of the integral membrane protein (Q5Y7A8); soluble tumor necrosis factor receptor superfamily member 1A (sTNFR-I, P19438); soluble tumor necrosis factor receptor superfamily member 1B (sTNFR-II, P20333); Tissue inhibitor of metalloproteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined with the kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney)

glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m² can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr\ corrected} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., *Nephrol. Dial. Transplant.* 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N J, 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1: Contrast-Induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:

Inclusion Criteria males and females 18 years of age or older;
undergoing a radiographic/angiographic procedure (such as a CT scan or coronary intervention) involving the intravascular administration of contrast media;
expected to be hospitalized for at least 48 hours after contrast administration.
able and willing to provide written informed consent for study participation and to comply with all study procedures.

Exclusion Criteria
renal transplant recipients;
acutely worsening renal function prior to the contrast procedure;
already receiving dialysis (either acute or chronic) or in imminent need of dialysis at enrollment;
expected to undergo a major surgical procedure (such as involving cardiopulmonary bypass) or an additional imaging procedure with contrast media with significant risk for further renal insult within the 48 hrs following contrast administration;
participation in an interventional clinical study with an experimental therapy within the previous 30 days;
known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 (±0.5), 8 (±1), 24 (±2) 48 (±2), and 72 (±2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Serum creatinine is assessed at the site immediately prior to the first contrast administration (after any pre-procedure hydration) and at 4 (±0.5), 8 (±1), 24 (±2) and 48 (±2)), and 72 (±2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure <80 mm Hg=5 points; intra-arterial balloon pump=5 points; congestive heart failure (Class III-IV or history of pulmonary edema)=5 points; age>75 yrs=4 points; hematocrit level<39% for men, <35% for women=3 points; diabetes=3 points; contrast media volume=1 point for each 100 mL; serum creatinine level>1.5 g/dL=4 points OR estimated GFR 40-60 mL/min/1.73 $m^2$=2 points, 20-40 mL/min/1.73 $m^2$=4 points, <20 mL/min/1.73 $m^2$=6 points. The risks assigned are as follows: risk for CIN and dialysis: 5 or less total points=risk of CIN—7.5%, risk of dialysis—0.04%; 6-10 total points=risk of CIN—14%, risk of dialysis—0.12%; 11-16 total points=risk of CIN—26.1%, risk of dialysis—1.09%; >16 total points=risk of CIN—57.3%, risk of dialysis—12.8%.

Example 2: Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:

Inclusion Criteria
males and females 18 years of age or older;
undergoing cardiovascular surgery;
Toronto/Ottawa Predictive Risk Index for Renal Replacement risk score of at least 2 (Wijeysundera et al., *JAMA* 297: 1801-9, 2007); and
able and willing to provide written informed consent for study participation and to comply with all study procedures.
Exclusion Criteria
known pregnancy;
previous renal transplantation;
acutely worsening renal function prior to enrollment (e.g., any category of RIFLE criteria);
already receiving dialysis (either acute or chronic) or in imminent need of dialysis at enrollment;
currently enrolled in another clinical study or expected to be enrolled in another clinical study within 7 days of cardiac surgery that involves drug infusion or a therapeutic intervention for AKI;
known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, Calif. The study urine samples are frozen and shipped to Astute Medical, Inc.

Example 3: Acutely Ill Subject Sample Collection

The objective of this study is to collect samples from acutely ill patients. Approximately 900 adults expected to be in the ICU for at least 48 hours will be enrolled. To be enrolled in the study, each patient must meet all of the following inclusion criteria and none of the following exclusion criteria:
Inclusion Criteria
males and females 18 years of age or older;
Study population 1: approximately 300 patients that have at least one of:
shock (SBP<90 mmHg and/or need for vasopressor support to maintain MAP>60 mmHg and/or documented drop in SBP of at least 40 mmHg); and
sepsis;
Study population 2: approximately 300 patients that have at least one of:
IV antibiotics ordered in computerized physician order entry (CPOE) within 24 hours of enrollment;
contrast media exposure within 24 hours of enrollment;
increased Intra-Abdominal Pressure with acute decompensated heart failure; and
severe trauma as the primary reason for ICU admission and likely to be hospitalized in the ICU for 48 hours after enrollment;
Study population 3: approximately 300 patients
expected to be hospitalized through acute care setting (ICU or ED) with a known risk factor for acute renal injury (e.g. sepsis, hypotension/shock (Shock=systolic BP<90 mmHg and/or the need for vasopressor support to maintain a MAP>60 mmHg and/or a documented drop in SBP>40 mmHg), major trauma, hemorrhage, or major surgery); and/or expected to be hospitalized to the ICU for at least 24 hours after enrollment.

Exclusion Criteria
known pregnancy;
institutionalized individuals;
previous renal transplantation;
known acutely worsening renal function prior to enrollment (e.g., any category of RIFLE criteria);
received dialysis (either acute or chronic) within 5 days prior to enrollment or in imminent need of dialysis at the time of enrollment;
known infection with human immunodeficiency virus (HIV) or a hepatitis virus;
meets only the SBP<90 mmHg inclusion criterion set forth above, and does not have shock in the attending physician's or principal investigator's opinion.

After providing informed consent, an EDTA anti-coagulated blood sample (10 mL) and a urine sample (25-30 mL) are collected from each patient. Blood and urine samples are then collected at 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Example 4. Immunoassay Format

Analytes are measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards. Units for Insulin-like growth factor-binding protein 2, Insulin-like growth factor-binding protein 3, Insulin-like growth factor-binding protein 4, and Insulin-like growth factor-binding protein 6 reported herein are ng/mL.

Example 5. Apparently Healthy Donor and Chronic Disease Patient Samples

Human urine samples from donors with no known chronic or acute disease ("Apparently Healthy Donors") were purchased from two vendors (Golden West Biologicals, Inc., 27625 Commerce Center Dr., Temecula, Calif. 92590 and Virginia Medical Research, Inc., 915 First Colonial Rd., Virginia Beach, Va. 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, Va. 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

Example 6. Use of CD97 Antigen for Evaluating Renal Status in Patients Admitted to the ICU: Recovery to RIFLE 0 from RIFLE I and F Patients from the intensive care unit (ICU) are enrolled in the following study. EDTA anti-coagulated blood samples (10 mL) and a urine samples (25-30 mL) are collected from each patient at enrollment, 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. CD97 antigen is measured in the earliest samples collected while the patients were in RIFLE I or F by standard immunoassay methods using commercially available assay reagents.

Kidney status is assessed by RIFLE criteria based on serum creatinine, urine output, or both serum creatinine and urine output during a period starting at 12, 24, 48, or 72 hours after sample collection or at any time within 7 days after sample collection. Two cohorts are defined to represent a "recovered" and a "non-recovered" population. "Recovered" indicates those patients whose maximum RIFLE stage during a period of 24, 48 or 72 hours is non-injury (RIFLE 0). "Non-recovered" indicates those patients whose maximum RIFLE stage during a period of 24, 48 or 72 hours is risk of injury (R), injury (I) or failure (F). If a patient dies or is placed on renal replacement therapy (RRT) within 9 days of enrollment, the patient is considered "non-recovered".

The ability to distinguish the "recovered" and "non-recovered" cohorts is determined using receiver operating characteristic (ROC) analysis.

Example 6. Use of Insulin-Like Growth Factor-Binding Protein 2 for Evaluating Renal Status in Patients Admitted to the ICU: Recovery to RIFLE 0 from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 2 is measured in the enrollment samples by standard immunoassay methods using commercially available assay reagents.

Kidney status is assessed by RIFLE criteria based on serum creatinine, urine output, or both serum creatinine and urine output during a period starting at 12, 24, 48, or 72 hours after sample collection or at any time within 7 days after sample collection. Two cohorts are defined to represent a "recovered" and a "non-recovered" population. "Recovered" indicates those patients whose maximum RIFLE stage during a period of 24, 48 or 72 hours is non-injury (RIFLE 0). "Non-recovered" indicates those patients whose maximum RIFLE stage during a period of 24, 48 or 72 hours is risk of injury (R), injury (I) or failure (F). If a patient dies or is placed on renal replacement therapy (RRT) at any time from sample collection to 12, 24, 48, or 72 hours after sample collection or at any time within 7 days after sample collection, the patient is considered "non-recovered".

The ability to distinguish the "recovered" and "non-recovered" cohorts is determined using receiver operating characteristic (ROC) analysis.

TABLE 6.1

Comparison of marker levels and the area under the ROC curve (AUC) in urine samples for the "recovered" and "non-recovered" cohorts where recovery starts at 12 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 1.23 | 5.74 | 0.497 | 5.72 | 0.497 | 5.72 |
| Average | 4.29 | 17.7 | 4.50 | 17.5 | 4.50 | 17.5 |
| Stdev | 9.77 | 26.8 | 10.3 | 26.7 | 10.3 | 26.7 |
| p (t-test) | | 0.12 | | 0.15 | | 0.15 |
| Min | 3.16E−5 | 0.0532 | 3.16E−5 | 0.0532 | 3.16E−5 | 0.0532 |
| Max | 31.9 | 112 | 31.9 | 112 | 31.9 | 112 |
| n (Patient) | 10 | 139 | 9 | 140 | 9 | 140 |
| sCr only | | | | | | |
| Median | 2.09 | 6.60 | 2.08 | 6.52 | 2.08 | 6.52 |
| Average | 5.77 | 18.8 | 5.74 | 18.7 | 5.74 | 18.7 |
| Stdev | 11.2 | 27.6 | 11.4 | 27.5 | 11.4 | 27.5 |
| p (t-test) | | 0.028 | | 0.032 | | 0.032 |
| Min | 3.16E−5 | 0.0532 | 3.16E−5 | 0.0532 | 3.16E−5 | 0.0532 |
| Max | 46.5 | 112 | 46.5 | 112 | 46.5 | 112 |
| n (Patient) | 23 | 126 | 22 | 127 | 22 | 127 |
| UO only | | | | | | |
| Median | 3.17 | 6.67 | 2.91 | 6.67 | 2.85 | 6.73 |
| Average | 13.4 | 20.4 | 12.9 | 20.2 | 11.3 | 21.1 |
| Stdev | 22.3 | 29.5 | 20.7 | 29.8 | 18.2 | 30.4 |
| p (t-test) | | 0.11 | | 0.091 | | 0.024 |
| Min | 3.16E−5 | 0.0645 | 3.16E−5 | 0.0645 | 3.16E−5 | 0.0645 |
| Max | 102 | 112 | 91.0 | 112 | 90.4 | 112 |
| n (Patient) | 75 | 73 | 67 | 81 | 64 | 84 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.78 | 0.71 | 0.61 | 0.79 | 0.72 | 0.62 | 0.79 | 0.72 | 0.63 |
| SE | 0.061 | 0.052 | 0.046 | 0.061 | 0.052 | 0.046 | 0.061 | 0.052 | 0.045 |
| p Value | 4.0E−6 | 7.8E−5 | 0.016 | 2.5E−6 | 3.2E−5 | 0.0097 | 2.5E−6 | 3.2E−5 | 0.0033 |
| nCohort Recovered | 10 | 23 | 75 | 9 | 22 | 67 | 9 | 22 | 64 |
| nCohort Non-recovered | 139 | 126 | 73 | 140 | 127 | 81 | 140 | 127 | 84 |
| Cutoff Quartile 2 | 1.89 | 1.89 | 1.93 | 1.89 | 1.89 | 1.93 | 1.89 | 1.89 | 1.93 |
| Sensitivity | 77% | 77% | 81% | 77% | 77% | 81% | 77% | 77% | 81% |
| Specificity | 50% | 35% | 31% | 56% | 36% | 33% | 56% | 36% | 33% |
| Cutoff Quartile 3 | 4.13 | 4.13 | 4.52 | 4.13 | 4.13 | 4.52 | 4.13 | 4.13 | 4.52 |
| Sensitivity | 53% | 56% | 58% | 53% | 57% | 58% | 53% | 57% | 58% |
| Specificity | 90% | 83% | 57% | 89% | 86% | 60% | 89% | 86% | 61% |
| Cutoff Quartile 4 | 20.0 | 20.0 | 20.2 | 20.0 | 20.0 | 20.2 | 20.0 | 20.0 | 20.2 |
| Sensitivity | 27% | 29% | 32% | 26% | 28% | 30% | 26% | 28% | 31% |
| Specificity | 90% | 91% | 81% | 89% | 91% | 81% | 89% | 91% | 83% |
| OR Quartile 2 | 3.34 | 1.78 | 1.86 | 4.22 | 1.93 | 2.15 | 4.22 | 1.93 | 2.08 |
| p Value | 0.069 | 0.23 | 0.11 | 0.040 | 0.18 | 0.048 | 0.040 | 0.18 | 0.058 |
| Lower limit of 95% CI | 0.910 | 0.688 | 0.870 | 1.07 | 0.738 | 1.01 | 1.07 | 0.738 | 0.976 |
| Upper limit of 95% CI | 12.3 | 4.63 | 3.99 | 16.6 | 5.06 | 4.59 | 16.6 | 5.06 | 4.41 |
| OR Quartile 3 | 10.2 | 6.13 | 1.82 | 8.97 | 8.29 | 2.05 | 8.97 | 8.29 | 2.18 |
| p Value | 0.029 | 0.0017 | 0.072 | 0.041 | 0.0011 | 0.033 | 0.041 | 0.0011 | 0.021 |
| Lower limit of 95% CI | 1.26 | 1.97 | 0.949 | 1.09 | 2.33 | 1.06 | 1.09 | 2.33 | 1.12 |
| Upper limit of 95% CI | 83.1 | 19.1 | 3.49 | 73.6 | 29.4 | 3.95 | 73.6 | 29.4 | 4.24 |
| OR Quartile 4 | 3.26 | 4.20 | 2.00 | 2.87 | 3.96 | 1.75 | 2.87 | 3.96 | 2.16 |
| p Value | 0.27 | 0.061 | 0.074 | 0.33 | 0.073 | 0.16 | 0.33 | 0.073 | 0.058 |

TABLE 6.1-continued

Comparison of marker levels and the area under the ROC curve (AUC) in urine samples for the "recovered" and "non-recovered" cohorts where recovery starts at 12 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 0.400 | 0.936 | 0.935 | 0.348 | 0.879 | 0.809 | 0.348 | 0.879 | 0.973 |
| Upper limit of 95% CI | 26.7 | 18.8 | 4.30 | 23.8 | 17.8 | 3.78 | 23.8 | 17.8 | 4.79 |

TABLE 6.2

Comparison of marker levels and the area under the ROC curve (AUC) in urine samples for the "recovered" and "non-recovered" cohorts where recovery starts at 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 2.21 | 6.52 | 2.01 | 6.39 | 1.96 | 6.06 |
| Average | 4.52 | 19.3 | 4.92 | 18.8 | 5.01 | 18.7 |
| Stdev | 6.85 | 28.0 | 7.40 | 27.7 | 7.57 | 27.6 |
| p (t-test) | | 0.0082 | | 0.021 | | 0.026 |
| Min | 3.16E−5 | 0.0532 | 3.16E−5 | 0.0532 | 3.16E−5 | 0.0532 |
| Max | 31.9 | 112 | 31.9 | 112 | 31.9 | 112 |
| n (Patient) | 26 | 123 | 22 | 127 | 21 | 128 |
| sCr only | | | | | | |
| Median | 2.35 | 6.86 | 2.34 | 6.73 | 2.22 | 6.67 |
| Average | 5.67 | 20.5 | 5.74 | 20.2 | 5.83 | 20.0 |
| Stdev | 9.35 | 28.8 | 9.62 | 28.6 | 9.76 | 28.6 |
| p (t-test) | | 0.0034 | | 0.0051 | | 0.0065 |
| Min | 3.16E−5 | 0.0532 | 3.16E−5 | 0.0532 | 3.16E−5 | 0.0532 |
| Max | 46.5 | 112 | 46.5 | 112 | 46.5 | 112 |
| n (Patient) | 35 | 112 | 33 | 114 | 32 | 115 |
| UO only | | | | | | |
| Median | 3.47 | 6.78 | 3.47 | 6.60 | 3.17 | 6.67 |
| Average | 12.9 | 21.5 | 11.4 | 21.9 | 11.0 | 21.9 |
| Stdev | 20.1 | 31.2 | 15.6 | 32.2 | 15.4 | 31.8 |
| p (t-test) | | 0.046 | | 0.015 | | 0.011 |
| Min | 3.16E−5 | 0.0645 | 3.16E−5 | 0.0645 | 3.16E−5 | 0.0645 |
| Max | 102 | 112 | 73.5 | 112 | 73.5 | 112 |
| n (Patient) | 81 | 63 | 72 | 72 | 69 | 75 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.72 | 0.69 | 0.61 | 0.71 | 0.69 | 0.60 | 0.71 | 0.69 | 0.62 |
| SE | 0.049 | 0.047 | 0.048 | 0.053 | 0.048 | 0.047 | 0.054 | 0.048 | 0.047 |
| p Value | 1.1E−5 | 6.2E−5 | 0.026 | 7.8E−5 | 4.6E−5 | 0.029 | 8.3E−5 | 5.5E−5 | 0.011 |
| nCohort Recovered | 26 | 35 | 81 | 22 | 33 | 72 | 21 | 32 | 69 |
| nCohort Non-recovered | 123 | 112 | 63 | 127 | 114 | 72 | 128 | 115 | 75 |
| Cutoff Quartile 2 | 1.89 | 1.91 | 1.93 | 1.89 | 1.91 | 1.93 | 1.89 | 1.91 | 1.93 |
| Sensitivity | 79% | 78% | 81% | 79% | 78% | 81% | 79% | 78% | 81% |
| Specificity | 42% | 34% | 30% | 45% | 36% | 31% | 48% | 38% | 32% |
| Cutoff Quartile 3 | 4.13 | 4.13 | 4.99 | 4.13 | 4.13 | 4.99 | 4.13 | 4.13 | 4.99 |
| Sensitivity | 56% | 58% | 57% | 54% | 58% | 56% | 54% | 57% | 56% |
| Specificity | 77% | 74% | 56% | 73% | 76% | 56% | 71% | 75% | 57% |
| Cutoff Quartile 4 | 20.0 | 20.5 | 20.2 | 20.0 | 20.5 | 20.2 | 20.0 | 20.5 | 20.2 |
| Sensitivity | 30% | 31% | 32% | 29% | 31% | 31% | 29% | 30% | 31% |
| Specificity | 96% | 94% | 80% | 95% | 94% | 81% | 95% | 94% | 81% |
| OR Quartile 2 | 2.74 | 1.82 | 1.79 | 3.09 | 2.03 | 1.82 | 3.40 | 2.16 | 2.04 |
| p Value | 0.027 | 0.16 | 0.15 | 0.019 | 0.096 | 0.13 | 0.012 | 0.073 | 0.070 |
| Lower limit of 95% CI | 1.12 | 0.794 | 0.813 | 1.20 | 0.881 | 0.844 | 1.31 | 0.931 | 0.944 |
| Upper limit of 95% CI | 6.66 | 4.15 | 3.94 | 7.91 | 4.70 | 3.93 | 8.85 | 5.01 | 4.41 |
| OR Quartile 3 | 4.26 | 4.00 | 1.67 | 3.17 | 4.30 | 1.56 | 2.92 | 4.04 | 1.65 |

TABLE 6.2-continued

Comparison of marker levels and the area under the ROC curve
(AUC) in urine samples for the "recovered" and "non-recovered" cohorts where recovery
starts at 24 hours after sample collection and renal status is assessed by serum creatinine
(sCr) only, urine output (UO) only, or serum creatinine or urine output RIFLE criteria.

| | | | | | | | | | |
|---|---|---|---|---|---|---|---|---|---|
| p Value | 0.0037 | 0.0013 | 0.13 | 0.024 | 0.0011 | 0.18 | 0.037 | 0.0019 | 0.13 |
| Lower limit of 95% CI | 1.60 | 1.71 | 0.858 | 1.17 | 1.78 | 0.810 | 1.07 | 1.67 | 0.856 |
| Upper limit of 95% CI | 11.3 | 9.31 | 3.24 | 8.63 | 10.3 | 3.02 | 8.02 | 9.76 | 3.20 |
| OR Quartile 4 | 10.8 | 7.50 | 1.89 | 8.63 | 6.87 | 1.82 | 8.13 | 6.56 | 1.91 |
| p Value | 0.022 | 0.0077 | 0.10 | 0.039 | 0.011 | 0.13 | 0.045 | 0.013 | 0.10 |
| Lower limit of 95% CI | 1.40 | 1.70 | 0.882 | 1.12 | 1.56 | 0.844 | 1.05 | 1.49 | 0.875 |
| Upper limit of 95% CI | 82.4 | 33.0 | 4.05 | 66.5 | 30.3 | 3.93 | 62.8 | 29.0 | 4.15 |

TABLE 6.3

Comparison of marker levels and the area under the ROC curve
(AUC) in urine samples for the "recovered" and "non-recovered" cohorts where recovery
starts at 48 hours after sample collection and renal status is assessed by serum creatinine
(sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 2.09 | 7.04 | 2.07 | 7.04 | 2.07 | 6.93 |
| Average | 3.90 | 21.2 | 3.59 | 20.9 | 3.72 | 20.4 |
| Stdev | 4.68 | 29.1 | 4.29 | 28.8 | 4.42 | 28.6 |
| p (t-test) | | 4.5E−4 | | 6.8E−4 | | 0.0016 |
| Min | 3.16E−5 | 0.0532 | 3.16E−5 | 0.0532 | 0.242 | 3.16E−5 |
| Max | 17.4 | 112 | 17.4 | 112 | 17.4 | 112 |
| n (Patient) | 37 | 109 | 34 | 112 | 31 | 115 |
| sCr only | | | | | | |
| Median | 2.30 | 8.85 | 2.09 | 8.85 | 2.09 | 8.85 |
| Average | 4.85 | 22.4 | 4.61 | 22.1 | 4.61 | 22.1 |
| Stdev | 7.76 | 29.9 | 7.71 | 29.6 | 7.71 | 29.6 |
| p (t-test) | | 1.6E−4 | | 2.0E−4 | | 2.0E−4 |
| Min | 3.16E−5 | 0.0532 | 3.16E−5 | 0.0532 | 3.16E−5 | 0.0532 |
| Max | 46.5 | 112 | 46.5 | 112 | 46.5 | 112 |
| n (Patient) | 45 | 100 | 43 | 102 | 43 | 102 |
| UO only | | | | | | |
| Median | 3.49 | 6.98 | 3.34 | 6.98 | 3.17 | 6.67 |
| Average | 14.8 | 21.4 | 14.7 | 21.2 | 15.7 | 19.6 |
| Stdev | 23.3 | 30.6 | 23.7 | 29.9 | 24.8 | 28.8 |
| p (t-test) | | 0.17 | | 0.17 | | 0.42 |
| Min | 3.16E−5 | 0.0645 | 3.16E−5 | 0.0645 | 0.0532 | 3.16E−5 |
| Max | 109 | 112 | 109 | 112 | 109 | 112 |
| n (Patient) | 70 | 58 | 66 | 62 | 59 | 69 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.74 | 0.73 | 0.60 | 0.75 | 0.74 | 0.61 | 0.73 | 0.74 | 0.59 |
| SE | 0.043 | 0.042 | 0.050 | 0.043 | 0.042 | 0.050 | 0.045 | 0.042 | 0.050 |
| p Value | 5.1E−8 | 4.0E−8 | 0.041 | 9.6E−9 | 7.9E−9 | 0.024 | 2.9E−7 | 7.9E−9 | 0.062 |
| nCohort Recovered | 37 | 45 | 70 | 34 | 43 | 66 | 31 | 43 | 59 |
| nCohort Non-recovered | 109 | 100 | 58 | 112 | 102 | 62 | 115 | 102 | 69 |
| Cutoff Quartile 2 | 1.90 | 1.89 | 1.89 | 1.90 | 1.89 | 1.89 | 1.90 | 1.89 | 1.89 |
| Sensitivity | 79% | 81% | 83% | 79% | 81% | 84% | 78% | 81% | 83% |
| Specificity | 38% | 38% | 31% | 41% | 40% | 33% | 39% | 40% | 34% |
| Cutoff Quartile 3 | 4.11 | 4.13 | 5.38 | 4.11 | 4.13 | 5.38 | 4.11 | 4.13 | 5.38 |
| Sensitivity | 60% | 62% | 59% | 59% | 62% | 58% | 58% | 62% | 57% |
| Specificity | 78% | 76% | 57% | 79% | 77% | 58% | 81% | 77% | 58% |
| Cutoff Quartile 4 | 19.7 | 20.0 | 22.3 | 19.7 | 20.0 | 22.3 | 19.7 | 20.0 | 22.3 |
| Sensitivity | 34% | 36% | 29% | 33% | 35% | 29% | 32% | 35% | 26% |
| Specificity | 100% | 98% | 79% | 100% | 98% | 79% | 100% | 98% | 76% |
| OR Quartile 2 | 2.28 | 2.59 | 2.20 | 2.71 | 2.86 | 2.60 | 2.27 | 2.86 | 2.44 |

TABLE 6.3-continued

Comparison of marker levels and the area under the ROC curve
(AUC) in urine samples for the "recovered" and "non-recovered" cohorts where recovery
starts at 48 hours after sample collection and renal status is assessed by serum creatinine
(sCr) only, urine output (UO) only, or serum creatinine or urine output RIFLE criteria.

| p Value | 0.046 | 0.017 | 0.068 | 0.018 | 0.0091 | 0.027 | 0.058 | 0.0091 | 0.034 |
|---|---|---|---|---|---|---|---|---|---|
| Lower limit of 95% CI | 1.01 | 1.18 | 0.942 | 1.19 | 1.30 | 1.11 | 0.974 | 1.30 | 1.07 |
| Upper limit of 95% CI | 5.11 | 5.66 | 5.14 | 6.17 | 6.29 | 6.07 | 5.31 | 6.29 | 5.55 |
| OR Quartile 3 | 5.36 | 5.04 | 1.89 | 5.53 | 5.33 | 1.88 | 5.82 | 5.33 | 1.77 |
| p Value | 1.6E−4 | 6.1E−5 | 0.077 | 2.4E−4 | 5.4E−5 | 0.078 | 3.5E−4 | 5.4E−5 | 0.11 |
| Lower limit of 95% CI | 2.24 | 2.29 | 0.933 | 2.22 | 2.37 | 0.931 | 2.22 | 2.37 | 0.876 |
| Upper limit of 95% CI | 12.8 | 11.1 | 3.82 | 13.8 | 12.0 | 3.79 | 15.3 | 12.0 | 3.57 |
| OR Quartile 4 | 38.8 | 24.8 | 1.52 | 34.3 | 22.9 | 1.52 | 30.1 | 22.9 | 1.13 |
| p Value | 0.011 | 0.0019 | 0.31 | 0.014 | 0.0024 | 0.31 | 0.018 | 0.0024 | 0.76 |
| Lower limit of 95% CI | 2.32 | 3.27 | 0.681 | 2.04 | 3.03 | 0.679 | 1.79 | 3.03 | 0.507 |
| Upper limit of 95% CI | 650 | 187 | 3.40 | 575 | 173 | 3.40 | 505 | 173 | 2.54 |

TABLE 6.4

Comparison of marker levels and the area under the ROC curve
(AUC) in urine samples for the "recovered" and "non-recovered" cohorts where recovery
starts at 72 hours after sample collection and renal status is assessed by serum creatinine
(sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 2.30 | 7.74 | 2.20 | 7.04 | 2.20 | 7.04 |
| Average | 6.89 | 21.7 | 7.15 | 20.9 | 7.30 | 20.6 |
| Stdev | 12.2 | 29.8 | 12.8 | 29.3 | 13.1 | 29.1 |
| p (t-test) | | 0.0020 | | 0.0059 | | 0.0091 |
| Min | 3.16E−5 | 0.0532 | 0.242 | 3.16E−5 | 0.242 | 3.16E−5 |
| Max | 56.0 | 112 | 56.0 | 112 | 56.0 | 112 |
| n (Patient) | 43 | 99 | 38 | 104 | 36 | 106 |
| sCr only | | | | | | |
| Median | 2.32 | 9.30 | 2.32 | 9.30 | 2.32 | 8.42 |
| Average | 7.38 | 22.6 | 7.38 | 22.6 | 7.51 | 22.2 |
| Stdev | 12.7 | 30.5 | 12.7 | 30.5 | 12.9 | 30.3 |
| p (t-test) | | 9.7E−4 | | 9.7E−4 | | 0.0016 |
| Min | 3.16E−5 | 0.0532 | 3.16E−5 | 0.0532 | 3.16E−5 | 0.0532 |
| Max | 56.0 | 112 | 56.0 | 112 | 56.0 | 112 |
| n (Patient) | 50 | 92 | 50 | 92 | 48 | 94 |
| UO only | | | | | | |
| Median | 3.21 | 7.04 | 3.21 | 6.93 | 3.53 | 6.86 |
| Average | 15.8 | 21.0 | 17.3 | 19.2 | 18.1 | 18.4 |
| Stdev | 26.4 | 28.9 | 28.0 | 27.5 | 28.7 | 26.8 |
| p (t-test) | | 0.31 | | 0.71 | | 0.95 |
| Min | 3.16E−5 | 0.0645 | 3.16E−5 | 3.16E−5 | 0.0532 | 3.16E−5 |
| Max | 109 | 112 | 109 | 112 | 109 | 112 |
| n (Patient) | 62 | 57 | 54 | 65 | 50 | 70 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.70 | 0.63 | 0.70 | 0.70 | 0.61 | 0.69 | 0.69 | 0.57 |
| SE | 0.044 | 0.044 | 0.051 | 0.046 | 0.044 | 0.052 | 0.047 | 0.044 | 0.052 |
| p Value | 2.4E−6 | 3.8E−6 | 0.011 | 1.8E−5 | 3.8E−6 | 0.041 | 5.2E−5 | 1.2E−5 | 0.15 |
| nCohort Recovered | 43 | 50 | 62 | 38 | 50 | 54 | 36 | 48 | 50 |
| nCohort Non-recovered | 99 | 92 | 57 | 104 | 92 | 65 | 106 | 94 | 70 |
| Cutoff Quartile 2 | 1.90 | 1.90 | 1.88 | 1.90 | 1.90 | 1.88 | 1.90 | 1.90 | 1.89 |
| Sensitivity | 81% | 80% | 86% | 80% | 80% | 85% | 79% | 80% | 81% |
| Specificity | 40% | 36% | 35% | 39% | 36% | 37% | 39% | 35% | 34% |
| Cutoff Quartile 3 | 4.99 | 4.99 | 5.74 | 4.99 | 4.99 | 5.74 | 4.99 | 4.99 | 6.06 |
| Sensitivity | 59% | 61% | 60% | 58% | 61% | 57% | 58% | 61% | 54% |
| Specificity | 70% | 70% | 58% | 71% | 70% | 57% | 72% | 71% | 56% |
| Cutoff Quartile 4 | 20.7 | 20.7 | 22.6 | 20.7 | 20.7 | 22.6 | 20.7 | 20.7 | 22.3 |

TABLE 6.4-continued

Comparison of marker levels and the area under the ROC curve (AUC) in urine samples for the "recovered" and "non-recovered" cohorts where recovery starts at 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Sensitivity | 33% | 35% | 30% | 32% | 35% | 26% | 31% | 34% | 26% |
| Specificity | 93% | 92% | 79% | 92% | 92% | 76% | 92% | 92% | 76% |
| OR Quartile 2 | 2.75 | 2.31 | 3.37 | 2.58 | 2.31 | 3.24 | 2.43 | 2.16 | 2.26 |
| p Value | 0.012 | 0.034 | 0.0089 | 0.022 | 0.034 | 0.0083 | 0.033 | 0.051 | 0.057 |
| Lower limit of 95% CI | 1.25 | 1.07 | 1.36 | 1.15 | 1.07 | 1.35 | 1.07 | 0.996 | 0.975 |
| Upper limit of 95% CI | 6.07 | 5.01 | 8.37 | 5.78 | 5.01 | 7.73 | 5.51 | 4.71 | 5.23 |
| OR Quartile 3 | 3.26 | 3.63 | 2.05 | 3.35 | 3.63 | 1.78 | 3.52 | 3.74 | 1.51 |
| p Value | 0.0024 | 5.9E−4 | 0.055 | 0.0031 | 5.9E−4 | 0.12 | 0.0028 | 5.4E−4 | 0.27 |
| Lower limit of 95% CI | 1.52 | 1.74 | 0.985 | 1.50 | 1.74 | 0.859 | 1.54 | 1.77 | 0.728 |
| Upper limit of 95% CI | 7.01 | 7.57 | 4.25 | 7.46 | 7.57 | 3.69 | 8.04 | 7.90 | 3.14 |
| OR Quartile 4 | 6.67 | 6.13 | 1.60 | 5.42 | 6.13 | 1.12 | 4.97 | 5.68 | 1.10 |
| p Value | 0.0028 | 0.0013 | 0.27 | 0.0080 | 0.0013 | 0.79 | 0.012 | 0.0021 | 0.83 |
| Lower limit of 95% CI | 1.92 | 2.03 | 0.696 | 1.55 | 2.03 | 0.485 | 1.42 | 1.87 | 0.472 |
| Upper limit of 95% CI | 23.2 | 18.6 | 3.69 | 18.9 | 18.6 | 2.57 | 17.4 | 17.2 | 2.54 |

TABLE 6.5

Comparison of marker levels and the area under the ROC curve (AUC) in urine samples for the "recovered" and "non-recovered" cohorts where recovery starts within 7 days after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 3.09 | 7.74 | 3.15 | 7.39 | 3.15 | 7.39 |
| Average | 13.8 | 20.8 | 13.9 | 20.5 | 13.9 | 20.5 |
| Stdev | 23.3 | 29.3 | 23.4 | 29.2 | 23.4 | 29.2 |
| p (t-test) | | 0.10 | | 0.13 | | 0.13 |
| Min | 3.16E−5 | 0.0645 | 3.16E−5 | 0.0645 | 3.16E−5 | 0.0645 |
| Max | 109 | 112 | 109 | 112 | 109 | 112 |
| n (Patient) | 86 | 63 | 85 | 64 | 85 | 64 |
| sCr only | | | | | | |
| Median | 2.65 | 10.8 | 2.79 | 10.2 | 2.79 | 10.2 |
| Average | 9.32 | 23.5 | 9.56 | 23.0 | 9.56 | 23.0 |
| Stdev | 15.7 | 31.5 | 15.9 | 31.3 | 15.9 | 31.3 |
| p (t-test) | | 7.8E−4 | | 0.0016 | | 0.0016 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 71 | 78 | 69 | 80 | 69 | 80 |
| UO only | | | | | | |
| Median | 3.32 | 7.39 | 3.47 | 7.04 | 3.49 | 6.91 |
| Average | 15.0 | 20.2 | 15.3 | 19.6 | 15.6 | 19.0 |
| Stdev | 25.1 | 28.1 | 25.3 | 27.8 | 25.5 | 27.5 |
| p (t-test) | | 0.25 | | 0.34 | | 0.45 |
| Min | 3.16E−5 | 0.0645 | 3.16E−5 | 0.0645 | 3.16E−5 | 0.0645 |
| Max | 109 | 112 | 109 | 112 | 109 | 112 |
| n (Patient) | 96 | 52 | 94 | 54 | 92 | 56 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.62 | 0.67 | 0.62 | 0.62 | 0.65 | 0.61 | 0.62 | 0.65 | 0.59 |
| SE | 0.047 | 0.044 | 0.049 | 0.047 | 0.045 | 0.049 | 0.047 | 0.045 | 0.049 |
| p Value | 0.010 | 9.5E−5 | 0.016 | 0.012 | 7.1E−4 | 0.026 | 0.012 | 7.1E−4 | 0.058 |
| nCohort Recovered | 86 | 71 | 96 | 85 | 69 | 94 | 85 | 69 | 92 |
| nCohort Non-recovered | 63 | 78 | 52 | 64 | 80 | 54 | 64 | 80 | 56 |
| Cutoff Quartile 2 | 1.89 | 1.89 | 1.93 | 1.89 | 1.89 | 1.93 | 1.89 | 1.89 | 1.93 |
| Sensitivity | 81% | 81% | 83% | 81% | 79% | 83% | 81% | 79% | 82% |
| Specificity | 29% | 31% | 29% | 29% | 29% | 30% | 29% | 29% | 29% |

TABLE 6.5-continued

Comparison of marker levels and the area under the ROC curve
(AUC) in urine samples for the "recovered" and "non-recovered" cohorts where recovery
starts within 7 days after sample collection and renal status is assessed by serum
creatinine (sCr) only, urine output (UO) only, or serum creatinine or urine output RIFLE criteria.

| | | | | | | | | | |
|---|---|---|---|---|---|---|---|---|---|
| Cutoff Quartile 3 | 4.13 | 4.13 | 4.52 | 4.13 | 4.13 | 4.52 | 4.13 | 4.13 | 4.52 |
| Sensitivity | 62% | 64% | 63% | 61% | 62% | 61% | 61% | 62% | 59% |
| Specificity | 58% | 65% | 57% | 58% | 64% | 56% | 58% | 64% | 55% |
| Cutoff Quartile 4 | 20.0 | 20.0 | 20.2 | 20.0 | 20.0 | 20.2 | 20.0 | 20.0 | 20.2 |
| Sensitivity | 33% | 36% | 33% | 33% | 35% | 31% | 33% | 35% | 30% |
| Specificity | 80% | 86% | 79% | 80% | 86% | 79% | 80% | 86% | 78% |
| OR Quartile 2 | 1.74 | 1.89 | 1.97 | 1.81 | 1.51 | 2.12 | 1.81 | 1.51 | 1.91 |
| p Value | 0.16 | 0.100 | 0.12 | 0.14 | 0.28 | 0.080 | 0.14 | 0.28 | 0.12 |
| Lower limit of 95% CI | 0.797 | 0.886 | 0.847 | 0.826 | 0.717 | 0.915 | 0.826 | 0.717 | 0.843 |
| Upper limit of 95% CI | 3.81 | 4.01 | 4.57 | 3.95 | 3.19 | 4.92 | 3.95 | 3.19 | 4.33 |
| OR Quartile 3 | 2.26 | 3.29 | 2.33 | 2.12 | 2.93 | 2.03 | 2.12 | 2.93 | 1.78 |
| p Value | 0.016 | 5.2E−4 | 0.017 | 0.026 | 0.0016 | 0.042 | 0.026 | 0.0016 | 0.091 |
| Lower limit of 95% CI | 1.16 | 1.68 | 1.16 | 1.10 | 1.50 | 1.03 | 1.10 | 1.50 | 0.911 |
| Upper limit of 95% CI | 4.39 | 6.43 | 4.67 | 4.11 | 5.72 | 4.02 | 4.11 | 5.72 | 3.50 |
| OR Quartile 4 | 2.03 | 3.42 | 1.85 | 1.95 | 3.18 | 1.70 | 1.95 | 3.18 | 1.57 |
| p Value | 0.063 | 0.0031 | 0.11 | 0.078 | 0.0053 | 0.17 | 0.078 | 0.0053 | 0.24 |
| Lower limit of 95% CI | 0.963 | 1.51 | 0.863 | 0.928 | 1.41 | 0.797 | 0.928 | 1.41 | 0.738 |
| Upper limit of 95% CI | 4.28 | 7.70 | 3.95 | 4.11 | 7.16 | 3.63 | 4.11 | 7.16 | 3.34 |

Example 7. Use of Insulin-Like Growth Factor-Binding Protein 2 for Evaluating Renal Status in Patients Admitted to the ICU: Recovery to RIFLE 0 and R from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 2 is measured in the enrollment samples by standard immunoassay methods using commercially available assay reagents.

Kidney status is assessed by RIFLE criteria based on serum creatinine, urine output, or both serum creatinine and urine output during a period starting at 12, 24, 48, or 72 hours after sample collection or at any time within 7 days after sample collection. Two cohorts are defined to represent a "recovered" and a "non-recovered" population. "Recovered" indicates those patients whose maximum RIFLE stage during a period of 24, 48 or 72 hours is non-injury (RIFLE 0) or risk of injury (R). "Non-recovered" indicates those patients whose maximum RIFLE stage during a period of 24, 48 or 72 hours is injury (I) or failure (F). If a patient dies or is placed on renal replacement therapy (RRT) at any time from sample collection to 12, 24, 48, or 72 hours after sample collection or at any time within 7 days after sample collection, the patient is considered "non-recovered".

The ability to distinguish the "recovered" and "non-recovered" cohorts is determined using receiver operating characteristic (ROC) analysis.

TABLE 7.1

Comparison of marker levels and the area under the ROC curve
(AUC) in urine samples for the "recovered" and "non-recovered" cohorts where recovery
starts at 12 hours after sample collection and renal status is assessed by serum creatinine
(sCr) only, urine output (UO) only, or serum creatinine or urine output RIFLE criteria.

| | | Recovery Period Duration (hr) | | | | |
|---|---|---|---|---|---|---|
| | | 24 | | 48 | | 72 | |
| | | Recovered Cohort | Non-recovered Cohort | Recovered Cohort | Non-recovered Cohort | Recovered Cohort | Non-recovered Cohort |
| sCr or UO | | | | | | | |
| | Median | 2.52 | 6.86 | 2.52 | 6.73 | 2.44 | 6.67 |
| | Average | 6.75 | 20.1 | 6.91 | 19.8 | 7.01 | 19.6 |
| | Stdev | 13.8 | 28.4 | 14.1 | 28.2 | 14.3 | 28.2 |
| | p (t-test) | | 0.0068 | | 0.010 | | 0.013 |
| | Min | 3.16E−5 | 0.0532 | 3.16E−5 | 0.0532 | 3.16E−5 | 0.0532 |
| | Max | 78.7 | 112 | 78.7 | 112 | 78.7 | 112 |
| | n (Patient) | 37 | 112 | 35 | 114 | 34 | 115 |
| sCr only | | | | | | | |
| | Median | 2.79 | 7.04 | 2.79 | 7.04 | 2.68 | 7.04 |
| | Average | 7.47 | 21.3 | 7.47 | 21.3 | 7.55 | 21.1 |
| | Stdev | 13.4 | 29.5 | 13.4 | 29.5 | 13.5 | 29.4 |
| | p (t-test) | | 0.0022 | | 0.0022 | | 0.0028 |
| | Min | 3.16E−5 | 0.0532 | 3.16E−5 | 0.0532 | 3.16E−5 | 0.0532 |
| | Max | 78.7 | 112 | 78.7 | 112 | 78.7 | 112 |
| | n (Patient) | 49 | 100 | 49 | 100 | 48 | 101 |

TABLE 7.1-continued

Comparison of marker levels and the area under the ROC curve
(AUC) in urine samples for the "recovered" and "non-recovered" cohorts where recovery
starts at 12 hours after sample collection and renal status is assessed by serum creatinine
(sCr) only, urine output (UO) only, or serum creatinine or urine output RIFLE criteria.

| UO only | | | | | | |
|---|---|---|---|---|---|---|
| Median | 3.47 | 7.04 | 3.16 | 6.98 | 3.15 | 7.04 |
| Average | 14.2 | 21.4 | 14.6 | 20.1 | 13.9 | 20.8 |
| Stdev | 23.7 | 29.7 | 24.5 | 28.5 | 23.4 | 29.3 |
| p (t-test) | | 0.11 | | 0.21 | | 0.11 |
| Min | 3.16E−5 | 0.0645 | 3.16E−5 | 0.0645 | 3.16E−5 | 0.0645 |
| Max | 109 | 112 | 109 | 112 | 109 | 112 |
| n (Patient) | 94 | 54 | 88 | 60 | 85 | 63 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.68 | 0.65 | 0.62 | 0.68 | 0.65 | 0.62 | 0.68 | 0.65 | 0.63 |
| SE | 0.047 | 0.046 | 0.049 | 0.048 | 0.046 | 0.047 | 0.048 | 0.046 | 0.047 |
| p Value | 1.2E−4 | 8.0E−4 | 0.013 | 2.1E−4 | 8.0E−4 | 0.011 | 1.9E−4 | 8.0E−4 | 0.0067 |
| nCohort Recovered | 37 | 49 | 94 | 35 | 49 | 88 | 34 | 48 | 85 |
| nCohort Non-recovered | 112 | 100 | 54 | 114 | 100 | 60 | 115 | 101 | 63 |
| Cutoff Quartile 2 | 1.89 | 1.89 | 1.93 | 1.89 | 1.89 | 1.93 | 1.89 | 1.89 | 1.93 |
| Sensitivity | 79% | 78% | 83% | 79% | 78% | 83% | 79% | 78% | 83% |
| Specificity | 38% | 31% | 30% | 37% | 31% | 31% | 38% | 31% | 31% |
| Cutoff Quartile 3 | 4.13 | 4.13 | 4.52 | 4.13 | 4.13 | 4.52 | 4.13 | 4.13 | 4.52 |
| Sensitivity | 58% | 58% | 63% | 58% | 58% | 63% | 57% | 57% | 63% |
| Specificity | 73% | 65% | 57% | 74% | 65% | 59% | 74% | 65% | 60% |
| Cutoff Quartile 4 | 20.0 | 20.0 | 20.2 | 20.0 | 20.0 | 20.2 | 20.0 | 20.0 | 20.2 |
| Sensitivity | 32% | 35% | 35% | 32% | 35% | 32% | 31% | 35% | 32% |
| Specificity | 95% | 94% | 81% | 94% | 94% | 80% | 94% | 94% | 80% |
| OR Quartile 2 | 2.36 | 1.56 | 2.12 | 2.22 | 1.56 | 2.21 | 2.35 | 1.63 | 2.08 |
| p Value | 0.038 | 0.25 | 0.080 | 0.057 | 0.25 | 0.056 | 0.043 | 0.21 | 0.071 |
| Lower limit of 95% CI | 1.05 | 0.724 | 0.915 | 0.976 | 0.724 | 0.978 | 1.03 | 0.754 | 0.938 |
| Upper limit of 95% CI | 5.28 | 3.38 | 4.92 | 5.03 | 3.38 | 5.01 | 5.36 | 3.53 | 4.62 |
| OR Quartile 3 | 3.73 | 2.60 | 2.30 | 3.97 | 2.60 | 2.49 | 3.74 | 2.46 | 2.61 |
| p Value | 0.0016 | 0.0083 | 0.018 | 0.0014 | 0.0083 | 0.0080 | 0.0023 | 0.013 | 0.0052 |
| Lower limit of 95% CI | 1.65 | 1.28 | 1.15 | 1.71 | 1.28 | 1.27 | 1.60 | 1.21 | 1.33 |
| Upper limit of 95% CI | 8.45 | 5.29 | 4.56 | 9.24 | 5.29 | 4.90 | 8.73 | 5.01 | 5.11 |
| OR Quartile 4 | 8.29 | 8.26 | 2.29 | 7.62 | 8.26 | 1.80 | 7.29 | 7.95 | 1.86 |
| p Value | 0.0051 | 8.3E−4 | 0.032 | 0.0072 | 8.3E−4 | 0.12 | 0.0086 | 0.0010 | 0.11 |
| Lower limit of 95% CI | 1.89 | 2.39 | 1.07 | 1.73 | 2.39 | 0.850 | 1.66 | 2.31 | 0.878 |
| Upper limit of 95% CI | 36.4 | 28.5 | 4.90 | 33.5 | 28.5 | 3.82 | 32.1 | 27.4 | 3.94 |

TABLE 7.2

Comparison of marker levels and the area under the ROC curve
(AUC) in urine samples for the "recovered" and "non-recovered" cohorts where recovery
starts at 24 hours after sample collection and renal status is assessed by serum creatinine
(sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 2.34 | 7.81 | 2.34 | 7.04 | 2.34 | 7.04 |
| Average | 6.95 | 21.9 | 7.13 | 21.5 | 7.13 | 21.5 |
| Stdev | 13.1 | 29.7 | 13.3 | 29.5 | 13.3 | 29.5 |
| p (t-test) | | 8.1E−4 | | 0.0015 | | 0.0015 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 51 | 98 | 49 | 100 | 49 | 100 |
| sCr only | | | | | | |
| Median | 2.35 | 10.0 | 2.34 | 9.57 | 2.34 | 9.57 |
| Average | 7.37 | 22.8 | 7.44 | 22.6 | 7.44 | 22.6 |
| Stdev | 13.6 | 30.3 | 13.7 | 30.2 | 13.7 | 30.2 |
| p (t-test) | | 4.4E−4 | | 5.9E−4 | | 5.9E−4 |

TABLE 7.2-continued

Comparison of marker levels and the area under the ROC curve
(AUC) in urine samples for the "recovered" and "non-recovered" cohorts where recovery
starts at 24 hours after sample collection and renal status is assessed by serum creatinine
(sCr) only, urine output (UO) only, or serum creatinine or urine output RIFLE criteria.

|  | | | | | | |
|---|---|---|---|---|---|---|
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 56 | 91 | 55 | 92 | 55 | 92 |
| UO only | | | | | | |
| Median | 3.49 | 6.86 | 3.47 | 6.93 | 3.47 | 6.93 |
| Average | 13.8 | 22.0 | 13.2 | 22.2 | 13.2 | 22.2 |
| Stdev | 22.3 | 30.8 | 21.3 | 31.1 | 21.3 | 31.1 |
| p (t-test) | | 0.072 | | 0.043 | | 0.043 |
| Min | 3.16E−5 | 0.0645 | 3.16E−5 | 0.0645 | 3.16E−5 | 0.0645 |
| Max | 109 | 112 | 109 | 112 | 109 | 112 |
| n (Patient) | 94 | 50 | 89 | 55 | 89 | 55 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.70 | 0.61 | 0.69 | 0.70 | 0.61 | 0.69 | 0.70 | 0.61 |
| SE | 0.043 | 0.043 | 0.050 | 0.044 | 0.043 | 0.049 | 0.044 | 0.043 | 0.049 |
| p Value | 4.7E−6 | 5.3E−6 | 0.034 | 1.4E−5 | 5.3E−6 | 0.027 | 1.4E−5 | 5.3E−6 | 0.027 |
| nCohort Recovered | 51 | 56 | 94 | 49 | 55 | 89 | 49 | 55 | 89 |
| nCohort Non-recovered | 98 | 91 | 50 | 100 | 92 | 55 | 100 | 92 | 55 |
| Cutoff Quartile 2 | 1.89 | 1.91 | 1.93 | 1.89 | 1.91 | 1.93 | 1.89 | 1.91 | 1.93 |
| Sensitivity | 81% | 79% | 82% | 80% | 79% | 80% | 80% | 79% | 80% |
| Specificity | 35% | 32% | 29% | 35% | 33% | 28% | 35% | 33% | 28% |
| Cutoff Quartile 3 | 4.13 | 4.13 | 4.99 | 4.13 | 4.13 | 4.99 | 4.13 | 4.13 | 4.99 |
| Sensitivity | 61% | 63% | 58% | 60% | 62% | 58% | 60% | 62% | 58% |
| Specificity | 71% | 70% | 54% | 69% | 69% | 55% | 69% | 69% | 55% |
| Cutoff Quartile 4 | 20.0 | 20.5 | 20.2 | 20.0 | 20.5 | 20.2 | 20.0 | 20.5 | 20.2 |
| Sensitivity | 36% | 36% | 36% | 35% | 36% | 35% | 35% | 36% | 35% |
| Specificity | 94% | 93% | 81% | 94% | 93% | 81% | 94% | 93% | 81% |
| OR Quartile 2 | 2.27 | 1.80 | 1.84 | 2.12 | 1.87 | 1.56 | 2.12 | 1.87 | 1.56 |
| p Value | 0.035 | 0.13 | 0.16 | 0.054 | 0.11 | 0.28 | 0.054 | 0.11 | 0.28 |
| Lower limit of 95% CI | 1.06 | 0.844 | 0.786 | 0.988 | 0.877 | 0.698 | 0.988 | 0.877 | 0.698 |
| Upper limit of 95% CI | 4.86 | 3.82 | 4.29 | 4.57 | 3.98 | 3.50 | 4.57 | 3.98 | 3.50 |
| OR Quartile 3 | 3.79 | 3.85 | 1.64 | 3.40 | 3.64 | 1.70 | 3.40 | 3.64 | 1.70 |
| p Value | 3.3E−4 | 2.0E−4 | 0.16 | 9.8E−4 | 3.6E−4 | 0.12 | 9.8E−4 | 3.6E−4 | 0.12 |
| Lower limit of 95% CI | 1.83 | 1.89 | 0.819 | 1.64 | 1.79 | 0.864 | 1.64 | 1.79 | 0.864 |
| Upper limit of 95% CI | 7.84 | 7.83 | 3.27 | 7.04 | 7.41 | 3.36 | 7.04 | 7.41 | 3.36 |
| OR Quartile 4 | 8.89 | 7.40 | 2.38 | 8.26 | 7.13 | 2.24 | 8.26 | 7.13 | 2.24 |
| p Value | 5.4E−4 | 3.8E−4 | 0.028 | 8.3E−4 | 4.8E−4 | 0.040 | 8.3E−4 | 4.8E−4 | 0.040 |
| Lower limit of 95% CI | 2.58 | 2.45 | 1.10 | 2.39 | 2.37 | 1.04 | 2.39 | 2.37 | 1.04 |
| Upper limit of 95% CI | 30.6 | 22.3 | 5.14 | 28.5 | 21.5 | 4.81 | 28.5 | 21.5 | 4.81 |

TABLE 7.3

Comparison of marker levels and the area under the ROC curve
(AUC) in urine samples for the "recovered" and "non-recovered" cohorts where recovery
starts at 48 hours after sample collection and renal status is assessed by serum creatinine
(sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 2.56 | 7.04 | 2.56 | 7.04 | 2.52 | 7.04 |
| Average | 9.30 | 22.6 | 9.30 | 22.6 | 9.21 | 22.3 |
| Stdev | 14.6 | 31.5 | 14.6 | 31.5 | 14.8 | 31.1 |
| p (t-test) | | 0.0023 | | 0.0023 | | 0.0028 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 63 | 83 | 63 | 83 | 61 | 85 |

TABLE 7.3-continued

Comparison of marker levels and the area under the ROC curve (AUC) in urine samples for the "recovered" and "non-recovered" cohorts where recovery starts at 48 hours after sample collection and renal status is assessed by serum creatinine (sCr) only, urine output (UO) only, or serum creatinine or urine output RIFLE criteria.

| sCr only | | | | | | |
|---|---|---|---|---|---|---|
| Median | 2.65 | 8.16 | 2.65 | 8.16 | 2.61 | 8.58 |
| Average | 9.56 | 23.3 | 9.56 | 23.3 | 9.45 | 23.2 |
| Stdev | 14.9 | 32.0 | 14.9 | 32.0 | 15.0 | 31.8 |
| p (t-test) | | 0.0016 | | 0.0016 | | 0.0016 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 67 | 78 | 67 | 78 | 66 | 79 |
| UO only | | | | | | |
| Median | 3.49 | 7.39 | 3.49 | 7.39 | 3.47 | 7.04 |
| Average | 14.9 | 22.7 | 14.9 | 22.7 | 15.2 | 21.7 |
| Stdev | 24.2 | 30.7 | 24.2 | 30.7 | 24.6 | 30.1 |
| p (t-test) | | 0.11 | | 0.11 | | 0.19 |
| Min | 3.16E−5 | 0.0645 | 3.16E−5 | 0.0645 | 3.16E−5 | 0.0645 |
| Max | 109 | 112 | 109 | 112 | 109 | 112 |
| n (Patient) | 80 | 48 | 80 | 48 | 77 | 51 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.65 | 0.62 | 0.64 | 0.65 | 0.62 | 0.65 | 0.65 | 0.61 |
| SE | 0.045 | 0.045 | 0.052 | 0.045 | 0.045 | 0.052 | 0.045 | 0.045 | 0.052 |
| p Value | 0.0016 | 0.0010 | 0.025 | 0.0016 | 0.0010 | 0.025 | 7.2E−4 | 5.7E−4 | 0.031 |
| nCohort Recovered | 63 | 67 | 80 | 63 | 67 | 80 | 61 | 66 | 77 |
| nCohort Non-recovered | 83 | 78 | 48 | 83 | 78 | 48 | 85 | 79 | 51 |
| Cutoff Quartile 2 | 1.90 | 1.89 | 1.89 | 1.90 | 1.89 | 1.89 | 1.90 | 1.89 | 1.89 |
| Sensitivity | 77% | 79% | 81% | 77% | 79% | 81% | 78% | 80% | 82% |
| Specificity | 29% | 30% | 29% | 29% | 30% | 29% | 30% | 30% | 30% |
| Cutoff Quartile 3 | 4.11 | 4.13 | 5.38 | 4.11 | 4.13 | 5.38 | 4.11 | 4.13 | 5.38 |
| Sensitivity | 59% | 60% | 60% | 59% | 60% | 60% | 60% | 61% | 61% |
| Specificity | 62% | 61% | 56% | 62% | 61% | 56% | 64% | 62% | 57% |
| Cutoff Quartile 4 | 19.7 | 20.0 | 22.3 | 19.7 | 20.0 | 22.3 | 19.7 | 20.0 | 22.3 |
| Sensitivity | 35% | 36% | 33% | 35% | 36% | 33% | 34% | 35% | 31% |
| Specificity | 87% | 87% | 80% | 87% | 87% | 80% | 87% | 86% | 79% |
| OR Quartile 2 | 1.35 | 1.65 | 1.75 | 1.35 | 1.65 | 1.75 | 1.45 | 1.71 | 1.99 |
| p Value | 0.44 | 0.20 | 0.21 | 0.44 | 0.20 | 0.21 | 0.33 | 0.17 | 0.12 |
| Lower limit of 95% CI | 0.637 | 0.772 | 0.731 | 0.637 | 0.772 | 0.731 | 0.687 | 0.801 | 0.833 |
| Upper limit of 95% CI | 2.85 | 3.52 | 4.18 | 2.85 | 3.52 | 4.18 | 3.08 | 3.66 | 4.74 |
| OR Quartile 3 | 2.34 | 2.39 | 1.96 | 2.34 | 2.39 | 1.96 | 2.66 | 2.54 | 2.07 |
| p Value | 0.013 | 0.011 | 0.069 | 0.013 | 0.011 | 0.069 | 0.0048 | 0.0066 | 0.048 |
| Lower limit of 95% CI | 1.20 | 1.23 | 0.948 | 1.20 | 1.23 | 0.948 | 1.35 | 1.30 | 1.01 |
| Upper limit of 95% CI | 4.58 | 4.67 | 4.06 | 4.58 | 4.67 | 4.06 | 5.24 | 4.97 | 4.25 |
| OR Quartile 4 | 3.69 | 3.61 | 2.00 | 3.69 | 3.61 | 2.00 | 3.43 | 3.48 | 1.74 |
| p Value | 0.0032 | 0.0028 | 0.095 | 0.0032 | 0.0028 | 0.095 | 0.0054 | 0.0037 | 0.18 |
| Lower limit of 95% CI | 1.55 | 1.56 | 0.887 | 1.55 | 1.56 | 0.887 | 1.44 | 1.50 | 0.777 |
| Upper limit of 95% CI | 8.80 | 8.37 | 4.51 | 8.80 | 8.37 | 4.51 | 8.17 | 8.06 | 3.91 |

TABLE 7.4

Comparison of marker levels and the area under the ROC curve (AUC) in urine samples for the "recovered" and "non-recovered" cohorts where recovery starts at 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 2.79 | 10.3 | 2.65 | 10.0 | 2.61 | 10.2 |
| Average | 9.37 | 25.1 | 9.50 | 24.1 | 9.44 | 23.6 |
| Stdev | 15.1 | 32.8 | 15.4 | 32.2 | 15.7 | 31.7 |
| p (t-test) | | 3.4E−4 | | 9.0E−4 | | 0.0014 |

TABLE 7.4-continued

Comparison of marker levels and the area under the ROC curve (AUC) in urine samples for the "recovered" and "non-recovered" cohorts where recovery starts at 72 hours after sample collection and renal status is assessed by serum creatinine (sCr) only, urine output (UO) only, or serum creatinine or urine output RIFLE criteria.

|  |  |  |  |  |  |  |
|---|---|---|---|---|---|---|
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 71 | 71 | 67 | 75 | 64 | 78 |
| sCr only |  |  |  |  |  |  |
| Median | 2.79 | 10.3 | 2.72 | 10.8 | 2.65 | 11.3 |
| Average | 9.77 | 25.1 | 9.67 | 25.0 | 9.54 | 24.9 |
| Stdev | 15.5 | 33.0 | 15.6 | 32.8 | 15.7 | 32.6 |
| p (t-test) |  | 4.8E−4 |  | 4.8E−4 |  | 4.6E−4 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 73 | 69 | 72 | 70 | 71 | 71 |
| UO only |  |  |  |  |  |  |
| Median | 3.49 | 8.58 | 3.49 | 7.04 | 3.51 | 7.04 |
| Average | 15.9 | 22.3 | 15.6 | 21.9 | 15.9 | 21.3 |
| Stdev | 26.3 | 29.6 | 25.6 | 30.0 | 25.8 | 29.5 |
| p (t-test) |  | 0.22 |  | 0.22 |  | 0.29 |
| Min | 3.16E−5 | 0.0645 | 3.16E−5 | 0.0645 | 3.16E−5 | 0.0645 |
| Max | 109 | 112 | 109 | 112 | 109 | 112 |
| n (Patient) | 74 | 45 | 68 | 51 | 67 | 53 |

| | Recovery Period Duration (hr) | | | | | | | |
|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.67 | 0.64 | 0.67 | 0.67 | 0.63 | 0.67 | 0.68 | 0.62 |
| SE | 0.045 | 0.045 | 0.053 | 0.045 | 0.045 | 0.052 | 0.045 | 0.045 | 0.052 |
| p Value | 2.1E−4 | 2.7E−4 | 0.011 | 1.9E−4 | 1.5E−4 | 0.014 | 1.7E−4 | 7.0E−5 | 0.027 |
| nCohort Recovered | 71 | 73 | 74 | 67 | 72 | 68 | 64 | 71 | 67 |
| nCohort Non-recovered | 71 | 69 | 45 | 75 | 70 | 51 | 78 | 71 | 53 |
| Cutoff Quartile 2 | 1.90 | 1.90 | 1.88 | 1.90 | 1.90 | 1.88 | 1.90 | 1.90 | 1.89 |
| Sensitivity | 77% | 78% | 82% | 79% | 79% | 84% | 78% | 79% | 83% |
| Specificity | 28% | 29% | 30% | 30% | 29% | 32% | 30% | 30% | 31% |
| Cutoff Quartile 3 | 4.99 | 4.99 | 5.74 | 4.99 | 4.99 | 5.74 | 4.99 | 4.99 | 6.06 |
| Sensitivity | 65% | 65% | 64% | 64% | 66% | 63% | 64% | 66% | 60% |
| Specificity | 65% | 64% | 58% | 66% | 65% | 59% | 67% | 66% | 58% |
| Cutoff Quartile 4 | 20.7 | 20.7 | 22.6 | 20.7 | 20.7 | 22.6 | 20.7 | 20.7 | 22.3 |
| Sensitivity | 38% | 38% | 33% | 36% | 37% | 31% | 35% | 37% | 30% |
| Specificity | 87% | 86% | 80% | 87% | 86% | 79% | 86% | 86% | 79% |
| OR Quartile 2 | 1.35 | 1.45 | 1.96 | 1.57 | 1.51 | 2.57 | 1.52 | 1.57 | 2.23 |
| p Value | 0.44 | 0.34 | 0.15 | 0.25 | 0.29 | 0.042 | 0.28 | 0.25 | 0.075 |
| Lower limit of 95% CI | 0.631 | 0.677 | 0.786 | 0.733 | 0.703 | 1.03 | 0.709 | 0.730 | 0.922 |
| Upper limit of 95% CI | 2.88 | 3.12 | 4.87 | 3.36 | 3.24 | 6.38 | 3.24 | 3.37 | 5.40 |
| OR Quartile 3 | 3.39 | 3.39 | 2.51 | 3.40 | 3.60 | 2.41 | 3.66 | 3.84 | 2.12 |
| p Value | 5.2E−4 | 5.2E−4 | 0.018 | 5.1E−4 | 2.8E−4 | 0.021 | 2.7E−4 | 1.5E−4 | 0.044 |
| Lower limit of 95% CI | 1.70 | 1.70 | 1.17 | 1.71 | 1.80 | 1.14 | 1.82 | 1.91 | 1.02 |
| Upper limit of 95% CI | 6.74 | 6.75 | 5.40 | 6.78 | 7.20 | 5.07 | 7.34 | 7.69 | 4.42 |
| OR Quartile 4 | 4.23 | 3.81 | 1.97 | 3.62 | 3.66 | 1.76 | 3.24 | 3.52 | 1.64 |
| p Value | 8.6E−4 | 0.0015 | 0.11 | 0.0028 | 0.0020 | 0.18 | 0.0065 | 0.0028 | 0.25 |
| Lower limit of 95% CI | 1.81 | 1.67 | 0.849 | 1.56 | 1.60 | 0.766 | 1.39 | 1.54 | 0.713 |
| Upper limit of 95% CI | 9.87 | 8.70 | 4.55 | 8.45 | 8.36 | 4.06 | 7.53 | 8.04 | 3.76 |

TABLE 7.5

Comparison of marker levels and the area under the ROC curve (AUC) in urine samples for the "recovered" and "non-recovered" cohorts where recovery starts within 7 days after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 3.03 | 8.85 | 3.09 | 8.58 | 3.15 | 8.16 |
| Average | 13.3 | 22.6 | 13.4 | 22.2 | 13.5 | 21.9 |
| Stdev | 22.6 | 30.6 | 22.7 | 30.4 | 22.8 | 30.3 |
| p (t-test) | | 0.035 | | 0.044 | | 0.055 |
| Min | 3.16E−5 | 0.0645 | 3.16E−5 | 0.0645 | 3.16E−5 | 0.0645 |
| Max | 109 | 112 | 109 | 112 | 109 | 112 |
| n (Patient) | 93 | 56 | 92 | 57 | 91 | 58 |
| sCr only | | | | | | |
| Median | 2.91 | 9.73 | 2.91 | 9.73 | 2.91 | 9.73 |
| Average | 9.79 | 25.5 | 9.79 | 25.5 | 9.79 | 25.5 |
| Stdev | 15.0 | 33.7 | 15.0 | 33.7 | 15.0 | 33.7 |
| p (t-test) | | 2.0E−4 | | 2.0E−4 | | 2.0E−4 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 83 | 66 | 83 | 66 | 83 | 66 |
| UO only | | | | | | |
| Median | 3.32 | 9.46 | 3.32 | 9.46 | 3.47 | 8.16 |
| Average | 14.6 | 21.7 | 14.6 | 21.7 | 14.8 | 20.9 |
| Stdev | 24.7 | 28.8 | 24.7 | 28.8 | 24.9 | 28.5 |
| p (t-test) | | 0.12 | | 0.12 | | 0.18 |
| Min | 3.16E−5 | 0.0645 | 3.16E−5 | 0.0645 | 3.16E−5 | 0.0645 |
| Max | 109 | 112 | 109 | 112 | 109 | 112 |
| n (Patient) | 100 | 48 | 100 | 48 | 98 | 50 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.66 | 0.64 | 0.64 | 0.66 | 0.64 | 0.64 | 0.66 | 0.63 |
| SE | 0.048 | 0.045 | 0.050 | 0.048 | 0.045 | 0.050 | 0.047 | 0.045 | 0.050 |
| p Value | 0.0024 | 5.1E−4 | 0.0057 | 0.0034 | 5.1E−4 | 0.0057 | 0.0044 | 5.1E−4 | 0.010 |
| nCohort Recovered | 93 | 83 | 100 | 92 | 83 | 100 | 91 | 83 | 98 |
| nCohort Non-recovered | 56 | 66 | 48 | 57 | 66 | 48 | 58 | 66 | 50 |
| Cutoff Quartile 2 | 1.89 | 1.89 | 1.93 | 1.89 | 1.89 | 1.93 | 1.89 | 1.89 | 1.93 |
| Sensitivity | 82% | 80% | 81% | 82% | 80% | 81% | 83% | 80% | 82% |
| Specificity | 29% | 29% | 28% | 29% | 29% | 28% | 30% | 29% | 29% |
| Cutoff Quartile 3 | 4.13 | 4.13 | 4.52 | 4.13 | 4.13 | 4.52 | 4.13 | 4.13 | 4.52 |
| Sensitivity | 64% | 64% | 67% | 63% | 64% | 67% | 62% | 64% | 64% |
| Specificity | 58% | 60% | 58% | 58% | 60% | 58% | 57% | 60% | 57% |
| Cutoff Quartile 4 | 20.0 | 20.0 | 20.2 | 20.0 | 20.0 | 20.2 | 20.0 | 20.0 | 20.2 |
| Sensitivity | 36% | 38% | 35% | 35% | 38% | 35% | 34% | 38% | 34% |
| Specificity | 81% | 84% | 80% | 80% | 84% | 80% | 80% | 84% | 80% |
| OR Quartile 2 | 1.88 | 1.66 | 1.69 | 1.95 | 1.66 | 1.69 | 2.02 | 1.66 | 1.82 |
| p Value | 0.13 | 0.20 | 0.23 | 0.11 | 0.20 | 0.23 | 0.090 | 0.20 | 0.16 |
| Lower limit of 95% CI | 0.831 | 0.768 | 0.723 | 0.863 | 0.768 | 0.723 | 0.895 | 0.768 | 0.783 |
| Upper limit of 95% CI | 4.26 | 3.58 | 3.93 | 4.42 | 3.58 | 3.93 | 4.58 | 3.58 | 4.24 |
| OR Quartile 3 | 2.49 | 2.65 | 2.76 | 2.33 | 2.65 | 2.76 | 2.18 | 2.65 | 2.37 |
| p Value | 0.0089 | 0.0042 | 0.0057 | 0.015 | 0.0042 | 0.0057 | 0.023 | 0.0042 | 0.016 |
| Lower limit of 95% CI | 1.26 | 1.36 | 1.34 | 1.18 | 1.36 | 1.34 | 1.11 | 1.36 | 1.17 |
| Upper limit of 95% CI | 4.94 | 5.17 | 5.67 | 4.59 | 5.17 | 5.67 | 4.28 | 5.17 | 4.79 |
| OR Quartile 4 | 2.31 | 3.28 | 2.19 | 2.22 | 3.28 | 2.19 | 2.13 | 3.28 | 2.01 |
| p Value | 0.028 | 0.0026 | 0.045 | 0.037 | 0.0026 | 0.045 | 0.047 | 0.0026 | 0.073 |
| Lower limit of 95% CI | 1.09 | 1.52 | 1.02 | 1.05 | 1.52 | 1.02 | 1.01 | 1.52 | 0.936 |
| Upper limit of 95% CI | 4.90 | 7.11 | 4.73 | 4.70 | 7.11 | 4.73 | 4.51 | 7.11 | 4.31 |

Example 8. Use of Insulin-Like Growth Factor-Binding Protein 3 for Evaluating Renal Status in Patients Admitted to the ICU: Recovery to RIFLE 0 from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 3 is measured in the enrollment samples by standard immunoassay methods using commercially available assay reagents.

Kidney status is assessed by RIFLE criteria based on serum creatinine, urine output, or both serum creatinine and urine output during a period starting at 12, 24, 48, or 72 hours after sample collection or at any time within 7 days after sample collection. Two cohorts are defined to represent a "recovered" and a "non-recovered" population. "Recovered" indicates those patients whose maximum RIFLE stage during a period of 24, 48 or 72 hours is non-injury (RIFLE 0). "Non-recovered" indicates those patients whose maximum RIFLE stage during a period of 24, 48 or 72 hours is risk of injury (R), injury (I) or failure (F). If a patient dies or is placed on renal replacement therapy (RRT) at any time from sample collection to 12, 24, 48, or 72 hours after sample collection or at any time within 7 days after sample collection, the patient is considered "non-recovered".

The ability to distinguish the "recovered" and "non-recovered" cohorts is determined using receiver operating characteristic (ROC) analysis.

TABLE 8.1

Comparison of marker levels and the area under the ROC curve (AUC) in urine samples for the "recovered" and "non-recovered" cohorts where recovery starts at 12 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 375 | 822 | 316 | 824 | 316 | 824 |
| Average | 662 | 2930 | 486 | 2930 | 486 | 2930 |
| Stdev | 763 | 5170 | 555 | 5160 | 555 | 5160 |
| p (t-test) | | 0.17 | | 0.16 | | 0.16 |
| Min | 30.5 | 20.6 | 30.5 | 20.6 | 30.5 | 20.6 |
| Max | 2240 | 18800 | 1890 | 18800 | 1890 | 18800 |
| n (Patient) | 10 | 139 | 9 | 140 | 9 | 140 |
| sCr only | | | | | | |
| Median | 463 | 828 | 457 | 826 | 457 | 826 |
| Average | 1470 | 3020 | 1510 | 3000 | 1510 | 3000 |
| Stdev | 3810 | 5200 | 3900 | 5180 | 3900 | 5180 |
| p (t-test) | | 0.18 | | 0.20 | | 0.20 |
| Min | 30.5 | 20.6 | 30.5 | 20.6 | 30.5 | 20.6 |
| Max | 18800 | 18800 | 18800 | 18800 | 18800 | 18800 |
| n (Patient) | 23 | 126 | 22 | 127 | 22 | 127 |
| UO only | | | | | | |
| Median | 615 | 1010 | 569 | 1000 | 567 | 1010 |
| Average | 2050 | 3570 | 1900 | 3540 | 1640 | 3680 |
| Stdev | 4200 | 5720 | 3920 | 5740 | 3380 | 5880 |
| p (t-test) | | 0.066 | | 0.049 | | 0.014 |
| Min | 20.6 | 172 | 20.6 | 172 | 20.6 | 172 |
| Max | 18800 | 18800 | 18800 | 18800 | 18800 | 18800 |
| n (Patient) | 75 | 73 | 67 | 81 | 64 | 84 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.63 | 0.65 | 0.76 | 0.63 | 0.66 | 0.76 | 0.63 | 0.68 |
| SE | 0.074 | 0.059 | 0.045 | 0.068 | 0.060 | 0.044 | 0.068 | 0.060 | 0.043 |
| p Value | 0.0063 | 0.027 | 9.2E-4 | 1.4E-4 | 0.033 | 2.6E-4 | 1.4E-4 | 0.033 | 3.9E-5 |
| nCohort Recovered | 10 | 23 | 75 | 9 | 22 | 67 | 9 | 22 | 64 |
| nCohort Non-recovered | 139 | 126 | 73 | 140 | 127 | 81 | 140 | 127 | 84 |
| Cutoff Quartile 2 | 401 | 401 | 410 | 401 | 401 | 410 | 401 | 401 | 410 |
| Sensitivity | 77% | 76% | 85% | 77% | 76% | 85% | 77% | 76% | 86% |
| Specificity | 50% | 30% | 35% | 56% | 32% | 37% | 56% | 32% | 39% |
| Cutoff Quartile 3 | 794 | 794 | 801 | 794 | 794 | 801 | 794 | 794 | 801 |
| Sensitivity | 53% | 54% | 63% | 53% | 54% | 60% | 53% | 54% | 61% |
| Specificity | 80% | 70% | 63% | 89% | 68% | 63% | 89% | 68% | 64% |
| Cutoff Quartile 4 | 1830 | 1830 | 1840 | 1830 | 1830 | 1840 | 1830 | 1830 | 1840 |
| Sensitivity | 26% | 28% | 27% | 26% | 28% | 28% | 26% | 28% | 30% |

TABLE 8.1-continued

Comparison of marker levels and the area under the ROC curve
(AUC) in urine samples for the "recovered" and "non-recovered" cohorts where recovery
starts at 12 hours after sample collection and renal status is assessed by serum creatinine
(sCr) only, urine output (UO) only, or serum creatinine or urine output RIFLE criteria.

| | | | | | | | | | |
|---|---|---|---|---|---|---|---|---|---|
| Specificity | 80% | 87% | 77% | 89% | 86% | 79% | 89% | 86% | 81% |
| OR Quartile 2 | 3.34 | 1.40 | 2.99 | 4.22 | 1.51 | 3.42 | 4.22 | 1.51 | 3.85 |
| p Value | 0.069 | 0.50 | 0.0072 | 0.040 | 0.41 | 0.0022 | 0.040 | 0.41 | 8.4E−4 |
| Lower limit of 95% CI | 0.910 | 0.526 | 1.35 | 1.07 | 0.563 | 1.56 | 1.07 | 0.563 | 1.74 |
| Upper limit of 95% CI | 12.3 | 3.72 | 6.64 | 16.6 | 4.05 | 7.53 | 16.6 | 4.05 | 8.48 |
| OR Quartile 3 | 4.42 | 2.68 | 2.86 | 8.97 | 2.47 | 2.57 | 8.97 | 2.47 | 2.75 |
| p Value | 0.066 | 0.043 | 0.0020 | 0.041 | 0.066 | 0.0054 | 0.041 | 0.066 | 0.0031 |
| Lower limit of 95% CI | 0.907 | 1.03 | 1.47 | 1.09 | 0.943 | 1.32 | 1.09 | 0.943 | 1.41 |
| Upper limit of 95% CI | 21.6 | 6.96 | 5.57 | 73.6 | 6.47 | 5.01 | 73.6 | 6.47 | 5.40 |
| OR Quartile 4 | 1.40 | 2.56 | 1.29 | 2.87 | 2.41 | 1.50 | 2.87 | 2.41 | 1.84 |
| p Value | 0.68 | 0.15 | 0.51 | 0.33 | 0.18 | 0.30 | 0.33 | 0.18 | 0.13 |
| Lower limit of 95% CI | 0.284 | 0.717 | 0.610 | 0.348 | 0.671 | 0.701 | 0.348 | 0.671 | 0.839 |
| Upper limit of 95% CI | 6.89 | 9.17 | 2.72 | 23.8 | 8.65 | 3.22 | 23.8 | 8.65 | 4.02 |

TABLE 8.2

Comparison of marker levels and the area under the ROC curve
(AUC) in urine samples for the "recovered" and "non-recovered" cohorts where recovery
starts at 24 hours after sample collection and renal status is assessed by serum creatinine
(sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 416 | 907 | 321 | 907 | 316 | 911 |
| Average | 578 | 3250 | 494 | 3180 | 467 | 3160 |
| Stdev | 545 | 5420 | 454 | 5350 | 448 | 5330 |
| p (t-test) | | 0.013 | | 0.020 | | 0.022 |
| Min | 30.5 | 20.6 | 30.5 | 20.6 | 30.5 | 20.6 |
| Max | 2240 | 18800 | 1890 | 18800 | 1890 | 18800 |
| n (Patient) | 26 | 123 | 22 | 127 | 21 | 128 |
| sCr only | | | | | | |
| Median | 463 | 911 | 451 | 904 | 442 | 907 |
| Average | 1200 | 3320 | 1230 | 3270 | 1240 | 3250 |
| Stdev | 3100 | 5440 | 3190 | 5410 | 3240 | 5390 |
| p (t-test) | | 0.030 | | 0.041 | | 0.046 |
| Min | 30.5 | 20.6 | 30.5 | 20.6 | 30.5 | 20.6 |
| Max | 18800 | 18800 | 18800 | 18800 | 18800 | 18800 |
| n (Patient) | 35 | 112 | 33 | 114 | 32 | 115 |
| UO only | | | | | | |
| Median | 626 | 1070 | 611 | 1060 | 569 | 1070 |
| Average | 2110 | 3710 | 1770 | 3850 | 1610 | 3920 |
| Stdev | 4330 | 5830 | 3610 | 6070 | 3440 | 6040 |
| p (t-test) | | 0.062 | | 0.014 | | 0.0061 |
| Min | 20.6 | 172 | 20.6 | 172 | 20.6 | 172 |
| Max | 18800 | 18800 | 18800 | 18800 | 18800 | 18800 |
| n (Patient) | 81 | 63 | 72 | 72 | 69 | 75 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.66 | 0.66 | 0.77 | 0.66 | 0.68 | 0.78 | 0.66 | 0.70 |
| SE | 0.048 | 0.049 | 0.046 | 0.047 | 0.051 | 0.045 | 0.045 | 0.051 | 0.043 |
| p Value | 1.2E−6 | 0.0013 | 4.9E−4 | 1.3E−8 | 0.0022 | 7.0E−5 | 4.8E−10 | 0.0013 | 4.8E−6 |
| nCohort Recovered | 26 | 35 | 81 | 22 | 33 | 72 | 21 | 32 | 69 |
| nCohort Non-recovered | 123 | 112 | 63 | 127 | 114 | 72 | 128 | 115 | 75 |
| Cutoff Quartile 2 | 401 | 407 | 399 | 401 | 407 | 399 | 401 | 407 | 399 |
| Sensitivity | 80% | 78% | 89% | 80% | 78% | 89% | 80% | 78% | 89% |
| Specificity | 46% | 34% | 36% | 55% | 36% | 39% | 57% | 38% | 41% |
| Cutoff Quartile 3 | 794 | 808 | 812 | 794 | 808 | 812 | 794 | 808 | 812 |
| Sensitivity | 56% | 57% | 65% | 56% | 56% | 64% | 56% | 57% | 65% |

TABLE 8.2-continued

Comparison of marker levels and the area under the ROC curve (AUC) in urine samples for the "recovered" and "non-recovered" cohorts where recovery starts at 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Specificity | 77% | 71% | 62% | 82% | 70% | 64% | 86% | 72% | 67% |
| Cutoff Quartile 4 | 1830 | 1850 | 1840 | 1830 | 1850 | 1840 | 1830 | 1850 | 1840 |
| Sensitivity | 29% | 30% | 29% | 29% | 30% | 29% | 29% | 30% | 31% |
| Specificity | 92% | 91% | 78% | 95% | 91% | 79% | 95% | 91% | 81% |
| OR Quartile 2 | 3.36 | 1.82 | 4.46 | 4.90 | 2.03 | 5.09 | 5.49 | 2.16 | 5.72 |
| p Value | 0.0074 | 0.16 | 0.0012 | 0.0010 | 0.096 | 2.6E−4 | 5.7E−4 | 0.073 | 9.7E−5 |
| Lower limit of 95% CI | 1.38 | 0.794 | 1.80 | 1.90 | 0.881 | 2.12 | 2.09 | 0.931 | 2.38 |
| Upper limit of 95% CI | 8.16 | 4.15 | 11.1 | 12.6 | 4.70 | 12.2 | 14.5 | 5.01 | 13.7 |
| OR Quartile 3 | 4.26 | 3.33 | 3.01 | 5.71 | 2.94 | 3.13 | 7.71 | 3.32 | 3.77 |
| p Value | 0.0037 | 0.0042 | 0.0016 | 0.0027 | 0.011 | 0.0010 | 0.0016 | 0.0059 | 1.7E−4 |
| Lower limit of 95% CI | 1.60 | 1.46 | 1.52 | 1.83 | 1.28 | 1.59 | 2.16 | 1.41 | 1.89 |
| Upper limit of 95% CI | 11.3 | 7.59 | 5.96 | 17.8 | 6.75 | 6.18 | 27.5 | 7.81 | 7.52 |
| OR Quartile 4 | 4.97 | 4.65 | 1.40 | 8.63 | 4.25 | 1.56 | 8.13 | 4.06 | 1.91 |
| p Value | 0.036 | 0.016 | 0.38 | 0.039 | 0.024 | 0.25 | 0.045 | 0.029 | 0.10 |
| Lower limit of 95% CI | 1.11 | 1.33 | 0.657 | 1.12 | 1.21 | 0.730 | 1.05 | 1.16 | 0.875 |
| Upper limit of 95% CI | 22.1 | 16.2 | 2.98 | 66.5 | 14.9 | 3.35 | 62.8 | 14.2 | 4.15 |

TABLE 8.3

Comparison of marker levels and the area under the ROC curve (AUC) in urine samples for the "recovered" and "non-recovered" cohorts where recovery starts at 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 451 | 942 | 442 | 962 | 434 | 942 |
| Average | 863 | 3470 | 528 | 3500 | 525 | 3430 |
| Stdev | 2000 | 5620 | 333 | 5620 | 324 | 5570 |
| p (t-test) | | 0.0065 | | 0.0025 | | 0.0044 |
| Min | 30.5 | 20.6 | 30.5 | 20.6 | 88.7 | 20.6 |
| Max | 12500 | 18800 | 1430 | 18800 | 1430 | 18800 |
| n (Patient) | 37 | 109 | 34 | 112 | 31 | 115 |
| sCr only | | | | | | |
| Median | 540 | 911 | 512 | 929 | 512 | 929 |
| Average | 1330 | 3500 | 1070 | 3560 | 1070 | 3560 |
| Stdev | 3220 | 5620 | 2800 | 5640 | 2800 | 5640 |
| p (t-test) | | 0.017 | | 0.0067 | | 0.0067 |
| Min | 30.5 | 20.6 | 30.5 | 20.6 | 30.5 | 20.6 |
| Max | 18800 | 18800 | 18800 | 18800 | 18800 | 18800 |
| n (Patient) | 45 | 100 | 43 | 102 | 43 | 102 |
| UO only | | | | | | |
| Median | 685 | 1120 | 637 | 1120 | 766 | 1000 |
| Average | 2180 | 4160 | 2060 | 4160 | 2230 | 3800 |
| Stdev | 4250 | 6280 | 4170 | 6190 | 4380 | 5970 |
| p (t-test) | | 0.036 | | 0.025 | | 0.099 |
| Min | 20.6 | 172 | 20.6 | 172 | 20.6 | 30.5 |
| Max | 18800 | 18800 | 18800 | 18800 | 18800 | 18800 |
| n (Patient) | 70 | 58 | 66 | 62 | 59 | 69 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.65 | 0.66 | 0.74 | 0.67 | 0.67 | 0.73 | 0.67 | 0.63 |
| SE | 0.045 | 0.047 | 0.049 | 0.044 | 0.047 | 0.048 | 0.046 | 0.047 | 0.049 |
| p Value | 2.5E−6 | 0.0018 | 8.6E−4 | 1.0E−7 | 3.0E−4 | 2.6E−4 | 3.5E−7 | 3.0E−4 | 0.0056 |
| nCohort Recovered | 37 | 45 | 70 | 34 | 43 | 66 | 31 | 43 | 59 |
| nCohort Non-recovered | 109 | 100 | 58 | 112 | 102 | 62 | 115 | 102 | 69 |
| Cutoff Quartile 2 | 404 | 401 | 414 | 404 | 401 | 414 | 404 | 401 | 414 |
| Sensitivity | 80% | 78% | 90% | 79% | 78% | 89% | 79% | 78% | 87% |

TABLE 8.3-continued

Comparison of marker levels and the area under the ROC curve
(AUC) in urine samples for the "recovered" and "non-recovered" cohorts where recovery
starts at 48 hours after sample collection and renal status is assessed by serum creatinine
(sCr) only, urine output (UO) only, or serum creatinine or urine output RIFLE criteria.

| | | | | | | | | | |
|---|---|---|---|---|---|---|---|---|---|
| Specificity | 41% | 31% | 37% | 41% | 33% | 38% | 42% | 33% | 39% |
| Cutoff Quartile 3 | 790 | 794 | 878 | 790 | 794 | 878 | 790 | 794 | 878 |
| Sensitivity | 58% | 56% | 62% | 58% | 57% | 61% | 57% | 57% | 57% |
| Specificity | 73% | 62% | 60% | 76% | 65% | 61% | 77% | 65% | 58% |
| Cutoff Quartile 4 | 1770 | 1790 | 2020 | 1770 | 1790 | 2020 | 1770 | 1790 | 2020 |
| Sensitivity | 33% | 34% | 31% | 33% | 34% | 32% | 32% | 34% | 29% |
| Specificity | 97% | 93% | 80% | 100% | 95% | 82% | 100% | 95% | 80% |
| OR Quartile 2 | 2.70 | 1.60 | 5.12 | 2.71 | 1.76 | 4.79 | 2.74 | 1.76 | 4.26 |
| p Value | 0.016 | 0.24 | 0.0010 | 0.018 | 0.16 | 9.7E−4 | 0.019 | 0.16 | 0.0012 |
| Lower limit of 95% CI | 1.20 | 0.728 | 1.93 | 1.19 | 0.794 | 1.89 | 1.18 | 0.794 | 1.78 |
| Upper limit of 95% CI | 6.04 | 3.52 | 13.6 | 6.17 | 3.88 | 12.1 | 6.36 | 3.88 | 10.2 |
| OR Quartile 3 | 3.70 | 2.10 | 2.45 | 4.49 | 2.46 | 2.44 | 4.62 | 2.46 | 1.77 |
| p Value | 0.0018 | 0.044 | 0.014 | 7.8E−4 | 0.017 | 0.014 | 0.0011 | 0.017 | 0.11 |
| Lower limit of 95% CI | 1.63 | 1.02 | 1.20 | 1.87 | 1.17 | 1.20 | 1.84 | 1.17 | 0.876 |
| Upper limit of 95% CI | 8.39 | 4.31 | 5.01 | 10.8 | 5.15 | 4.96 | 11.6 | 5.15 | 3.57 |
| OR Quartile 4 | 17.8 | 7.21 | 1.80 | 34.3 | 10.7 | 2.14 | 30.1 | 10.7 | 1.60 |
| p Value | 0.0054 | 0.0018 | 0.15 | 0.014 | 0.0017 | 0.069 | 0.018 | 0.0017 | 0.26 |
| Lower limit of 95% CI | 2.34 | 2.08 | 0.803 | 2.04 | 2.45 | 0.942 | 1.79 | 2.45 | 0.704 |
| Upper limit of 95% CI | 135 | 25.0 | 4.04 | 575 | 46.9 | 4.87 | 505 | 46.9 | 3.63 |

TABLE 8.4

Comparison of marker levels and the area under the ROC curve
(AUC) in urine samples for the "recovered" and "non-recovered" cohorts where recovery
starts at 72 hours after sample collection and renal status is assessed by serum creatinine
(sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 463 | 1070 | 427 | 1050 | 427 | 1050 |
| Average | 963 | 3710 | 967 | 3580 | 980 | 3530 |
| Stdev | 2490 | 5740 | 2640 | 5630 | 2710 | 5590 |
| p (t-test) | | 0.0030 | | 0.0068 | | 0.0097 |
| Min | 21.1 | 20.6 | 21.1 | 20.6 | 88.7 | 20.6 |
| Max | 16600 | 18800 | 16600 | 18800 | 16600 | 18800 |
| n (Patient) | 43 | 99 | 38 | 104 | 36 | 106 |
| sCr only | | | | | | |
| Median | 526 | 1060 | 526 | 1060 | 526 | 1060 |
| Average | 1330 | 3720 | 1330 | 3720 | 1360 | 3660 |
| Stdev | 3420 | 5700 | 3420 | 5700 | 3480 | 5660 |
| p (t-test) | | 0.0075 | | 0.0075 | | 0.011 |
| Min | 21.1 | 20.6 | 21.1 | 20.6 | 30.5 | 20.6 |
| Max | 18800 | 18800 | 18800 | 18800 | 18800 | 18800 |
| n (Patient) | 50 | 92 | 50 | 92 | 48 | 94 |
| UO only | | | | | | |
| Median | 747 | 1070 | 776 | 1040 | 797 | 992 |
| Average | 2530 | 4040 | 2760 | 3660 | 2890 | 3500 |
| Stdev | 4770 | 6130 | 5070 | 5830 | 5220 | 5670 |
| p (t-test) | | 0.14 | | 0.37 | | 0.55 |
| Min | 20.6 | 172 | 20.6 | 30.5 | 20.6 | 21.1 |
| Max | 18800 | 18800 | 18800 | 18800 | 18800 | 18800 |
| n (Patient) | 62 | 57 | 54 | 65 | 50 | 70 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.72 | 0.68 | 0.63 | 0.73 | 0.68 | 0.61 | 0.72 | 0.68 | 0.58 |
| SE | 0.044 | 0.045 | 0.051 | 0.044 | 0.045 | 0.051 | 0.045 | 0.046 | 0.052 |
| p Value | 5.5E−7 | 5.0E−5 | 0.0092 | 2.8E−7 | 5.0E−5 | 0.030 | 6.4E−7 | 1.1E−4 | 0.13 |
| nCohort Recovered | 43 | 50 | 62 | 38 | 50 | 54 | 36 | 48 | 50 |

TABLE 8.4-continued

Comparison of marker levels and the area under the ROC curve (AUC) in urine samples for the "recovered" and "non-recovered" cohorts where recovery starts at 72 hours after sample collection and renal status is assessed by serum creatinine (sCr) only, urine output (UO) only, or serum creatinine or urine output RIFLE criteria.

| nCohort Non-recovered | 99 | 92 | 57 | 104 | 92 | 65 | 106 | 94 | 70 |
|---|---|---|---|---|---|---|---|---|---|
| Cutoff Quartile 2 | 397 | 397 | 419 | 397 | 397 | 419 | 397 | 397 | 420 |
| Sensitivity | 81% | 80% | 84% | 81% | 80% | 83% | 80% | 80% | 81% |
| Specificity | 40% | 36% | 34% | 42% | 36% | 35% | 42% | 35% | 34% |
| Cutoff Quartile 3 | 812 | 812 | 901 | 812 | 812 | 901 | 812 | 812 | 904 |
| Sensitivity | 62% | 61% | 60% | 61% | 61% | 57% | 60% | 61% | 54% |
| Specificity | 77% | 70% | 58% | 79% | 70% | 57% | 81% | 71% | 56% |
| Cutoff Quartile 4 | 1870 | 1870 | 2240 | 1870 | 1870 | 2240 | 1870 | 1870 | 2240 |
| Sensitivity | 34% | 36% | 28% | 34% | 36% | 28% | 33% | 35% | 27% |
| Specificity | 95% | 94% | 77% | 97% | 94% | 78% | 97% | 94% | 78% |
| OR Quartile 2 | 2.75 | 2.31 | 2.73 | 3.05 | 2.31 | 2.66 | 2.89 | 2.16 | 2.26 |
| p Value | 0.012 | 0.034 | 0.026 | 0.0067 | 0.034 | 0.025 | 0.011 | 0.051 | 0.057 |
| Lower limit of 95% CI | 1.25 | 1.07 | 1.13 | 1.36 | 1.07 | 1.13 | 1.28 | 0.996 | 0.975 |
| Upper limit of 95% CI | 6.07 | 5.01 | 6.62 | 6.85 | 5.01 | 6.27 | 6.54 | 4.71 | 5.23 |
| OR Quartile 3 | 5.30 | 3.63 | 2.05 | 5.76 | 3.63 | 1.78 | 6.31 | 3.74 | 1.51 |
| p Value | 6.1E−5 | 5.9E−4 | 0.055 | 8.5E−5 | 5.9E−4 | 0.12 | 7.6E−5 | 5.4E−4 | 0.27 |
| Lower limit of 95% CI | 2.34 | 1.74 | 0.985 | 2.41 | 1.74 | 0.859 | 2.53 | 1.77 | 0.728 |
| Upper limit of 95% CI | 12.0 | 7.57 | 4.25 | 13.8 | 7.57 | 3.69 | 15.7 | 7.90 | 3.14 |
| OR Quartile 4 | 10.7 | 8.76 | 1.34 | 18.8 | 8.76 | 1.34 | 17.3 | 8.11 | 1.32 |
| p Value | 0.0017 | 6.2E−4 | 0.49 | 0.0046 | 6.2E−4 | 0.49 | 0.0059 | 9.6E−4 | 0.52 |
| Lower limit of 95% CI | 2.44 | 2.53 | 0.584 | 2.47 | 2.53 | 0.578 | 2.27 | 2.34 | 0.564 |
| Upper limit of 95% CI | 47.0 | 30.4 | 3.07 | 143 | 30.4 | 3.11 | 131 | 28.1 | 3.10 |

TABLE 8.5

Comparison of marker levels and the area under the ROC curve (AUC) in urine samples for the "recovered" and "non-recovered" cohorts where recovery starts within 7 days after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 747 | 942 | 729 | 1000 | 729 | 1000 |
| Average | 2110 | 3690 | 2130 | 3660 | 2130 | 3660 |
| Stdev | 4460 | 5630 | 4480 | 5600 | 4480 | 5600 |
| p (t-test) | 0.058 | | 0.066 | | 0.066 | |
| Min | 20.6 | 166 | 20.6 | 166 | 20.6 | 166 |
| Max | 18800 | 18800 | 18800 | 18800 | 18800 | 18800 |
| n (Patient) | 86 | 63 | 85 | 64 | 85 | 64 |
| sCr only | | | | | | |
| Median | 569 | 1070 | 583 | 1070 | 583 | 1070 |
| Average | 1430 | 4010 | 1470 | 3920 | 1470 | 3920 |
| Stdev | 3400 | 5910 | 3450 | 5860 | 3450 | 5860 |
| p (t-test) | 0.0015 | | 0.0027 | | 0.0027 | |
| Min | 21.1 | 20.6 | 21.1 | 20.6 | 21.1 | 20.6 |
| Max | 18800 | 18800 | 18800 | 18800 | 18800 | 18800 |
| n (Patient) | 71 | 78 | 69 | 80 | 69 | 80 |
| UO only | | | | | | |
| Median | 747 | 1030 | 747 | 1030 | 682 | 1030 |
| Average | 2200 | 3910 | 2230 | 3790 | 2210 | 3760 |
| Stdev | 4320 | 6050 | 4360 | 5970 | 4400 | 5870 |
| p (t-test) | 0.048 | | 0.069 | | 0.070 | |
| Min | 20.6 | 175 | 20.6 | 172 | 20.6 | 172 |
| Max | 18800 | 18800 | 18800 | 18800 | 18800 | 18800 |
| n (Patient) | 96 | 52 | 94 | 54 | 92 | 56 |

TABLE 8.5-continued

Comparison of marker levels and the area under the ROC curve
(AUC) in urine samples for the "recovered" and "non-recovered" cohorts where recovery
starts within 7 days after sample collection and renal status is assessed by serum
creatinine (sCr) only, urine output (UO) only, or serum creatinine or urine output RIFLE
criteria.

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.62 | 0.69 | 0.63 | 0.62 | 0.67 | 0.62 | 0.62 | 0.67 | 0.63 |
| SE | 0.047 | 0.043 | 0.049 | 0.047 | 0.044 | 0.049 | 0.047 | 0.044 | 0.048 |
| p Value | 0.013 | 8.5E−6 | 0.011 | 0.010 | 1.2E−4 | 0.018 | 0.010 | 1.2E−4 | 0.0090 |
| nCohort Recovered | 86 | 71 | 96 | 85 | 69 | 94 | 85 | 69 | 92 |
| nCohort Non-recovered | 63 | 78 | 52 | 64 | 80 | 54 | 64 | 80 | 56 |
| Cutoff Quartile 2 | 401 | 401 | 410 | 401 | 401 | 410 | 401 | 401 | 410 |
| Sensitivity | 84% | 85% | 88% | 84% | 82% | 87% | 84% | 82% | 88% |
| Specificity | 31% | 35% | 32% | 32% | 33% | 32% | 32% | 33% | 33% |
| Cutoff Quartile 3 | 794 | 794 | 801 | 794 | 794 | 801 | 794 | 794 | 801 |
| Sensitivity | 56% | 62% | 60% | 56% | 60% | 59% | 56% | 60% | 61% |
| Specificity | 53% | 62% | 55% | 54% | 61% | 55% | 54% | 61% | 57% |
| Cutoff Quartile 4 | 1830 | 1830 | 1840 | 1830 | 1830 | 1840 | 1830 | 1830 | 1840 |
| Sensitivity | 33% | 40% | 29% | 33% | 39% | 28% | 33% | 39% | 29% |
| Specificity | 80% | 90% | 77% | 80% | 90% | 77% | 80% | 90% | 77% |
| OR Quartile 2 | 2.43 | 2.99 | 3.66 | 2.51 | 2.36 | 3.15 | 2.51 | 2.36 | 3.39 |
| p Value | 0.033 | 0.0062 | 0.0076 | 0.027 | 0.028 | 0.013 | 0.027 | 0.028 | 0.0082 |
| Lower limit of 95% CI | 1.07 | 1.36 | 1.41 | 1.11 | 1.10 | 1.27 | 1.11 | 1.10 | 1.37 |
| Upper limit of 95% CI | 5.48 | 6.55 | 9.48 | 5.68 | 5.06 | 7.78 | 5.68 | 5.06 | 8.36 |
| OR Quartile 3 | 1.44 | 2.61 | 1.82 | 1.52 | 2.33 | 1.80 | 1.52 | 2.33 | 2.01 |
| p Value | 0.28 | 0.0045 | 0.087 | 0.21 | 0.012 | 0.089 | 0.21 | 0.012 | 0.043 |
| Lower limit of 95% CI | 0.748 | 1.35 | 0.918 | 0.790 | 1.21 | 0.914 | 0.790 | 1.21 | 1.02 |
| Upper limit of 95% CI | 2.76 | 5.05 | 3.61 | 2.91 | 4.51 | 3.55 | 2.91 | 4.51 | 3.95 |
| OR Quartile 4 | 2.03 | 6.03 | 1.36 | 1.95 | 5.60 | 1.26 | 1.95 | 5.60 | 1.35 |
| p Value | 0.063 | 9.5E−5 | 0.43 | 0.078 | 1.8E−4 | 0.55 | 0.078 | 1.8E−4 | 0.43 |
| Lower limit of 95% CI | 0.963 | 2.45 | 0.634 | 0.928 | 2.27 | 0.587 | 0.928 | 2.27 | 0.634 |
| Upper limit of 95% CI | 4.28 | 14.9 | 2.93 | 4.11 | 13.8 | 2.70 | 4.11 | 13.8 | 2.88 |

Example 9. Use of Insulin-Like Growth Factor-Binding Protein 3 for Evaluating Renal Status in Patients Admitted to the ICU: Recovery to RIFLE 0 and R from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 3 is measured in the enrollment samples by standard immunoassay methods using commercially available assay reagents.

Kidney status is assessed by RIFLE criteria based on serum creatinine, urine output, or both serum creatinine and urine output during a period starting at 12, 24, 48, or 72 hours after sample collection or at any time within 7 days after sample collection. Two cohorts are defined to represent a "recovered" and a "non-recovered" population. "Recovered" indicates those patients whose maximum RIFLE stage during a period of 24, 48 or 72 hours is non-injury (RIFLE 0) or risk of injury (R). "Non-recovered" indicates those patients whose maximum RIFLE stage during a period of 24, 48 or 72 hours is injury (I) or failure (F). If a patient dies or is placed on renal replacement therapy (RRT) at any time from sample collection to 12, 24, 48, or 72 hours after sample collection or at any time within 7 days after sample collection, the patient is considered "non-recovered".

The ability to distinguish the "recovered" and "non-recovered" cohorts is determined using receiver operating characteristic (ROC) analysis.

TABLE 9.1

Comparison of marker levels and the area under the ROC curve
(AUC) in urine samples for the "recovered" and "non-recovered" cohorts where recovery
starts at 12 hours after sample collection and renal status is assessed by serum creatinine
(sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 553 | 904 | 463 | 904 | 448 | 901 |
| Average | 1110 | 3330 | 1110 | 3300 | 1120 | 3270 |

TABLE 9.1-continued

Comparison of marker levels and the area under the ROC curve
(AUC) in urine samples for the "recovered" and "non-recovered" cohorts where recovery
starts at 12 hours after sample collection and renal status is assessed by serum creatinine
(sCr) only, urine output (UO) only, or serum creatinine or urine output RIFLE criteria.

| | | | | | | |
|---|---|---|---|---|---|---|
| Stdev | 2570 | 5510 | 2640 | 5470 | 2680 | 5450 |
| p (t-test) | | 0.019 | | 0.024 | | 0.028 |
| Min | 30.5 | 20.6 | 30.5 | 20.6 | 30.5 | 20.6 |
| Max | 15900 | 18800 | 15900 | 18800 | 15900 | 18800 |
| n (Patient) | 37 | 112 | 35 | 114 | 34 | 115 |
| sCr only | | | | | | |
| Median | 601 | 920 | 601 | 920 | 592 | 916 |
| Average | 1400 | 3460 | 1400 | 3460 | 1410 | 3440 |
| Stdev | 3380 | 5560 | 3380 | 5560 | 3410 | 5540 |
| p (t-test) | | 0.018 | | 0.018 | | 0.021 |
| Min | 30.5 | 20.6 | 30.5 | 20.6 | 30.5 | 20.6 |
| Max | 18800 | 18800 | 18800 | 18800 | 18800 | 18800 |
| n (Patient) | 49 | 100 | 49 | 100 | 48 | 101 |
| UO only | | | | | | |
| Median | 637 | 1130 | 630 | 1120 | 626 | 1070 |
| Average | 2300 | 3660 | 2380 | 3410 | 2230 | 3570 |
| Stdev | 4630 | 5640 | 4770 | 5400 | 4510 | 5630 |
| p (t-test) | | 0.11 | | 0.23 | | 0.11 |
| Min | 20.6 | 172 | 20.6 | 172 | 20.6 | 172 |
| Max | 18800 | 18800 | 18800 | 18800 | 18800 | 18800 |
| n (Patient) | 94 | 54 | 88 | 60 | 85 | 63 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.63 | 0.66 | 0.66 | 0.63 | 0.66 | 0.66 | 0.63 | 0.67 |
| SE | 0.049 | 0.047 | 0.048 | 0.049 | 0.047 | 0.046 | 0.049 | 0.047 | 0.046 |
| p Value | 0.0022 | 0.0050 | 0.0012 | 0.0012 | 0.0050 | 7.3E−4 | 9.1E−4 | 0.0044 | 2.9E−4 |
| nCohort Recovered | 37 | 49 | 94 | 35 | 49 | 88 | 34 | 48 | 85 |
| nCohort Non-recovered | 112 | 100 | 54 | 114 | 100 | 60 | 115 | 101 | 63 |
| Cutoff Quartile 2 | 401 | 401 | 410 | 401 | 401 | 410 | 401 | 401 | 410 |
| Sensitivity | 79% | 77% | 89% | 79% | 77% | 90% | 79% | 77% | 90% |
| Specificity | 35% | 29% | 33% | 37% | 29% | 35% | 38% | 29% | 36% |
| Cutoff Quartile 3 | 794 | 794 | 801 | 794 | 794 | 801 | 794 | 794 | 801 |
| Sensitivity | 54% | 56% | 65% | 54% | 56% | 63% | 55% | 56% | 63% |
| Specificity | 62% | 61% | 59% | 63% | 61% | 59% | 65% | 62% | 60% |
| Cutoff Quartile 4 | 1830 | 1830 | 1840 | 1830 | 1830 | 1840 | 1830 | 1830 | 1840 |
| Sensitivity | 30% | 33% | 31% | 30% | 33% | 30% | 30% | 33% | 30% |
| Specificity | 89% | 90% | 79% | 89% | 90% | 78% | 88% | 90% | 79% |
| OR Quartile 2 | 1.99 | 1.34 | 3.94 | 2.22 | 1.34 | 4.89 | 2.35 | 1.40 | 5.45 |
| p Value | 0.098 | 0.46 | 0.0048 | 0.057 | 0.46 | 0.0011 | 0.043 | 0.40 | 4.7E−4 |
| Lower limit of 95% CI | 0.882 | 0.617 | 1.52 | 0.976 | 0.617 | 1.89 | 1.03 | 0.642 | 2.11 |
| Upper limit of 95% CI | 4.47 | 2.91 | 10.2 | 5.03 | 2.91 | 12.7 | 5.36 | 3.04 | 14.1 |
| OR Quartile 3 | 1.96 | 2.01 | 2.60 | 2.02 | 2.01 | 2.49 | 2.22 | 2.16 | 2.61 |
| p Value | 0.082 | 0.050 | 0.0069 | 0.077 | 0.050 | 0.0080 | 0.049 | 0.032 | 0.0052 |
| Lower limit of 95% CI | 0.918 | 1.00 | 1.30 | 0.926 | 1.00 | 1.27 | 1.00 | 1.07 | 1.33 |
| Upper limit of 95% CI | 4.21 | 4.04 | 5.20 | 4.39 | 4.04 | 4.90 | 4.91 | 4.37 | 5.11 |
| OR Quartile 4 | 3.60 | 4.33 | 1.70 | 3.29 | 4.33 | 1.56 | 3.15 | 4.17 | 1.61 |
| p Value | 0.024 | 0.0046 | 0.17 | 0.036 | 0.0046 | 0.25 | 0.044 | 0.0058 | 0.21 |
| Lower limit of 95% CI | 1.18 | 1.57 | 0.797 | 1.08 | 1.57 | 0.735 | 1.03 | 1.51 | 0.760 |
| Upper limit of 95% CI | 10.9 | 12.0 | 3.63 | 10.1 | 12.0 | 3.30 | 9.62 | 11.5 | 3.40 |

TABLE 9.2

Comparison of marker levels and the area under the ROC curve (AUC) in urine samples for the "recovered" and "non-recovered" cohorts where recovery starts at 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 553 | 992 | 540 | 992 | 540 | 992 |
| Average | 1290 | 3560 | 1290 | 3520 | 1290 | 3520 |
| Stdev | 3110 | 5650 | 3170 | 5600 | 3170 | 5600 |
| p (t-test) | | 0.0083 | | 0.011 | | 0.011 |
| Min | 30.5 | 20.6 | 30.5 | 20.6 | 30.5 | 20.6 |
| Max | 16600 | 18800 | 16600 | 18800 | 16600 | 18800 |
| n (Patient) | 51 | 98 | 49 | 100 | 49 | 100 |
| sCr only | | | | | | |
| Median | 576 | 1070 | 569 | 1020 | 569 | 1020 |
| Average | 1570 | 3580 | 1590 | 3550 | 1590 | 3550 |
| Stdev | 3770 | 5590 | 3810 | 5570 | 3810 | 5570 |
| p (t-test) | | 0.019 | | 0.022 | | 0.022 |
| Min | 30.5 | 20.6 | 30.5 | 20.6 | 30.5 | 20.6 |
| Max | 18800 | 18800 | 18800 | 18800 | 18800 | 18800 |
| n (Patient) | 56 | 91 | 55 | 92 | 55 | 92 |
| UO only | | | | | | |
| Median | 672 | 1190 | 640 | 1180 | 640 | 1180 |
| Average | 2280 | 3800 | 2160 | 3870 | 2160 | 3870 |
| Stdev | 4600 | 5810 | 4380 | 5950 | 4380 | 5950 |
| p (t-test) | | 0.088 | | 0.049 | | 0.049 |
| Min | 20.6 | 172 | 20.6 | 172 | 20.6 | 172 |
| Max | 18800 | 18800 | 18800 | 18800 | 18800 | 18800 |
| n (Patient) | 94 | 50 | 89 | 55 | 89 | 55 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.65 | 0.66 | 0.68 | 0.65 | 0.67 | 0.68 | 0.65 | 0.67 |
| SE | 0.045 | 0.045 | 0.049 | 0.044 | 0.045 | 0.047 | 0.044 | 0.045 | 0.047 |
| p Value | 1.1E−4 | 8.6E−4 | 8.9E−4 | 3.3E−5 | 7.7E−4 | 2.7E−4 | 3.3E−5 | 7.7E−4 | 2.7E−4 |
| nCohort Recovered | 51 | 56 | 94 | 49 | 55 | 89 | 49 | 55 | 89 |
| nCohort Non-recovered | 98 | 91 | 50 | 100 | 92 | 55 | 100 | 92 | 55 |
| Cutoff Quartile 2 | 401 | 407 | 399 | 401 | 407 | 399 | 401 | 407 | 399 |
| Sensitivity | 81% | 79% | 90% | 81% | 79% | 91% | 81% | 79% | 91% |
| Specificity | 35% | 32% | 33% | 37% | 33% | 35% | 37% | 33% | 35% |
| Cutoff Quartile 3 | 794 | 808 | 812 | 794 | 808 | 812 | 794 | 808 | 812 |
| Sensitivity | 59% | 59% | 68% | 60% | 60% | 67% | 60% | 60% | 67% |
| Specificity | 67% | 64% | 60% | 69% | 65% | 61% | 69% | 65% | 61% |
| Cutoff Quartile 4 | 1830 | 1850 | 1840 | 1830 | 1850 | 1840 | 1830 | 1850 | 1840 |
| Sensitivity | 34% | 34% | 32% | 33% | 34% | 31% | 33% | 34% | 31% |
| Specificity | 90% | 89% | 79% | 90% | 89% | 79% | 90% | 89% | 79% |
| OR Quartile 2 | 2.27 | 1.80 | 4.43 | 2.48 | 1.87 | 5.34 | 2.48 | 1.87 | 5.34 |
| p Value | 0.035 | 0.13 | 0.0042 | 0.020 | 0.11 | 0.0012 | 0.020 | 0.11 | 0.0012 |
| Lower limit of 95% CI | 1.06 | 0.844 | 1.60 | 1.15 | 0.877 | 1.93 | 1.15 | 0.877 | 1.93 |
| Upper limit of 95% CI | 4.86 | 3.82 | 12.3 | 5.33 | 3.98 | 14.8 | 5.33 | 3.98 | 14.8 |
| OR Quartile 3 | 2.90 | 2.63 | 3.13 | 3.40 | 2.82 | 3.17 | 3.40 | 2.82 | 3.17 |
| p Value | 0.0032 | 0.0060 | 0.0020 | 9.8E−4 | 0.0035 | 0.0013 | 9.8E−4 | 0.0035 | 0.0013 |
| Lower limit of 95% CI | 1.43 | 1.32 | 1.52 | 1.64 | 1.41 | 1.57 | 1.64 | 1.41 | 1.57 |
| Upper limit of 95% CI | 5.89 | 5.23 | 6.45 | 7.04 | 5.64 | 6.42 | 7.04 | 5.64 | 6.42 |
| OR Quartile 4 | 4.67 | 4.31 | 1.74 | 4.33 | 4.15 | 1.65 | 4.33 | 4.15 | 1.65 |
| p Value | 0.0029 | 0.0026 | 0.16 | 0.0046 | 0.0034 | 0.20 | 0.0046 | 0.0034 | 0.20 |
| Lower limit of 95% CI | 1.70 | 1.66 | 0.804 | 1.57 | 1.60 | 0.768 | 1.57 | 1.60 | 0.768 |
| Upper limit of 95% CI | 12.9 | 11.1 | 3.77 | 12.0 | 10.7 | 3.54 | 12.0 | 10.7 | 3.54 |

TABLE 9.3

Comparison of marker levels and the area under the ROC curve
(AUC) in urine samples for the "recovered" and "non-recovered" cohorts where recovery
starts at 48 hours after sample collection and renal status is assessed by serum creatinine
(sCr) only, urine output (UO) only, or serum creatinine or urine output RIFLE criteria.

|  | Recovery Period Duration (hr) | | | | | |
|---|---|---|---|---|---|---|
|  | 24 | | 48 | | 72 | |
|  | Recovered Cohort | Non-recovered Cohort | Recovered Cohort | Non-recovered Cohort | Recovered Cohort | Non-recovered Cohort |
| sCr or UO | | | | | | |
| Median | 569 | 1070 | 569 | 1070 | 569 | 1070 |
| Average | 1430 | 3860 | 1430 | 3860 | 1270 | 3920 |
| Stdev | 3210 | 5940 | 3210 | 5940 | 2920 | 5960 |
| p (t-test) | | 0.0039 | | 0.0039 | | 0.0017 |
| Min | 21.1 | 20.6 | 21.1 | 20.6 | 21.1 | 20.6 |
| Max | 16600 | 18800 | 16600 | 18800 | 16600 | 18800 |
| n (Patient) | 63 | 83 | 63 | 83 | 61 | 85 |
| sCr only | | | | | | |
| Median | 601 | 1020 | 601 | 1020 | 592 | 1070 |
| Average | 1680 | 3810 | 1680 | 3810 | 1520 | 3920 |
| Stdev | 3760 | 5850 | 3760 | 5850 | 3540 | 5900 |
| p (t-test) | | 0.012 | | 0.012 | | 0.0044 |
| Min | 21.1 | 20.6 | 21.1 | 20.6 | 21.1 | 20.6 |
| Max | 18800 | 18800 | 18800 | 18800 | 18800 | 18800 |
| n (Patient) | 67 | 78 | 67 | 78 | 66 | 79 |
| UO only | | | | | | |
| Median | 722 | 1200 | 722 | 1200 | 766 | 1070 |
| Average | 2260 | 4430 | 2260 | 4430 | 2340 | 4190 |
| Stdev | 4410 | 6420 | 4410 | 6420 | 4480 | 6300 |
| p (t-test) | | 0.026 | | 0.026 | | 0.054 |
| Min | 20.6 | 194 | 20.6 | 194 | 20.6 | 172 |
| Max | 18800 | 18800 | 18800 | 18800 | 18800 | 18800 |
| n (Patient) | 80 | 48 | 80 | 48 | 77 | 51 |

|  | Recovery Period Duration (hr) | | | | | | | | |
|---|---|---|---|---|---|---|---|---|---|
|  | 24 | | | 48 | | | 72 | | |
|  | sCr or UO | sCr only | UO only | sCr or UO | sCr only | UO only | sCr or UO | sCr only | UO only |
| AUC | 0.68 | 0.65 | 0.67 | 0.68 | 0.65 | 0.67 | 0.68 | 0.66 | 0.64 |
| SE | 0.044 | 0.045 | 0.051 | 0.044 | 0.045 | 0.051 | 0.044 | 0.045 | 0.051 |
| p Value | 4.2E−5 | 6.6E−4 | 9.0E−4 | 4.2E−5 | 6.6E−4 | 9.0E−4 | 3.0E−5 | 2.2E−4 | 0.0076 |
| nCohort Recovered | 63 | 67 | 80 | 63 | 67 | 80 | 61 | 66 | 77 |
| nCohort Non-recovered | 83 | 78 | 48 | 83 | 78 | 48 | 85 | 79 | 51 |
| Cutoff Quartile 2 | 404 | 401 | 414 | 404 | 401 | 414 | 404 | 401 | 414 |
| Sensitivity | 82% | 81% | 92% | 82% | 81% | 92% | 81% | 81% | 88% |
| Specificity | 35% | 31% | 35% | 35% | 31% | 35% | 34% | 32% | 34% |
| Cutoff Quartile 3 | 790 | 794 | 878 | 790 | 794 | 878 | 790 | 794 | 878 |
| Sensitivity | 61% | 60% | 65% | 61% | 60% | 65% | 61% | 61% | 61% |
| Specificity | 65% | 61% | 59% | 65% | 61% | 59% | 66% | 62% | 57% |
| Cutoff Quartile 4 | 1770 | 1790 | 2020 | 1770 | 1790 | 2020 | 1770 | 1790 | 2020 |
| Sensitivity | 36% | 37% | 31% | 36% | 37% | 31% | 36% | 38% | 29% |
| Specificity | 89% | 88% | 79% | 89% | 88% | 79% | 90% | 89% | 78% |
| OR Quartile 2 | 2.43 | 1.92 | 5.92 | 2.43 | 1.92 | 5.92 | 2.26 | 1.99 | 3.82 |
| p Value | 0.022 | 0.095 | 0.0019 | 0.022 | 0.095 | 0.0019 | 0.035 | 0.077 | 0.0070 |
| Lower limit of 95% CI | 1.14 | 0.893 | 1.93 | 1.14 | 0.893 | 1.93 | 1.06 | 0.927 | 1.44 |
| Upper limit of 95% CI | 5.21 | 4.12 | 18.2 | 5.21 | 4.12 | 18.2 | 4.83 | 4.28 | 10.1 |
| OR Quartile 3 | 2.97 | 2.39 | 2.60 | 2.97 | 2.39 | 2.60 | 3.00 | 2.54 | 2.07 |
| p Value | 0.0017 | 0.011 | 0.012 | 0.0017 | 0.011 | 0.012 | 0.0017 | 0.0066 | 0.048 |
| Lower limit of 95% CI | 1.50 | 1.23 | 1.24 | 1.50 | 1.23 | 1.24 | 1.51 | 1.30 | 1.01 |
| Upper limit of 95% CI | 5.87 | 4.67 | 5.45 | 5.87 | 4.67 | 5.45 | 5.95 | 4.97 | 4.25 |
| OR Quartile 4 | 4.53 | 4.36 | 1.68 | 4.53 | 4.36 | 1.68 | 5.26 | 5.16 | 1.47 |
| p Value | 0.0011 | 9.0E−4 | 0.21 | 0.0011 | 9.0E−4 | 0.21 | 6.2E−4 | 3.8E−4 | 0.35 |
| Lower limit of 95% CI | 1.83 | 1.83 | 0.748 | 1.83 | 1.83 | 0.748 | 2.03 | 2.09 | 0.656 |
| Upper limit of 95% CI | 11.2 | 10.4 | 3.79 | 11.2 | 10.4 | 3.79 | 13.6 | 12.8 | 3.30 |

TABLE 9.4

Comparison of marker levels and the area under the ROC curve (AUC) in urine samples for the "recovered" and "non-recovered" cohorts where recovery starts at 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 583 | 1250 | 583 | 1220 | 573 | 1240 |
| Average | 1360 | 4400 | 1230 | 4360 | 1220 | 4240 |
| Stdev | 3030 | 6260 | 2790 | 6210 | 2850 | 6120 |
| p (t-test) | | 3.3E−4 | | 2.2E−4 | | 4.0E−4 |
| Min | 21.1 | 20.6 | 21.1 | 20.6 | 21.1 | 20.6 |
| Max | 16600 | 18800 | 16600 | 18800 | 16600 | 18800 |
| n (Patient) | 71 | 71 | 67 | 75 | 64 | 78 |
| sCr only | | | | | | |
| Median | 601 | 1180 | 592 | 1210 | 583 | 1250 |
| Average | 1600 | 4230 | 1450 | 4350 | 1440 | 4320 |
| Stdev | 3620 | 6100 | 3400 | 6140 | 3420 | 6100 |
| p (t-test) | | 0.0020 | | 6.3E−4 | | 6.9E−4 |
| Min | 21.1 | 20.6 | 21.1 | 20.6 | 21.1 | 20.6 |
| Max | 18800 | 18800 | 18800 | 18800 | 18800 | 18800 |
| n (Patient) | 73 | 69 | 72 | 70 | 71 | 71 |
| UO only | | | | | | |
| Median | 776 | 1180 | 797 | 1070 | 808 | 1070 |
| Average | 2680 | 4200 | 2600 | 4120 | 2650 | 4000 |
| Stdev | 4940 | 6240 | 4730 | 6310 | 4760 | 6220 |
| p (t-test) | | 0.14 | | 0.14 | | 0.18 |
| Min | 20.6 | 194 | 20.6 | 172 | 20.6 | 169 |
| Max | 18800 | 18800 | 18800 | 18800 | 18800 | 18800 |
| n (Patient) | 74 | 45 | 68 | 51 | 67 | 53 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.69 | 0.64 | 0.70 | 0.70 | 0.61 | 0.70 | 0.71 | 0.60 |
| SE | 0.043 | 0.045 | 0.053 | 0.043 | 0.044 | 0.053 | 0.043 | 0.043 | 0.052 |
| p Value | 1.7E−6 | 2.4E−5 | 0.0087 | 3.3E−6 | 5.7E−6 | 0.033 | 2.1E−6 | 1.9E−6 | 0.064 |
| nCohort Recovered | 71 | 73 | 74 | 67 | 72 | 68 | 64 | 71 | 67 |
| nCohort Non-recovered | 71 | 69 | 45 | 75 | 70 | 51 | 78 | 71 | 53 |
| Cutoff Quartile 2 | 397 | 397 | 419 | 397 | 397 | 419 | 397 | 397 | 420 |
| Sensitivity | 85% | 84% | 89% | 83% | 84% | 84% | 82% | 85% | 83% |
| Specificity | 35% | 34% | 34% | 34% | 35% | 32% | 34% | 35% | 31% |
| Cutoff Quartile 3 | 812 | 812 | 901 | 812 | 812 | 901 | 812 | 812 | 904 |
| Sensitivity | 65% | 64% | 62% | 64% | 64% | 59% | 64% | 65% | 58% |
| Specificity | 65% | 63% | 57% | 66% | 64% | 56% | 67% | 65% | 57% |
| Cutoff Quartile 4 | 1870 | 1870 | 2240 | 1870 | 1870 | 2240 | 1870 | 1870 | 2240 |
| Sensitivity | 39% | 39% | 29% | 39% | 40% | 27% | 38% | 41% | 26% |
| Specificity | 89% | 88% | 77% | 90% | 89% | 76% | 91% | 90% | 76% |
| OR Quartile 2 | 2.96 | 2.75 | 4.08 | 2.49 | 2.85 | 2.57 | 2.39 | 2.96 | 2.23 |
| p Value | 0.0083 | 0.014 | 0.0085 | 0.022 | 0.011 | 0.042 | 0.027 | 0.0083 | 0.075 |
| Lower limit of 95% CI | 1.32 | 1.23 | 1.43 | 1.14 | 1.27 | 1.03 | 1.10 | 1.32 | 0.922 |
| Upper limit of 95% CI | 6.64 | 6.15 | 11.6 | 5.45 | 6.39 | 6.38 | 5.20 | 6.64 | 5.40 |
| OR Quartile 3 | 3.39 | 3.00 | 2.16 | 3.40 | 3.18 | 1.81 | 3.66 | 3.39 | 1.85 |
| p Value | 5.2E−4 | 0.0016 | 0.046 | 5.1E−4 | 9.3E−4 | 0.11 | 2.7E−4 | 5.2E−4 | 0.099 |
| Lower limit of 95% CI | 1.70 | 1.51 | 1.01 | 1.71 | 1.60 | 0.868 | 1.82 | 1.70 | 0.890 |
| Upper limit of 95% CI | 6.74 | 5.94 | 4.61 | 6.78 | 6.32 | 3.77 | 7.34 | 6.74 | 3.83 |
| OR Quartile 4 | 5.13 | 4.57 | 1.36 | 5.40 | 5.33 | 1.23 | 6.04 | 6.31 | 1.14 |
| p Value | 2.6E−4 | 4.5E−4 | 0.47 | 2.8E−4 | 1.8E−4 | 0.63 | 2.3E−4 | 7.6E−5 | 0.75 |
| Lower limit of 95% CI | 2.14 | 1.96 | 0.587 | 2.17 | 2.22 | 0.535 | 2.32 | 2.53 | 0.499 |
| Upper limit of 95% CI | 12.3 | 10.7 | 3.16 | 13.4 | 12.8 | 2.83 | 15.7 | 15.7 | 2.62 |

TABLE 9.5

Comparison of marker levels and the area under the ROC curve (AUC) in urine samples for the "recovered" and "non-recovered" cohorts where recovery starts within 7 days after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 642 | 1070 | 686 | 1070 | 642 | 1070 |
| Average | 2060 | 3980 | 2080 | 3920 | 2090 | 3870 |
| Stdev | 4310 | 5890 | 4330 | 5860 | 4360 | 5820 |
| p (t-test) | | 0.023 | | 0.030 | | 0.035 |
| Min | 20.6 | 166 | 20.6 | 166 | 20.6 | 166 |
| Max | 18800 | 18800 | 18800 | 18800 | 18800 | 18800 |
| n (Patient) | 93 | 56 | 92 | 57 | 91 | 58 |
| sCr only | | | | | | |
| Median | 622 | 1070 | 622 | 1070 | 622 | 1070 |
| Average | 1480 | 4420 | 1480 | 4420 | 1480 | 4420 |
| Stdev | 3210 | 6310 | 3210 | 6310 | 3210 | 6310 |
| p (t-test) | | 3.1E−4 | | 3.1E−4 | | 3.1E−4 |
| Min | 21.1 | 20.6 | 21.1 | 20.6 | 21.1 | 20.6 |
| Max | 18800 | 18800 | 18800 | 18800 | 18800 | 18800 |
| n (Patient) | 83 | 66 | 83 | 66 | 83 | 66 |
| UO only | | | | | | |
| Median | 747 | 1070 | 747 | 1070 | 747 | 1070 |
| Average | 2140 | 4170 | 2140 | 4170 | 2170 | 4040 |
| Stdev | 4250 | 6230 | 4250 | 6230 | 4280 | 6140 |
| p (t-test) | | 0.021 | | 0.021 | | 0.033 |
| Min | 20.6 | 175 | 20.6 | 175 | 20.6 | 172 |
| Max | 18800 | 18800 | 18800 | 18800 | 18800 | 18800 |
| n (Patient) | 100 | 48 | 100 | 48 | 98 | 50 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.68 | 0.63 | 0.62 | 0.68 | 0.63 | 0.63 | 0.68 | 0.62 |
| SE | 0.048 | 0.045 | 0.050 | 0.048 | 0.045 | 0.050 | 0.048 | 0.045 | 0.050 |
| p Value | 0.0045 | 8.8E−5 | 0.0077 | 0.011 | 8.8E−5 | 0.0077 | 0.0080 | 8.8E−5 | 0.014 |
| nCohort Recovered | 93 | 83 | 100 | 92 | 83 | 100 | 91 | 83 | 98 |
| nCohort Non-recovered | 56 | 66 | 48 | 57 | 66 | 48 | 58 | 66 | 50 |
| Cutoff Quartile 2 | 401 | 401 | 410 | 401 | 401 | 410 | 401 | 401 | 410 |
| Sensitivity | 86% | 85% | 88% | 84% | 85% | 88% | 84% | 85% | 86% |
| Specificity | 31% | 33% | 31% | 30% | 33% | 31% | 31% | 33% | 31% |
| Cutoff Quartile 3 | 794 | 794 | 801 | 794 | 794 | 801 | 794 | 794 | 801 |
| Sensitivity | 59% | 62% | 60% | 58% | 62% | 60% | 59% | 62% | 60% |
| Specificity | 55% | 59% | 55% | 54% | 59% | 55% | 55% | 59% | 55% |
| Cutoff Quartile 4 | 1830 | 1830 | 1840 | 1830 | 1830 | 1840 | 1830 | 1830 | 1840 |
| Sensitivity | 34% | 38% | 31% | 33% | 38% | 31% | 33% | 38% | 30% |
| Specificity | 80% | 84% | 78% | 79% | 84% | 78% | 79% | 84% | 78% |
| OR Quartile 2 | 2.72 | 2.70 | 3.14 | 2.33 | 2.70 | 3.14 | 2.42 | 2.70 | 2.71 |
| p Value | 0.024 | 0.017 | 0.019 | 0.048 | 0.017 | 0.019 | 0.039 | 0.017 | 0.031 |
| Lower limit of 95% CI | 1.14 | 1.20 | 1.21 | 1.01 | 1.20 | 1.21 | 1.05 | 1.20 | 1.09 |
| Upper limit of 95% CI | 6.47 | 6.10 | 8.17 | 5.40 | 6.10 | 8.17 | 5.60 | 6.10 | 6.71 |
| OR Quartile 3 | 1.74 | 2.36 | 1.87 | 1.64 | 2.36 | 1.87 | 1.73 | 2.36 | 1.84 |
| p Value | 0.10 | 0.011 | 0.081 | 0.15 | 0.011 | 0.081 | 0.11 | 0.011 | 0.084 |
| Lower limit of 95% CI | 0.891 | 1.22 | 0.926 | 0.840 | 1.22 | 0.926 | 0.888 | 1.22 | 0.922 |
| Upper limit of 95% CI | 3.41 | 4.58 | 3.76 | 3.19 | 4.58 | 3.76 | 3.36 | 4.58 | 3.68 |
| OR Quartile 4 | 2.00 | 3.28 | 1.61 | 1.92 | 3.28 | 1.61 | 1.85 | 3.28 | 1.48 |
| p Value | 0.069 | 0.0026 | 0.23 | 0.087 | 0.0026 | 0.23 | 0.11 | 0.0026 | 0.32 |
| Lower limit of 95% CI | 0.946 | 1.52 | 0.744 | 0.910 | 1.52 | 0.744 | 0.876 | 1.52 | 0.686 |
| Upper limit of 95% CI | 4.23 | 7.11 | 3.49 | 4.05 | 7.11 | 3.49 | 3.89 | 7.11 | 3.19 |

Example 10. Use of Insulin-Like Growth Factor-Binding Protein 4 for Evaluating Renal Status in Patients Admitted to the ICU: Recovery to RIFLE 0 from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 4 is measured in the enrollment samples by standard immunoassay methods using commercially available assay reagents.

Kidney status is assessed by RIFLE criteria based on serum creatinine, urine output, or both serum creatinine and urine output during a period starting at 12, 24, 48, or 72 hours after sample collection or at any time within 7 days after sample collection. Two cohorts are defined to represent a "recovered" and a "non-recovered" population. "Recovered" indicates those patients whose maximum RIFLE stage during a period of 24, 48 or 72 hours is non-injury (RIFLE 0). "Non-recovered" indicates those patients whose maximum RIFLE stage during a period of 24, 48 or 72 hours is risk of injury (R), injury (I) or failure (F). If a patient dies or is placed on renal replacement therapy (RRT) at any time from sample collection to 12, 24, 48, or 72 hours after sample collection or at any time within 7 days after sample collection, the patient is considered "non-recovered".

The ability to distinguish the "recovered" and "non-recovered" cohorts is determined using receiver operating characteristic (ROC) analysis.

TABLE 10.1

Comparison of marker levels and the area under the ROC curve (AUC) in urine samples for the "recovered" and "non-recovered" cohorts where recovery starts at 12 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 0.000286 | 0.394 | 0.000286 | 0.341 | 0.000286 | 0.341 |
| Average | 0.236 | 8.15 | 0.262 | 8.09 | 0.262 | 8.09 |
| Stdev | 0.746 | 19.5 | 0.786 | 19.4 | 0.786 | 19.4 |
| p (t-test) | | 0.20 | | 0.23 | | 0.23 |
| Min | 0.000212 | 0.000212 | 0.000212 | 0.000212 | 0.000212 | 0.000212 |
| Max | 2.36 | 120 | 2.36 | 120 | 2.36 | 120 |
| n (Patient) | 10 | 139 | 9 | 140 | 9 | 140 |
| sCr only | | | | | | |
| Median | 0.000339 | 0.538 | 0.000339 | 0.443 | 0.000339 | 0.443 |
| Average | 0.740 | 8.87 | 0.773 | 8.80 | 0.773 | 8.80 |
| Stdev | 2.66 | 20.3 | 2.72 | 20.3 | 2.72 | 20.3 |
| p (t-test) | | 0.058 | | 0.066 | | 0.066 |
| Min | 0.000212 | 0.000212 | 0.000212 | 0.000212 | 0.000212 | 0.000212 |
| Max | 12.7 | 120 | 12.7 | 120 | 12.7 | 120 |
| n (Patient) | 23 | 126 | 22 | 127 | 22 | 127 |
| UO only | | | | | | |
| Median | 0.126 | 0.394 | 0.165 | 0.265 | 0.142 | 0.330 |
| Average | 7.26 | 8.08 | 7.17 | 8.07 | 4.67 | 9.95 |
| Stdev | 19.8 | 18.3 | 19.7 | 18.5 | 12.3 | 22.6 |
| p (t-test) | | 0.79 | | 0.77 | | 0.094 |
| Min | 0.000212 | 0.000212 | 0.000212 | 0.000212 | 0.000212 | 0.000212 |
| Max | 120 | 110 | 120 | 110 | 73.0 | 120 |
| n (Patient) | 75 | 73 | 67 | 81 | 64 | 84 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.86 | 0.75 | 0.54 | 0.87 | 0.75 | 0.55 | 0.87 | 0.75 | 0.57 |
| SE | 0.045 | 0.048 | 0.047 | 0.042 | 0.049 | 0.047 | 0.042 | 0.049 | 0.047 |
| p Value | 2.2E−15 | 1.0E−7 | 0.35 | 0 | 2.7E−7 | 0.28 | 0 | 2.7E−7 | 0.15 |
| nCohort Recovered | 10 | 23 | 75 | 9 | 22 | 67 | 9 | 22 | 64 |
| nCohort Non-recovered | 139 | 126 | 73 | 140 | 127 | 81 | 140 | 127 | 84 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 85% | 85% | 84% | 85% | 85% | 85% | 85% | 85% | 85% |
| Specificity | 70% | 39% | 20% | 78% | 41% | 22% | 78% | 41% | 22% |
| Cutoff Quartile 3 | 0.170 | 0.170 | 0.205 | 0.170 | 0.170 | 0.205 | 0.170 | 0.170 | 0.205 |
| Sensitivity | 53% | 55% | 52% | 53% | 54% | 51% | 53% | 54% | 51% |
| Specificity | 90% | 74% | 52% | 89% | 73% | 51% | 89% | 73% | 52% |
| Cutoff Quartile 4 | 2.99 | 2.99 | 3.01 | 2.99 | 2.99 | 3.01 | 2.99 | 2.99 | 3.01 |
| Sensitivity | 27% | 29% | 30% | 27% | 29% | 28% | 27% | 29% | 30% |

TABLE 10.1-continued

Comparison of marker levels and the area under the ROC curve (AUC) in urine samples for the "recovered" and "non-recovered" cohorts where recovery starts at 12 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Specificity | 100% | 96% | 80% | 100% | 95% | 79% | 100% | 95% | 81% |
| OR Quartile 2 | 13.1 | 3.62 | 1.27 | 19.8 | 3.94 | 1.66 | 19.8 | 3.94 | 1.53 |
| p Value | 4.2E−4 | 0.0093 | 0.58 | 3.5E−4 | 0.0061 | 0.24 | 3.5E−4 | 0.0061 | 0.32 |
| Lower limit of 95% CI | 3.14 | 1.37 | 0.549 | 3.85 | 1.48 | 0.716 | 3.85 | 1.48 | 0.662 |
| Upper limit of 95% CI | 54.8 | 9.54 | 2.94 | 102 | 10.5 | 3.84 | 102 | 10.5 | 3.53 |
| OR Quartile 3 | 10.2 | 3.43 | 1.18 | 8.97 | 3.17 | 1.06 | 8.97 | 3.17 | 1.12 |
| p Value | 0.029 | 0.015 | 0.62 | 0.041 | 0.024 | 0.87 | 0.041 | 0.024 | 0.74 |
| Lower limit of 95% CI | 1.26 | 1.27 | 0.617 | 1.09 | 1.17 | 0.553 | 1.09 | 1.17 | 0.582 |
| Upper limit of 95% CI | 83.1 | 9.27 | 2.24 | 73.6 | 8.63 | 2.02 | 73.6 | 8.63 | 2.14 |
| OR Quartile 4 | 7.97 | 9.15 | 1.73 | 7.14 | 8.63 | 1.50 | 7.14 | 8.63 | 1.84 |
| p Value | 0.16 | 0.033 | 0.16 | 0.18 | 0.039 | 0.30 | 0.18 | 0.039 | 0.13 |
| Lower limit of 95% CI | 0.456 | 1.19 | 0.811 | 0.405 | 1.12 | 0.701 | 0.405 | 1.12 | 0.839 |
| Upper limit of 95% CI | 139 | 70.4 | 3.67 | 126 | 66.5 | 3.22 | 126 | 66.5 | 4.02 |

TABLE 10.2

Comparison of marker levels and the area under the ROC curve (AUC) in urine samples for the "recovered" and "non-recovered" cohorts where recovery starts at 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 0.000457 | 0.633 | 0.000391 | 0.449 | 0.000339 | 0.446 |
| Average | 0.209 | 9.18 | 0.234 | 8.89 | 0.224 | 8.83 |
| Stdev | 0.501 | 20.5 | 0.542 | 20.2 | 0.553 | 20.2 |
| p (t-test) | | 0.028 | | 0.047 | | 0.053 |
| Min | 0.000212 | 0.000212 | 0.000212 | 0.000212 | 0.000212 | 0.000212 |
| Max | 2.36 | 120 | 2.36 | 120 | 2.36 | 120 |
| n (Patient) | 26 | 123 | 22 | 127 | 21 | 128 |
| sCr only | | | | | | |
| Median | 0.000471 | 0.752 | 0.000471 | 0.685 | 0.000471 | 0.659 |
| Average | 0.550 | 9.94 | 0.580 | 9.77 | 0.584 | 9.69 |
| Stdev | 2.16 | 21.3 | 2.23 | 21.2 | 2.26 | 21.1 |
| p (t-test) | | 0.010 | | 0.014 | | 0.016 |
| Min | 0.000212 | 0.000212 | 0.000212 | 0.000212 | 0.000212 | 0.000212 |
| Max | 12.7 | 120 | 12.7 | 120 | 12.7 | 120 |
| n (Patient) | 35 | 112 | 33 | 114 | 32 | 115 |
| UO only | | | | | | |
| Median | 0.118 | 0.555 | 0.102 | 0.422 | 0.0851 | 0.449 |
| Average | 6.50 | 9.12 | 4.74 | 10.6 | 3.86 | 11.1 |
| Stdev | 18.9 | 19.5 | 13.0 | 23.4 | 11.3 | 23.7 |
| p (t-test) | | 0.42 | | 0.067 | | 0.022 |
| Min | 0.000212 | 0.000212 | 0.000212 | 0.000212 | 0.000212 | 0.000212 |
| Max | 120 | 110 | 73.0 | 120 | 73.0 | 120 |
| n (Patient) | 81 | 63 | 72 | 72 | 69 | 75 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.75 | 0.74 | 0.58 | 0.75 | 0.73 | 0.59 | 0.76 | 0.74 | 0.60 |
| SE | 0.046 | 0.044 | 0.048 | 0.048 | 0.045 | 0.047 | 0.048 | 0.044 | 0.047 |
| p Value | 1.1E−7 | 7.2E−8 | 0.099 | 1.7E−7 | 1.3E−7 | 0.067 | 2.6E−8 | 4.8E−8 | 0.033 |
| nCohort Recovered | 26 | 35 | 81 | 22 | 33 | 72 | 21 | 32 | 69 |
| nCohort Non-recovered | 123 | 112 | 63 | 127 | 114 | 72 | 128 | 115 | 75 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 85% | 85% | 84% | 84% | 85% | 85% | 84% | 85% | 84% |
| Specificity | 35% | 29% | 21% | 36% | 30% | 22% | 38% | 31% | 22% |
| Cutoff Quartile 3 | 0.170 | 0.170 | 0.218 | 0.170 | 0.170 | 0.218 | 0.170 | 0.170 | 0.218 |

TABLE 10.2-continued

Comparison of marker levels and the area under the ROC curve
(AUC) in urine samples for the "recovered" and "non-recovered" cohorts where recovery
starts at 24 hours after sample collection and renal status is assessed by serum creatinine
(sCr) only, urine output (UO) only, or serum creatinine or urine output RIFLE criteria.

| | | | | | | | | | |
|---|---|---|---|---|---|---|---|---|---|
| Sensitivity | 56% | 58% | 56% | 55% | 57% | 53% | 55% | 57% | 53% |
| Specificity | 77% | 74% | 54% | 77% | 73% | 53% | 81% | 75% | 54% |
| Cutoff Quartile 4 | 2.99 | 3.02 | 3.01 | 2.99 | 3.02 | 3.01 | 2.99 | 3.02 | 3.01 |
| Sensitivity | 31% | 32% | 32% | 30% | 32% | 32% | 30% | 31% | 33% |
| Specificity | 100% | 97% | 80% | 100% | 97% | 82% | 100% | 97% | 84% |
| OR Quartile 2 | 2.90 | 2.24 | 1.41 | 3.06 | 2.48 | 1.58 | 3.32 | 2.62 | 1.46 |
| p Value | 0.027 | 0.079 | 0.44 | 0.027 | 0.049 | 0.29 | 0.019 | 0.038 | 0.38 |
| Lower limit of 95% CI | 1.13 | 0.912 | 0.595 | 1.13 | 1.00 | 0.678 | 1.22 | 1.06 | 0.629 |
| Upper limit of 95% CI | 7.45 | 5.48 | 3.33 | 8.24 | 6.12 | 3.70 | 9.05 | 6.49 | 3.38 |
| OR Quartile 3 | 4.26 | 4.00 | 1.49 | 4.18 | 3.54 | 1.25 | 5.29 | 4.04 | 1.32 |
| p Value | 0.0037 | 0.0013 | 0.24 | 0.0080 | 0.0036 | 0.51 | 0.0043 | 0.0019 | 0.40 |
| Lower limit of 95% CI | 1.60 | 1.71 | 0.767 | 1.45 | 1.51 | 0.649 | 1.69 | 1.67 | 0.686 |
| Upper limit of 95% CI | 11.3 | 9.31 | 2.88 | 12.0 | 8.29 | 2.40 | 16.6 | 9.76 | 2.55 |
| OR Quartile 4 | 23.9 | 16.1 | 1.89 | 19.4 | 14.8 | 2.13 | 18.3 | 14.1 | 2.64 |
| p Value | 0.028 | 0.0072 | 0.10 | 0.040 | 0.0093 | 0.057 | 0.044 | 0.011 | 0.018 |
| Lower limit of 95% CI | 1.42 | 2.12 | 0.882 | 1.14 | 1.94 | 0.978 | 1.08 | 1.86 | 1.18 |
| Upper limit of 95% CI | 402 | 122 | 4.05 | 327 | 112 | 4.64 | 310 | 108 | 5.89 |

TABLE 10.3

Comparison of marker levels and the area under the ROC curve
(AUC) in urine samples for the "recovered" and "non-recovered" cohorts where recovery
starts at 48 hours after sample collection and renal status is assessed by serum creatinine
(sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| Cohort | Recovered Cohort | Non-recovered Cohort | Recovered Cohort | Non-recovered Cohort | Recovered Cohort | Non-recovered Cohort |
| sCr or UO | | | | | | |
| Median | 0.000443 | 0.710 | 0.000339 | 0.685 | 0.000443 | 0.633 |
| Average | 0.555 | 10.2 | 0.201 | 10.0 | 0.220 | 9.78 |
| Stdev | 2.20 | 21.6 | 0.497 | 21.3 | 0.517 | 21.1 |
| p (t-test) | | 0.0076 | | 0.0081 | | 0.013 |
| Min | 0.000212 | 0.000212 | 0.000212 | 0.000212 | 0.000212 | 0.000212 |
| Max | 13.2 | 120 | 2.56 | 120 | 2.56 | 120 |
| n (Patient) | 37 | 109 | 34 | 112 | 31 | 115 |
| sCr only | | | | | | |
| Median | 0.000471 | 0.866 | 0.000443 | 0.866 | 0.000443 | 0.866 |
| Average | 0.750 | 11.0 | 0.467 | 10.9 | 0.467 | 10.9 |
| Stdev | 2.70 | 22.3 | 1.96 | 22.1 | 1.96 | 22.1 |
| p (t-test) | | 0.0027 | | 0.0025 | | 0.0025 |
| Min | 0.000212 | 0.000212 | 0.000212 | 0.000212 | 0.000212 | 0.000212 |
| Max | 13.2 | 120 | 12.7 | 120 | 12.7 | 120 |
| n (Patient) | 45 | 100 | 43 | 102 | 43 | 102 |
| UO only | | | | | | |
| Median | 0.341 | 0.706 | 0.341 | 0.706 | 0.404 | 0.265 |
| Average | 7.43 | 9.90 | 6.75 | 10.5 | 7.51 | 9.44 |
| Stdev | 19.3 | 21.1 | 18.6 | 21.5 | 19.6 | 20.6 |
| p (t-test) | | 0.49 | | 0.30 | | 0.59 |
| Min | 0.000212 | 0.000212 | 0.000212 | 0.000212 | 0.000212 | 0.000212 |
| Max | 110 | 120 | 110 | 120 | 110 | 120 |
| n (Patient) | 70 | 58 | 66 | 62 | 59 | 69 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.75 | 0.76 | 0.57 | 0.78 | 0.78 | 0.58 | 0.74 | 0.78 | 0.54 |
| SE | 0.042 | 0.040 | 0.051 | 0.040 | 0.038 | 0.050 | 0.045 | 0.038 | 0.051 |
| p Value | 1.9E-9 | 4.0E-11 | 0.15 | 4.8E-12 | 1.5E-13 | 0.10 | 5.4E-8 | 1.5E-13 | 0.42 |
| nCohort Recovered | 37 | 45 | 70 | 34 | 43 | 66 | 31 | 43 | 59 |
| nCohort Non-recovered | 109 | 100 | 58 | 112 | 102 | 62 | 115 | 102 | 69 |

TABLE 10.3-continued

Comparison of marker levels and the area under the ROC curve (AUC) in urine samples for the "recovered" and "non-recovered" cohorts where recovery starts at 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Cutoff Quartile 2 | 0.000339 | 0.000339 | 0.000471 | 0.000339 | 0.000339 | 0.000471 | 0.000339 | 0.000339 | 0.000471 |
| Sensitivity | 85% | 87% | 81% | 86% | 87% | 81% | 83% | 87% | 78% |
| Specificity | 30% | 31% | 29% | 32% | 33% | 29% | 26% | 33% | 27% |
| Cutoff Quartile 3 | 0.168 | 0.165 | 0.399 | 0.168 | 0.165 | 0.399 | 0.168 | 0.165 | 0.399 |
| Sensitivity | 59% | 62% | 52% | 59% | 63% | 52% | 57% | 63% | 49% |
| Specificity | 76% | 73% | 51% | 79% | 77% | 52% | 77% | 77% | 49% |
| Cutoff Quartile 4 | 3.04 | 3.05 | 4.89 | 3.04 | 3.05 | 4.89 | 3.04 | 3.05 | 4.89 |
| Sensitivity | 33% | 35% | 29% | 33% | 35% | 31% | 32% | 35% | 28% |
| Specificity | 97% | 96% | 79% | 100% | 98% | 80% | 100% | 98% | 78% |
| OR Quartile 2 | 2.46 | 3.02 | 1.71 | 2.87 | 3.31 | 1.68 | 1.76 | 3.31 | 1.34 |
| p Value | 0.046 | 0.012 | 0.21 | 0.021 | 0.0067 | 0.22 | 0.24 | 0.0067 | 0.48 |
| Lower limit of 95% CI | 1.02 | 1.28 | 0.740 | 1.18 | 1.39 | 0.738 | 0.684 | 1.39 | 0.596 |
| Upper limit of 95% CI | 5.94 | 7.14 | 3.95 | 7.00 | 7.84 | 3.84 | 4.51 | 7.84 | 3.01 |
| OR Quartile 3 | 4.42 | 4.49 | 1.13 | 5.53 | 5.56 | 1.13 | 4.62 | 5.56 | 0.939 |
| p Value | 5.4E−4 | 1.4E−4 | 0.72 | 2.4E−4 | 3.6E−5 | 0.72 | 0.0011 | 3.6E−5 | 0.86 |
| Lower limit of 95% CI | 1.91 | 2.07 | 0.565 | 2.22 | 2.46 | 0.566 | 1.84 | 2.46 | 0.469 |
| Upper limit of 95% CI | 10.3 | 9.73 | 2.28 | 13.8 | 12.5 | 2.27 | 11.6 | 12.5 | 1.88 |
| OR Quartile 4 | 17.8 | 11.6 | 1.52 | 34.3 | 22.9 | 1.80 | 30.1 | 22.9 | 1.34 |
| p Value | 0.0054 | 0.0011 | 0.31 | 0.014 | 0.0024 | 0.16 | 0.018 | 0.0024 | 0.47 |
| Lower limit of 95% CI | 2.34 | 2.65 | 0.681 | 2.04 | 3.03 | 0.800 | 1.79 | 3.03 | 0.597 |
| Upper limit of 95% CI | 135 | 50.7 | 3.40 | 575 | 173 | 4.06 | 505 | 173 | 3.03 |

TABLE 10.4

Comparison of marker levels and the area under the ROC curve (AUC) in urine samples for the "recovered" and "non-recovered" cohorts where recovery starts at 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 0.000471 | 0.857 | 0.000471 | 0.646 | 0.000471 | 0.646 |
| Average | 1.29 | 10.9 | 1.46 | 10.3 | 1.52 | 10.1 |
| Stdev | 5.58 | 22.3 | 5.93 | 21.9 | 6.09 | 21.7 |
| p (t-test) | | 0.0063 | | 0.015 | | 0.020 |
| Min | 0.000212 | 0.000212 | 0.000212 | 0.000212 | 0.000212 | 0.000212 |
| Max | 35.9 | 120 | 35.9 | 120 | 35.9 | 120 |
| n (Patient) | 43 | 99 | 38 | 104 | 36 | 106 |
| sCr only | | | | | | |
| Median | 0.000472 | 0.869 | 0.000472 | 0.869 | 0.000472 | 0.866 |
| Average | 1.38 | 11.5 | 1.38 | 11.5 | 1.42 | 11.3 |
| Stdev | 5.44 | 22.9 | 5.44 | 22.9 | 5.55 | 22.8 |
| p (t-test) | | 0.0025 | | 0.0025 | | 0.0036 |
| Min | 0.000212 | 0.000212 | 0.000212 | 0.000212 | 0.000212 | 0.000212 |
| Max | 35.9 | 120 | 35.9 | 120 | 35.9 | 120 |
| n (Patient) | 50 | 92 | 50 | 92 | 48 | 94 |
| UO only | | | | | | |
| Median | 0.142 | 0.866 | 0.399 | 0.555 | 0.446 | 0.330 |
| Average | 7.83 | 10.1 | 8.92 | 8.96 | 9.71 | 8.45 |
| Stdev | 20.4 | 21.3 | 21.6 | 20.1 | 22.3 | 19.5 |
| p (t-test) | | 0.54 | | 0.99 | | 0.74 |
| Min | 0.000212 | 0.000286 | 0.000212 | 0.000212 | 0.000212 | 0.000212 |
| Max | 110 | 120 | 110 | 120 | 110 | 120 |
| n (Patient) | 62 | 57 | 54 | 65 | 50 | 70 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.74 | 0.74 | 0.59 | 0.70 | 0.74 | 0.54 | 0.70 | 0.73 | 0.52 |
| SE | 0.042 | 0.041 | 0.052 | 0.046 | 0.041 | 0.053 | 0.047 | 0.042 | 0.054 |

TABLE 10.4-continued

Comparison of marker levels and the area under the ROC curve
(AUC) in urine samples for the "recovered" and "non-recovered" cohorts where recovery
starts at 72 hours after sample collection and renal status is assessed by serum creatinine
(sCr) only, urine output (UO) only, or serum creatinine or urine output RIFLE criteria.

| | | | | | | | | | |
|---|---|---|---|---|---|---|---|---|---|
| p Value | 9.4E−9 | 1.1E−8 | 0.071 | 9.8E−6 | 1.1E−8 | 0.40 | 1.6E−5 | 2.3E−8 | 0.73 |
| nCohort Recovered | 43 | 50 | 62 | 38 | 50 | 54 | 36 | 48 | 50 |
| nCohort Non-recovered | 99 | 92 | 57 | 104 | 92 | 65 | 106 | 94 | 70 |
| Cutoff Quartile 2 | 0.000365 | 0.000365 | 0.000471 | 0.000365 | 0.000365 | 0.000471 | 0.000365 | 0.000365 | 0.000471 |
| Sensitivity | 83% | 83% | 82% | 81% | 83% | 80% | 80% | 82% | 79% |
| Specificity | 44% | 40% | 29% | 42% | 40% | 28% | 42% | 40% | 26% |
| Cutoff Quartile 3 | 0.205 | 0.205 | 0.404 | 0.205 | 0.205 | 0.404 | 0.205 | 0.205 | 0.424 |
| Sensitivity | 61% | 63% | 54% | 58% | 63% | 51% | 58% | 63% | 49% |
| Specificity | 74% | 74% | 53% | 71% | 74% | 50% | 72% | 75% | 48% |
| Cutoff Quartile 4 | 3.58 | 3.58 | 4.63 | 3.58 | 3.58 | 4.63 | 3.58 | 3.58 | 4.89 |
| Sensitivity | 34% | 36% | 32% | 33% | 36% | 28% | 32% | 35% | 26% |
| Specificity | 95% | 94% | 81% | 95% | 94% | 78% | 94% | 94% | 76% |
| OR Quartile 2 | 3.82 | 3.17 | 1.92 | 3.05 | 3.17 | 1.54 | 2.89 | 2.97 | 1.29 |
| p Value | 9.8E−4 | 0.0038 | 0.14 | 0.0067 | 0.0038 | 0.32 | 0.011 | 0.0064 | 0.56 |
| Lower limit of 95% CI | 1.72 | 1.45 | 0.801 | 1.36 | 1.45 | 0.657 | 1.28 | 1.36 | 0.550 |
| Upper limit of 95% CI | 8.47 | 6.92 | 4.62 | 6.85 | 6.92 | 3.60 | 6.54 | 6.48 | 3.02 |
| OR Quartile 3 | 4.48 | 4.86 | 1.36 | 3.35 | 4.86 | 1.03 | 3.52 | 5.06 | 0.872 |
| p Value | 2.2E−4 | 4.7E−5 | 0.41 | 0.0031 | 4.7E−5 | 0.93 | 0.0028 | 4.2E−5 | 0.71 |
| Lower limit of 95% CI | 2.02 | 2.27 | 0.659 | 1.50 | 2.27 | 0.501 | 1.54 | 2.33 | 0.422 |
| Upper limit of 95% CI | 9.91 | 10.4 | 2.79 | 7.46 | 10.4 | 2.12 | 8.04 | 11.0 | 1.80 |
| OR Quartile 4 | 10.7 | 8.76 | 1.92 | 8.74 | 8.76 | 1.34 | 8.03 | 8.11 | 1.10 |
| p Value | 0.0017 | 6.2E−4 | 0.13 | 0.0041 | 6.2E−4 | 0.49 | 0.0059 | 9.6E−4 | 0.83 |
| Lower limit of 95% CI | 2.44 | 2.53 | 0.829 | 1.99 | 2.53 | 0.578 | 1.82 | 2.34 | 0.472 |
| Upper limit of 95% CI | 47.0 | 30.4 | 4.46 | 38.5 | 30.4 | 3.11 | 35.4 | 28.1 | 2.54 |

TABLE 10.5

Comparison of marker levels and the area under the ROC curve
(AUC) in urine samples for the "recovered" and "non-recovered" cohorts where recovery
starts within 7 days after sample collection and renal status is assessed by serum
creatinine (sCr) only, urine output (UO) only, or serum creatinine or urine output RIFLE
criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 0.0328 | 0.872 | 0.0328 | 0.869 | 0.0328 | 0.869 |
| Average | 6.80 | 8.72 | 6.88 | 8.59 | 6.88 | 8.59 |
| Stdev | 21.2 | 15.5 | 21.3 | 15.4 | 21.3 | 15.4 |
| p (t-test) | | 0.54 | | 0.59 | | 0.59 |
| Min | 0.000212 | 0.000212 | 0.000212 | 0.000212 | 0.000212 | 0.000212 |
| Max | 120 | 59.1 | 120 | 59.1 | 120 | 59.1 |
| n (Patient) | 86 | 63 | 85 | 64 | 85 | 64 |
| sCr only | | | | | | |
| Median | 0.000473 | 1.17 | 0.000473 | 1.13 | 0.000473 | 1.13 |
| Average | 2.89 | 11.9 | 2.97 | 11.6 | 2.97 | 11.6 |
| Stdev | 13.8 | 21.9 | 13.9 | 21.7 | 13.9 | 21.7 |
| p (t-test) | | 0.0033 | | 0.0051 | | 0.0051 |
| Min | 0.000212 | 0.000212 | 0.000212 | 0.000212 | 0.000212 | 0.000212 |
| Max | 110 | 120 | 110 | 120 | 110 | 120 |
| n (Patient) | 71 | 78 | 69 | 80 | 69 | 80 |
| UO only | | | | | | |
| Median | 0.0873 | 0.899 | 0.104 | 0.869 | 0.0873 | 0.869 |
| Average | 7.22 | 8.48 | 7.38 | 8.17 | 7.44 | 8.04 |
| Stdev | 20.9 | 14.9 | 21.1 | 14.7 | 21.4 | 14.4 |
| p (t-test) | | 0.70 | | 0.81 | | 0.85 |
| Min | 0.000212 | 0.000212 | 0.000212 | 0.000212 | 0.000212 | 0.000212 |
| Max | 120 | 50.9 | 120 | 50.9 | 120 | 50.9 |
| n (Patient) | 96 | 52 | 94 | 54 | 92 | 56 |

TABLE 10.5-continued

Comparison of marker levels and the area under the ROC curve (AUC) in urine samples for the "recovered" and "non-recovered" cohorts where recovery starts within 7 days after sample collection and renal status is assessed by serum creatinine (sCr) only, urine output (UO) only, or serum creatinine or urine output RIFLE criteria.

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.66 | 0.73 | 0.60 | 0.66 | 0.72 | 0.59 | 0.66 | 0.72 | 0.60 |
| SE | 0.046 | 0.041 | 0.050 | 0.046 | 0.041 | 0.049 | 0.046 | 0.041 | 0.049 |
| p Value | 4.0E-4 | 1.6E-8 | 0.040 | 6.0E-4 | 9.2E-8 | 0.069 | 6.0E-4 | 9.2E-8 | 0.046 |
| nCohort Recovered | 86 | 71 | 96 | 85 | 69 | 94 | 85 | 69 | 92 |
| nCohort Non-recovered | 63 | 78 | 52 | 64 | 80 | 54 | 64 | 80 | 56 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 89% | 87% | 85% | 89% | 88% | 85% | 89% | 88% | 86% |
| Specificity | 24% | 25% | 20% | 25% | 26% | 20% | 25% | 26% | 21% |
| Cutoff Quartile 3 | 0.170 | 0.170 | 0.205 | 0.170 | 0.170 | 0.205 | 0.170 | 0.170 | 0.205 |
| Sensitivity | 65% | 67% | 58% | 64% | 65% | 56% | 64% | 65% | 55% |
| Specificity | 60% | 68% | 54% | 60% | 67% | 53% | 60% | 67% | 53% |
| Cutoff Quartile 4 | 2.99 | 2.99 | 3.01 | 2.99 | 2.99 | 3.01 | 2.99 | 2.99 | 3.01 |
| Sensitivity | 33% | 40% | 35% | 33% | 39% | 33% | 33% | 39% | 34% |
| Specificity | 80% | 90% | 80% | 80% | 90% | 80% | 80% | 90% | 80% |
| OR Quartile 2 | 2.58 | 2.31 | 1.36 | 2.67 | 2.47 | 1.46 | 2.67 | 2.47 | 1.56 |
| p Value | 0.045 | 0.054 | 0.51 | 0.038 | 0.038 | 0.41 | 0.038 | 0.038 | 0.33 |
| Lower limit of 95% CI | 1.02 | 0.985 | 0.549 | 1.06 | 1.05 | 0.590 | 1.06 | 1.05 | 0.633 |
| Upper limit of 95% CI | 6.53 | 5.42 | 3.36 | 6.75 | 5.80 | 3.60 | 6.75 | 5.80 | 3.85 |
| OR Quartile 3 | 2.85 | 4.17 | 1.61 | 2.67 | 3.71 | 1.42 | 2.67 | 3.71 | 1.41 |
| p Value | 0.0023 | 4.3E-5 | 0.17 | 0.0040 | 1.5E-4 | 0.31 | 0.0040 | 1.5E-4 | 0.31 |
| Lower limit of 95% CI | 1.45 | 2.10 | 0.816 | 1.37 | 1.88 | 0.725 | 1.37 | 1.88 | 0.725 |
| Upper limit of 95% CI | 5.60 | 8.28 | 3.18 | 5.23 | 7.33 | 2.78 | 5.23 | 7.33 | 2.75 |
| OR Quartile 4 | 2.03 | 6.03 | 2.15 | 1.95 | 5.60 | 1.97 | 1.95 | 5.60 | 2.11 |
| p Value | 0.063 | 9.5E-5 | 0.049 | 0.078 | 1.8E-4 | 0.078 | 0.078 | 1.8E-4 | 0.053 |
| Lower limit of 95% CI | 0.963 | 2.45 | 1.00 | 0.928 | 2.27 | 0.925 | 0.928 | 2.27 | 0.991 |
| Upper limit of 95% CI | 4.28 | 14.9 | 4.59 | 4.11 | 13.8 | 4.21 | 4.11 | 13.8 | 4.50 |

Example 11. Use of Insulin-Like Growth Factor-Binding Protein 4 for Evaluating Renal Status in Patients Admitted to the ICU: Recovery to RIFLE 0 and R from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 4 is measured in the enrollment samples by standard immunoassay methods using commercially available assay reagents.

Kidney status is assessed by RIFLE criteria based on serum creatinine, urine output, or both serum creatinine and urine output during a period starting at 12, 24, 48, or 72 hours after sample collection or at any time within 7 days after sample collection. Two cohorts are defined to represent a "recovered" and a "non-recovered" population. "Recovered" indicates those patients whose maximum RIFLE stage during a period of 24, 48 or 72 hours is non-injury (RIFLE 0) or risk of injury (R). "Non-recovered" indicates those patients whose maximum RIFLE stage during a period of 24, 48 or 72 hours is injury (I) or failure (F). If a patient dies or is placed on renal replacement therapy (RRT) at any time from sample collection to 12, 24, 48, or 72 hours after sample collection or at any time within 7 days after sample collection, the patient is considered "non-recovered".

The ability to distinguish the "recovered" and "non-recovered" cohorts is determined using receiver operating characteristic (ROC) analysis.

TABLE 11.1

Comparison of marker levels and the area under the ROC curve (AUC) in urine samples for the "recovered" and "non-recovered" cohorts where recovery starts at 12 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 0.000471 | 0.685 | 0.000471 | 0.646 | 0.000471 | 0.633 |
| Average | 3.59 | 8.94 | 3.78 | 8.79 | 3.89 | 8.71 |

TABLE 11.1-continued

Comparison of marker levels and the area under the ROC curve (AUC) in urine samples for the "recovered" and "non-recovered" cohorts where recovery starts at 12 hours after sample collection and renal status is assessed by serum creatinine (sCr) only, urine output (UO) only, or serum creatinine or urine output RIFLE criteria.

| | | | | | | |
|---|---|---|---|---|---|---|
| Stdev | 18.1 | 19.1 | 18.6 | 19.0 | 18.9 | 18.9 |
| p (t-test) | | 0.14 | | 0.17 | | 0.19 |
| Min | 0.000212 | 0.000212 | 0.000212 | 0.000212 | 0.000212 | 0.000212 |
| Max | 110 | 120 | 110 | 120 | 110 | 120 |
| n (Patient) | 37 | 112 | 35 | 114 | 34 | 115 |
| sCr only | | | | | | |
| Median | 0.000471 | 0.866 | 0.000471 | 0.866 | 0.000472 | 0.866 |
| Average | 3.00 | 9.87 | 3.00 | 9.87 | 3.07 | 9.78 |
| Stdev | 15.8 | 20.0 | 15.8 | 20.0 | 16.0 | 19.9 |
| p (t-test) | | 0.037 | | 0.037 | | 0.043 |
| Min | 0.000212 | 0.000212 | 0.000212 | 0.000212 | 0.000212 | 0.000212 |
| Max | 110 | 120 | 110 | 120 | 110 | 120 |
| n (Patient) | 49 | 100 | 49 | 100 | 48 | 101 |
| UO only | | | | | | |
| Median | 0.122 | 0.679 | 0.122 | 0.594 | 0.118 | 0.633 |
| Average | 7.32 | 8.27 | 7.73 | 7.57 | 6.55 | 9.17 |
| Stdev | 20.8 | 15.4 | 21.5 | 14.8 | 18.0 | 20.3 |
| p (t-test) | | 0.77 | | 0.96 | | 0.41 |
| Min | 0.000212 | 0.000212 | 0.000212 | 0.000212 | 0.000212 | 0.000212 |
| Max | 120 | 59.1 | 120 | 59.1 | 110 | 120 |
| n (Patient) | 94 | 54 | 88 | 60 | 85 | 63 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.73 | 0.57 | 0.71 | 0.73 | 0.57 | 0.69 | 0.72 | 0.58 |
| SE | 0.046 | 0.041 | 0.049 | 0.046 | 0.041 | 0.048 | 0.047 | 0.042 | 0.048 |
| p Value | 7.5E−6 | 3.3E−8 | 0.15 | 8.6E−6 | 3.3E−8 | 0.15 | 4.5E−5 | 2.4E−7 | 0.087 |
| nCohort Recovered | 37 | 49 | 94 | 35 | 49 | 88 | 34 | 48 | 85 |
| nCohort Non-recovered | 112 | 100 | 54 | 114 | 100 | 60 | 115 | 101 | 63 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 85% | 87% | 83% | 85% | 87% | 85% | 84% | 86% | 86% |
| Specificity | 30% | 31% | 19% | 31% | 31% | 20% | 29% | 29% | 21% |
| Cutoff Quartile 3 | 0.170 | 0.170 | 0.205 | 0.170 | 0.170 | 0.205 | 0.170 | 0.170 | 0.205 |
| Sensitivity | 57% | 61% | 56% | 57% | 61% | 55% | 57% | 60% | 56% |
| Specificity | 70% | 71% | 53% | 71% | 71% | 53% | 71% | 71% | 54% |
| Cutoff Quartile 4 | 2.99 | 2.99 | 3.01 | 2.99 | 2.99 | 3.01 | 2.99 | 2.99 | 3.01 |
| Sensitivity | 32% | 35% | 33% | 32% | 35% | 32% | 31% | 35% | 33% |
| Specificity | 95% | 94% | 80% | 94% | 94% | 80% | 94% | 94% | 81% |
| OR Quartile 2 | 2.36 | 2.95 | 1.18 | 2.62 | 2.95 | 1.46 | 2.25 | 2.56 | 1.61 |
| p Value | 0.054 | 0.012 | 0.71 | 0.032 | 0.012 | 0.40 | 0.076 | 0.028 | 0.29 |
| Lower limit of 95% CI | 0.987 | 1.27 | 0.491 | 1.08 | 1.27 | 0.606 | 0.919 | 1.10 | 0.671 |
| Upper limit of 95% CI | 5.66 | 6.85 | 2.86 | 6.31 | 6.85 | 3.51 | 5.48 | 5.93 | 3.87 |
| OR Quartile 3 | 3.15 | 3.91 | 1.42 | 3.32 | 3.91 | 1.40 | 3.12 | 3.70 | 1.47 |
| p Value | 0.0048 | 3.0E−4 | 0.31 | 0.0042 | 3.0E−4 | 0.32 | 0.0068 | 5.2E−4 | 0.25 |
| Lower limit of 95% CI | 1.42 | 1.87 | 0.725 | 1.46 | 1.87 | 0.725 | 1.37 | 1.77 | 0.766 |
| Upper limit of 95% CI | 7.00 | 8.18 | 2.78 | 7.54 | 8.18 | 2.71 | 7.12 | 7.76 | 2.84 |
| OR Quartile 4 | 8.29 | 8.26 | 1.97 | 7.62 | 8.26 | 1.80 | 7.29 | 7.95 | 2.16 |
| p Value | 0.0051 | 8.3E−4 | 0.078 | 0.0072 | 8.3E−4 | 0.12 | 0.0086 | 0.0010 | 0.046 |
| Lower limit of 95% CI | 1.89 | 2.39 | 0.925 | 1.73 | 2.39 | 0.850 | 1.66 | 2.31 | 1.01 |
| Upper limit of 95% CI | 36.4 | 28.5 | 4.21 | 33.5 | 28.5 | 3.82 | 32.1 | 27.4 | 4.59 |

TABLE 11.2

Comparison of marker levels and the area under the ROC curve (AUC) in urine samples for the "recovered" and "non-recovered" cohorts where recovery starts at 24 hours after sample collection and renal status is assessed by serum creatinine (sCr) only, urine output (UO) only, or serum creatinine or urine output RIFLE criteria.

|  | Recovery Period Duration (hr) | | | | | |
|---|---|---|---|---|---|---|
|  | 24 | | 48 | | 72 | |
|  | Recovered Cohort | Non-recovered Cohort | Recovered Cohort | Non-recovered Cohort | Recovered Cohort | Non-recovered Cohort |
| sCr or UO | | | | | | |
| Median | 0.000473 | 0.866 | 0.000473 | 0.862 | 0.000473 | 0.862 |
| Average | 2.71 | 10.2 | 2.81 | 9.97 | 2.81 | 9.97 |
| Stdev | 15.4 | 20.1 | 15.8 | 20.0 | 15.8 | 20.0 |
| p (t-test) |  | 0.022 |  | 0.030 |  | 0.030 |
| Min | 0.000212 | 0.000212 | 0.000212 | 0.000212 | 0.000212 | 0.000212 |
| Max | 110 | 120 | 110 | 120 | 110 | 120 |
| n (Patient) | 51 | 98 | 49 | 100 | 49 | 100 |
| sCr only | | | | | | |
| Median | 0.000473 | 0.927 | 0.000473 | 0.899 | 0.000473 | 0.899 |
| Average | 2.66 | 10.8 | 2.71 | 10.7 | 2.71 | 10.7 |
| Stdev | 14.8 | 20.7 | 14.9 | 20.6 | 14.9 | 20.6 |
| p (t-test) |  | 0.011 |  | 0.013 |  | 0.013 |
| Min | 0.000212 | 0.000212 | 0.000212 | 0.000212 | 0.000212 | 0.000212 |
| Max | 110 | 120 | 110 | 120 | 110 | 120 |
| n (Patient) | 56 | 91 | 55 | 92 | 55 | 92 |
| UO only | | | | | | |
| Median | 0.122 | 0.869 | 0.118 | 0.866 | 0.118 | 0.866 |
| Average | 7.03 | 8.82 | 6.02 | 10.3 | 6.02 | 10.3 |
| Stdev | 20.7 | 15.9 | 17.4 | 21.5 | 17.4 | 21.5 |
| p (t-test) |  | 0.59 |  | 0.19 |  | 0.19 |
| Min | 0.000212 | 0.000212 | 0.000212 | 0.000212 | 0.000212 | 0.000212 |
| Max | 120 | 59.1 | 110 | 120 | 110 | 120 |
| n (Patient) | 94 | 50 | 89 | 55 | 89 | 55 |

|  | Recovery Period Duration (hr) | | | | | | | | |
|---|---|---|---|---|---|---|---|---|---|
|  | 24 | | | 48 | | | 72 | | |
|  | sCr or UO | sCr only | UO only | sCr or UO | sCr only | UO only | sCr or UO | sCr only | UO only |
| AUC | 0.71 | 0.74 | 0.59 | 0.70 | 0.73 | 0.60 | 0.70 | 0.73 | 0.60 |
| SE | 0.042 | 0.040 | 0.051 | 0.043 | 0.041 | 0.049 | 0.043 | 0.041 | 0.049 |
| p Value | 9.2E−7 | 3.9E−9 | 0.082 | 3.1E−6 | 3.3E−8 | 0.045 | 3.1E−6 | 3.3E−8 | 0.045 |
| nCohort Recovered | 51 | 56 | 94 | 49 | 55 | 89 | 49 | 55 | 89 |
| nCohort Non-recovered | 98 | 91 | 50 | 100 | 92 | 55 | 100 | 92 | 55 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 85% | 87% | 84% | 84% | 86% | 85% | 84% | 86% | 85% |
| Specificity | 25% | 27% | 20% | 24% | 25% | 21% | 24% | 25% | 21% |
| Cutoff Quartile 3 | 0.170 | 0.170 | 0.218 | 0.170 | 0.170 | 0.218 | 0.170 | 0.170 | 0.218 |
| Sensitivity | 60% | 64% | 56% | 60% | 63% | 56% | 60% | 63% | 56% |
| Specificity | 69% | 71% | 53% | 69% | 71% | 54% | 69% | 71% | 54% |
| Cutoff Quartile 4 | 2.99 | 3.02 | 3.01 | 2.99 | 3.02 | 3.01 | 2.99 | 3.02 | 3.01 |
| Sensitivity | 37% | 37% | 36% | 36% | 37% | 36% | 36% | 37% | 36% |
| Specificity | 96% | 95% | 81% | 96% | 95% | 82% | 96% | 95% | 82% |
| OR Quartile 2 | 1.89 | 2.41 | 1.33 | 1.70 | 2.08 | 1.59 | 1.70 | 2.08 | 1.59 |
| p Value | 0.13 | 0.042 | 0.54 | 0.22 | 0.090 | 0.31 | 0.22 | 0.090 | 0.31 |
| Lower limit of 95% CI | 0.820 | 1.03 | 0.536 | 0.733 | 0.892 | 0.645 | 0.733 | 0.892 | 0.645 |
| Upper limit of 95% CI | 4.37 | 5.62 | 3.30 | 3.95 | 4.83 | 3.94 | 3.95 | 4.83 | 3.94 |
| OR Quartile 3 | 3.31 | 4.39 | 1.45 | 3.40 | 4.16 | 1.51 | 3.40 | 4.16 | 1.51 |
| p Value | 0.0011 | 5.6E−5 | 0.29 | 9.8E−4 | 1.0E−4 | 0.23 | 9.8E−4 | 1.0E−4 | 0.23 |
| Lower limit of 95% CI | 1.62 | 2.14 | 0.725 | 1.64 | 2.02 | 0.769 | 1.64 | 2.02 | 0.769 |
| Upper limit of 95% CI | 6.78 | 9.03 | 2.88 | 7.04 | 8.54 | 2.97 | 7.04 | 8.54 | 2.97 |
| OR Quartile 4 | 14.2 | 10.5 | 2.38 | 13.2 | 10.2 | 2.61 | 13.2 | 10.2 | 2.61 |
| p Value | 4.1E−4 | 1.9E−4 | 0.028 | 5.9E−4 | 2.4E−4 | 0.015 | 5.9E−4 | 2.4E−4 | 0.015 |
| Lower limit of 95% CI | 3.26 | 3.05 | 1.10 | 3.03 | 2.95 | 1.21 | 3.03 | 2.95 | 1.21 |
| Upper limit of 95% CI | 62.0 | 36.4 | 5.14 | 57.7 | 35.1 | 5.64 | 57.7 | 35.1 | 5.64 |

TABLE 11.3

Comparison of marker levels and the area under the ROC curve (AUC) in urine samples for the "recovered" and "non-recovered" cohorts where recovery starts at 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 0.0328 | 0.866 | 0.0328 | 0.866 | 0.0328 | 0.866 |
| Average | 3.63 | 10.9 | 3.63 | 10.9 | 3.52 | 10.8 |
| Stdev | 14.7 | 21.4 | 14.7 | 21.4 | 14.9 | 21.2 |
| p (t-test) | | 0.023 | | 0.023 | | 0.023 |
| Min | 0.000212 | 0.000212 | 0.000212 | 0.000212 | 0.000212 | 0.000212 |
| Max | 110 | 120 | 110 | 120 | 110 | 120 |
| n (Patient) | 63 | 83 | 63 | 83 | 61 | 85 |
| sCr only | | | | | | |
| Median | 0.0328 | 0.899 | 0.0328 | 0.899 | 0.0169 | 0.927 |
| Average | 3.61 | 11.4 | 3.61 | 11.4 | 3.46 | 11.4 |
| Stdev | 14.3 | 21.9 | 14.3 | 21.9 | 14.4 | 21.8 |
| p (t-test) | | 0.014 | | 0.014 | | 0.012 |
| Min | 0.000212 | 0.000212 | 0.000212 | 0.000212 | 0.000212 | 0.000212 |
| Max | 110 | 120 | 110 | 120 | 110 | 120 |
| n (Patient) | 67 | 78 | 67 | 78 | 66 | 79 |
| UO only | | | | | | |
| Median | 0.146 | 0.899 | 0.146 | 0.899 | 0.165 | 0.866 |
| Average | 7.31 | 10.6 | 7.31 | 10.6 | 7.58 | 10.0 |
| Stdev | 19.2 | 21.6 | 19.2 | 21.6 | 19.5 | 21.1 |
| p (t-test) | | 0.37 | | 0.37 | | 0.51 |
| Min | 0.000212 | 0.000212 | 0.000212 | 0.000212 | 0.000212 | 0.000212 |
| Max | 110 | 120 | 110 | 120 | 110 | 120 |
| n (Patient) | 80 | 48 | 80 | 48 | 77 | 51 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.67 | 0.60 | 0.65 | 0.67 | 0.60 | 0.67 | 0.68 | 0.59 |
| SE | 0.045 | 0.044 | 0.052 | 0.045 | 0.044 | 0.052 | 0.044 | 0.044 | 0.052 |
| p Value | 5.9E-4 | 1.4E-4 | 0.051 | 5.9E-4 | 1.4E-4 | 0.051 | 1.6E-4 | 4.3E-5 | 0.078 |
| nCohort Recovered | 63 | 67 | 80 | 63 | 67 | 80 | 61 | 66 | 77 |
| nCohort Non-recovered | 83 | 78 | 48 | 83 | 78 | 48 | 85 | 79 | 51 |
| Cutoff Quartile 2 | 0.000339 | 0.000339 | 0.000471 | 0.000339 | 0.000339 | 0.000471 | 0.000339 | 0.000339 | 0.000471 |
| Sensitivity | 83% | 85% | 81% | 83% | 85% | 81% | 84% | 85% | 82% |
| Specificity | 21% | 22% | 28% | 21% | 22% | 28% | 21% | 23% | 29% |
| Cutoff Quartile 3 | 0.168 | 0.165 | 0.399 | 0.168 | 0.165 | 0.399 | 0.168 | 0.165 | 0.399 |
| Sensitivity | 59% | 62% | 58% | 59% | 62% | 58% | 60% | 62% | 57% |
| Specificity | 62% | 61% | 55% | 62% | 61% | 55% | 64% | 62% | 55% |
| Cutoff Quartile 4 | 3.04 | 3.05 | 4.89 | 3.04 | 3.05 | 4.89 | 3.04 | 3.05 | 4.89 |
| Sensitivity | 35% | 36% | 33% | 35% | 36% | 33% | 35% | 37% | 31% |
| Specificity | 87% | 87% | 80% | 87% | 87% | 80% | 89% | 88% | 79% |
| OR Quartile 2 | 1.28 | 1.59 | 1.64 | 1.28 | 1.59 | 1.64 | 1.37 | 1.64 | 1.87 |
| p Value | 0.56 | 0.28 | 0.27 | 0.56 | 0.28 | 0.27 | 0.46 | 0.25 | 0.16 |
| Lower limit of 95% CI | 0.554 | 0.684 | 0.685 | 0.554 | 0.684 | 0.685 | 0.594 | 0.708 | 0.779 |
| Upper limit of 95% CI | 2.96 | 3.68 | 3.94 | 2.96 | 3.68 | 3.94 | 3.18 | 3.81 | 4.47 |
| OR Quartile 3 | 2.34 | 2.52 | 1.71 | 2.34 | 2.52 | 1.71 | 2.66 | 2.68 | 1.58 |
| p Value | 0.013 | 0.0068 | 0.15 | 0.013 | 0.0068 | 0.15 | 0.0048 | 0.0041 | 0.21 |
| Lower limit of 95% CI | 1.20 | 1.29 | 0.830 | 1.20 | 1.29 | 0.830 | 1.35 | 1.37 | 0.775 |
| Upper limit of 95% CI | 4.58 | 4.93 | 3.53 | 4.58 | 4.93 | 3.53 | 5.24 | 5.25 | 3.23 |
| OR Quartile 4 | 3.69 | 3.61 | 2.00 | 3.69 | 3.61 | 2.00 | 4.21 | 4.20 | 1.74 |
| p Value | 0.0032 | 0.0028 | 0.095 | 0.0032 | 0.0028 | 0.095 | 0.0018 | 0.0012 | 0.18 |
| Lower limit of 95% CI | 1.55 | 1.56 | 0.887 | 1.55 | 1.56 | 0.887 | 1.70 | 1.76 | 0.777 |
| Upper limit of 95% CI | 8.80 | 8.37 | 4.51 | 8.80 | 8.37 | 4.51 | 10.4 | 10.0 | 3.91 |

TABLE 11.4

Comparison of marker levels and the area under the ROC curve (AUC) in urine samples for the "recovered" and "non-recovered" cohorts where recovery starts at 72 hours after sample collection and renal status is assessed by serum creatinine (sCr) only, urine output (UO) only, or serum creatinine or urine output RIFLE criteria.

| Cohort | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 0.000473 | 1.21 | 0.000473 | 1.14 | 0.000473 | 1.13 |
| Average | 3.27 | 12.6 | 3.26 | 12.2 | 3.21 | 11.9 |
| Stdev | 13.9 | 22.7 | 14.3 | 22.2 | 14.5 | 21.8 |
| p (t-test) | | 0.0035 | | 0.0057 | | 0.0075 |
| Min | 0.000212 | 0.000212 | 0.000212 | 0.000212 | 0.000212 | 0.000212 |
| Max | 110 | 120 | 110 | 120 | 110 | 120 |
| n (Patient) | 71 | 71 | 67 | 75 | 64 | 78 |
| sCr only | | | | | | |
| Median | 0.00102 | 1.21 | 0.000747 | 1.28 | 0.000473 | 1.35 |
| Average | 3.36 | 12.8 | 3.22 | 12.8 | 3.09 | 12.8 |
| Stdev | 13.8 | 23.0 | 13.8 | 22.8 | 13.9 | 22.6 |
| p (t-test) | | 0.0032 | | 0.0028 | | 0.0024 |
| Min | 0.000212 | 0.000212 | 0.000212 | 0.000212 | 0.000212 | 0.000212 |
| Max | 110 | 120 | 110 | 120 | 110 | 120 |
| n (Patient) | 73 | 69 | 72 | 70 | 71 | 71 |
| UO only | | | | | | |
| Median | 0.0873 | 1.13 | 0.0873 | 0.872 | 0.118 | 0.866 |
| Average | 9.20 | 8.52 | 8.23 | 9.89 | 8.55 | 9.52 |
| Stdev | 23.8 | 14.7 | 20.6 | 21.1 | 20.7 | 20.8 |
| p (t-test) | | 0.86 | | 0.67 | | 0.80 |
| Min | 0.000212 | 0.000286 | 0.000212 | 0.000286 | 0.000212 | 0.000286 |
| Max | 120 | 50.9 | 110 | 120 | 110 | 120 |
| n (Patient) | 74 | 45 | 68 | 51 | 67 | 53 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.70 | 0.63 | 0.72 | 0.71 | 0.61 | 0.72 | 0.72 | 0.59 |
| SE | 0.043 | 0.044 | 0.054 | 0.043 | 0.043 | 0.053 | 0.042 | 0.043 | 0.053 |
| p Value | 6.7E−7 | 3.5E−6 | 0.019 | 4.2E−7 | 8.0E−7 | 0.038 | 3.6E−7 | 1.6E−7 | 0.097 |
| nCohort Recovered | 71 | 73 | 74 | 67 | 72 | 68 | 64 | 71 | 67 |
| nCohort Non-recovered | 71 | 69 | 45 | 75 | 70 | 51 | 78 | 71 | 53 |
| Cutoff Quartile 2 | 0.000365 | 0.000365 | 0.000471 | 0.000365 | 0.000365 | 0.000471 | 0.000365 | 0.000365 | 0.000471 |
| Sensitivity | 82% | 81% | 84% | 83% | 81% | 84% | 82% | 82% | 83% |
| Specificity | 32% | 32% | 28% | 34% | 32% | 29% | 34% | 32% | 28% |
| Cutoff Quartile 3 | 0.205 | 0.205 | 0.404 | 0.205 | 0.205 | 0.404 | 0.205 | 0.205 | 0.424 |
| Sensitivity | 66% | 65% | 62% | 65% | 66% | 59% | 64% | 66% | 57% |
| Specificity | 66% | 64% | 57% | 67% | 65% | 56% | 67% | 66% | 55% |
| Cutoff Quartile 4 | 3.58 | 3.58 | 4.63 | 3.58 | 3.58 | 4.63 | 3.58 | 3.58 | 4.89 |
| Sensitivity | 39% | 39% | 33% | 39% | 40% | 31% | 38% | 41% | 28% |
| Specificity | 89% | 88% | 80% | 90% | 89% | 79% | 91% | 90% | 78% |
| OR Quartile 2 | 2.14 | 1.98 | 2.15 | 2.49 | 2.06 | 2.24 | 2.39 | 2.14 | 1.94 |
| p Value | 0.056 | 0.086 | 0.11 | 0.022 | 0.070 | 0.085 | 0.027 | 0.056 | 0.15 |
| Lower limit of 95% CI | 0.980 | 0.909 | 0.831 | 1.14 | 0.943 | 0.895 | 1.10 | 0.980 | 0.793 |
| Upper limit of 95% CI | 4.66 | 4.32 | 5.57 | 5.45 | 4.49 | 5.61 | 5.20 | 4.66 | 4.72 |
| OR Quartile 3 | 3.84 | 3.39 | 2.16 | 3.85 | 3.60 | 1.81 | 3.66 | 3.84 | 1.61 |
| p Value | 1.5E−4 | 5.2E−4 | 0.046 | 1.5E−4 | 2.8E−4 | 0.11 | 2.7E−4 | 1.5E−4 | 0.20 |
| Lower limit of 95% CI | 1.91 | 1.70 | 1.01 | 1.92 | 1.80 | 0.868 | 1.82 | 1.91 | 0.778 |
| Upper limit of 95% CI | 7.69 | 6.75 | 4.61 | 7.74 | 7.20 | 3.77 | 7.34 | 7.69 | 3.32 |
| OR Quartile 4 | 5.13 | 4.57 | 1.97 | 5.40 | 5.33 | 1.76 | 6.04 | 6.31 | 1.37 |
| p Value | 2.6E−4 | 4.5E−4 | 0.11 | 2.8E−4 | 1.8E−4 | 0.18 | 2.3E−4 | 7.6E−5 | 0.46 |
| Lower limit of 95% CI | 2.14 | 1.96 | 0.849 | 2.17 | 2.22 | 0.766 | 2.32 | 2.53 | 0.597 |
| Upper limit of 95% CI | 12.3 | 10.7 | 4.55 | 13.4 | 12.8 | 4.06 | 15.7 | 15.7 | 3.13 |

TABLE 11.5

Comparison of marker levels and the area under the ROC curve (AUC) in urine samples for the "recovered" and "non-recovered" cohorts where recovery starts within 7 days after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 0.0328 | 1.13 | 0.0328 | 1.13 | 0.0328 | 1.03 |
| Average | 6.41 | 9.62 | 6.48 | 9.45 | 6.55 | 9.29 |
| Stdev | 20.4 | 16.2 | 20.5 | 16.1 | 20.6 | 16.0 |
| p (t-test) | | 0.32 | | 0.35 | | 0.39 |
| Min | 0.000212 | 0.000212 | 0.000212 | 0.000212 | 0.000212 | 0.000212 |
| Max | 120 | 59.1 | 120 | 59.1 | 120 | 59.1 |
| n (Patient) | 93 | 56 | 92 | 57 | 91 | 58 |
| sCr only | | | | | | |
| Median | 0.00102 | 1.28 | 0.00102 | 1.28 | 0.00102 | 1.28 |
| Average | 3.04 | 13.4 | 3.04 | 13.4 | 3.04 | 13.4 |
| Stdev | 12.9 | 23.4 | 12.9 | 23.4 | 12.9 | 23.4 |
| p (t-test) | | 8.0E−4 | | 8.0E−4 | | 8.0E−4 |
| Min | 0.000212 | 0.000212 | 0.000212 | 0.000212 | 0.000212 | 0.000212 |
| Max | 110 | 120 | 110 | 120 | 110 | 120 |
| n (Patient) | 83 | 66 | 83 | 66 | 83 | 66 |
| UO only | | | | | | |
| Median | 0.0851 | 1.13 | 0.0851 | 1.13 | 0.0873 | 1.03 |
| Average | 6.94 | 9.19 | 6.94 | 9.19 | 7.08 | 8.82 |
| Stdev | 20.6 | 15.3 | 20.6 | 15.3 | 20.8 | 15.1 |
| p (t-test) | | 0.50 | | 0.50 | | 0.60 |
| Min | 0.000212 | 0.000212 | 0.000212 | 0.000212 | 0.000212 | 0.000212 |
| Max | 120 | 50.9 | 120 | 50.9 | 120 | 50.9 |
| n (Patient) | 100 | 48 | 100 | 48 | 98 | 50 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.72 | 0.64 | 0.67 | 0.72 | 0.64 | 0.66 | 0.72 | 0.63 |
| SE | 0.047 | 0.043 | 0.050 | 0.047 | 0.043 | 0.050 | 0.047 | 0.043 | 0.050 |
| p Value | 2.2E−4 | 4.0E−7 | 0.0051 | 3.9E−4 | 4.0E−7 | 0.0051 | 5.9E−4 | 4.0E−7 | 0.011 |
| nCohort Recovered | 93 | 83 | 100 | 92 | 83 | 100 | 91 | 83 | 98 |
| nCohort Non-recovered | 56 | 66 | 48 | 57 | 66 | 48 | 58 | 66 | 50 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 89% | 88% | 88% | 89% | 88% | 88% | 90% | 88% | 88% |
| Specificity | 24% | 24% | 21% | 24% | 24% | 21% | 24% | 24% | 21% |
| Cutoff Quartile 3 | 0.170 | 0.170 | 0.205 | 0.170 | 0.170 | 0.205 | 0.170 | 0.170 | 0.205 |
| Sensitivity | 64% | 65% | 62% | 63% | 65% | 62% | 62% | 65% | 60% |
| Specificity | 58% | 61% | 56% | 58% | 61% | 56% | 57% | 61% | 55% |
| Cutoff Quartile 4 | 2.99 | 2.99 | 3.01 | 2.99 | 2.99 | 3.01 | 2.99 | 2.99 | 3.01 |
| Sensitivity | 36% | 41% | 38% | 35% | 41% | 38% | 34% | 41% | 36% |
| Specificity | 81% | 87% | 81% | 80% | 87% | 81% | 80% | 87% | 81% |
| OR Quartile 2 | 2.58 | 2.30 | 1.86 | 2.67 | 2.30 | 1.86 | 2.76 | 2.30 | 2.00 |
| p Value | 0.056 | 0.068 | 0.21 | 0.048 | 0.068 | 0.21 | 0.040 | 0.068 | 0.17 |
| Lower limit of 95% CI | 0.976 | 0.941 | 0.697 | 1.01 | 0.941 | 0.697 | 1.05 | 0.941 | 0.751 |
| Upper limit of 95% CI | 6.83 | 5.63 | 4.97 | 7.06 | 5.63 | 4.97 | 7.30 | 5.63 | 5.33 |
| OR Quartile 3 | 2.49 | 2.98 | 2.12 | 2.33 | 2.98 | 2.12 | 2.18 | 2.98 | 1.84 |
| p Value | 0.0089 | 0.0015 | 0.037 | 0.015 | 0.0015 | 0.037 | 0.023 | 0.0015 | 0.084 |
| Lower limit of 95% CI | 1.26 | 1.52 | 1.05 | 1.18 | 1.52 | 1.05 | 1.11 | 1.52 | 0.922 |
| Upper limit of 95% CI | 4.94 | 5.84 | 4.29 | 4.59 | 5.84 | 4.29 | 4.28 | 5.84 | 3.68 |
| OR Quartile 4 | 2.31 | 4.53 | 2.56 | 2.22 | 4.53 | 2.56 | 2.13 | 4.53 | 2.34 |
| p Value | 0.028 | 2.2E−4 | 0.017 | 0.037 | 2.2E−4 | 0.017 | 0.047 | 2.2E−4 | 0.029 |
| Lower limit of 95% CI | 1.09 | 2.03 | 1.19 | 1.05 | 2.03 | 1.19 | 1.01 | 2.03 | 1.09 |
| Upper limit of 95% CI | 4.90 | 10.1 | 5.52 | 4.70 | 10.1 | 5.52 | 4.51 | 10.1 | 5.02 |

Example 12. Use of Insulin-Like Growth Factor-Binding Protein 6 for Evaluating Renal Status in Patients Admitted to the ICU: Recovery to RIFLE 0 from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 6 is measured in the enrollment samples by standard immunoassay methods using commercially available assay reagents.

Kidney status is assessed by RIFLE criteria based on serum creatinine, urine output, or both serum creatinine and urine output during a period starting at 12, 24, 48, or 72 hours after sample collection or at any time within 7 days after sample collection. Two cohorts are defined to represent a "recovered" and a "non-recovered" population. "Recovered" indicates those patients whose maximum RIFLE stage during a period of 24, 48 or 72 hours is non-injury (RIFLE 0). "Non-recovered" indicates those patients whose maximum RIFLE stage during a period of 24, 48 or 72 hours is risk of injury (R), injury (I) or failure (F). If a patient dies or is placed on renal replacement therapy (RRT) at any time from sample collection to 12, 24, 48, or 72 hours after sample collection or at any time within 7 days after sample collection, the patient is considered "non-recovered".

The ability to distinguish the "recovered" and "non-recovered" cohorts is determined using receiver operating characteristic (ROC) analysis.

TABLE 12.1

Comparison of marker levels and the area under the ROC curve (AUC) in urine samples for the "recovered" and "non-recovered" cohorts where recovery starts at 12 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 7.89 | 86.4 | 7.31 | 85.4 | 7.31 | 85.4 |
| Average | 70.0 | 296 | 71.2 | 294 | 71.2 | 294 |
| Stdev | 142 | 551 | 150 | 549 | 150 | 549 |
| p (t-test) | | 0.20 | | 0.23 | | 0.23 |
| Min | 0.352 | 0.259 | 0.352 | 0.259 | 0.352 | 0.259 |
| Max | 460 | 3600 | 460 | 3600 | 460 | 3600 |
| n (Patient) | 10 | 139 | 9 | 140 | 9 | 140 |
| sCr only | | | | | | |
| Median | 8.47 | 93.9 | 8.47 | 93.8 | 8.47 | 93.8 |
| Average | 70.6 | 319 | 72.8 | 317 | 72.8 | 317 |
| Stdev | 141 | 572 | 144 | 570 | 144 | 570 |
| p (t-test) | | 0.041 | | 0.049 | | 0.049 |
| Min | 0.352 | 0.259 | 0.352 | 0.259 | 0.352 | 0.259 |
| Max | 532 | 3600 | 532 | 3600 | 532 | 3600 |
| n (Patient) | 23 | 126 | 22 | 127 | 22 | 127 |
| UO only | | | | | | |
| Median | 63.7 | 98.2 | 63.7 | 93.8 | 61.7 | 94.8 |
| Average | 212 | 354 | 213 | 340 | 181 | 360 |
| Stdev | 381 | 655 | 381 | 635 | 320 | 648 |
| p (t-test) | | 0.11 | | 0.16 | | 0.045 |
| Min | 0.259 | 1.14 | 0.259 | 1.14 | 0.259 | 1.14 |
| Max | 1830 | 3600 | 1830 | 3600 | 1650 | 3600 |
| n (Patient) | 75 | 73 | 67 | 81 | 64 | 84 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.74 | 0.58 | 0.75 | 0.74 | 0.58 | 0.75 | 0.74 | 0.59 |
| SE | 0.069 | 0.049 | 0.047 | 0.069 | 0.050 | 0.047 | 0.069 | 0.050 | 0.047 |
| p Value | 6.7E-4 | 8.4E-7 | 0.073 | 2.7E-4 | 1.6E-6 | 0.081 | 2.7E-4 | 1.6E-6 | 0.042 |
| nCohort Recovered | 10 | 23 | 75 | 9 | 22 | 67 | 9 | 22 | 64 |
| nCohort Non-recovered | 139 | 126 | 73 | 140 | 127 | 81 | 140 | 127 | 84 |
| Cutoff Quartile 2 | 17.2 | 17.2 | 17.6 | 17.2 | 17.2 | 17.6 | 17.2 | 17.2 | 17.6 |
| Sensitivity | 78% | 81% | 79% | 78% | 81% | 81% | 78% | 81% | 81% |
| Specificity | 60% | 57% | 29% | 67% | 59% | 33% | 67% | 59% | 33% |
| Cutoff Quartile 3 | 78.3 | 78.3 | 80.9 | 78.3 | 78.3 | 80.9 | 78.3 | 78.3 | 80.9 |
| Sensitivity | 53% | 56% | 56% | 52% | 55% | 53% | 52% | 55% | 54% |
| Specificity | 80% | 78% | 56% | 78% | 77% | 54% | 78% | 77% | 55% |
| Cutoff Quartile 4 | 331 | 331 | 331 | 331 | 331 | 331 | 331 | 331 | 331 |
| Sensitivity | 27% | 29% | 30% | 26% | 28% | 28% | 26% | 28% | 30% |

TABLE 12.1-continued

Comparison of marker levels and the area under the ROC curve
(AUC) in urine samples for the "recovered" and "non-recovered" cohorts where recovery
starts at 12 hours after sample collection and renal status is assessed by serum creatinine
(sCr) only, urine output (UO) only, or serum creatinine or urine output RIFLE criteria.

| | | | | | | | | | |
|---|---|---|---|---|---|---|---|---|---|
| Specificity | 90% | 91% | 80% | 89% | 91% | 79% | 89% | 91% | 81% |
| OR Quartile 2 | 5.23 | 5.52 | 1.61 | 7.03 | 6.20 | 2.15 | 7.03 | 6.20 | 2.08 |
| p Value | 0.015 | 3.5E−4 | 0.22 | 0.0080 | 1.9E−4 | 0.048 | 0.0080 | 1.9E−4 | 0.058 |
| Lower limit of 95% CI | 1.39 | 2.17 | 0.755 | 1.66 | 2.38 | 1.01 | 1.66 | 2.38 | 0.976 |
| Upper limit of 95% CI | 19.7 | 14.1 | 3.41 | 29.7 | 16.2 | 4.59 | 29.7 | 16.2 | 4.41 |
| OR Quartile 3 | 4.42 | 4.50 | 1.63 | 3.81 | 4.18 | 1.31 | 3.81 | 4.18 | 1.39 |
| p Value | 0.066 | 0.0050 | 0.14 | 0.10 | 0.0080 | 0.41 | 0.10 | 0.0080 | 0.32 |
| Lower limit of 95% CI | 0.907 | 1.57 | 0.852 | 0.765 | 1.45 | 0.687 | 0.765 | 1.45 | 0.725 |
| Upper limit of 95% CI | 21.6 | 12.9 | 3.12 | 19.0 | 12.0 | 2.51 | 19.0 | 12.0 | 2.67 |
| OR Quartile 4 | 3.26 | 4.20 | 1.73 | 2.87 | 3.96 | 1.50 | 2.87 | 3.96 | 1.84 |
| p Value | 0.27 | 0.061 | 0.16 | 0.33 | 0.073 | 0.30 | 0.33 | 0.073 | 0.13 |
| Lower limit of 95% CI | 0.400 | 0.936 | 0.811 | 0.348 | 0.879 | 0.701 | 0.348 | 0.879 | 0.839 |
| Upper limit of 95% CI | 26.7 | 18.8 | 3.67 | 23.8 | 17.8 | 3.22 | 23.8 | 17.8 | 4.02 |

TABLE 12.2

Comparison of marker levels and the area under the ROC curve
(AUC) in urine samples for the "recovered" and "non-recovered" cohorts where recovery
starts at 24 hours after sample collection and renal status is assessed by serum creatinine
(sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 15.1 | 95.7 | 12.9 | 93.8 | 8.47 | 93.6 |
| Average | 52.2 | 329 | 55.2 | 320 | 57.0 | 317 |
| Stdev | 94.7 | 577 | 102 | 570 | 104 | 569 |
| p (t-test) | | 0.016 | | 0.032 | | 0.039 |
| Min | 0.352 | 0.259 | 0.352 | 0.259 | 0.352 | 0.259 |
| Max | 460 | 3600 | 460 | 3600 | 460 | 3600 |
| n (Patient) | 26 | 123 | 22 | 127 | 21 | 128 |
| sCr only | | | | | | |
| Median | 19.4 | 98.7 | 17.2 | 97.0 | 16.2 | 95.7 |
| Average | 72.5 | 350 | 74.1 | 345 | 75.9 | 342 |
| Stdev | 124 | 599 | 128 | 595 | 129 | 593 |
| p (t-test) | | 0.0073 | | 0.011 | | 0.013 |
| Min | 0.352 | 0.259 | 0.352 | 0.259 | 0.352 | 0.259 |
| Max | 532 | 3600 | 532 | 3600 | 532 | 3600 |
| n (Patient) | 35 | 112 | 33 | 114 | 32 | 115 |
| UO only | | | | | | |
| Median | 59.7 | 99.2 | 59.3 | 98.7 | 58.8 | 99.2 |
| Average | 213 | 380 | 188 | 384 | 177 | 386 |
| Stdev | 372 | 697 | 320 | 688 | 315 | 677 |
| p (t-test) | | 0.067 | | 0.030 | | 0.021 |
| Min | 0.259 | 2.24 | 0.259 | 2.24 | 0.259 | 2.24 |
| Max | 1830 | 3600 | 1650 | 3600 | 1650 | 3600 |
| n (Patient) | 81 | 63 | 72 | 72 | 69 | 75 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.75 | 0.73 | 0.60 | 0.74 | 0.73 | 0.61 | 0.74 | 0.72 | 0.62 |
| SE | 0.046 | 0.045 | 0.048 | 0.050 | 0.045 | 0.047 | 0.051 | 0.046 | 0.046 |
| p Value | 8.4E−8 | 4.5E−7 | 0.037 | 1.2E−6 | 6.6E−7 | 0.023 | 3.3E−6 | 1.8E−6 | 0.0076 |
| nCohort Recovered | 26 | 35 | 81 | 22 | 33 | 72 | 21 | 32 | 69 |
| nCohort Non-recovered | 123 | 112 | 63 | 127 | 114 | 72 | 128 | 115 | 75 |
| Cutoff Quartile 2 | 17.2 | 17.5 | 16.5 | 17.2 | 17.5 | 16.5 | 17.2 | 17.5 | 16.5 |
| Sensitivity | 80% | 82% | 83% | 80% | 82% | 82% | 80% | 82% | 83% |
| Specificity | 50% | 49% | 31% | 50% | 52% | 32% | 52% | 50% | 33% |
| Cutoff Quartile 3 | 78.3 | 83.5 | 80.9 | 78.3 | 83.5 | 80.9 | 78.3 | 83.5 | 80.9 |
| Sensitivity | 57% | 58% | 57% | 55% | 57% | 56% | 55% | 57% | 56% |

TABLE 12.2-continued

Comparison of marker levels and the area under the ROC curve (AUC) in urine samples for the "recovered" and "non-recovered" cohorts where recovery starts at 24 hours after sample collection and renal status is assessed by serum creatinine (sCr) only, urine output (UO) only, or serum creatinine or urine output RIFLE criteria.

| Specificity | 81% | 74% | 56% | 77% | 73% | 56% | 76% | 72% | 57% |
|---|---|---|---|---|---|---|---|---|---|
| Cutoff Quartile 4 | 331 | 332 | 331 | 331 | 332 | 331 | 331 | 332 | 331 |
| Sensitivity | 30% | 31% | 30% | 29% | 31% | 29% | 29% | 30% | 31% |
| Specificity | 96% | 94% | 79% | 95% | 94% | 79% | 95% | 94% | 81% |
| OR Quartile 2 | 4.12 | 4.34 | 2.11 | 3.88 | 4.99 | 2.13 | 4.32 | 4.48 | 2.38 |
| p Value | 0.0018 | 4.5E−4 | 0.068 | 0.0047 | 1.6E−4 | 0.057 | 0.0028 | 4.6E−4 | 0.029 |
| Lower limit of 95% CI | 1.70 | 1.91 | 0.945 | 1.52 | 2.16 | 0.978 | 1.65 | 1.93 | 1.09 |
| Upper limit of 95% CI | 10.0 | 9.87 | 4.71 | 9.95 | 11.5 | 4.64 | 11.3 | 10.4 | 5.20 |
| OR Quartile 3 | 5.55 | 4.00 | 1.67 | 4.18 | 3.54 | 1.56 | 3.86 | 3.32 | 1.65 |
| p Value | 0.0012 | 0.0013 | 0.13 | 0.0080 | 0.0036 | 0.18 | 0.013 | 0.0059 | 0.13 |
| Lower limit of 95% CI | 1.96 | 1.71 | 0.858 | 1.45 | 1.51 | 0.810 | 1.33 | 1.41 | 0.856 |
| Upper limit of 95% CI | 15.7 | 9.31 | 3.24 | 12.0 | 8.29 | 3.02 | 11.2 | 7.81 | 3.20 |
| OR Quartile 4 | 10.8 | 7.50 | 1.63 | 8.63 | 6.87 | 1.56 | 8.13 | 6.56 | 1.91 |
| p Value | 0.022 | 0.0077 | 0.21 | 0.039 | 0.011 | 0.25 | 0.045 | 0.013 | 0.10 |
| Lower limit of 95% CI | 1.40 | 1.70 | 0.761 | 1.12 | 1.56 | 0.730 | 1.05 | 1.49 | 0.875 |
| Upper limit of 95% CI | 82.4 | 33.0 | 3.47 | 66.5 | 30.3 | 3.35 | 62.8 | 29.0 | 4.15 |

TABLE 12.3

Comparison of marker levels and the area under the ROC curve (AUC) in urine samples for the "recovered" and "non-recovered" cohorts where recovery starts at 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 20.6 | 103 | 20.8 | 101 | 26.8 | 98.2 |
| Average | 54.4 | 360 | 47.7 | 354 | 51.6 | 345 |
| Stdev | 80.0 | 605 | 62.2 | 599 | 63.8 | 593 |
| p (t-test) | | 0.0027 | | 0.0035 | | 0.0069 |
| Min | 0.352 | 0.259 | 0.352 | 0.259 | 1.13 | 0.259 |
| Max | 367 | 3600 | 225 | 3600 | 225 | 3600 |
| n (Patient) | 37 | 109 | 34 | 112 | 31 | 115 |
| sCr only | | | | | | |
| Median | 21.0 | 106 | 21.0 | 106 | 21.0 | 106 |
| Average | 70.6 | 380 | 64.9 | 377 | 64.9 | 377 |
| Stdev | 110 | 626 | 102 | 621 | 102 | 621 |
| p (t-test) | | 0.0013 | | 0.0014 | | 0.0014 |
| Min | 0.352 | 0.259 | 0.352 | 0.259 | 0.352 | 0.259 |
| Max | 532 | 3600 | 532 | 3600 | 532 | 3600 |
| n (Patient) | 45 | 100 | 43 | 102 | 43 | 102 |
| UO only | | | | | | |
| Median | 61.7 | 114 | 61.7 | 114 | 63.7 | 99.2 |
| Average | 230 | 410 | 224 | 404 | 246 | 368 |
| Stdev | 404 | 713 | 406 | 695 | 424 | 667 |
| p (t-test) | | 0.076 | | 0.074 | | 0.23 |
| Min | 0.259 | 2.24 | 0.259 | 2.24 | 0.259 | 0.352 |
| Max | 2160 | 3600 | 2160 | 3600 | 2160 | 3600 |
| n (Patient) | 70 | 58 | 66 | 62 | 59 | 69 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.75 | 0.73 | 0.62 | 0.75 | 0.74 | 0.62 | 0.72 | 0.74 | 0.58 |
| SE | 0.042 | 0.042 | 0.050 | 0.043 | 0.042 | 0.050 | 0.046 | 0.042 | 0.050 |
| p Value | 2.9E−9 | 2.7E−8 | 0.020 | 3.7E−9 | 9.2E−9 | 0.014 | 1.8E−6 | 9.2E−9 | 0.13 |
| nCohort Recovered | 37 | 45 | 70 | 34 | 43 | 66 | 31 | 43 | 59 |
| nCohort Non-recovered | 109 | 100 | 58 | 112 | 102 | 62 | 115 | 102 | 69 |
| Cutoff Quartile 2 | 17.4 | 17.2 | 20.7 | 17.4 | 17.2 | 20.7 | 17.4 | 17.2 | 20.7 |
| Sensitivity | 82% | 83% | 83% | 80% | 83% | 82% | 79% | 83% | 80% |

TABLE 12.3-continued

Comparison of marker levels and the area under the ROC curve
(AUC) in urine samples for the "recovered" and "non-recovered" cohorts where recovery
starts at 48 hours after sample collection and renal status is assessed by serum creatinine
(sCr) only, urine output (UO) only, or serum creatinine or urine output RIFLE criteria.

| | | | | | | | | | |
|---|---|---|---|---|---|---|---|---|---|
| Specificity | 46% | 42% | 31% | 44% | 44% | 32% | 42% | 44% | 31% |
| Cutoff Quartile 3 | 80.9 | 83.5 | 87.1 | 80.9 | 83.5 | 87.1 | 80.9 | 83.5 | 87.1 |
| Sensitivity | 59% | 60% | 57% | 58% | 60% | 56% | 57% | 60% | 54% |
| Specificity | 76% | 71% | 56% | 76% | 72% | 56% | 74% | 72% | 54% |
| Cutoff Quartile 4 | 325 | 331 | 369 | 325 | 331 | 369 | 325 | 331 | 369 |
| Sensitivity | 33% | 35% | 29% | 33% | 35% | 29% | 32% | 35% | 26% |
| Specificity | 97% | 96% | 79% | 100% | 98% | 79% | 100% | 98% | 76% |
| OR Quartile 2 | 3.78 | 3.57 | 2.20 | 3.23 | 3.96 | 2.16 | 2.74 | 3.96 | 1.72 |
| p Value | 0.0013 | 0.0016 | 0.068 | 0.0052 | 7.0E−4 | 0.069 | 0.019 | 7.0E−4 | 0.19 |
| Lower limit of 95% CI | 1.69 | 1.62 | 0.942 | 1.42 | 1.79 | 0.941 | 1.18 | 1.79 | 0.770 |
| Upper limit of 95% CI | 8.49 | 7.85 | 5.14 | 7.35 | 8.77 | 4.97 | 6.36 | 8.77 | 3.87 |
| OR Quartile 3 | 4.42 | 3.69 | 1.66 | 4.49 | 3.84 | 1.65 | 3.74 | 3.84 | 1.37 |
| p Value | 5.4E−4 | 7.4E−4 | 0.16 | 7.8E−4 | 6.6E−4 | 0.16 | 0.0035 | 6.6E−4 | 0.38 |
| Lower limit of 95% CI | 1.91 | 1.73 | 0.823 | 1.87 | 1.77 | 0.822 | 1.54 | 1.77 | 0.682 |
| Upper limit of 95% CI | 10.3 | 7.88 | 3.35 | 10.8 | 8.34 | 3.33 | 9.06 | 8.34 | 2.75 |
| OR Quartile 4 | 17.8 | 11.6 | 1.52 | 34.3 | 22.9 | 1.52 | 30.1 | 22.9 | 1.13 |
| p Value | 0.0054 | 0.0011 | 0.31 | 0.014 | 0.0024 | 0.31 | 0.018 | 0.0024 | 0.76 |
| Lower limit of 95% CI | 2.34 | 2.65 | 0.681 | 2.04 | 3.03 | 0.679 | 1.79 | 3.03 | 0.507 |
| Upper limit of 95% CI | 135 | 50.7 | 3.40 | 575 | 173 | 3.40 | 505 | 173 | 2.54 |

TABLE 12.4

Comparison of marker levels and the area under the ROC curve (AUC) in urine samples for the "recovered"
and "non-recovered" cohorts where recovery starts at 72 hours after sample collection and renal status
is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 22.2 | 108 | 24.5 | 98.7 | 24.5 | 98.7 |
| Average | 100 | 370 | 109 | 354 | 112 | 348 |
| Stdev | 239 | 619 | 253 | 608 | 259 | 604 |
| p (t-test) | | 0.0065 | | 0.018 | | 0.024 |
| Min | 0.352 | 0.259 | 1.13 | 0.259 | 1.13 | 0.259 |
| Max | 1440 | 3600 | 1440 | 3600 | 1440 | 3600 |
| n (Patient) | 43 | 99 | 38 | 104 | 36 | 106 |
| | sCr only | | | | | |
| Median | 33.4 | 106 | 33.4 | 106 | 33.4 | 106 |
| Average | 111 | 385 | 111 | 385 | 113 | 378 |
| Stdev | 232 | 638 | 232 | 638 | 236 | 633 |
| p (t-test) | | 0.0040 | | 0.0040 | | 0.0059 |
| Min | 0.352 | 0.259 | 0.352 | 0.259 | 0.352 | 0.259 |
| Max | 1440 | 3600 | 1440 | 3600 | 1440 | 3600 |
| n (Patient) | 50 | 92 | 50 | 92 | 48 | 94 |
| | UO only | | | | | |
| Median | 61.3 | 117 | 71.0 | 99.2 | 86.1 | 94.8 |
| Average | 245 | 403 | 266 | 365 | 289 | 348 |
| Stdev | 433 | 712 | 456 | 676 | 470 | 656 |
| p (t-test) | | 0.14 | | 0.36 | | 0.59 |
| Min | 0.259 | 2.91 | 0.259 | 0.352 | 0.259 | 0.352 |
| Max | 2160 | 3600 | 2160 | 3600 | 2160 | 3600 |
| n (Patient) | 62 | 57 | 54 | 65 | 50 | 70 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.70 | 0.63 | 0.70 | 0.70 | 0.58 | 0.70 | 0.69 | 0.55 |
| SE | 0.043 | 0.044 | 0.051 | 0.046 | 0.044 | 0.052 | 0.047 | 0.045 | 0.053 |
| p Value | 1.4E−7 | 7.0E−6 | 0.011 | 1.0E−5 | 7.0E−6 | 0.11 | 2.3E−5 | 1.7E−5 | 0.38 |
| nCohort Recovered | 43 | 50 | 62 | 38 | 50 | 54 | 36 | 48 | 50 |
| nCohort Non-recovered | 99 | 92 | 57 | 104 | 92 | 65 | 106 | 94 | 70 |

TABLE 12.4-continued

Comparison of marker levels and the area under the ROC curve (AUC) in urine samples for the "recovered" and "non-recovered" cohorts where recovery starts at 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Cutoff Quartile 2 | 17.4 | 17.4 | 25.6 | 17.4 | 17.4 | 25.6 | 17.4 | 17.4 | 25.8 |
| Sensitivity | 82% | 82% | 84% | 81% | 82% | 80% | 80% | 81% | 79% |
| Specificity | 42% | 38% | 34% | 42% | 38% | 31% | 42% | 38% | 30% |
| Cutoff Quartile 3 | 80.9 | 80.9 | 87.9 | 80.9 | 80.9 | 87.9 | 80.9 | 80.9 | 90.6 |
| Sensitivity | 60% | 60% | 58% | 58% | 60% | 54% | 58% | 60% | 51% |
| Specificity | 72% | 68% | 56% | 71% | 68% | 54% | 72% | 69% | 52% |
| Cutoff Quartile 4 | 332 | 332 | 364 | 332 | 332 | 364 | 332 | 332 | 369 |
| Sensitivity | 33% | 35% | 28% | 32% | 35% | 26% | 31% | 34% | 24% |
| Specificity | 93% | 92% | 77% | 92% | 92% | 76% | 92% | 92% | 74% |
| OR Quartile 2 | 3.24 | 2.70 | 2.73 | 3.05 | 2.70 | 1.84 | 2.89 | 2.53 | 1.57 |
| p Value | 0.0036 | 0.012 | 0.026 | 0.0067 | 0.012 | 0.15 | 0.011 | 0.019 | 0.29 |
| Lower limit of 95% CI | 1.47 | 1.24 | 1.13 | 1.36 | 1.24 | 0.796 | 1.28 | 1.16 | 0.684 |
| Upper limit of 95% CI | 7.16 | 5.88 | 6.62 | 6.85 | 5.88 | 4.24 | 6.54 | 5.52 | 3.61 |
| OR Quartile 3 | 3.81 | 3.16 | 1.78 | 3.35 | 3.16 | 1.35 | 3.52 | 3.24 | 1.15 |
| p Value | 7.5E−4 | 0.0019 | 0.12 | 0.0031 | 0.0019 | 0.41 | 0.0028 | 0.0017 | 0.71 |
| Lower limit of 95% CI | 1.75 | 1.53 | 0.862 | 1.50 | 1.53 | 0.656 | 1.54 | 1.55 | 0.555 |
| Upper limit of 95% CI | 8.30 | 6.53 | 3.69 | 7.46 | 6.53 | 2.79 | 8.04 | 6.77 | 2.37 |
| OR Quartile 4 | 6.67 | 6.13 | 1.34 | 5.42 | 6.13 | 1.12 | 4.97 | 5.68 | 0.913 |
| p Value | 0.0028 | 0.0013 | 0.49 | 0.0080 | 0.0013 | 0.79 | 0.012 | 0.0021 | 0.83 |
| Lower limit of 95% CI | 1.92 | 2.03 | 0.584 | 1.55 | 2.03 | 0.485 | 1.42 | 1.87 | 0.396 |
| Upper limit of 95% CI | 23.2 | 18.6 | 3.07 | 18.9 | 18.6 | 2.57 | 17.4 | 17.2 | 2.10 |

TABLE 12.5

Comparison of marker levels and the area under the ROC curve (AUC) in urine samples for the "recovered" and "non-recovered" cohorts where recovery starts within 7 days after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 44.2 | 117 | 40.8 | 118 | 40.8 | 118 |
| Average | 206 | 382 | 207 | 379 | 207 | 379 |
| Stdev | 393 | 675 | 396 | 670 | 396 | 670 |
| p (t-test) | | 0.047 | | 0.052 | | 0.052 |
| Min | 0.259 | 2.91 | 0.259 | 2.91 | 0.259 | 2.91 |
| Max | 2160 | 3600 | 2160 | 3600 | 2160 | 3600 |
| n (Patient) | 86 | 63 | 85 | 64 | 85 | 64 |
| | sCr only | | | | | |
| Median | 36.8 | 123 | 36.8 | 119 | 36.8 | 119 |
| Average | 137 | 412 | 140 | 402 | 140 | 402 |
| Stdev | 322 | 649 | 326 | 644 | 326 | 644 |
| p (t-test) | | 0.0015 | | 0.0026 | | 0.0026 |
| Min | 0.259 | 0.723 | 0.259 | 0.723 | 0.259 | 0.723 |
| Max | 2160 | 3600 | 2160 | 3600 | 2160 | 3600 |
| n (Patient) | 71 | 78 | 69 | 80 | 69 | 80 |
| | UO only | | | | | |
| Median | 58.9 | 113 | 58.9 | 113 | 58.9 | 113 |
| Average | 214 | 408 | 217 | 396 | 216 | 391 |
| Stdev | 380 | 733 | 383 | 722 | 386 | 711 |
| p (t-test) | | 0.035 | | 0.051 | | 0.054 |
| Min | 0.259 | 3.02 | 0.259 | 2.91 | 0.259 | 2.91 |
| Max | 2160 | 3600 | 2160 | 3600 | 2160 | 3600 |
| n (Patient) | 96 | 52 | 94 | 54 | 92 | 56 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.72 | 0.62 | 0.66 | 0.71 | 0.61 | 0.66 | 0.71 | 0.61 |
| SE | 0.046 | 0.041 | 0.049 | 0.046 | 0.042 | 0.049 | 0.046 | 0.042 | 0.049 |
| p Value | 8.2E−4 | 8.6E−8 | 0.019 | 5.5E−4 | 4.6E−7 | 0.031 | 5.5E−4 | 4.6E−7 | 0.028 |
| nCohort Recovered | 86 | 71 | 96 | 85 | 69 | 94 | 85 | 69 | 92 |

TABLE 12.5-continued

Comparison of marker levels and the area under the ROC curve (AUC) in urine samples for the "recovered" and "non-recovered" cohorts where recovery starts within 7 days after sample collection and renal status is assessed by serum creatinine (sCr) only, urine output (UO) only, or serum creatinine or urine output RIFLE criteria.

| nCohort Non-recovered | 63 | 78 | 52 | 64 | 80 | 54 | 64 | 80 | 56 |
|---|---|---|---|---|---|---|---|---|---|
| Cutoff Quartile 2 | 17.2 | 17.2 | 17.6 | 17.2 | 17.2 | 17.6 | 17.2 | 17.2 | 17.6 |
| Sensitivity | 84% | 86% | 83% | 84% | 85% | 81% | 84% | 85% | 80% |
| Specificity | 31% | 37% | 29% | 32% | 36% | 29% | 32% | 36% | 28% |
| Cutoff Quartile 3 | 78.3 | 78.3 | 80.9 | 78.3 | 78.3 | 80.9 | 78.3 | 78.3 | 80.9 |
| Sensitivity | 65% | 67% | 62% | 66% | 65% | 61% | 66% | 65% | 61% |
| Specificity | 60% | 68% | 56% | 61% | 67% | 56% | 61% | 67% | 57% |
| Cutoff Quartile 4 | 331 | 331 | 331 | 331 | 331 | 331 | 331 | 331 | 331 |
| Sensitivity | 33% | 38% | 31% | 33% | 38% | 30% | 33% | 38% | 30% |
| Specificity | 80% | 89% | 78% | 80% | 88% | 78% | 80% | 88% | 78% |
| OR Quartile 2 | 2.43 | 3.52 | 1.97 | 2.51 | 3.22 | 1.77 | 2.51 | 3.22 | 1.61 |
| p Value | 0.033 | 0.0020 | 0.12 | 0.027 | 0.0035 | 0.17 | 0.027 | 0.0035 | 0.24 |
| Lower limit of 95% CI | 1.07 | 1.58 | 0.847 | 1.11 | 1.47 | 0.782 | 1.11 | 1.47 | 0.724 |
| Upper limit of 95% CI | 5.48 | 7.83 | 4.57 | 5.68 | 7.07 | 4.02 | 5.68 | 7.07 | 3.59 |
| OR Quartile 3 | 2.85 | 4.17 | 2.06 | 3.01 | 3.71 | 2.03 | 3.01 | 3.71 | 2.01 |
| p Value | 0.0023 | 4.3E−5 | 0.040 | 0.0014 | 1.5E−4 | 0.042 | 0.0014 | 1.5E−4 | 0.043 |
| Lower limit of 95% CI | 1.45 | 2.10 | 1.03 | 1.53 | 1.88 | 1.03 | 1.53 | 1.88 | 1.02 |
| Upper limit of 95% CI | 5.60 | 8.28 | 4.10 | 5.91 | 7.33 | 4.02 | 5.91 | 7.33 | 3.95 |
| OR Quartile 4 | 2.03 | 4.92 | 1.59 | 1.95 | 4.58 | 1.46 | 1.95 | 4.58 | 1.57 |
| p Value | 0.063 | 3.1E−4 | 0.23 | 0.078 | 5.7E−4 | 0.33 | 0.078 | 5.7E−4 | 0.24 |
| Lower limit of 95% CI | 0.963 | 2.07 | 0.741 | 0.928 | 1.93 | 0.685 | 0.928 | 1.93 | 0.738 |
| Upper limit of 95% CI | 4.28 | 11.7 | 3.40 | 4.11 | 10.9 | 3.13 | 4.11 | 10.9 | 3.34 |

Example 13. Use of Insulin-Like Growth Factor-Binding Protein 6 for Evaluating Renal Status in Patients Admitted to the ICU: Recovery to RIFLE 0 and R from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 6 is measured in the enrollment samples by standard immunoassay methods using commercially available assay reagents.

Kidney status is assessed by RIFLE criteria based on serum creatinine, urine output, or both serum creatinine and urine output during a period starting at 12, 24, 48, or 72 hours after sample collection or at any time within 7 days after sample collection. Two cohorts are defined to represent a "recovered" and a "non-recovered" population. "Recovered" indicates those patients whose maximum RIFLE stage during a period of 24, 48 or 72 hours is non-injury (RIFLE 0) or risk of injury (R). "Non-recovered" indicates those patients whose maximum RIFLE stage during a period of 24, 48 or 72 hours is injury (I) or failure (F). If a patient dies or is placed on renal replacement therapy (RRT) at any time from sample collection to 12, 24, 48, or 72 hours after sample collection or at any time within 7 days after sample collection, the patient is considered "non-recovered".

The ability to distinguish the "recovered" and "non-recovered" cohorts is determined using receiver operating characteristic (ROC) analysis.

TABLE 13.1

Comparison of marker levels and the area under the ROC curve (AUC) in urine samples for the "recovered" and "non-recovered" cohorts where recovery starts at 12 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 20.6 | 98.7 | 17.2 | 97.0 | 18.9 | 95.7 |
| Average | 125 | 332 | 131 | 327 | 135 | 324 |
| Stdev | 368 | 573 | 378 | 569 | 383 | 568 |
| p (t-test) | | 0.042 | | 0.059 | | 0.070 |
| Min | 0.259 | 0.723 | 0.259 | 0.723 | 0.259 | 0.723 |
| Max | 2160 | 3600 | 2160 | 3600 | 2160 | 3600 |
| n (Patient) | 37 | 112 | 35 | 114 | 34 | 115 |
| sCr only | | | | | | |
| Median | 21.0 | 106 | 21.0 | 106 | 21.6 | 103 |
| Average | 121 | 359 | 121 | 359 | 124 | 355 |
| Stdev | 328 | 599 | 328 | 599 | 331 | 597 |
| p (t-test) | | 0.011 | | 0.011 | | 0.013 |
| Min | 0.259 | 0.723 | 0.259 | 0.723 | 0.259 | 0.723 |

TABLE 13.1-continued

Comparison of marker levels and the area under the ROC curve (AUC) in urine samples for the "recovered" and "non-recovered" cohorts where recovery starts at 12 hours after sample collection and renal status is assessed by serum creatinine (sCr) only, urine output (UO) only, or serum creatinine or urine output RIFLE criteria.

| | | | | | | |
|---|---|---|---|---|---|---|
| Max | 2160 | 3600 | 2160 | 3600 | 2160 | 3600 |
| n (Patient) | 49 | 100 | 49 | 100 | 48 | 101 |
| | | | UO only | | | |
| Median | 58.5 | 121 | 58.9 | 104 | 58.8 | 108 |
| Average | 212 | 405 | 223 | 369 | 206 | 386 |
| Stdev | 405 | 699 | 416 | 672 | 384 | 682 |
| p (t-test) | | 0.034 | | 0.11 | | 0.043 |
| Min | 0.259 | 2.91 | 0.259 | 2.91 | 0.259 | 2.91 |
| Max | 2160 | 3600 | 2160 | 3600 | 2160 | 3600 |
| n (Patient) | 94 | 54 | 88 | 60 | 85 | 63 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.72 | 0.65 | 0.72 | 0.72 | 0.62 | 0.71 | 0.72 | 0.63 |
| SE | 0.044 | 0.042 | 0.048 | 0.045 | 0.042 | 0.048 | 0.046 | 0.042 | 0.047 |
| p Value | 1.9E−7 | 6.5E−8 | 0.0022 | 5.0E−7 | 6.5E−8 | 0.015 | 2.8E−6 | 3.6E−7 | 0.0065 |
| nCohort Recovered | 37 | 49 | 94 | 35 | 49 | 88 | 34 | 48 | 85 |
| nCohort Non-recovered | 112 | 100 | 54 | 114 | 100 | 60 | 115 | 101 | 63 |
| Cutoff Quartile 2 | 17.2 | 17.2 | 17.6 | 17.2 | 17.2 | 17.6 | 17.2 | 17.2 | 17.6 |
| Sensitivity | 82% | 84% | 85% | 82% | 84% | 85% | 82% | 83% | 86% |
| Specificity | 46% | 43% | 31% | 49% | 43% | 32% | 47% | 42% | 33% |
| Cutoff Quartile 3 | 78.3 | 78.3 | 80.9 | 78.3 | 78.3 | 80.9 | 78.3 | 78.3 | 80.9 |
| Sensitivity | 59% | 61% | 65% | 58% | 61% | 60% | 57% | 60% | 60% |
| Specificity | 76% | 71% | 59% | 74% | 71% | 57% | 74% | 71% | 58% |
| Cutoff Quartile 4 | 331 | 331 | 331 | 331 | 331 | 331 | 331 | 331 | 331 |
| Sensitivity | 31% | 34% | 35% | 31% | 34% | 32% | 30% | 34% | 32% |
| Specificity | 92% | 92% | 81% | 91% | 92% | 80% | 91% | 92% | 80% |
| OR Quartile 2 | 3.91 | 3.94 | 2.57 | 4.44 | 3.94 | 2.64 | 3.98 | 3.53 | 2.95 |
| p Value | 9.3E−4 | 5.6E−4 | 0.034 | 3.7E−4 | 5.6E−4 | 0.023 | 0.0010 | 0.0014 | 0.011 |
| Lower limit of 95% CI | 1.74 | 1.81 | 1.08 | 1.96 | 1.81 | 1.14 | 1.75 | 1.63 | 1.27 |
| Upper limit of 95% CI | 8.77 | 8.58 | 6.12 | 10.1 | 8.58 | 6.12 | 9.06 | 7.66 | 6.81 |
| OR Quartile 3 | 4.46 | 3.91 | 2.60 | 3.97 | 3.91 | 1.97 | 3.74 | 3.70 | 2.07 |
| p Value | 4.8E−4 | 3.0E−4 | 0.0069 | 0.0014 | 3.0E−4 | 0.046 | 0.0023 | 5.2E−4 | 0.032 |
| Lower limit of 95% CI | 1.93 | 1.87 | 1.30 | 1.71 | 1.87 | 1.01 | 1.60 | 1.77 | 1.07 |
| Upper limit of 95% CI | 10.3 | 8.18 | 5.20 | 9.24 | 8.18 | 3.84 | 8.73 | 7.76 | 4.02 |
| OR Quartile 4 | 5.15 | 5.80 | 2.29 | 4.73 | 5.80 | 1.80 | 4.52 | 5.58 | 1.86 |
| p Value | 0.0099 | 0.0018 | 0.032 | 0.015 | 0.0018 | 0.12 | 0.018 | 0.0023 | 0.11 |
| Lower limit of 95% CI | 1.48 | 1.92 | 1.07 | 1.36 | 1.92 | 0.850 | 1.30 | 1.85 | 0.878 |
| Upper limit of 95% CI | 17.9 | 17.5 | 4.90 | 16.5 | 17.5 | 3.82 | 15.8 | 16.8 | 3.94 |

TABLE 13.2

Comparison of marker levels and the area under the ROC curve (AUC) in urine samples for the "recovered" and "non-recovered" cohorts where recovery starts at 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | | | sCr or UO | | | |
| Median | 26.8 | 110 | 26.8 | 109 | 26.8 | 109 |
| Average | 121 | 363 | 125 | 357 | 125 | 357 |
| Stdev | 323 | 603 | 329 | 599 | 329 | 599 |
| p (t-test) | | 0.0084 | | 0.013 | | 0.013 |
| Min | 0.259 | 0.723 | 0.259 | 0.723 | 0.259 | 0.723 |
| Max | 2160 | 3600 | 2160 | 3600 | 2160 | 3600 |
| n (Patient) | 51 | 98 | 49 | 100 | 49 | 100 |
| | | | sCr only | | | |
| Median | 28.9 | 111 | 30.9 | 110 | 30.9 | 110 |
| Average | 125 | 382 | 127 | 378 | 127 | 378 |
| Stdev | 314 | 621 | 316 | 618 | 316 | 618 |
| p (t-test) | | 0.0047 | | 0.0060 | | 0.0060 |

TABLE 13.2-continued

Comparison of marker levels and the area under the ROC curve (AUC) in urine samples for the "recovered" and "non-recovered" cohorts where recovery starts at 24 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 0.259 | 0.723 | 0.259 | 0.723 | 0.259 | 0.723 |
| Max | 2160 | 3600 | 2160 | 3600 | 2160 | 3600 |
| n (Patient) | 56 | 91 | 55 | 92 | 55 | 92 |

UO only

| | | | | | | |
|---|---|---|---|---|---|---|
| Median | 58.5 | 114 | 58.8 | 109 | 58.8 | 109 |
| Average | 217 | 414 | 204 | 417 | 204 | 417 |
| Stdev | 405 | 724 | 377 | 722 | 377 | 722 |
| p (t-test) | | 0.038 | | 0.022 | | 0.022 |
| Min | 0.259 | 2.91 | 0.259 | 2.91 | 0.259 | 2.91 |
| Max | 2160 | 3600 | 2160 | 3600 | 2160 | 3600 |
| n (Patient) | 94 | 50 | 89 | 55 | 89 | 55 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.72 | 0.72 | 0.64 | 0.71 | 0.71 | 0.64 | 0.71 | 0.71 | 0.64 |
| SE | 0.042 | 0.042 | 0.050 | 0.043 | 0.042 | 0.048 | 0.043 | 0.042 | 0.048 |
| p Value | 1.7E−7 | 2.4E−7 | 0.0040 | 1.2E−6 | 1.2E−6 | 0.0036 | 1.2E−6 | 1.2E−6 | 0.0036 |
| nCohort Recovered | 51 | 56 | 94 | 49 | 55 | 89 | 49 | 55 | 89 |
| nCohort Non-recovered | 98 | 91 | 50 | 100 | 92 | 55 | 100 | 92 | 55 |
| Cutoff Quartile 2 | 17.2 | 17.5 | 16.5 | 17.2 | 17.5 | 16.5 | 17.2 | 17.5 | 16.5 |
| Sensitivity | 84% | 85% | 86% | 83% | 84% | 87% | 83% | 84% | 87% |
| Specificity | 41% | 41% | 31% | 41% | 40% | 33% | 41% | 40% | 33% |
| Cutoff Quartile 3 | 78.3 | 83.5 | 80.9 | 78.3 | 83.5 | 80.9 | 78.3 | 83.5 | 80.9 |
| Sensitivity | 62% | 63% | 64% | 61% | 62% | 62% | 61% | 62% | 62% |
| Specificity | 73% | 70% | 57% | 71% | 69% | 57% | 71% | 69% | 57% |
| Cutoff Quartile 4 | 331 | 332 | 331 | 331 | 332 | 331 | 331 | 332 | 331 |
| Sensitivity | 35% | 35% | 34% | 34% | 35% | 33% | 34% | 35% | 33% |
| Specificity | 92% | 91% | 80% | 92% | 91% | 80% | 92% | 91% | 80% |
| OR Quartile 2 | 3.59 | 3.83 | 2.74 | 3.37 | 3.42 | 3.31 | 3.37 | 3.42 | 3.31 |
| p Value | 0.0012 | 7.3E−4 | 0.030 | 0.0021 | 0.0018 | 0.0097 | 0.0021 | 0.0018 | 0.0097 |
| Lower limit of 95% CI | 1.66 | 1.76 | 1.10 | 1.56 | 1.58 | 1.34 | 1.56 | 1.58 | 1.34 |
| Upper limit of 95% CI | 7.77 | 8.36 | 6.81 | 7.29 | 7.41 | 8.22 | 7.29 | 7.41 | 8.22 |
| OR Quartile 3 | 4.36 | 3.85 | 2.40 | 3.91 | 3.64 | 2.17 | 3.91 | 3.64 | 2.17 |
| p Value | 9.3E−5 | 2.0E−4 | 0.015 | 3.0E−4 | 3.6E−4 | 0.027 | 3.0E−4 | 3.6E−4 | 0.027 |
| Lower limit of 95% CI | 2.08 | 1.89 | 1.18 | 1.87 | 1.79 | 1.09 | 1.87 | 1.79 | 1.09 |
| Upper limit of 95% CI | 9.12 | 7.83 | 4.87 | 8.18 | 7.41 | 4.32 | 8.18 | 7.41 | 4.32 |
| OR Quartile 4 | 6.24 | 5.53 | 2.03 | 5.80 | 5.33 | 1.92 | 5.80 | 5.33 | 1.92 |
| p Value | 0.0011 | 9.5E−4 | 0.072 | 0.0018 | 0.0012 | 0.095 | 0.0018 | 0.0012 | 0.095 |
| Lower limit of 95% CI | 2.07 | 2.01 | 0.940 | 1.92 | 1.93 | 0.893 | 1.92 | 1.93 | 0.893 |
| Upper limit of 95% CI | 18.8 | 15.3 | 4.40 | 17.5 | 14.7 | 4.12 | 17.5 | 14.7 | 4.12 |

TABLE 13.3

Comparison of marker levels and the area under the ROC curve (AUC) in urine samples for the "recovered" and "non-recovered" cohorts where recovery starts at 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort | sCr or UO

| | | | | | | |
|---|---|---|---|---|---|---|
| Median | 31.3 | 111 | 31.3 | 111 | 31.3 | 111 |
| Average | 154 | 380 | 154 | 380 | 153 | 376 |
| Stdev | 345 | 636 | 345 | 636 | 349 | 629 |
| p (t-test) | | 0.012 | | 0.012 | | 0.014 |
| Min | 0.259 | 0.723 | 0.259 | 0.723 | 0.259 | 0.723 |
| Max | 2160 | 3600 | 2160 | 3600 | 2160 | 3600 |
| n (Patient) | 63 | 83 | 63 | 83 | 61 | 85 | sCr only

| | | | | | | |
|---|---|---|---|---|---|---|
| Median | 32.9 | 110 | 32.9 | 110 | 32.1 | 111 |
| Average | 157 | 394 | 157 | 394 | 154 | 393 |
| Stdev | 339 | 652 | 339 | 652 | 340 | 648 |

TABLE 13.3-continued

Comparison of marker levels and the area under the ROC curve (AUC) in urine samples for the "recovered"
and "non-recovered" cohorts where recovery starts at 48 hours after sample collection and renal status
is assessed by serum creatinine (sCr) only, urine output (UO) only, or serum creatinine or urine output RIFLE criteria.

| | | | | | | |
|---|---|---|---|---|---|---|
| p (t-test) | | 0.0082 | | 0.0082 | | 0.0075 |
| Min | 0.259 | 0.723 | 0.259 | 0.723 | 0.259 | 0.723 |
| Max | 2160 | 3600 | 2160 | 3600 | 2160 | 3600 |
| n (Patient) | 67 | 78 | 67 | 78 | 66 | 79 |

UO only

| | | | | | | |
|---|---|---|---|---|---|---|
| Median | 61.7 | 121 | 61.7 | 121 | 63.7 | 119 |
| Average | 231 | 446 | 231 | 446 | 238 | 423 |
| Stdev | 398 | 762 | 398 | 762 | 404 | 745 |
| p (t-test) | | 0.039 | | 0.039 | | 0.072 |
| Min | 0.259 | 3.55 | 0.259 | 3.55 | 0.259 | 2.91 |
| Max | 2160 | 3600 | 2160 | 3600 | 2160 | 3600 |
| n (Patient) | 80 | 48 | 80 | 48 | 77 | 51 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.69 | 0.64 | 0.69 | 0.69 | 0.64 | 0.69 | 0.69 | 0.61 |
| SE | 0.043 | 0.044 | 0.052 | 0.043 | 0.044 | 0.052 | 0.043 | 0.043 | 0.051 |
| p Value | 7.6E-6 | 2.0E-5 | 0.0079 | 7.6E-6 | 2.0E-5 | 0.0079 | 7.6E-6 | 7.0E-6 | 0.027 |
| nCohort Recovered | 63 | 67 | 80 | 63 | 67 | 80 | 61 | 66 | 77 |
| nCohort Non-recovered | 83 | 78 | 48 | 83 | 78 | 48 | 85 | 79 | 51 |
| Cutoff Quartile 2 | 17.4 | 17.2 | 20.7 | 17.4 | 17.2 | 20.7 | 17.4 | 17.2 | 20.7 |
| Sensitivity | 84% | 85% | 85% | 84% | 85% | 85% | 84% | 85% | 82% |
| Specificity | 38% | 36% | 31% | 38% | 36% | 31% | 38% | 36% | 30% |
| Cutoff Quartile 3 | 80.9 | 83.5 | 87.1 | 80.9 | 83.5 | 87.1 | 80.9 | 83.5 | 87.1 |
| Sensitivity | 64% | 64% | 60% | 64% | 64% | 60% | 64% | 65% | 59% |
| Specificity | 68% | 66% | 56% | 68% | 66% | 56% | 69% | 67% | 56% |
| Cutoff Quartile 4 | 325 | 331 | 369 | 325 | 331 | 369 | 325 | 331 | 369 |
| Sensitivity | 34% | 35% | 31% | 34% | 35% | 31% | 34% | 35% | 29% |
| Specificity | 86% | 85% | 79% | 86% | 85% | 79% | 87% | 86% | 78% |
| OR Quartile 2 | 3.31 | 3.07 | 2.66 | 3.31 | 3.07 | 2.66 | 3.07 | 3.19 | 1.99 |
| p Value | 0.0026 | 0.0055 | 0.039 | 0.0026 | 0.0055 | 0.039 | 0.0044 | 0.0041 | 0.12 |
| Lower limit of 95% CI | 1.52 | 1.39 | 1.05 | 1.52 | 1.39 | 1.05 | 1.42 | 1.44 | 0.833 |
| Upper limit of 95% CI | 7.23 | 6.78 | 6.75 | 7.23 | 6.78 | 6.75 | 6.65 | 7.05 | 4.74 |
| OR Quartile 3 | 3.80 | 3.42 | 1.96 | 3.80 | 3.42 | 1.96 | 3.85 | 3.64 | 1.81 |
| p Value | 1.6E-4 | 4.3E-4 | 0.069 | 1.6E-4 | 4.3E-4 | 0.069 | 1.6E-4 | 2.3E-4 | 0.11 |
| Lower limit of 95% CI | 1.90 | 1.72 | 0.948 | 1.90 | 1.72 | 0.948 | 1.91 | 1.83 | 0.883 |
| Upper limit of 95% CI | 7.60 | 6.77 | 4.06 | 7.60 | 6.77 | 4.06 | 7.75 | 7.25 | 3.70 |
| OR Quartile 4 | 3.05 | 3.02 | 1.68 | 3.05 | 3.02 | 1.68 | 3.43 | 3.48 | 1.47 |
| p Value | 0.0091 | 0.0081 | 0.21 | 0.0091 | 0.0081 | 0.21 | 0.0054 | 0.0037 | 0.35 |
| Lower limit of 95% CI | 1.32 | 1.33 | 0.748 | 1.32 | 1.33 | 0.748 | 1.44 | 1.50 | 0.656 |
| Upper limit of 95% CI | 7.07 | 6.84 | 3.79 | 7.07 | 6.84 | 3.79 | 8.17 | 8.06 | 3.30 |

TABLE 13.4

Comparison of marker levels and the area under the ROC curve (AUC) in urine samples for the "recovered"
and "non-recovered" cohorts where recovery starts at 72 hours after sample collection and renal status
is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort | sCr or UO

| | | | | | | |
|---|---|---|---|---|---|---|
| Median | 33.8 | 119 | 33.8 | 119 | 32.1 | 123 |
| Average | 144 | 432 | 145 | 416 | 136 | 413 |
| Stdev | 327 | 673 | 334 | 659 | 335 | 649 |
| p (t-test) | | 0.0015 | | 0.0029 | | 0.0024 |
| Min | 0.259 | 0.723 | 0.259 | 0.723 | 0.259 | 0.723 |
| Max | 2160 | 3600 | 2160 | 3600 | 2160 | 3600 |
| n (Patient) | 71 | 71 | 67 | 75 | 64 | 78 | sCr only

| | | | | | | |
|---|---|---|---|---|---|---|
| Median | 36.8 | 119 | 35.3 | 123 | 33.8 | 126 |
| Average | 148 | 437 | 145 | 436 | 138 | 439 |

TABLE 13.4-continued

Comparison of marker levels and the area under the ROC curve (AUC) in urine samples for the "recovered" and "non-recovered" cohorts where recovery starts at 72 hours after sample collection and renal status is assessed by serum creatinine (sCr) only, urine output (UO) only, or serum creatinine or urine output RIFLE criteria.

|  |  |  |  |  |  |  |
|---|---|---|---|---|---|---|
| Stdev | 325 | 681 | 327 | 677 | 323 | 672 |
| p (t-test) |  | 0.0015 |  | 0.0014 |  | 8.8E-4 |
| Min | 0.259 | 0.723 | 0.259 | 0.723 | 0.259 | 0.723 |
| Max | 2160 | 3600 | 2160 | 3600 | 2160 | 3600 |
| n (Patient) | 73 | 69 | 72 | 70 | 71 | 71 |

UO only

|  |  |  |  |  |  |  |
|---|---|---|---|---|---|---|
| Median | 72.2 | 109 | 72.2 | 109 | 75.9 | 109 |
| Average | 259 | 422 | 249 | 415 | 258 | 406 |
| Stdev | 447 | 757 | 422 | 746 | 427 | 733 |
| p (t-test) |  | 0.14 |  | 0.13 |  | 0.17 |
| Min | 0.259 | 5.59 | 0.259 | 2.91 | 0.259 | 2.91 |
| Max | 2160 | 3600 | 2160 | 3600 | 2160 | 3600 |
| n (Patient) | 74 | 45 | 68 | 51 | 67 | 53 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.72 | 0.71 | 0.62 | 0.71 | 0.72 | 0.61 | 0.72 | 0.73 | 0.60 |
| SE | 0.043 | 0.043 | 0.054 | 0.043 | 0.043 | 0.053 | 0.042 | 0.042 | 0.052 |
| p Value | 3.4E-7 | 9.8E-7 | 0.032 | 1.0E-6 | 3.0E-7 | 0.046 | 8.3E-8 | 4.5E-8 | 0.061 |
| nCohort Recovered | 71 | 73 | 74 | 67 | 72 | 68 | 64 | 71 | 67 |
| nCohort Non-recovered | 71 | 69 | 45 | 75 | 70 | 51 | 78 | 71 | 53 |
| Cutoff Quartile 2 | 17.4 | 17.4 | 25.6 | 17.4 | 17.4 | 25.6 | 17.4 | 17.4 | 25.8 |
| Sensitivity | 87% | 87% | 84% | 85% | 87% | 82% | 86% | 87% | 83% |
| Specificity | 38% | 37% | 31% | 37% | 38% | 31% | 39% | 38% | 31% |
| Cutoff Quartile 3 | 80.9 | 80.9 | 87.9 | 80.9 | 80.9 | 87.9 | 80.9 | 80.9 | 90.6 |
| Sensitivity | 66% | 67% | 58% | 65% | 67% | 57% | 65% | 68% | 57% |
| Specificity | 66% | 66% | 54% | 67% | 67% | 54% | 69% | 68% | 55% |
| Cutoff Quartile 4 | 332 | 332 | 364 | 332 | 332 | 364 | 332 | 332 | 369 |
| Sensitivity | 38% | 38% | 29% | 37% | 39% | 27% | 37% | 39% | 26% |
| Specificity | 87% | 86% | 77% | 88% | 88% | 76% | 89% | 89% | 76% |
| OR Quartile 2 | 4.23 | 3.91 | 2.45 | 3.46 | 4.07 | 2.09 | 3.90 | 4.23 | 2.23 |
| p Value | 8.6E-4 | 0.0016 | 0.063 | 0.0026 | 0.0012 | 0.10 | 0.0010 | 8.6E-4 | 0.075 |
| Lower limit of 95% CI | 1.81 | 1.68 | 0.952 | 1.54 | 1.74 | 0.861 | 1.73 | 1.81 | 0.922 |
| Upper limit of 95% CI | 9.87 | 9.12 | 6.30 | 7.78 | 9.49 | 5.05 | 8.79 | 9.87 | 5.40 |
| OR Quartile 3 | 3.84 | 3.84 | 1.61 | 3.85 | 4.09 | 1.57 | 4.16 | 4.36 | 1.61 |
| p Value | 1.5E-4 | 1.5E-4 | 0.21 | 1.5E-4 | 7.9E-5 | 0.22 | 7.5E-5 | 4.1E-5 | 0.20 |
| Lower limit of 95% CI | 1.91 | 1.91 | 0.762 | 1.92 | 2.03 | 0.757 | 2.05 | 2.16 | 0.778 |
| Upper limit of 95% CI | 7.69 | 7.70 | 3.40 | 7.74 | 8.22 | 3.27 | 8.41 | 8.80 | 3.32 |
| OR Quartile 4 | 4.23 | 3.81 | 1.36 | 4.39 | 4.40 | 1.23 | 4.82 | 5.13 | 1.14 |
| p Value | 8.6E-4 | 0.0015 | 0.47 | 9.0E-4 | 6.2E-4 | 0.63 | 7.0E-4 | 2.6E-4 | 0.75 |
| Lower limit of 95% CI | 1.81 | 1.67 | 0.587 | 1.83 | 1.88 | 0.535 | 1.94 | 2.14 | 0.499 |
| Upper limit of 95% CI | 9.87 | 8.70 | 3.16 | 10.5 | 10.3 | 2.83 | 12.0 | 12.3 | 2.62 |

TABLE 13.5

Comparison of marker levels and the area under the ROC curve (AUC) in urine samples for the "recovered" and "non-recovered" cohorts where recovery starts within 7 days after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort | sCr or UO

|  |  |  |  |  |  |  |
|---|---|---|---|---|---|---|
| Median | 40.8 | 118 | 44.2 | 117 | 40.8 | 118 |
| Average | 203 | 409 | 205 | 402 | 206 | 398 |
| Stdev | 383 | 708 | 384 | 703 | 386 | 698 |
| p (t-test) |  | 0.022 |  | 0.029 |  | 0.032 |
| Min | 0.259 | 5.59 | 0.259 | 2.91 | 0.259 | 2.91 |
| Max | 2160 | 3600 | 2160 | 3600 | 2160 | 3600 |
| n (Patient) | 93 | 56 | 92 | 57 | 91 | 58 |

TABLE 13.5-continued

Comparison of marker levels and the area under the ROC curve (AUC) in urine samples for the "recovered" and "non-recovered" cohorts where recovery starts within 7 days after sample collection and renal status is assessed by serum creatinine (sCr) only, urine output (UO) only, or serum creatinine or urine output RIFLE criteria.

| | sCr only | | | | | |
|---|---|---|---|---|---|---|
| Median | 38.1 | 123 | 38.1 | 123 | 38.1 | 123 |
| Average | 149 | 446 | 149 | 446 | 149 | 446 |
| Stdev | 312 | 694 | 312 | 694 | 312 | 694 |
| p (t-test) | | 6.5E−4 | | 6.5E−4 | | 6.5E−4 |
| Min | 0.259 | 0.723 | 0.259 | 0.723 | 0.259 | 0.723 |
| Max | 2160 | 3600 | 2160 | 3600 | 2160 | 3600 |
| n (Patient) | 83 | 66 | 83 | 66 | 83 | 66 |

| | UO only | | | | | |
|---|---|---|---|---|---|---|
| Median | 58.9 | 118 | 58.9 | 118 | 58.9 | 118 |
| Average | 208 | 437 | 208 | 437 | 211 | 423 |
| Stdev | 373 | 757 | 373 | 757 | 377 | 745 |
| p (t-test) | | 0.014 | | 0.014 | | 0.022 |
| Min | 0.259 | 3.55 | 0.259 | 3.55 | 0.259 | 2.91 |
| Max | 2160 | 3600 | 2160 | 3600 | 2160 | 3600 |
| n (Patient) | 100 | 48 | 100 | 48 | 98 | 50 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.72 | 0.64 | 0.66 | 0.72 | 0.64 | 0.66 | 0.72 | 0.63 |
| SE | 0.047 | 0.043 | 0.050 | 0.047 | 0.043 | 0.050 | 0.047 | 0.043 | 0.050 |
| p Value | 2.1E−4 | 4.0E−7 | 0.0065 | 6.7E−4 | 4.0E−7 | 0.0065 | 4.5E−4 | 4.0E−7 | 0.012 |
| nCohort Recovered | 93 | 83 | 100 | 92 | 83 | 100 | 91 | 83 | 98 |
| nCohort Non-recovered | 56 | 66 | 48 | 57 | 66 | 48 | 58 | 66 | 50 |
| Cutoff Quartile 2 | 17.2 | 17.2 | 17.6 | 17.2 | 17.2 | 17.6 | 17.2 | 17.2 | 17.6 |
| Sensitivity | 88% | 88% | 85% | 86% | 88% | 85% | 86% | 88% | 84% |
| Specificity | 32% | 35% | 30% | 32% | 35% | 30% | 32% | 35% | 30% |
| Cutoff Quartile 3 | 78.3 | 78.3 | 80.9 | 78.3 | 78.3 | 80.9 | 78.3 | 78.3 | 80.9 |
| Sensitivity | 68% | 68% | 62% | 67% | 68% | 62% | 67% | 68% | 62% |
| Specificity | 60% | 64% | 56% | 60% | 64% | 56% | 60% | 64% | 56% |
| Cutoff Quartile 4 | 331 | 331 | 331 | 331 | 331 | 331 | 331 | 331 | 331 |
| Sensitivity | 34% | 39% | 33% | 33% | 39% | 33% | 33% | 39% | 32% |
| Specificity | 80% | 86% | 79% | 79% | 86% | 79% | 79% | 86% | 79% |
| OR Quartile 2 | 3.33 | 3.89 | 2.51 | 2.82 | 3.89 | 2.51 | 2.92 | 3.89 | 2.21 |
| p Value | 0.0090 | 0.0021 | 0.047 | 0.019 | 0.0021 | 0.047 | 0.015 | 0.0021 | 0.075 |
| Lower limit of 95% CI | 1.35 | 1.64 | 1.01 | 1.18 | 1.64 | 1.01 | 1.23 | 1.64 | 0.923 |
| Upper limit of 95% CI | 8.23 | 9.26 | 6.23 | 6.71 | 9.26 | 6.23 | 6.96 | 9.26 | 5.28 |
| OR Quartile 3 | 3.20 | 3.79 | 2.12 | 2.97 | 3.79 | 2.12 | 3.14 | 3.79 | 2.09 |
| p Value | 0.0011 | 1.4E−4 | 0.037 | 0.0020 | 1.4E−4 | 0.037 | 0.0012 | 1.4E−4 | 0.038 |
| Lower limit of 95% CI | 1.59 | 1.91 | 1.05 | 1.49 | 1.91 | 1.05 | 1.57 | 1.91 | 1.04 |
| Upper limit of 95% CI | 6.42 | 7.51 | 4.29 | 5.93 | 7.51 | 4.29 | 6.26 | 7.51 | 4.19 |
| OR Quartile 4 | 2.00 | 3.85 | 1.88 | 1.92 | 3.85 | 1.88 | 1.85 | 3.85 | 1.73 |
| p Value | 0.069 | 7.8E−4 | 0.11 | 0.087 | 7.8E−4 | 0.11 | 0.11 | 7.8E−4 | 0.16 |
| Lower limit of 95% CI | 0.946 | 1.75 | 0.872 | 0.910 | 1.75 | 0.872 | 0.876 | 1.75 | 0.803 |
| Upper limit of 95% CI | 4.23 | 8.44 | 4.06 | 4.05 | 8.44 | 4.06 | 3.89 | 8.44 | 3.71 |

Example 14. Use of Insulin-Like Growth Factor-Binding Protein 2 for Evaluating Renal Status in Patients Admitted to the ICU: Persistent at RIFLE F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 2 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is failure (F) where the persistence period can start from the time of sample collection to 24, 48, 72, 96 or 168 hours after sample collection. "Non-persistent" indicates those patients who are not persistent at failure (F) and whose minimum RIFLE stage during a period of 24, 48 or 72 hours is non-injury (RIFLE 0), risk of injury (R), or injury (I) where the persistence period can start from the time of sample collection to 24, 48, 72, 96 or 168 hours after sample collection. If a patient dies after failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 14.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 3.47 | 15.6 | 3.49 | 15.6 | 3.53 | 11.3 |
| Average | 12.3 | 25.4 | 12.9 | 26.3 | 14.9 | 22.7 |
| Stdev | 21.5 | 31.8 | 22.2 | 32.4 | 25.0 | 29.1 |
| p (t-test) | | 0.0033 | | 0.0043 | | 0.12 |
| Min | 3.16E−5 | 0.0645 | 3.16E−5 | 0.0645 | 3.16E−5 | 0.0645 |
| Max | 111 | 112 | 111 | 112 | 111 | 112 |
| n (Patient) | 98 | 51 | 106 | 43 | 113 | 36 |
| | sCr only | | | | | |
| Median | 3.47 | 14.5 | 3.52 | 15.6 | 3.55 | 11.3 |
| Average | 12.4 | 24.9 | 12.9 | 26.3 | 15.0 | 22.0 |
| Stdev | 21.6 | 31.7 | 22.2 | 32.4 | 25.2 | 28.6 |
| p (t-test) | | 0.0049 | | 0.0042 | | 0.16 |
| Min | 3.16E−5 | 0.0645 | 3.16E−5 | 0.0645 | 3.16E−5 | 0.0645 |
| Max | 111 | 112 | 111 | 112 | 111 | 112 |
| n (Patient) | 97 | 52 | 106 | 43 | 111 | 38 |
| | UO only | | | | | |
| Median | 3.75 | 17.2 | 3.55 | 21.0 | 3.55 | 21.0 |
| Average | 15.9 | 23.7 | 15.8 | 24.9 | 15.8 | 24.9 |
| Stdev | 26.1 | 26.8 | 26.0 | 27.1 | 26.0 | 27.1 |
| p (t-test) | | 0.24 | | 0.18 | | 0.18 |
| Min | 3.16E−5 | 0.0645 | 3.16E−5 | 0.0645 | 3.16E−5 | 0.0645 |
| Max | 111 | 112 | 111 | 112 | 111 | 112 |
| n (Patient) | 130 | 18 | 131 | 17 | 131 | 17 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.62 | 0.68 | 0.65 | 0.63 | 0.70 | 0.61 | 0.59 | 0.70 |
| SE | 0.049 | 0.049 | 0.073 | 0.052 | 0.052 | 0.074 | 0.056 | 0.055 | 0.074 |
| p Value | 0.0050 | 0.012 | 0.012 | 0.0045 | 0.011 | 0.0078 | 0.044 | 0.098 | 0.0078 |
| nCohort Non-persistent | 98 | 97 | 130 | 106 | 106 | 131 | 113 | 111 | 131 |
| nCohort Persistent | 51 | 52 | 18 | 43 | 43 | 17 | 36 | 38 | 17 |
| Cutoff Quartile 2 | 1.89 | 1.89 | 1.93 | 1.89 | 1.89 | 1.93 | 1.89 | 1.89 | 1.93 |
| Sensitivity | 76% | 75% | 94% | 79% | 77% | 94% | 78% | 74% | 94% |
| Specificity | 26% | 25% | 28% | 26% | 25% | 27% | 26% | 24% | 27% |
| Cutoff Quartile 3 | 4.13 | 4.13 | 4.52 | 4.13 | 4.13 | 4.52 | 4.13 | 4.13 | 4.52 |
| Sensitivity | 65% | 63% | 78% | 65% | 63% | 82% | 64% | 61% | 82% |
| Specificity | 57% | 57% | 54% | 56% | 55% | 54% | 54% | 53% | 54% |
| Cutoff Quartile 4 | 20.0 | 20.0 | 20.2 | 20.0 | 20.0 | 20.2 | 20.0 | 20.0 | 20.2 |
| Sensitivity | 43% | 42% | 50% | 44% | 47% | 53% | 42% | 42% | 53% |
| Specificity | 84% | 84% | 78% | 82% | 83% | 79% | 80% | 80% | 79% |
| OR Quartile 2 | 1.11 | 0.986 | 6.51 | 1.36 | 1.13 | 6.06 | 1.21 | 0.900 | 6.06 |
| p Value | 0.79 | 0.97 | 0.074 | 0.48 | 0.78 | 0.086 | 0.68 | 0.81 | 0.086 |
| Lower limit of 95% CI | 0.505 | 0.453 | 0.836 | 0.578 | 0.491 | 0.776 | 0.495 | 0.388 | 0.776 |
| Upper limit of 95% CI | 2.45 | 2.15 | 50.7 | 3.18 | 2.59 | 47.4 | 2.95 | 2.09 | 47.4 |
| OR Quartile 3 | 2.44 | 2.27 | 4.08 | 2.34 | 2.04 | 5.52 | 2.08 | 1.74 | 5.52 |
| p Value | 0.012 | 0.020 | 0.018 | 0.023 | 0.055 | 0.0096 | 0.065 | 0.15 | 0.0096 |
| Lower limit of 95% CI | 1.21 | 1.14 | 1.28 | 1.12 | 0.986 | 1.51 | 0.957 | 0.822 | 1.51 |
| Upper limit of 95% CI | 4.92 | 4.55 | 13.1 | 4.89 | 4.22 | 20.1 | 4.50 | 3.68 | 20.1 |
| OR Quartile 4 | 3.89 | 3.71 | 3.64 | 3.62 | 4.25 | 4.14 | 2.80 | 2.94 | 4.14 |
| p Value | 5.5E−4 | 8.2E−4 | 0.012 | 0.0012 | 3.0E−4 | 0.0074 | 0.012 | 0.0078 | 0.0074 |
| Lower limit of 95% CI | 1.80 | 1.72 | 1.32 | 1.66 | 1.94 | 1.46 | 1.25 | 1.33 | 1.46 |
| Upper limit of 95% CI | 8.40 | 8.00 | 10.0 | 7.91 | 9.32 | 11.7 | 6.25 | 6.52 | 11.7 |

TABLE 14.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 3.15 | 10.8 | 3.19 | 13.4 | 3.47 | 10.2 |
| Average | 12.5 | 23.4 | 12.9 | 24.2 | 15.1 | 20.7 |
| Stdev | 22.2 | 30.4 | 22.9 | 30.3 | 25.8 | 26.9 |
| p (t-test) | | 0.013 | | 0.012 | | 0.23 |
| Min | 3.16E−5 | 0.0532 | 3.16E−5 | 0.0645 | 3.16E−5 | 0.0645 |
| Max | 111 | 112 | 111 | 112 | 111 | 112 |
| n (Patient) | 91 | 58 | 98 | 51 | 105 | 44 |
| sCr only | | | | | | |
| Median | 3.24 | 10.8 | 3.24 | 12.4 | 3.47 | 9.73 |
| Average | 12.6 | 23.3 | 13.0 | 23.8 | 15.3 | 19.9 |
| Stdev | 22.2 | 30.5 | 23.0 | 30.2 | 26.0 | 26.5 |
| p (t-test) | | 0.014 | | 0.016 | | 0.32 |
| Min | 3.16E−5 | 0.0532 | 3.16E−5 | 0.0645 | 3.16E−5 | 0.0645 |
| Max | 111 | 112 | 111 | 112 | 111 | 112 |
| n (Patient) | 91 | 58 | 97 | 52 | 103 | 46 |
| UO only | | | | | | |
| Median | 3.55 | 11.3 | 3.53 | 12.4 | 3.53 | 12.4 |
| Average | 16.3 | 19.8 | 16.2 | 20.5 | 16.2 | 20.5 |
| Stdev | 26.7 | 23.9 | 26.6 | 24.2 | 26.6 | 24.2 |
| p (t-test) | | 0.54 | | 0.46 | | 0.46 |
| Min | 3.16E−5 | 0.0645 | 3.16E−5 | 0.0645 | 3.16E−5 | 0.0645 |
| Max | 111 | 112 | 111 | 112 | 111 | 112 |
| n (Patient) | 123 | 25 | 124 | 24 | 124 | 24 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.62 | 0.64 | 0.65 | 0.64 | 0.65 | 0.62 | 0.60 | 0.65 |
| SE | 0.047 | 0.048 | 0.064 | 0.049 | 0.049 | 0.065 | 0.052 | 0.051 | 0.065 |
| p Value | 0.0049 | 0.013 | 0.029 | 0.0014 | 0.0035 | 0.023 | 0.022 | 0.064 | 0.023 |
| nCohort Non-persistent | 91 | 91 | 123 | 98 | 97 | 124 | 105 | 103 | 124 |
| nCohort Persistent | 58 | 58 | 25 | 51 | 52 | 24 | 44 | 46 | 24 |
| Cutoff Quartile 2 | 1.89 | 1.89 | 1.93 | 1.89 | 1.89 | 1.93 | 1.89 | 1.89 | 1.93 |
| Sensitivity | 78% | 76% | 88% | 80% | 79% | 88% | 80% | 76% | 88% |
| Specificity | 26% | 25% | 28% | 28% | 27% | 27% | 27% | 25% | 27% |
| Cutoff Quartile 3 | 4.13 | 4.13 | 4.52 | 4.13 | 4.13 | 4.52 | 4.13 | 4.13 | 4.52 |
| Sensitivity | 66% | 64% | 72% | 67% | 65% | 75% | 66% | 63% | 75% |
| Specificity | 59% | 58% | 54% | 58% | 58% | 55% | 56% | 55% | 55% |
| Cutoff Quartile 4 | 20.0 | 20.0 | 20.2 | 20.0 | 20.0 | 20.2 | 20.0 | 20.0 | 20.2 |
| Sensitivity | 40% | 40% | 40% | 43% | 42% | 42% | 39% | 37% | 42% |
| Specificity | 84% | 84% | 78% | 84% | 84% | 78% | 80% | 80% | 78% |
| OR Quartile 2 | 1.24 | 1.06 | 2.80 | 1.56 | 1.36 | 2.64 | 1.41 | 1.07 | 2.64 |
| p Value | 0.59 | 0.88 | 0.11 | 0.29 | 0.45 | 0.13 | 0.42 | 0.86 | 0.13 |
| Lower limit of 95% CI | 0.572 | 0.495 | 0.787 | 0.686 | 0.611 | 0.741 | 0.604 | 0.478 | 0.741 |
| Upper limit of 95% CI | 2.69 | 2.28 | 9.97 | 3.54 | 3.05 | 9.44 | 3.31 | 2.42 | 9.44 |
| OR Quartile 3 | 2.77 | 2.46 | 3.08 | 2.78 | 2.58 | 3.64 | 2.48 | 2.11 | 3.64 |
| p Value | 0.0035 | 0.0094 | 0.019 | 0.0046 | 0.0079 | 0.010 | 0.015 | 0.040 | 0.010 |
| Lower limit of 95% CI | 1.40 | 1.25 | 1.20 | 1.37 | 1.28 | 1.35 | 1.19 | 1.04 | 1.35 |
| Upper limit of 95% CI | 5.50 | 4.84 | 7.89 | 5.64 | 5.19 | 9.80 | 5.16 | 4.32 | 9.80 |
| OR Quartile 4 | 3.33 | 3.33 | 2.37 | 3.89 | 3.71 | 2.57 | 2.52 | 2.29 | 2.57 |
| p Value | 0.0020 | 0.0020 | 0.062 | 5.5E−4 | 8.2E−4 | 0.044 | 0.019 | 0.034 | 0.044 |
| Lower limit of 95% CI | 1.55 | 1.55 | 0.957 | 1.80 | 1.72 | 1.03 | 1.16 | 1.06 | 1.03 |
| Upper limit of 95% CI | 7.15 | 7.15 | 5.87 | 8.40 | 8.00 | 6.42 | 5.45 | 4.93 | 6.42 |

TABLE 14.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 3.09 | 10.3 | 2.97 | 13.4 | 3.19 | 10.3 |
| Average | 11.6 | 23.8 | 11.1 | 25.3 | 14.6 | 21.0 |
| Stdev | 20.2 | 31.4 | 19.9 | 31.9 | 25.4 | 27.4 |
| p (t-test) | | 0.0044 | | 0.0010 | | 0.16 |
| Min | 3.16E−5 | 0.0532 | 3.16E−5 | 0.0645 | 3.16E−5 | 0.0645 |
| Max | 111 | 112 | 111 | 112 | 111 | 112 |
| n (Patient) | 86 | 63 | 90 | 59 | 98 | 51 |
| | sCr only | | | | | |
| Median | 3.15 | 9.73 | 3.09 | 11.3 | 3.47 | 8.85 |
| Average | 11.7 | 23.5 | 11.4 | 25.0 | 14.9 | 20.1 |
| Stdev | 20.3 | 31.3 | 19.9 | 32.0 | 25.4 | 27.4 |
| p (t-test) | | 0.0062 | | 0.0017 | | 0.25 |
| Min | 3.16E−5 | 0.0532 | 3.16E−5 | 0.0645 | 3.16E−5 | 0.0645 |
| Max | 111 | 112 | 111 | 112 | 111 | 112 |
| n (Patient) | 85 | 64 | 90 | 59 | 97 | 52 |
| | UO only | | | | | |
| Median | 3.49 | 12.4 | 3.50 | 13.4 | 3.50 | 13.4 |
| Average | 15.7 | 21.2 | 15.6 | 21.8 | 15.6 | 21.8 |
| Stdev | 26.4 | 25.7 | 26.3 | 25.9 | 26.3 | 25.9 |
| p (t-test) | | 0.29 | | 0.24 | | 0.24 |
| Min | 3.16E−5 | 0.0645 | 3.16E−5 | 0.0645 | 3.16E−5 | 0.0645 |
| Max | 111 | 112 | 111 | 112 | 111 | 112 |
| n (Patient) | 116 | 32 | 117 | 31 | 117 | 31 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.63 | 0.65 | 0.68 | 0.66 | 0.66 | 0.63 | 0.60 | 0.66 |
| SE | 0.046 | 0.047 | 0.058 | 0.046 | 0.047 | 0.058 | 0.049 | 0.050 | 0.058 |
| p Value | 0.0027 | 0.0067 | 0.0089 | 1.1E−4 | 7.7E−4 | 0.0070 | 0.0087 | 0.047 | 0.0070 |
| nCohort Non-persistent | 86 | 85 | 116 | 90 | 90 | 117 | 98 | 97 | 117 |
| nCohort Persistent | 63 | 64 | 32 | 59 | 59 | 31 | 51 | 52 | 31 |
| Cutoff Quartile 2 | 1.89 | 1.89 | 1.93 | 1.89 | 1.89 | 1.93 | 1.89 | 1.89 | 1.93 |
| Sensitivity | 76% | 75% | 84% | 80% | 78% | 84% | 78% | 75% | 84% |
| Specificity | 26% | 25% | 28% | 28% | 27% | 27% | 27% | 25% | 27% |
| Cutoff Quartile 3 | 4.13 | 4.13 | 4.52 | 4.13 | 4.13 | 4.52 | 4.13 | 4.13 | 4.52 |
| Sensitivity | 65% | 64% | 72% | 68% | 66% | 74% | 67% | 63% | 74% |
| Specificity | 60% | 60% | 56% | 61% | 60% | 56% | 58% | 57% | 56% |
| Cutoff Quartile 4 | 20.0 | 20.0 | 20.2 | 20.0 | 20.0 | 20.2 | 20.0 | 20.0 | 20.2 |
| Sensitivity | 40% | 39% | 41% | 42% | 41% | 42% | 37% | 35% | 42% |
| Specificity | 85% | 85% | 79% | 86% | 84% | 79% | 81% | 79% | 79% |
| OR Quartile 2 | 1.10 | 0.984 | 2.06 | 1.51 | 1.29 | 1.96 | 1.31 | 0.986 | 1.96 |
| p Value | 0.80 | 0.97 | 0.17 | 0.31 | 0.52 | 0.21 | 0.51 | 0.97 | 0.21 |
| Lower limit of 95% CI | 0.517 | 0.465 | 0.729 | 0.688 | 0.594 | 0.692 | 0.588 | 0.453 | 0.692 |
| Upper limit of 95% CI | 2.34 | 2.08 | 5.81 | 3.30 | 2.79 | 5.54 | 2.93 | 2.15 | 5.54 |
| OR Quartile 3 | 2.85 | 2.67 | 3.26 | 3.31 | 2.92 | 3.72 | 2.78 | 2.27 | 3.72 |
| p Value | 0.0023 | 0.0040 | 0.0067 | 6.9E−4 | 0.0021 | 0.0036 | 0.0046 | 0.020 | 0.0036 |
| Lower limit of 95% CI | 1.45 | 1.37 | 1.39 | 1.66 | 1.48 | 1.54 | 1.37 | 1.14 | 1.54 |
| Upper limit of 95% CI | 5.60 | 5.23 | 7.65 | 6.60 | 5.80 | 9.00 | 5.64 | 4.55 | 9.00 |
| OR Quartile 4 | 3.69 | 3.55 | 2.62 | 4.36 | 3.72 | 2.80 | 2.47 | 2.04 | 2.80 |
| p Value | 9.7E−4 | 0.0014 | 0.024 | 2.3E−4 | 8.4E−4 | 0.017 | 0.019 | 0.064 | 0.017 |
| Lower limit of 95% CI | 1.70 | 1.64 | 1.14 | 1.99 | 1.72 | 1.20 | 1.16 | 0.959 | 1.20 |
| Upper limit of 95% CI | 8.03 | 7.71 | 6.05 | 9.52 | 8.05 | 6.50 | 5.26 | 4.33 | 6.50 |

TABLE 14.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 3.03 | 10.8 | 2.97 | 13.4 | 3.19 | 10.3 |
| Average | 11.2 | 24.2 | 11.1 | 25.3 | 14.1 | 21.6 |
| Stdev | 20.0 | 31.3 | 19.9 | 31.9 | 24.9 | 27.9 |
| p (t-test) | | 0.0024 | | 0.0010 | | 0.094 |
| Min | 3.16E−5 | 0.0532 | 3.16E−5 | 0.0645 | 3.16E−5 | 0.0645 |
| Max | 111 | 112 | 111 | 112 | 111 | 112 |
| n (Patient) | 85 | 64 | 90 | 59 | 96 | 53 |
| sCr only | | | | | | |
| Median | 3.15 | 9.73 | 3.03 | 12.4 | 3.24 | 9.73 |
| Average | 11.7 | 23.5 | 11.3 | 24.9 | 14.2 | 21.2 |
| Stdev | 20.3 | 31.3 | 20.0 | 31.8 | 25.0 | 27.8 |
| p (t-test) | | 0.0062 | | 0.0015 | | 0.12 |
| Min | 3.16E−5 | 0.0532 | 3.16E−5 | 0.0645 | 3.16E−5 | 0.0645 |
| Max | 111 | 112 | 111 | 112 | 111 | 112 |
| n (Patient) | 85 | 64 | 89 | 60 | 95 | 54 |
| UO only | | | | | | |
| Median | 3.35 | 12.4 | 3.47 | 12.4 | 3.47 | 12.4 |
| Average | 14.8 | 23.3 | 15.0 | 23.2 | 15.0 | 23.2 |
| Stdev | 25.3 | 28.4 | 25.3 | 28.7 | 25.3 | 28.7 |
| p (t-test) | | 0.090 | | 0.11 | | 0.11 |
| Min | 3.16E−5 | 0.0645 | 3.16E−5 | 0.0645 | 3.16E−5 | 0.0645 |
| Max | 111 | 112 | 111 | 112 | 111 | 112 |
| n (Patient) | 112 | 36 | 114 | 34 | 114 | 34 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.63 | 0.67 | 0.68 | 0.66 | 0.67 | 0.63 | 0.62 | 0.67 |
| SE | 0.046 | 0.047 | 0.054 | 0.046 | 0.046 | 0.056 | 0.049 | 0.049 | 0.056 |
| p Value | 0.0011 | 0.0067 | 0.0017 | 1.1E−4 | 3.8E−4 | 0.0031 | 0.0067 | 0.016 | 0.0031 |
| nCohort Non-persistent | 85 | 85 | 112 | 90 | 89 | 114 | 96 | 95 | 114 |
| nCohort Persistent | 64 | 64 | 36 | 59 | 60 | 34 | 53 | 54 | 34 |
| Cutoff Quartile 2 | 1.89 | 1.89 | 1.93 | 1.89 | 1.89 | 1.93 | 1.89 | 1.89 | 1.93 |
| Sensitivity | 77% | 75% | 86% | 80% | 78% | 85% | 77% | 76% | 85% |
| Specificity | 26% | 25% | 29% | 28% | 27% | 28% | 26% | 25% | 28% |
| Cutoff Quartile 3 | 4.13 | 4.13 | 4.52 | 4.13 | 4.13 | 4.52 | 4.13 | 4.13 | 4.52 |
| Sensitivity | 66% | 64% | 72% | 68% | 67% | 74% | 66% | 65% | 74% |
| Specificity | 61% | 60% | 57% | 61% | 61% | 57% | 58% | 58% | 57% |
| Cutoff Quartile 4 | 20.0 | 20.0 | 20.2 | 20.0 | 20.0 | 20.2 | 20.0 | 20.0 | 20.2 |
| Sensitivity | 41% | 39% | 42% | 42% | 42% | 41% | 38% | 37% | 41% |
| Specificity | 86% | 85% | 80% | 86% | 85% | 80% | 81% | 81% | 80% |
| OR Quartile 2 | 1.14 | 0.984 | 2.48 | 1.51 | 1.33 | 2.26 | 1.20 | 1.07 | 2.26 |
| p Value | 0.73 | 0.97 | 0.084 | 0.31 | 0.46 | 0.12 | 0.65 | 0.87 | 0.12 |
| Lower limit of 95% CI | 0.536 | 0.465 | 0.886 | 0.688 | 0.617 | 0.805 | 0.547 | 0.490 | 0.805 |
| Upper limit of 95% CI | 2.43 | 2.08 | 6.94 | 3.30 | 2.89 | 6.36 | 2.65 | 2.32 | 6.36 |
| OR Quartile 3 | 3.01 | 2.67 | 3.47 | 3.31 | 3.09 | 3.68 | 2.72 | 2.53 | 3.68 |
| p Value | 0.0014 | 0.0040 | 0.0030 | 6.9E−4 | 0.0013 | 0.0026 | 0.0049 | 0.0084 | 0.0026 |
| Lower limit of 95% CI | 1.53 | 1.37 | 1.53 | 1.66 | 1.56 | 1.58 | 1.35 | 1.27 | 1.58 |
| Upper limit of 95% CI | 5.91 | 5.23 | 7.87 | 6.60 | 6.12 | 8.60 | 5.47 | 5.06 | 8.60 |
| OR Quartile 4 | 4.16 | 3.55 | 2.92 | 4.36 | 4.18 | 2.77 | 2.63 | 2.52 | 2.77 |
| p Value | 3.9E−4 | 0.0014 | 0.0095 | 2.3E−4 | 3.3E−4 | 0.015 | 0.012 | 0.016 | 0.015 |
| Lower limit of 95% CI | 1.89 | 1.64 | 1.30 | 1.99 | 1.91 | 1.22 | 1.23 | 1.18 | 1.22 |
| Upper limit of 95% CI | 9.16 | 7.71 | 6.57 | 9.52 | 9.12 | 6.30 | 5.59 | 5.35 | 6.30 |

TABLE 14.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 2.97 | 11.3 | 2.85 | 15.6 | 3.15 | 10.8 |
| Average | 10.3 | 24.7 | 9.85 | 26.2 | 13.9 | 21.6 |
| Stdev | 18.3 | 31.8 | 17.9 | 32.2 | 25.0 | 27.5 |
| p (t-test) | | 6.6E−4 | | 1.2E−4 | | 0.081 |
| Min | 3.16E−5 | 0.0532 | 3.16E−5 | 0.0645 | 3.16E−5 | 0.0645 |
| Max | 111 | 112 | 111 | 112 | 111 | 112 |
| n (Patient) | 82 | 67 | 86 | 63 | 93 | 56 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 3.03 | 10.8 | 2.91 | 14.5 | 3.15 | 10.8 |
| Average | 10.7 | 24.4 | 10.3 | 25.9 | 13.4 | 22.4 |
| Stdev | 18.6 | 31.9 | 18.2 | 32.4 | 23.9 | 28.9 |
| p (t-test) | | 0.0013 | | 2.6E−4 | | 0.042 |
| Min | 3.16E−5 | 0.0532 | 3.16E−5 | 0.0645 | 3.16E−5 | 0.0645 |
| Max | 111 | 112 | 111 | 112 | 111 | 112 |
| n (Patient) | 83 | 66 | 87 | 62 | 93 | 56 |

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 3.24 | 13.4 | 3.35 | 14.5 | 3.35 | 14.5 |
| Average | 14.7 | 23.2 | 14.6 | 23.8 | 14.6 | 23.8 |
| Stdev | 25.4 | 28.0 | 25.3 | 28.2 | 25.3 | 28.2 |
| p (t-test) | | 0.089 | | 0.069 | | 0.069 |
| Min | 3.16E−5 | 0.0645 | 3.16E−5 | 0.0645 | 3.16E−5 | 0.0645 |
| Max | 111 | 112 | 111 | 112 | 111 | 112 |
| n (Patient) | 111 | 37 | 112 | 36 | 112 | 36 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.65 | 0.64 | 0.68 | 0.69 | 0.68 | 0.68 | 0.63 | 0.64 | 0.68 |
| SE | 0.045 | 0.046 | 0.054 | 0.045 | 0.045 | 0.054 | 0.048 | 0.048 | 0.054 |
| p Value | 6.8E−4 | 0.0017 | 9.7E−4 | 1.8E−5 | 6.2E−5 | 7.3E−4 | 0.0052 | 0.0047 | 7.3E−4 |
| nCohort Non-persistent | 82 | 83 | 111 | 86 | 87 | 112 | 93 | 93 | 112 |
| nCohort Persistent | 67 | 66 | 37 | 63 | 62 | 36 | 56 | 56 | 36 |
| Cutoff Quartile 2 | 1.89 | 1.89 | 1.93 | 1.89 | 1.89 | 1.93 | 1.89 | 1.89 | 1.93 |
| Sensitivity | 76% | 76% | 86% | 79% | 79% | 86% | 77% | 77% | 86% |
| Specificity | 26% | 25% | 29% | 28% | 28% | 29% | 26% | 26% | 29% |
| Cutoff Quartile 3 | 4.13 | 4.13 | 4.52 | 4.13 | 4.13 | 4.52 | 4.13 | 4.13 | 4.52 |
| Sensitivity | 66% | 65% | 73% | 68% | 68% | 75% | 66% | 66% | 75% |
| Specificity | 62% | 61% | 58% | 63% | 62% | 58% | 59% | 59% | 58% |
| Cutoff Quartile 4 | 20.0 | 20.0 | 20.2 | 20.0 | 20.0 | 20.2 | 20.0 | 20.0 | 20.2 |
| Sensitivity | 40% | 39% | 41% | 43% | 42% | 42% | 38% | 38% | 42% |
| Specificity | 87% | 86% | 80% | 87% | 86% | 80% | 82% | 82% | 80% |
| OR Quartile 2 | 1.10 | 1.06 | 2.59 | 1.49 | 1.44 | 2.48 | 1.15 | 1.15 | 2.48 |
| p Value | 0.81 | 0.88 | 0.069 | 0.31 | 0.36 | 0.084 | 0.72 | 0.72 | 0.084 |
| Lower limit of 95% CI | 0.519 | 0.500 | 0.927 | 0.689 | 0.664 | 0.886 | 0.530 | 0.530 | 0.886 |
| Upper limit of 95% CI | 2.32 | 2.24 | 7.25 | 3.22 | 3.11 | 6.94 | 2.50 | 2.50 | 6.94 |
| OR Quartile 3 | 3.15 | 2.98 | 3.68 | 3.63 | 3.44 | 4.15 | 2.82 | 2.82 | 4.15 |
| p Value | 8.5E−4 | 0.0015 | 0.0018 | 2.4E−4 | 4.2E−4 | 9.3E−4 | 0.0033 | 0.0033 | 9.3E−4 |
| Lower limit of 95% CI | 1.60 | 1.52 | 1.62 | 1.82 | 1.73 | 1.79 | 1.41 | 1.41 | 1.79 |
| Upper limit of 95% CI | 6.17 | 5.84 | 8.33 | 7.22 | 6.83 | 9.64 | 5.62 | 5.62 | 9.64 |
| OR Quartile 4 | 4.36 | 3.85 | 2.76 | 5.11 | 4.51 | 2.92 | 2.68 | 2.68 | 2.92 |
| p Value | 3.2E−4 | 7.8E−4 | 0.014 | 7.2E−5 | 1.9E−4 | 0.0095 | 0.010 | 0.010 | 0.0095 |

TABLE 14.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 1.96 | 1.75 | 1.23 | 2.28 | 2.05 | 1.30 | 1.26 | 1.26 | 1.30 |
| Upper limit of 95% CI | 9.71 | 8.44 | 6.17 | 11.4 | 9.96 | 6.57 | 5.70 | 5.70 | 6.57 |

Example 15. Use of Insulin-Like Growth Factor-Binding Protein 2 for Evaluating Renal Status in Patients Admitted to the ICU: Persistent at RIFLE I or F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 2 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is injury (I) or failure (F) where the persistence period can start from the time of sample collection to 24, 48, 72, 96 or 168 hours after sample collection. "Non-persistent" indicates those patients who are not persistent at injury (I) or failure (F) and whose minimum RIFLE stage during a period of 24, 48 or 72 hours is non-injury (RIFLE 0) or risk of injury (R) where the persistence period can start from the time of sample collection to 24, 48, 72, 96 or 168 hours after sample collection. If a patient dies after injury (I) or failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 15.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 2.31 | 9.57 | 2.97 | 7.04 | 2.97 | 11.3 |
| Average | 6.67 | 22.7 | 9.93 | 24.3 | 9.33 | 27.5 |
| Stdev | 12.6 | 30.0 | 14.8 | 33.1 | 14.1 | 34.7 |
| p (t-test) | | 2.5E−4 | | 7.0E−4 | | 1.9E−5 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 55 | 94 | 78 | 71 | 88 | 61 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 2.35 | 9.57 | 2.97 | 7.04 | 3.03 | 10.8 |
| Average | 7.38 | 22.6 | 10.3 | 23.5 | 9.80 | 27.1 |
| Stdev | 13.4 | 30.2 | 15.4 | 32.7 | 14.6 | 34.9 |
| p (t-test) | | 4.7E−4 | | 0.0019 | | 5.2E−5 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 57 | 92 | 76 | 73 | 89 | 60 |

TABLE 15.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 3.75 | 6.98 | 3.96 | 13.4 | 3.53 | 22.0 |
| Average | 15.1 | 22.7 | 14.7 | 26.4 | 14.3 | 30.6 |
| Stdev | 24.7 | 30.4 | 24.2 | 32.6 | 23.9 | 33.7 |
| p (t-test) | | 0.14 | | 0.037 | | 0.0060 |
| Min | 3.16E−5 | 0.0645 | 3.16E−5 | 0.0645 | 3.16E−5 | 0.0645 |
| Max | 109 | 112 | 109 | 112 | 109 | 112 |
| n (Patient) | 114 | 34 | 121 | 27 | 125 | 23 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.71 | 0.69 | 0.61 | 0.63 | 0.62 | 0.64 | 0.66 | 0.65 | 0.71 |
| SE | 0.042 | 0.043 | 0.057 | 0.046 | 0.046 | 0.062 | 0.046 | 0.047 | 0.064 |
| p Value | 5.6E−7 | 1.7E−5 | 0.050 | 0.0050 | 0.0092 | 0.020 | 4.7E−4 | 0.0013 | 0.0014 |
| nCohort Non-persistent | 55 | 57 | 114 | 78 | 76 | 121 | 88 | 89 | 125 |
| nCohort Persistent | 94 | 92 | 34 | 71 | 73 | 27 | 61 | 60 | 23 |
| Cutoff Quartile 2 | 1.89 | 1.89 | 1.93 | 1.89 | 1.89 | 1.93 | 1.89 | 1.89 | 1.93 |
| Sensitivity | 81% | 79% | 82% | 77% | 77% | 81% | 79% | 78% | 87% |
| Specificity | 35% | 32% | 27% | 27% | 26% | 26% | 27% | 27% | 27% |
| Cutoff Quartile 3 | 4.13 | 4.13 | 4.52 | 4.13 | 4.13 | 4.52 | 4.13 | 4.13 | 4.52 |
| Sensitivity | 63% | 62% | 62% | 59% | 60% | 67% | 64% | 65% | 78% |
| Specificity | 71% | 68% | 54% | 58% | 59% | 54% | 59% | 60% | 55% |
| Cutoff Quartile 4 | 20.0 | 20.0 | 20.2 | 20.0 | 20.0 | 20.2 | 20.0 | 20.0 | 20.2 |
| Sensitivity | 37% | 37% | 41% | 37% | 36% | 48% | 43% | 42% | 57% |
| Specificity | 95% | 93% | 80% | 85% | 84% | 80% | 86% | 85% | 81% |
| OR Quartile 2 | 2.23 | 1.77 | 1.74 | 1.27 | 1.18 | 1.58 | 1.38 | 1.33 | 2.49 |
| p Value | 0.038 | 0.14 | 0.26 | 0.54 | 0.67 | 0.39 | 0.41 | 0.46 | 0.16 |
| Lower limit of 95% CI | 1.05 | 0.835 | 0.658 | 0.599 | 0.558 | 0.553 | 0.640 | 0.617 | 0.695 |
| Upper limit of 95% CI | 4.75 | 3.76 | 4.61 | 2.68 | 2.48 | 4.53 | 3.00 | 2.89 | 8.92 |
| OR Quartile 3 | 4.11 | 3.53 | 1.86 | 1.97 | 2.20 | 2.32 | 2.56 | 2.73 | 4.44 |
| p Value | 1.1E−4 | 4.1E−4 | 0.12 | 0.041 | 0.018 | 0.060 | 0.0062 | 0.0037 | 0.0055 |
| Lower limit of 95% CI | 2.01 | 1.75 | 0.849 | 1.03 | 1.14 | 0.966 | 1.31 | 1.39 | 1.55 |
| Upper limit of 95% CI | 8.41 | 7.10 | 4.07 | 3.79 | 4.24 | 5.58 | 5.02 | 5.39 | 12.7 |
| OR Quartile 4 | 10.3 | 7.77 | 2.77 | 3.18 | 2.95 | 3.75 | 4.70 | 4.18 | 5.47 |
| p Value | 2.2E−4 | 2.6E−4 | 0.015 | 0.0038 | 0.0066 | 0.0031 | 1.3E−4 | 3.3E−4 | 3.8E−4 |
| Lower limit of 95% CI | 2.99 | 2.58 | 1.22 | 1.45 | 1.35 | 1.56 | 2.13 | 1.91 | 2.14 |
| Upper limit of 95% CI | 35.4 | 23.4 | 6.30 | 6.95 | 6.44 | 9.02 | 10.4 | 9.12 | 14.0 |

TABLE 15.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 2.30 | 9.12 | 2.65 | 8.16 | 2.61 | 11.3 |
| Average | 6.65 | 22.5 | 9.62 | 23.6 | 8.94 | 26.3 |
| Stdev | 12.7 | 29.9 | 15.1 | 32.2 | 14.4 | 33.3 |
| p (t-test) | | 3.0E−4 | | 9.4E−4 | | 3.6E−5 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 54 | 95 | 73 | 76 | 82 | 67 |

TABLE 15.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 2.35 | 9.12 | 2.79 | 7.39 | 2.72 | 10.3 |
| Average | 7.37 | 22.4 | 10.3 | 23.0 | 9.59 | 25.5 |
| Stdev | 13.6 | 30.1 | 15.7 | 32.2 | 15.0 | 33.4 |
| p (t-test) | | 5.6E−4 | | 0.0026 | | 1.6E−4 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 56 | 93 | 73 | 76 | 82 | 67 |

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 3.49 | 7.04 | 3.51 | 13.4 | 3.47 | 21.0 |
| Average | 14.5 | 23.0 | 14.1 | 25.9 | 13.7 | 28.9 |
| Stdev | 24.0 | 30.5 | 23.5 | 32.3 | 23.2 | 33.1 |
| p (t-test) | | 0.075 | | 0.020 | | 0.0038 |
| Min | 3.16E−5 | 0.0645 | 3.16E−5 | 0.0645 | 3.16E−5 | 0.0645 |
| Max | 109 | 112 | 109 | 112 | 109 | 112 |
| n (Patient) | 106 | 42 | 113 | 35 | 117 | 31 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.71 | 0.69 | 0.63 | 0.65 | 0.63 | 0.66 | 0.69 | 0.66 | 0.71 |
| SE | 0.042 | 0.043 | 0.052 | 0.045 | 0.045 | 0.055 | 0.044 | 0.045 | 0.057 |
| p Value | 2.8E−7 | 1.1E−5 | 0.012 | 7.2E−4 | 0.0048 | 0.0044 | 2.5E−5 | 3.9E−4 | 2.7E−4 |
| nCohort Non-persistent | 54 | 56 | 106 | 73 | 73 | 113 | 82 | 82 | 117 |
| nCohort Persistent | 95 | 93 | 42 | 76 | 76 | 35 | 67 | 67 | 31 |
| Cutoff Quartile 2 | 1.89 | 1.89 | 1.93 | 1.89 | 1.89 | 1.93 | 1.89 | 1.89 | 1.93 |
| Sensitivity | 81% | 80% | 83% | 79% | 78% | 83% | 81% | 79% | 87% |
| Specificity | 35% | 32% | 28% | 29% | 27% | 27% | 29% | 28% | 28% |
| Cutoff Quartile 3 | 4.13 | 4.13 | 4.52 | 4.13 | 4.13 | 4.52 | 4.13 | 4.13 | 4.52 |
| Sensitivity | 63% | 62% | 64% | 62% | 61% | 69% | 67% | 66% | 77% |
| Specificity | 72% | 70% | 56% | 62% | 60% | 56% | 63% | 62% | 57% |
| Cutoff Quartile 4 | 20.0 | 20.0 | 20.2 | 20.0 | 20.0 | 20.2 | 20.0 | 20.0 | 20.2 |
| Sensitivity | 37% | 37% | 40% | 37% | 36% | 46% | 42% | 40% | 52% |
| Specificity | 94% | 93% | 81% | 86% | 85% | 81% | 88% | 87% | 82% |
| OR Quartile 2 | 2.32 | 1.84 | 1.97 | 1.51 | 1.31 | 1.83 | 1.72 | 1.48 | 2.65 |
| p Value | 0.029 | 0.11 | 0.15 | 0.28 | 0.48 | 0.22 | 0.17 | 0.32 | 0.089 |
| Lower limit of 95% CI | 1.09 | 0.868 | 0.791 | 0.716 | 0.621 | 0.692 | 0.796 | 0.690 | 0.861 |
| Upper limit of 95% CI | 4.96 | 3.92 | 4.93 | 3.20 | 2.76 | 4.83 | 3.71 | 3.16 | 8.17 |
| OR Quartile 3 | 4.46 | 3.80 | 2.26 | 2.60 | 2.33 | 2.75 | 3.55 | 3.15 | 4.59 |
| p Value | 5.6E−5 | 2.2E−4 | 0.030 | 0.0045 | 0.012 | 0.014 | 2.6E−4 | 8.5E−4 | 0.0011 |
| Lower limit of 95% CI | 2.15 | 1.87 | 1.08 | 1.35 | 1.21 | 1.23 | 1.80 | 1.60 | 1.83 |
| Upper limit of 95% CI | 9.22 | 7.71 | 4.73 | 5.04 | 4.49 | 6.15 | 7.00 | 6.17 | 11.5 |
| OR Quartile 4 | 9.92 | 7.49 | 2.92 | 3.68 | 3.11 | 3.69 | 5.17 | 4.36 | 4.88 |
| p Value | 2.8E−4 | 3.4E−4 | 0.0074 | 0.0017 | 0.0052 | 0.0017 | 8.7E−5 | 3.2E−4 | 2.5E−4 |
| Lower limit of 95% CI | 2.88 | 2.49 | 1.33 | 1.63 | 1.40 | 1.63 | 2.28 | 1.96 | 2.09 |
| Upper limit of 95% CI | 34.2 | 22.5 | 6.41 | 8.29 | 6.88 | 8.35 | 11.7 | 9.71 | 11.4 |

TABLE 15.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 2.30 | 9.12 | 2.72 | 7.74 | 2.72 | 10.3 |
| Average | 6.65 | 22.5 | 9.72 | 23.3 | 9.19 | 25.1 |
| Stdev | 12.7 | 29.9 | 15.2 | 32.0 | 14.7 | 32.8 |
| p (t-test) | | 3.0E−4 | | 0.0013 | | 1.6E−4 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 54 | 95 | 72 | 77 | 78 | 71 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 2.35 | 9.12 | 2.85 | 7.04 | 2.85 | 9.12 |
| Average | 7.37 | 22.4 | 10.4 | 22.7 | 9.79 | 24.4 |
| Stdev | 13.6 | 30.1 | 15.7 | 32.0 | 15.3 | 32.8 |
| p (t-test) | | 5.6E−4 | | 0.0036 | | 5.3E−4 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 56 | 93 | 72 | 77 | 78 | 71 |

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 3.49 | 7.04 | 3.49 | 10.8 | 3.47 | 14.5 |
| Average | 14.9 | 20.9 | 14.3 | 23.4 | 13.8 | 25.6 |
| Stdev | 24.6 | 29.1 | 24.1 | 30.3 | 23.7 | 31.1 |
| p (t-test) | | 0.19 | | 0.056 | | 0.016 |
| Min | 3.16E−5 | 0.0645 | 3.16E−5 | 0.0645 | 3.16E−5 | 0.0645 |
| Max | 109 | 112 | 109 | 112 | 109 | 112 |
| n (Patient) | 100 | 48 | 106 | 42 | 110 | 38 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.71 | 0.69 | 0.61 | 0.65 | 0.62 | 0.64 | 0.67 | 0.64 | 0.68 |
| SE | 0.042 | 0.043 | 0.051 | 0.045 | 0.046 | 0.052 | 0.044 | 0.045 | 0.053 |
| p Value | 2.8E−7 | 1.1E−5 | 0.031 | 0.0011 | 0.0069 | 0.0083 | 1.6E−4 | 0.0014 | 9.3E−4 |
| nCohort Non-persistent | 54 | 56 | 100 | 72 | 72 | 106 | 78 | 78 | 110 |
| nCohort Persistent | 95 | 93 | 48 | 77 | 77 | 42 | 71 | 71 | 38 |
| Cutoff Quartile 2 | 1.89 | 1.89 | 1.93 | 1.89 | 1.89 | 1.93 | 1.89 | 1.89 | 1.93 |
| Sensitivity | 81% | 80% | 79% | 79% | 78% | 79% | 79% | 77% | 82% |
| Specificity | 35% | 32% | 27% | 29% | 28% | 26% | 28% | 27% | 27% |
| Cutoff Quartile 3 | 4.13 | 4.13 | 4.52 | 4.13 | 4.13 | 4.52 | 4.13 | 4.13 | 4.52 |
| Sensitivity | 63% | 62% | 62% | 61% | 60% | 67% | 65% | 63% | 74% |
| Specificity | 72% | 70% | 56% | 61% | 60% | 57% | 63% | 62% | 58% |
| Cutoff Quartile 4 | 20.0 | 20.0 | 20.2 | 20.0 | 20.0 | 20.2 | 20.0 | 20.0 | 20.2 |
| Sensitivity | 37% | 37% | 35% | 36% | 35% | 40% | 39% | 38% | 45% |
| Specificity | 94% | 93% | 80% | 86% | 85% | 81% | 87% | 86% | 82% |
| OR Quartile 2 | 2.32 | 1.84 | 1.41 | 1.57 | 1.36 | 1.32 | 1.47 | 1.27 | 1.66 |
| p Value | 0.029 | 0.11 | 0.42 | 0.24 | 0.42 | 0.53 | 0.32 | 0.54 | 0.28 |
| Lower limit of 95% CI | 1.09 | 0.868 | 0.616 | 0.742 | 0.644 | 0.560 | 0.690 | 0.599 | 0.661 |
| Upper limit of 95% CI | 4.96 | 3.92 | 3.21 | 3.32 | 2.86 | 3.09 | 3.12 | 2.68 | 4.17 |
| OR Quartile 3 | 4.46 | 3.80 | 2.12 | 2.46 | 2.20 | 2.61 | 3.11 | 2.77 | 3.90 |
| p Value | 5.6E−5 | 2.2E−4 | 0.037 | 0.0074 | 0.018 | 0.012 | 9.0E−4 | 0.0027 | 0.0011 |
| Lower limit of 95% CI | 2.15 | 1.87 | 1.05 | 1.27 | 1.14 | 1.24 | 1.59 | 1.43 | 1.72 |
| Upper limit of 95% CI | 9.22 | 7.71 | 4.29 | 4.76 | 4.24 | 5.51 | 6.07 | 5.38 | 8.80 |
| OR Quartile 4 | 9.92 | 7.49 | 2.19 | 3.54 | 2.99 | 2.92 | 4.43 | 3.74 | 3.64 |
| p Value | 2.8E−4 | 3.4E−4 | 0.045 | 0.0023 | 0.0068 | 0.0074 | 3.6E−4 | 0.0012 | 0.0016 |

TABLE 15.3-continued

Comparison of marker levels and the area under the ROC curve
(AUC) in urine samples for the "persistent" and "non-persistent" cohorts where
persistence starts within 72 hours after sample collection and renal status is assessed by
serum creatinine (sCr) only, urine output (UO) only, or serum creatinine or urine output
RIFLE criteria.

| | | | | | | | | | |
|---|---|---|---|---|---|---|---|---|---|
| Lower limit of 95% CI | 2.88 | 2.49 | 1.02 | 1.57 | 1.35 | 1.33 | 1.96 | 1.68 | 1.63 |
| Upper limit of 95% CI | 34.2 | 22.5 | 4.73 | 7.99 | 6.63 | 6.41 | 10.0 | 8.30 | 8.13 |

TABLE 15.4

Comparison of marker levels and the area under the ROC curve
(AUC) in urine samples for the "persistent" and "non-persistent" cohorts where
persistence starts within 96 hours after sample collection and renal status is assessed by
serum creatinine (sCr) only, urine output (UO) only, or serum creatinine or urine output
RIFLE criteria.

sCr or UO

| Persistence Period Duration (hr) | 24 | | 48 | | 72 | |
|---|---|---|---|---|---|---|
| | Non-persistent Cohort | Persistent Cohort | Non-persistent Cohort | Persistent Cohort | Non-persistent Cohort | Persistent Cohort |
| Median | 2.30 | 9.12 | 2.72 | 7.74 | 2.72 | 10.3 |
| Average | 6.65 | 22.5 | 9.72 | 23.3 | 9.19 | 25.1 |
| Stdev | 12.7 | 29.9 | 15.2 | 32.0 | 14.7 | 32.8 |
| p (t-test) | | 3.0E−4 | | 0.0013 | | 1.6E−4 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 54 | 95 | 72 | 77 | 78 | 71 | sCr only

| Persistence Period Duration (hr) | 24 | | 48 | | 72 | |
|---|---|---|---|---|---|---|
| | Non-persistent Cohort | Persistent Cohort | Non-persistent Cohort | Persistent Cohort | Non-persistent Cohort | Persistent Cohort |
| Median | 2.35 | 9.12 | 2.85 | 7.04 | 2.85 | 9.12 |
| Average | 7.37 | 22.4 | 10.4 | 22.7 | 9.79 | 24.4 |
| Stdev | 13.6 | 30.1 | 15.7 | 32.0 | 15.3 | 32.8 |
| p (t-test) | | 5.6E−4 | | 0.0036 | | 5.3E−4 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 56 | 93 | 72 | 77 | 78 | 71 |

UO only

| Persistence Period Duration (hr) | 24 | | 48 | | 72 | |
|---|---|---|---|---|---|---|
| | Non-persistent Cohort | Persistent Cohort | Non-persistent Cohort | Persistent Cohort | Non-persistent Cohort | Persistent Cohort |
| Median | 3.49 | 6.98 | 3.47 | 8.58 | 3.47 | 11.3 |
| Average | 15.1 | 20.3 | 14.6 | 22.1 | 14.1 | 24.0 |
| Stdev | 24.8 | 28.7 | 24.4 | 29.7 | 24.0 | 30.4 |
| p (t-test) | | 0.26 | | 0.11 | | 0.039 |
| Min | 3.16E−5 | 0.0645 | 3.16E−5 | 0.0645 | 3.16E−5 | 0.0645 |
| Max | 109 | 112 | 109 | 112 | 109 | 112 |
| n (Patient) | 98 | 50 | 103 | 45 | 107 | 41 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.71 | 0.69 | 0.60 | 0.65 | 0.62 | 0.62 | 0.67 | 0.64 | 0.66 |
| SE | 0.042 | 0.043 | 0.050 | 0.045 | 0.046 | 0.051 | 0.044 | 0.045 | 0.052 |
| p Value | 2.8E−7 | 1.1E−5 | 0.047 | 0.0011 | 0.0069 | 0.016 | 1.6E−4 | 0.0014 | 0.0023 |
| nCohort Non-persistent | 54 | 56 | 98 | 72 | 72 | 103 | 78 | 78 | 107 |
| nCohort Persistent | 95 | 93 | 50 | 77 | 77 | 45 | 71 | 71 | 41 |
| Cutoff Quartile 2 | 1.89 | 1.89 | 1.93 | 1.89 | 1.89 | 1.93 | 1.89 | 1.89 | 1.93 |
| Sensitivity | 81% | 80% | 78% | 79% | 78% | 78% | 79% | 77% | 80% |
| Specificity | 35% | 32% | 27% | 29% | 28% | 26% | 28% | 27% | 27% |
| Cutoff Quartile 3 | 4.13 | 4.13 | 4.52 | 4.13 | 4.13 | 4.52 | 4.13 | 4.13 | 4.52 |
| Sensitivity | 63% | 62% | 62% | 61% | 60% | 64% | 65% | 63% | 71% |
| Specificity | 72% | 70% | 56% | 61% | 60% | 56% | 63% | 62% | 58% |

TABLE 15.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| Cutoff Quartile 4 | 20.0 | 20.0 | 20.2 | 20.0 | 20.0 | 20.2 | 20.0 | 20.0 | 20.2 |
|---|---|---|---|---|---|---|---|---|---|
| Sensitivity | 37% | 37% | 34% | 36% | 35% | 38% | 39% | 38% | 41% |
| Specificity | 94% | 93% | 80% | 86% | 85% | 81% | 87% | 86% | 81% |
| OR Quartile 2 | 2.32 | 1.84 | 1.28 | 1.57 | 1.36 | 1.24 | 1.47 | 1.27 | 1.53 |
| p Value | 0.029 | 0.11 | 0.55 | 0.24 | 0.42 | 0.61 | 0.32 | 0.54 | 0.34 |
| Lower limit of 95% CI | 1.09 | 0.868 | 0.572 | 0.742 | 0.644 | 0.543 | 0.690 | 0.599 | 0.635 |
| Upper limit of 95% CI | 4.96 | 3.92 | 2.87 | 3.32 | 2.86 | 2.85 | 3.12 | 2.68 | 3.71 |
| OR Quartile 3 | 4.46 | 3.80 | 2.09 | 2.46 | 2.20 | 2.34 | 3.11 | 2.77 | 3.33 |
| p Value | 5.6E−5 | 2.2E−4 | 0.038 | 0.0074 | 0.018 | 0.022 | 9.0E−4 | 0.0027 | 0.0023 |
| Lower limit of 95% CI | 2.15 | 1.87 | 1.04 | 1.27 | 1.14 | 1.13 | 1.59 | 1.43 | 1.53 |
| Upper limit of 95% CI | 9.22 | 7.71 | 4.19 | 4.76 | 4.24 | 4.82 | 6.07 | 5.38 | 7.22 |
| OR Quartile 4 | 9.92 | 7.49 | 2.01 | 3.54 | 2.99 | 2.52 | 4.43 | 3.74 | 3.08 |
| p Value | 2.8E−4 | 3.4E−4 | 0.073 | 0.0023 | 0.0068 | 0.020 | 3.6E−4 | 0.0012 | 0.0052 |
| Lower limit of 95% CI | 2.88 | 2.49 | 0.936 | 1.57 | 1.35 | 1.16 | 1.96 | 1.68 | 1.40 |
| Upper limit of 95% CI | 34.2 | 22.5 | 4.31 | 7.99 | 6.63 | 5.47 | 10.0 | 8.30 | 6.78 |

TABLE 15.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

sCr or UO

| | 24 | | 48 | | 72 | |
|---|---|---|---|---|---|---|
| Persistence Period Duration (hr) | Non-persistent Cohort | Persistent Cohort | Non-persistent Cohort | Persistent Cohort | Non-persistent Cohort | Persistent Cohort |
| Median | 2.30 | 9.12 | 2.65 | 7.39 | 2.72 | 9.12 |
| Average | 6.53 | 22.2 | 9.85 | 22.7 | 9.38 | 24.0 |
| Stdev | 12.8 | 29.7 | 15.4 | 31.6 | 15.0 | 32.2 |
| p (t-test) | | 3.8E−4 | | 0.0025 | | 5.1E−4 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 52 | 97 | 69 | 80 | 74 | 75 | sCr only

| | 24 | | 48 | | 72 | |
|---|---|---|---|---|---|---|
| Persistence Period Duration (hr) | Non-persistent Cohort | Persistent Cohort | Non-persistent Cohort | Persistent Cohort | Non-persistent Cohort | Persistent Cohort |
| Median | 2.34 | 9.57 | 2.72 | 7.74 | 2.72 | 10.3 |
| Average | 7.17 | 22.4 | 10.1 | 22.6 | 9.57 | 24.2 |
| Stdev | 13.6 | 29.9 | 15.9 | 31.6 | 15.4 | 32.4 |
| p (t-test) | | 5.1E−4 | | 0.0034 | | 5.1E−4 |
| Min | 3.16E−5 | 0.0532 | 3.16E−5 | 0.0532 | 3.16E−5 | 0.0532 |
| Max | 78.7 | 112 | 78.7 | 112 | 78.7 | 112 |
| n (Patient) | 55 | 94 | 70 | 79 | 76 | 73 |

UO only

| | 24 | | 48 | | 72 | |
|---|---|---|---|---|---|---|
| Persistence Period Duration (hr) | Non-persistent Cohort | Persistent Cohort | Non-persistent Cohort | Persistent Cohort | Non-persistent Cohort | Persistent Cohort |
| Median | 3.47 | 7.04 | 3.47 | 8.58 | 3.47 | 10.8 |
| Average | 15.1 | 20.2 | 14.7 | 21.2 | 14.4 | 22.4 |
| Stdev | 25.1 | 28.1 | 24.8 | 28.7 | 24.5 | 29.2 |
| p (t-test) | | 0.26 | | 0.16 | | 0.084 |
| Min | 3.16E−5 | 0.0645 | 3.16E−5 | 0.0645 | 3.16E−5 | 0.0645 |
| Max | 109 | 112 | 109 | 112 | 109 | 112 |
| n (Patient) | 96 | 52 | 99 | 49 | 102 | 46 |

TABLE 15.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.71 | 0.70 | 0.61 | 0.64 | 0.64 | 0.63 | 0.65 | 0.66 | 0.65 |
| SE | 0.042 | 0.043 | 0.049 | 0.045 | 0.045 | 0.050 | 0.045 | 0.045 | 0.050 |
| p Value | 4.8E−7 | 3.4E−6 | 0.024 | 0.0022 | 0.0026 | 0.012 | 5.3E−4 | 4.3E−4 | 0.0025 |
| nCohort Non-persistent | 52 | 55 | 96 | 69 | 70 | 99 | 74 | 76 | 102 |
| nCohort Persistent | 97 | 94 | 52 | 80 | 79 | 49 | 75 | 73 | 46 |
| Cutoff Quartile 2 | 1.89 | 1.89 | 1.93 | 1.89 | 1.89 | 1.93 | 1.89 | 1.89 | 1.93 |
| Sensitivity | 80% | 80% | 79% | 79% | 78% | 80% | 79% | 78% | 83% |
| Specificity | 35% | 33% | 27% | 29% | 29% | 27% | 28% | 28% | 28% |
| Cutoff Quartile 3 | 4.13 | 4.13 | 4.52 | 4.13 | 4.13 | 4.52 | 4.13 | 4.13 | 4.52 |
| Sensitivity | 63% | 63% | 63% | 60% | 61% | 63% | 63% | 64% | 67% |
| Specificity | 73% | 71% | 57% | 61% | 61% | 57% | 62% | 63% | 58% |
| Cutoff Quartile 4 | 20.0 | 20.0 | 20.2 | 20.0 | 20.0 | 20.2 | 20.0 | 20.0 | 20.2 |
| Sensitivity | 36% | 36% | 33% | 35% | 34% | 35% | 37% | 37% | 37% |
| Specificity | 94% | 93% | 79% | 86% | 84% | 80% | 86% | 86% | 80% |
| OR Quartile 2 | 2.17 | 1.92 | 1.38 | 1.51 | 1.46 | 1.46 | 1.46 | 1.36 | 1.89 |
| p Value | 0.045 | 0.090 | 0.43 | 0.28 | 0.32 | 0.37 | 0.32 | 0.42 | 0.16 |
| Lower limit of 95% CI | 1.02 | 0.902 | 0.620 | 0.717 | 0.692 | 0.642 | 0.691 | 0.643 | 0.786 |
| Upper limit of 95% CI | 4.65 | 4.09 | 3.09 | 3.19 | 3.08 | 3.33 | 3.09 | 2.88 | 4.53 |
| OR Quartile 3 | 4.60 | 4.11 | 2.33 | 2.33 | 2.47 | 2.24 | 2.76 | 3.10 | 2.84 |
| p Value | 5.1E−5 | 1.1E−4 | 0.017 | 0.012 | 0.0074 | 0.024 | 0.0027 | 9.1E−4 | 0.0052 |
| Lower limit of 95% CI | 2.20 | 2.01 | 1.16 | 1.21 | 1.27 | 1.11 | 1.42 | 1.59 | 1.37 |
| Upper limit of 95% CI | 9.62 | 8.41 | 4.67 | 4.51 | 4.77 | 4.53 | 5.35 | 6.05 | 5.89 |
| OR Quartile 4 | 9.22 | 7.22 | 1.85 | 3.18 | 2.78 | 2.10 | 3.81 | 3.47 | 2.40 |
| p Value | 4.3E−4 | 4.3E−4 | 0.11 | 0.0053 | 0.011 | 0.058 | 0.0013 | 0.0022 | 0.026 |
| Lower limit of 95% CI | 2.68 | 2.40 | 0.863 | 1.41 | 1.26 | 0.976 | 1.69 | 1.56 | 1.11 |
| Upper limit of 95% CI | 31.8 | 21.7 | 3.95 | 7.16 | 6.16 | 4.51 | 8.61 | 7.69 | 5.21 |

Example 16. Use of Insulin-Like Growth Factor-Binding Protein 3 for Evaluating Renal Status in Patients Admitted to the ICU: Persistent at RIFLE F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 3 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is failure (F) where the persistence period can start from the time of sample collection to 24, 48, 72, 96 or 168 hours after sample collection. "Non-persistent" indicates those patients who are not persistent at failure (F) and whose minimum RIFLE stage during a period of 24, 48 or 72 hours is non-injury (RIFLE 0), risk of injury (R), or injury (I) where the persistence period can start from the time of sample collection to 24, 48, 72, 96 or 168 hours after sample collection. If a patient dies after failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 16.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 637 | 1250 | 637 | 1350 | 702 | 1160 |
| Average | 1820 | 4620 | 1960 | 4820 | 2360 | 4100 |
| Stdev | 3970 | 6250 | 4060 | 6480 | 4660 | 5940 |

TABLE 16.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | | 0.0011 | | 0.0015 | | 0.072 |
| Min | 20.6 | 158 | 20.6 | 158 | 20.6 | 158 |
| Max | 18800 | 18800 | 18800 | 18800 | 18800 | 18800 |
| n (Patient) | 98 | 51 | 106 | 43 | 113 | 36 | sCr only

| | 24 | | 48 | | 72 | |
|---|---|---|---|---|---|---|
| Persistence Period Duration (hr) | Non-persistent Cohort | Persistent Cohort | Non-persistent Cohort | Persistent Cohort | Non-persistent Cohort | Persistent Cohort |
| Median | 640 | 1210 | 641 | 1400 | 702 | 1160 |
| Average | 1840 | 4540 | 1840 | 5110 | 2280 | 4250 |
| Stdev | 3990 | 6220 | 3880 | 6620 | 4560 | 6050 |
| p (t-test) | | 0.0016 | | 2.6E−4 | | 0.037 |
| Min | 20.6 | 158 | 20.6 | 158 | 20.6 | 158 |
| Max | 18800 | 18800 | 18800 | 18800 | 18800 | 18800 |
| n (Patient) | 97 | 52 | 106 | 43 | 111 | 38 |

UO only

| | 24 | | 48 | | 72 | |
|---|---|---|---|---|---|---|
| Persistence Period Duration (hr) | Non-persistent Cohort | Persistent Cohort | Non-persistent Cohort | Persistent Cohort | Non-persistent Cohort | Persistent Cohort |
| Median | 747 | 1380 | 766 | 1400 | 766 | 1400 |
| Average | 2440 | 5410 | 2430 | 5670 | 2430 | 5670 |
| Stdev | 4550 | 7420 | 4530 | 7560 | 4530 | 7560 |
| p (t-test) | | 0.019 | | 0.012 | | 0.012 |
| Min | 20.6 | 322 | 20.6 | 322 | 20.6 | 322 |
| Max | 18800 | 18800 | 18800 | 18800 | 18800 | 18800 |
| n (Patient) | 130 | 18 | 131 | 17 | 131 | 17 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.68 | 0.67 | 0.70 | 0.70 | 0.69 | 0.70 | 0.65 | 0.64 | 0.70 |
| SE | 0.048 | 0.048 | 0.072 | 0.050 | 0.050 | 0.074 | 0.055 | 0.054 | 0.074 |
| p Value | 1.3E−4 | 4.6E−4 | 0.0058 | 7.9E−5 | 1.1E−4 | 0.0057 | 0.0048 | 0.0098 | 0.0057 |
| nCohort Non-persistent | 98 | 97 | 130 | 106 | 106 | 131 | 113 | 111 | 131 |
| nCohort Persistent | 51 | 52 | 18 | 43 | 43 | 17 | 36 | 38 | 17 |
| Cutoff Quartile 2 | 401 | 401 | 410 | 401 | 401 | 410 | 401 | 401 | 410 |
| Sensitivity | 84% | 83% | 89% | 86% | 84% | 88% | 86% | 82% | 88% |
| Specificity | 30% | 29% | 27% | 29% | 28% | 27% | 28% | 27% | 27% |
| Cutoff Quartile 3 | 794 | 794 | 801 | 794 | 794 | 801 | 794 | 794 | 801 |
| Sensitivity | 67% | 65% | 78% | 72% | 72% | 76% | 69% | 68% | 76% |
| Specificity | 58% | 58% | 54% | 58% | 58% | 53% | 56% | 56% | 53% |
| Cutoff Quartile 4 | 1830 | 1830 | 1840 | 1830 | 1830 | 1840 | 1830 | 1830 | 1840 |
| Sensitivity | 41% | 40% | 33% | 42% | 44% | 35% | 36% | 37% | 35% |
| Specificity | 83% | 82% | 76% | 81% | 82% | 76% | 78% | 78% | 76% |
| OR Quartile 2 | 2.26 | 1.94 | 2.95 | 2.55 | 2.03 | 2.73 | 2.45 | 1.64 | 2.73 |
| p Value | 0.067 | 0.12 | 0.16 | 0.056 | 0.13 | 0.20 | 0.088 | 0.29 | 0.20 |
| Lower limit of 95% CI | 0.946 | 0.835 | 0.644 | 0.977 | 0.814 | 0.595 | 0.875 | 0.653 | 0.595 |
| Upper limit of 95% CI | 5.39 | 4.50 | 13.5 | 6.65 | 5.06 | 12.6 | 6.86 | 4.12 | 12.6 |
| OR Quartile 3 | 2.78 | 2.58 | 4.08 | 3.64 | 3.64 | 3.73 | 2.86 | 2.74 | 3.73 |
| p Value | 0.0046 | 0.0079 | 0.018 | 0.0010 | 0.0010 | 0.028 | 0.0100 | 0.011 | 0.028 |
| Lower limit of 95% CI | 1.37 | 1.28 | 1.28 | 1.68 | 1.68 | 1.16 | 1.29 | 1.26 | 1.16 |
| Upper limit of 95% CI | 5.64 | 5.19 | 13.1 | 7.86 | 7.86 | 12.0 | 6.38 | 5.98 | 12.0 |
| OR Quartile 4 | 3.34 | 3.19 | 1.60 | 3.10 | 3.62 | 1.76 | 1.99 | 2.11 | 1.76 |
| p Value | 0.0020 | 0.0029 | 0.39 | 0.0044 | 0.0012 | 0.30 | 0.097 | 0.066 | 0.30 |
| Lower limit of 95% CI | 1.55 | 1.49 | 0.553 | 1.42 | 1.66 | 0.602 | 0.883 | 0.951 | 0.602 |
| Upper limit of 95% CI | 7.16 | 6.83 | 4.61 | 6.73 | 7.91 | 5.15 | 4.48 | 4.70 | 5.15 |

TABLE 16.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 626 | 1210 | 624 | 1400 | 640 | 1210 |
| Average | 1880 | 4200 | 1850 | 4570 | 2310 | 3920 |
| Stdev | 4110 | 5970 | 4030 | 6210 | 4680 | 5690 |
| p (t-test) | 0.0055 | | 0.0015 | | 0.074 | |
| Min | 21.1 | 20.6 | 20.6 | 158 | 20.6 | 158 |
| Max | 18800 | 18800 | 18800 | 18800 | 18800 | 18800 |
| n (Patient) | 91 | 58 | 98 | 51 | 105 | 44 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 634 | 1120 | 626 | 1300 | 642 | 1070 |
| Average | 1900 | 4170 | 1880 | 4470 | 2360 | 3740 |
| Stdev | 4110 | 5990 | 4040 | 6190 | 4710 | 5630 |
| p (t-test) | 0.0067 | | 0.0025 | | 0.12 | |
| Min | 21.1 | 20.6 | 20.6 | 158 | 20.6 | 158 |
| Max | 18800 | 18800 | 18800 | 18800 | 18800 | 18800 |
| n (Patient) | 91 | 58 | 97 | 52 | 103 | 46 |

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 718 | 1350 | 724 | 1380 | 724 | 1380 |
| Average | 2490 | 4330 | 2480 | 4470 | 2480 | 4470 |
| Stdev | 4660 | 6520 | 4640 | 6630 | 4640 | 6630 |
| p (t-test) | 0.097 | | 0.076 | | 0.076 | |
| Min | 20.6 | 322 | 20.6 | 322 | 20.6 | 322 |
| Max | 18800 | 18800 | 18800 | 18800 | 18800 | 18800 |
| n (Patient) | 123 | 25 | 124 | 24 | 124 | 24 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.68 | 0.66 | 0.68 | 0.71 | 0.70 | 0.69 | 0.67 | 0.64 | 0.69 |
| SE | 0.046 | 0.047 | 0.063 | 0.046 | 0.047 | 0.064 | 0.051 | 0.051 | 0.064 |
| p Value | 1.2E−4 | 7.6E−4 | 0.0036 | 3.7E−6 | 3.0E−5 | 0.0037 | 8.3E−4 | 0.0069 | 0.0037 |
| nCohort Non-persistent | 91 | 91 | 123 | 98 | 97 | 124 | 105 | 103 | 124 |
| nCohort Persistent | 58 | 58 | 25 | 51 | 52 | 24 | 44 | 46 | 24 |
| Cutoff Quartile 2 | 401 | 401 | 410 | 401 | 401 | 410 | 401 | 401 | 410 |
| Sensitivity | 84% | 83% | 92% | 88% | 87% | 92% | 89% | 85% | 92% |
| Specificity | 31% | 30% | 28% | 32% | 31% | 28% | 30% | 29% | 28% |
| Cutoff Quartile 3 | 794 | 794 | 801 | 794 | 794 | 801 | 794 | 794 | 801 |
| Sensitivity | 66% | 64% | 76% | 71% | 69% | 75% | 68% | 65% | 75% |
| Specificity | 59% | 58% | 55% | 60% | 60% | 55% | 57% | 56% | 55% |
| Cutoff Quartile 4 | 1830 | 1830 | 1840 | 1830 | 1830 | 1840 | 1830 | 1830 | 1840 |
| Sensitivity | 40% | 38% | 32% | 43% | 40% | 33% | 36% | 33% | 33% |
| Specificity | 84% | 82% | 76% | 84% | 82% | 77% | 79% | 78% | 77% |
| OR Quartile 2 | 2.42 | 2.02 | 4.57 | 3.47 | 2.88 | 4.33 | 3.42 | 2.29 | 4.33 |
| p Value | 0.039 | 0.090 | 0.047 | 0.010 | 0.022 | 0.056 | 0.018 | 0.074 | 0.056 |
| Lower limit of 95% CI | 1.05 | 0.895 | 1.02 | 1.34 | 1.16 | 0.966 | 1.23 | 0.922 | 0.966 |
| Upper limit of 95% CI | 5.60 | 4.58 | 20.4 | 8.99 | 7.12 | 19.4 | 9.48 | 5.69 | 19.4 |
| OR Quartile 3 | 2.77 | 2.46 | 3.92 | 3.63 | 3.35 | 3.64 | 2.86 | 2.42 | 3.64 |
| p Value | 0.0035 | 0.0094 | 0.0066 | 5.0E−4 | 9.3E−4 | 0.010 | 0.0056 | 0.016 | 0.010 |
| Lower limit of 95% CI | 1.40 | 1.25 | 1.46 | 1.76 | 1.64 | 1.35 | 1.36 | 1.18 | 1.35 |
| Upper limit of 95% CI | 5.50 | 4.84 | 10.5 | 7.50 | 6.84 | 9.80 | 6.01 | 4.97 | 9.80 |
| OR Quartile 4 | 3.33 | 2.86 | 1.53 | 3.89 | 3.19 | 1.64 | 2.16 | 1.68 | 1.64 |
| p Value | 0.0020 | 0.0064 | 0.38 | 5.5E−4 | 0.0029 | 0.31 | 0.052 | 0.19 | 0.31 |

TABLE 16.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 1.55 | 1.34 | 0.597 | 1.80 | 1.49 | 0.637 | 0.995 | 0.778 | 0.637 |
| Upper limit of 95% CI | 7.15 | 6.11 | 3.90 | 8.40 | 6.83 | 4.21 | 4.67 | 3.64 | 4.21 |

TABLE 16.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 624 | 1070 | 608 | 1250 | 630 | 1070 |
| Average | 1750 | 4190 | 1680 | 4460 | 2290 | 3720 |
| Stdev | 3830 | 6070 | 3760 | 6180 | 4690 | 5570 |
| p (t-test) | | 0.0031 | | 8.3E-4 | | 0.099 |
| Min | 21.1 | 20.6 | 20.6 | 158 | 20.6 | 158 |
| Max | 18800 | 18800 | 18800 | 18800 | 18800 | 18800 |
| n (Patient) | 86 | 63 | 90 | 59 | 98 | 51 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 626 | 1070 | 619 | 1250 | 642 | 1070 |
| Average | 1770 | 4130 | 1690 | 4450 | 2320 | 3650 |
| Stdev | 3850 | 6040 | 3750 | 6190 | 4700 | 5540 |
| p (t-test) | | 0.0042 | | 9.1E-4 | | 0.13 |
| Min | 21.1 | 20.6 | 20.6 | 158 | 20.6 | 158 |
| Max | 18800 | 18800 | 18800 | 18800 | 18800 | 18800 |
| n (Patient) | 85 | 64 | 90 | 59 | 97 | 52 |

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 724 | 1210 | 729 | 1250 | 729 | 1250 |
| Average | 2450 | 4070 | 2430 | 4170 | 2430 | 4170 |
| Stdev | 4660 | 6160 | 4640 | 6240 | 4640 | 6240 |
| p (t-test) | | 0.11 | | 0.088 | | 0.088 |
| Min | 20.6 | 233 | 20.6 | 233 | 20.6 | 233 |
| Max | 18800 | 18800 | 18800 | 18800 | 18800 | 18800 |
| n (Patient) | 116 | 32 | 117 | 31 | 117 | 31 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.67 | 0.66 | 0.65 | 0.71 | 0.70 | 0.66 | 0.65 | 0.63 | 0.66 |
| SE | 0.045 | 0.046 | 0.058 | 0.044 | 0.045 | 0.058 | 0.049 | 0.049 | 0.058 |
| p Value | 2.2E-4 | 6.9E-4 | 0.0071 | 2.4E-6 | 1.3E-5 | 0.0077 | 0.0018 | 0.0093 | 0.0077 |
| nCohort Non-persistent | 86 | 85 | 116 | 90 | 90 | 117 | 98 | 97 | 117 |
| nCohort Persistent | 63 | 64 | 32 | 59 | 59 | 31 | 51 | 52 | 31 |
| Cutoff Quartile 2 | 401 | 401 | 410 | 401 | 401 | 410 | 401 | 401 | 410 |
| Sensitivity | 84% | 83% | 91% | 88% | 86% | 90% | 88% | 85% | 90% |
| Specificity | 31% | 31% | 29% | 33% | 32% | 29% | 32% | 30% | 29% |
| Cutoff Quartile 3 | 794 | 794 | 801 | 794 | 794 | 801 | 794 | 794 | 801 |
| Sensitivity | 63% | 62% | 69% | 68% | 66% | 68% | 65% | 62% | 68% |
| Specificity | 59% | 59% | 55% | 61% | 60% | 55% | 57% | 56% | 55% |

TABLE 16.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Cutoff Quartile 4 | 1830 | 1830 | 1840 | 1830 | 1830 | 1840 | 1830 | 1830 | 1840 |
| Sensitivity | 38% | 38% | 31% | 41% | 41% | 32% | 33% | 33% | 32% |
| Specificity | 84% | 84% | 77% | 84% | 84% | 77% | 79% | 78% | 77% |
| OR Quartile 2 | 2.43 | 2.12 | 4.01 | 3.71 | 3.03 | 3.82 | 3.47 | 2.35 | 3.82 |
| p Value | 0.033 | 0.064 | 0.030 | 0.0044 | 0.012 | 0.036 | 0.010 | 0.055 | 0.036 |
| Lower limit of 95% CI | 1.07 | 0.957 | 1.14 | 1.51 | 1.27 | 1.09 | 1.34 | 0.983 | 1.09 |
| Upper limit of 95% CI | 5.48 | 4.71 | 14.0 | 9.16 | 7.21 | 13.4 | 8.99 | 5.60 | 13.4 |
| OR Quartile 3 | 2.53 | 2.38 | 2.71 | 3.31 | 2.92 | 2.54 | 2.44 | 2.01 | 2.54 |
| p Value | 0.0065 | 0.011 | 0.019 | 6.9E−4 | 0.0021 | 0.029 | 0.012 | 0.047 | 0.029 |
| Lower limit of 95% CI | 1.30 | 1.22 | 1.18 | 1.66 | 1.48 | 1.10 | 1.21 | 1.01 | 1.10 |
| Upper limit of 95% CI | 4.95 | 4.63 | 6.22 | 6.60 | 5.80 | 5.85 | 4.92 | 4.00 | 5.85 |
| OR Quartile 4 | 3.16 | 3.04 | 1.50 | 3.72 | 3.72 | 1.59 | 1.83 | 1.76 | 1.59 |
| p Value | 0.0032 | 0.0043 | 0.36 | 8.4E−4 | 8.4E−4 | 0.30 | 0.12 | 0.14 | 0.30 |
| Lower limit of 95% CI | 1.47 | 1.42 | 0.632 | 1.72 | 1.72 | 0.667 | 0.861 | 0.827 | 0.667 |
| Upper limit of 95% CI | 6.81 | 6.54 | 3.55 | 8.05 | 8.05 | 3.78 | 3.91 | 3.74 | 3.78 |

TABLE 16.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

sCr or UO

| | 24 | | 48 | | 72 | |
|---|---|---|---|---|---|---|
| Persistence Period Duration (hr) | Non-persistent Cohort | Persistent Cohort | Non-persistent Cohort | Persistent Cohort | Non-persistent Cohort | Persistent Cohort |
| Median | 622 | 1120 | 608 | 1250 | 630 | 1070 |
| Average | 1550 | 4420 | 1680 | 4460 | 2140 | 3940 |
| Stdev | 3370 | 6290 | 3760 | 6180 | 4420 | 5860 |
| p (t-test) | | 4.6E−4 | | 8.3E−4 | | 0.036 |
| Min | 21.1 | 20.6 | 20.6 | 158 | 20.6 | 158 |
| Max | 18800 | 18800 | 18800 | 18800 | 18800 | 18800 |
| n (Patient) | 85 | 64 | 90 | 59 | 96 | 53 | sCr only

| | 24 | | 48 | | 72 | |
|---|---|---|---|---|---|---|
| Persistence Period Duration (hr) | Non-persistent Cohort | Persistent Cohort | Non-persistent Cohort | Persistent Cohort | Non-persistent Cohort | Persistent Cohort |
| Median | 626 | 1070 | 615 | 1210 | 634 | 1070 |
| Average | 1770 | 4130 | 1700 | 4390 | 2160 | 3870 |
| Stdev | 3850 | 6040 | 3770 | 6150 | 4430 | 5830 |
| p (t-test) | | 0.0042 | | 0.0012 | | 0.046 |
| Min | 21.1 | 20.6 | 20.6 | 158 | 20.6 | 158 |
| Max | 18800 | 18800 | 18800 | 18800 | 18800 | 18800 |
| n (Patient) | 85 | 64 | 89 | 60 | 95 | 54 |

UO only

| | 24 | | 48 | | 72 | |
|---|---|---|---|---|---|---|
| Persistence Period Duration (hr) | Non-persistent Cohort | Persistent Cohort | Non-persistent Cohort | Persistent Cohort | Non-persistent Cohort | Persistent Cohort |
| Median | 724 | 1210 | 747 | 1210 | 747 | 1210 |
| Average | 2220 | 4590 | 2360 | 4280 | 2360 | 4280 |
| Stdev | 4310 | 6610 | 4540 | 6310 | 4540 | 6310 |
| p (t-test) | | 0.014 | | 0.050 | | 0.050 |
| Min | 20.6 | 233 | 20.6 | 233 | 20.6 | 233 |
| Max | 18800 | 18800 | 18800 | 18800 | 18800 | 18800 |
| n (Patient) | 112 | 36 | 114 | 34 | 114 | 34 |

TABLE 16.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.68 | 0.66 | 0.66 | 0.71 | 0.70 | 0.65 | 0.65 | 0.64 | 0.65 |
| SE | 0.045 | 0.046 | 0.055 | 0.044 | 0.045 | 0.056 | 0.048 | 0.048 | 0.056 |
| p Value | 5.9E-5 | 6.9E-4 | 0.0026 | 2.4E-6 | 1.2E-5 | 0.0076 | 0.0013 | 0.0036 | 0.0076 |
| nCohort Non-persistent | 85 | 85 | 112 | 90 | 89 | 114 | 96 | 95 | 114 |
| nCohort Persistent | 64 | 64 | 36 | 59 | 60 | 34 | 53 | 54 | 34 |
| Cutoff Quartile 2 | 401 | 401 | 410 | 401 | 401 | 410 | 401 | 401 | 410 |
| Sensitivity | 84% | 83% | 92% | 88% | 87% | 91% | 87% | 85% | 91% |
| Specificity | 32% | 31% | 30% | 33% | 33% | 30% | 31% | 31% | 30% |
| Cutoff Quartile 3 | 794 | 794 | 801 | 794 | 794 | 801 | 794 | 794 | 801 |
| Sensitivity | 64% | 62% | 67% | 68% | 67% | 65% | 64% | 63% | 65% |
| Specificity | 60% | 59% | 55% | 61% | 61% | 54% | 57% | 57% | 54% |
| Cutoff Quartile 4 | 1830 | 1830 | 1840 | 1830 | 1830 | 1840 | 1830 | 1830 | 1840 |
| Sensitivity | 39% | 38% | 33% | 41% | 40% | 32% | 34% | 33% | 32% |
| Specificity | 85% | 84% | 78% | 84% | 84% | 77% | 79% | 79% | 77% |
| OR Quartile 2 | 2.51 | 2.12 | 4.79 | 3.71 | 3.14 | 4.39 | 2.99 | 2.53 | 4.39 |
| p Value | 0.027 | 0.064 | 0.014 | 0.0044 | 0.0096 | 0.020 | 0.018 | 0.036 | 0.020 |
| Lower limit of 95% CI | 1.11 | 0.957 | 1.38 | 1.51 | 1.32 | 1.26 | 1.21 | 1.06 | 1.26 |
| Upper limit of 95% CI | 5.68 | 4.71 | 16.7 | 9.16 | 7.47 | 15.3 | 7.38 | 6.02 | 15.3 |
| OR Quartile 3 | 2.67 | 2.38 | 2.48 | 3.31 | 3.09 | 2.19 | 2.40 | 2.24 | 2.19 |
| p Value | 0.0040 | 0.011 | 0.024 | 6.9E-4 | 0.0013 | 0.054 | 0.013 | 0.021 | 0.054 |
| Lower limit of 95% CI | 1.37 | 1.22 | 1.13 | 1.66 | 1.56 | 0.988 | 1.20 | 1.13 | 0.988 |
| Upper limit of 95% CI | 5.23 | 4.63 | 5.45 | 6.60 | 6.12 | 4.84 | 4.80 | 4.44 | 4.84 |
| OR Quartile 4 | 3.55 | 3.04 | 1.74 | 3.72 | 3.57 | 1.62 | 1.95 | 1.88 | 1.62 |
| p Value | 0.0014 | 0.0043 | 0.19 | 8.4E-4 | 0.0012 | 0.26 | 0.081 | 0.10 | 0.26 |
| Lower limit of 95% CI | 1.64 | 1.42 | 0.764 | 1.72 | 1.65 | 0.698 | 0.921 | 0.885 | 0.698 |
| Upper limit of 95% CI | 7.71 | 6.54 | 3.96 | 8.05 | 7.71 | 3.75 | 4.15 | 3.97 | 3.75 |

TABLE 16.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 611 | 1180 | 592 | 1350 | 626 | 1070 |
| Average | 1220 | 4690 | 1180 | 4970 | 1870 | 4290 |
| Stdev | 2550 | 6480 | 2500 | 6590 | 3980 | 6160 |
| p (t-test) | | 1.7E-5 | | 2.6E-6 | | 0.0041 |
| Min | 21.1 | 20.6 | 20.6 | 158 | 20.6 | 158 |
| Max | 16600 | 18800 | 16600 | 18800 | 18800 | 18800 |
| n (Patient) | 82 | 67 | 86 | 63 | 93 | 56 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 622 | 1120 | 601 | 1300 | 626 | 1070 |
| Average | 1430 | 4480 | 1380 | 4750 | 1870 | 4290 |
| Stdev | 3190 | 6290 | 3120 | 6400 | 3980 | 6160 |
| p (t-test) | | 1.8E-4 | | 3.6E-5 | | 0.0041 |
| Min | 21.1 | 20.6 | 20.6 | 158 | 20.6 | 158 |
| Max | 18800 | 18800 | 18800 | 18800 | 18800 | 18800 |
| n (Patient) | 83 | 66 | 87 | 62 | 93 | 56 |

TABLE 16.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 718 | 1180 | 724 | 1210 | 724 | 1210 |
| Average | 2230 | 4500 | 2220 | 4600 | 2220 | 4600 |
| Stdev | 4320 | 6540 | 4310 | 6610 | 4310 | 6610 |
| p (t-test) | | 0.018 | | 0.014 | | 0.014 |
| Min | 20.6 | 233 | 20.6 | 233 | 20.6 | 233 |
| Max | 18800 | 18800 | 18800 | 18800 | 18800 | 18800 |
| n (Patient) | 111 | 37 | 112 | 36 | 112 | 36 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.69 | 0.68 | 0.67 | 0.73 | 0.72 | 0.67 | 0.66 | 0.66 | 0.67 |
| SE | 0.044 | 0.045 | 0.054 | 0.043 | 0.043 | 0.055 | 0.047 | 0.047 | 0.055 |
| p Value | 1.5E−5 | 6.5E−5 | 0.0021 | 5.9E−8 | 4.6E−7 | 0.0023 | 5.1E−4 | 5.1E−4 | 0.0023 |
| nCohort Non-persistent | 82 | 83 | 111 | 86 | 87 | 112 | 93 | 93 | 112 |
| nCohort Persistent | 67 | 66 | 37 | 63 | 62 | 36 | 56 | 56 | 36 |
| Cutoff Quartile 2 | 401 | 401 | 410 | 401 | 401 | 410 | 401 | 401 | 410 |
| Sensitivity | 84% | 83% | 92% | 87% | 87% | 92% | 86% | 86% | 92% |
| Specificity | 32% | 31% | 31% | 34% | 33% | 30% | 31% | 31% | 30% |
| Cutoff Quartile 3 | 794 | 794 | 801 | 794 | 794 | 801 | 794 | 794 | 801 |
| Sensitivity | 64% | 64% | 68% | 68% | 68% | 67% | 64% | 64% | 67% |
| Specificity | 61% | 60% | 56% | 63% | 62% | 55% | 58% | 58% | 55% |
| Cutoff Quartile 4 | 1830 | 1830 | 1840 | 1830 | 1830 | 1840 | 1830 | 1830 | 1840 |
| Sensitivity | 40% | 39% | 32% | 43% | 42% | 33% | 36% | 36% | 33% |
| Specificity | 87% | 86% | 77% | 87% | 86% | 78% | 81% | 81% | 78% |
| OR Quartile 2 | 2.36 | 2.28 | 5.00 | 3.50 | 3.38 | 4.79 | 2.72 | 2.72 | 4.79 |
| p Value | 0.034 | 0.042 | 0.011 | 0.0046 | 0.0059 | 0.014 | 0.024 | 0.024 | 0.014 |
| Lower limit of 95% CI | 1.07 | 1.03 | 1.44 | 1.47 | 1.42 | 1.38 | 1.14 | 1.14 | 1.38 |
| Upper limit of 95% CI | 5.24 | 5.06 | 17.4 | 8.32 | 8.02 | 16.7 | 6.47 | 6.47 | 16.7 |
| OR Quartile 3 | 2.80 | 2.65 | 2.64 | 3.63 | 3.44 | 2.48 | 2.49 | 2.49 | 2.48 |
| p Value | 0.0025 | 0.0042 | 0.015 | 2.4E−4 | 4.2E−4 | 0.024 | 0.0089 | 0.0089 | 0.024 |
| Lower limit of 95% CI | 1.44 | 1.36 | 1.20 | 1.82 | 1.73 | 1.13 | 1.26 | 1.26 | 1.13 |
| Upper limit of 95% CI | 5.46 | 5.17 | 5.77 | 7.22 | 6.83 | 5.45 | 4.94 | 4.94 | 5.45 |
| OR Quartile 4 | 4.36 | 3.85 | 1.65 | 5.11 | 4.51 | 1.74 | 2.31 | 2.31 | 1.74 |
| p Value | 3.2E−4 | 7.8E−4 | 0.23 | 7.2E−5 | 1.9E−4 | 0.19 | 0.028 | 0.028 | 0.19 |
| Lower limit of 95% CI | 1.96 | 1.75 | 0.727 | 2.28 | 2.05 | 0.764 | 1.09 | 1.09 | 0.764 |
| Upper limit of 95% CI | 9.71 | 8.44 | 3.75 | 11.4 | 9.96 | 3.96 | 4.90 | 4.90 | 3.96 |

Example 17. Use of Insulin-Like Growth Factor-Binding Protein 3 for Evaluating Renal Status in Patients Admitted to the ICU: Persistent at RIFLE I or F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 3 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is injury (I) or failure (F) where the persistence period can start from the time of sample collection to 24, 48, 72, 96 or 168 hours after sample collection. "Non-persistent" indicates those patients who are not persistent at injury (I) or failure (F) and whose minimum RIFLE stage during a period of 24, 48 or 72 hours is non-injury (RIFLE 0) or risk of injury (R) where the persistence period can start from the time of sample collection to 24, 48, 72, 96 or 168 hours after sample collection. If a patient dies after injury (I) or failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 17.1

Comparison of marker levels and the area under the ROC curve
(AUC) in urine samples for the "persistent" and "non-persistent" cohorts where
persistence starts within 24 hours after sample collection and renal status is assessed by
serum creatinine (sCr) only, urine output (UO) only, or serum creatinine or urine output
RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 553 | 1070 | 630 | 983 | 624 | 1070 |
| Average | 1240 | 3690 | 1580 | 4110 | 1470 | 4670 |
| Stdev | 3000 | 5730 | 3240 | 6210 | 3070 | 6530 |
| p (t-test) | | 0.0038 | | 0.0019 | | 9.6E−5 |
| Min | 30.5 | 20.6 | 21.1 | 20.6 | 21.1 | 20.6 |
| Max | 16600 | 18800 | 16600 | 18800 | 16600 | 18800 |
| n (Patient) | 55 | 94 | 78 | 71 | 88 | 61 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 583 | 1020 | 624 | 1070 | 622 | 1300 |
| Average | 1560 | 3540 | 1630 | 3980 | 1530 | 4640 |
| Stdev | 3740 | 5570 | 3550 | 6010 | 3310 | 6420 |
| p (t-test) | | 0.019 | | 0.0042 | | 1.6E−4 |
| Min | 30.5 | 20.6 | 21.1 | 20.6 | 21.1 | 20.6 |
| Max | 18800 | 18800 | 18800 | 18800 | 18800 | 18800 |
| n (Patient) | 57 | 92 | 76 | 73 | 89 | 60 |

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 672 | 1240 | 715 | 1350 | 718 | 1400 |
| Average | 2310 | 4450 | 2290 | 5070 | 2250 | 5780 |
| Stdev | 4440 | 6510 | 4340 | 7110 | 4270 | 7490 |
| p (t-test) | | 0.029 | | 0.0091 | | 0.0018 |
| Min | 20.6 | 172 | 20.6 | 194 | 20.6 | 194 |
| Max | 18800 | 18800 | 18800 | 18800 | 18800 | 18800 |
| n (Patient) | 114 | 34 | 121 | 27 | 125 | 23 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.68 | 0.64 | 0.66 | 0.64 | 0.64 | 0.68 | 0.68 | 0.69 | 0.70 |
| SE | 0.044 | 0.045 | 0.056 | 0.046 | 0.045 | 0.061 | 0.045 | 0.045 | 0.065 |
| p Value | 4.1E−5 | 0.0015 | 0.0037 | 0.0027 | 0.0018 | 0.0031 | 5.1E−5 | 2.4E−5 | 0.0018 |
| nCohort Non-persistent | 55 | 57 | 114 | 78 | 76 | 121 | 88 | 89 | 125 |
| nCohort Persistent | 94 | 92 | 34 | 71 | 73 | 27 | 61 | 60 | 23 |
| Cutoff Quartile 2 | 401 | 401 | 410 | 401 | 401 | 410 | 401 | 401 | 410 |
| Sensitivity | 80% | 78% | 85% | 80% | 79% | 85% | 85% | 83% | 87% |
| Specificity | 33% | 30% | 28% | 29% | 29% | 27% | 32% | 30% | 27% |
| Cutoff Quartile 3 | 794 | 794 | 801 | 794 | 794 | 801 | 794 | 794 | 801 |
| Sensitivity | 61% | 59% | 74% | 59% | 60% | 78% | 62% | 67% | 78% |
| Specificity | 67% | 63% | 57% | 58% | 59% | 56% | 58% | 61% | 55% |
| Cutoff Quartile 4 | 1830 | 1830 | 1840 | 1830 | 1830 | 1840 | 1830 | 1830 | 1840 |
| Sensitivity | 35% | 35% | 32% | 37% | 37% | 33% | 41% | 42% | 39% |
| Specificity | 91% | 89% | 77% | 85% | 86% | 77% | 85% | 85% | 78% |
| OR Quartile 2 | 1.92 | 1.53 | 2.26 | 1.70 | 1.58 | 2.16 | 2.70 | 2.18 | 2.49 |
| p Value | 0.090 | 0.27 | 0.12 | 0.17 | 0.24 | 0.18 | 0.020 | 0.061 | 0.16 |
| Lower limit of 95% CI | 0.902 | 0.720 | 0.805 | 0.796 | 0.741 | 0.693 | 1.17 | 0.963 | 0.695 |
| Upper limit of 95% CI | 4.09 | 3.25 | 6.36 | 3.64 | 3.35 | 6.71 | 6.23 | 4.92 | 8.92 |
| OR Quartile 3 | 3.17 | 2.44 | 3.68 | 1.97 | 2.20 | 4.49 | 2.28 | 3.09 | 4.44 |
| p Value | 0.0012 | 0.010 | 0.0026 | 0.041 | 0.018 | 0.0026 | 0.016 | 0.0013 | 0.0055 |
| Lower limit of 95% CI | 1.57 | 1.23 | 1.58 | 1.03 | 1.14 | 1.69 | 1.17 | 1.56 | 1.55 |
| Upper limit of 95% CI | 6.37 | 4.81 | 8.60 | 3.79 | 4.24 | 11.9 | 4.45 | 6.12 | 12.7 |
| OR Quartile 4 | 5.41 | 4.53 | 1.62 | 3.18 | 3.47 | 1.66 | 4.01 | 4.18 | 2.23 |
| p Value | 0.0011 | 0.0018 | 0.26 | 0.0038 | 0.0022 | 0.27 | 4.8E−4 | 3.3E−4 | 0.094 |

TABLE 17.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 1.97 | 1.76 | 0.698 | 1.45 | 1.56 | 0.672 | 1.84 | 1.91 | 0.873 |
| Upper limit of 95% CI | 14.9 | 11.7 | 3.75 | 6.95 | 7.69 | 4.10 | 8.73 | 9.12 | 5.68 |

TABLE 17.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | Persistence Period Duration (hr) | | | | | |
| | 24 | | 48 | | 72 | |
| | Non-persistent Cohort | Persistent Cohort | Non-persistent Cohort | Persistent Cohort | Non-persistent Cohort | Persistent Cohort |
| Median | 547 | 1070 | 601 | 1070 | 576 | 1250 |
| Average | 1250 | 3660 | 1400 | 4110 | 1310 | 4580 |
| Stdev | 3020 | 5710 | 3000 | 6140 | 2840 | 6400 |
| p (t-test) | | 0.0046 | | 8.7E−4 | | 5.5E−5 |
| Min | 30.5 | 20.6 | 21.1 | 20.6 | 21.1 | 20.6 |
| Max | 16600 | 18800 | 16600 | 18800 | 16600 | 18800 |
| n (Patient) | 54 | 95 | 73 | 76 | 82 | 67 |

| | sCr only | | | | | |
|---|---|---|---|---|---|---|
| | Persistence Period Duration (hr) | | | | | |
| | 24 | | 48 | | 72 | |
| | Non-persistent Cohort | Persistent Cohort | Non-persistent Cohort | Persistent Cohort | Non-persistent Cohort | Persistent Cohort |
| Median | 576 | 983 | 622 | 1020 | 592 | 1180 |
| Average | 1570 | 3510 | 1650 | 3870 | 1530 | 4310 |
| Stdev | 3770 | 5550 | 3610 | 5920 | 3430 | 6170 |
| p (t-test) | | 0.022 | | 0.0069 | | 6.8E−4 |
| Min | 30.5 | 20.6 | 21.1 | 20.6 | 21.1 | 20.6 |
| Max | 18800 | 18800 | 18800 | 18800 | 18800 | 18800 |
| n (Patient) | 56 | 93 | 73 | 76 | 82 | 67 |

| | UO only | | | | | |
|---|---|---|---|---|---|---|
| | Persistence Period Duration (hr) | | | | | |
| | 24 | | 48 | | 72 | |
| | Non-persistent Cohort | Persistent Cohort | Non-persistent Cohort | Persistent Cohort | Non-persistent Cohort | Persistent Cohort |
| Median | 637 | 1300 | 642 | 1400 | 702 | 1440 |
| Average | 2110 | 4540 | 2110 | 5040 | 2070 | 5560 |
| Stdev | 4260 | 6370 | 4160 | 6810 | 4090 | 7080 |
| p (t-test) | | 0.0079 | | 0.0024 | | 5.0E−4 |
| Min | 20.6 | 172 | 20.6 | 194 | 20.6 | 194 |
| Max | 18800 | 18800 | 18800 | 18800 | 18800 | 18800 |
| n (Patient) | 106 | 42 | 113 | 35 | 117 | 31 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.68 | 0.64 | 0.69 | 0.67 | 0.64 | 0.70 | 0.71 | 0.69 | 0.72 |
| SE | 0.044 | 0.045 | 0.051 | 0.044 | 0.045 | 0.054 | 0.043 | 0.044 | 0.056 |
| p Value | 4.1E−5 | 0.0015 | 1.8E−4 | 1.5E−4 | 0.0015 | 1.5E−4 | 5.7E−7 | 8.6E−6 | 8.5E−5 |
| nCohort Non-persistent | 54 | 56 | 106 | 73 | 73 | 113 | 82 | 82 | 117 |

TABLE 17.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| nCohort Persistent | 95 | 93 | 42 | 76 | 76 | 35 | 67 | 67 | 31 |
|---|---|---|---|---|---|---|---|---|---|
| Cutoff Quartile 2 | 401 | 401 | 410 | 401 | 401 | 410 | 401 | 401 | 410 |
| Sensitivity | 80% | 78% | 88% | 82% | 80% | 89% | 87% | 85% | 90% |
| Specificity | 33% | 30% | 30% | 32% | 30% | 29% | 34% | 33% | 29% |
| Cutoff Quartile 3 | 794 | 794 | 801 | 794 | 794 | 801 | 794 | 794 | 801 |
| Sensitivity | 60% | 58% | 74% | 61% | 59% | 77% | 64% | 64% | 77% |
| Specificity | 67% | 62% | 59% | 60% | 59% | 58% | 61% | 61% | 57% |
| Cutoff Quartile 4 | 1830 | 1830 | 1840 | 1830 | 1830 | 1840 | 1830 | 1830 | 1840 |
| Sensitivity | 35% | 34% | 36% | 38% | 37% | 37% | 42% | 40% | 42% |
| Specificity | 91% | 89% | 79% | 88% | 86% | 79% | 88% | 87% | 79% |
| OR Quartile 2 | 2.00 | 1.59 | 3.20 | 2.04 | 1.75 | 3.20 | 3.34 | 2.80 | 3.82 |
| p Value | 0.073 | 0.23 | 0.026 | 0.067 | 0.14 | 0.042 | 0.0048 | 0.013 | 0.036 |
| Lower limit of 95% CI | 0.938 | 0.748 | 1.15 | 0.951 | 0.825 | 1.05 | 1.45 | 1.24 | 1.09 |
| Upper limit of 95% CI | 4.26 | 3.38 | 8.89 | 4.36 | 3.73 | 9.77 | 7.72 | 6.32 | 13.4 |
| OR Quartile 3 | 3.00 | 2.31 | 4.13 | 2.33 | 2.08 | 4.74 | 2.80 | 2.80 | 4.59 |
| p Value | 0.0021 | 0.016 | 4.3E−4 | 0.012 | 0.028 | 4.8E−4 | 0.0025 | 0.0025 | 0.0011 |
| Lower limit of 95% CI | 1.49 | 1.17 | 1.87 | 1.21 | 1.08 | 1.98 | 1.44 | 1.44 | 1.83 |
| Upper limit of 95% CI | 6.04 | 4.55 | 9.09 | 4.49 | 4.00 | 11.3 | 5.46 | 5.46 | 11.5 |
| OR Quartile 4 | 5.22 | 4.37 | 2.12 | 4.39 | 3.68 | 2.19 | 5.17 | 4.36 | 2.80 |
| p Value | 0.0014 | 0.0023 | 0.061 | 5.4E−4 | 0.0017 | 0.061 | 8.7E−5 | 3.2E−4 | 0.017 |
| Lower limit of 95% CI | 1.90 | 1.69 | 0.966 | 1.90 | 1.63 | 0.965 | 2.28 | 1.96 | 1.20 |
| Upper limit of 95% CI | 14.4 | 11.3 | 4.66 | 10.1 | 8.29 | 4.98 | 11.7 | 9.71 | 6.50 |

TABLE 17.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | Persistence Period Duration (hr) | | | | | |
| | 24 | | 48 | | 72 | |
| | Non-persistent Cohort | Persistent Cohort | Non-persistent Cohort | Persistent Cohort | Non-persistent Cohort | Persistent Cohort |
| Median | 547 | 1070 | 611 | 1070 | 592 | 1070 |
| Average | 1250 | 3660 | 1420 | 4060 | 1360 | 4350 |
| Stdev | 3020 | 5710 | 3010 | 6120 | 2910 | 6280 |
| p (t-test) | | 0.0046 | | 0.0012 | | 2.2E−4 |
| Min | 30.5 | 20.6 | 21.1 | 20.6 | 21.1 | 20.6 |
| Max | 16600 | 18800 | 16600 | 18800 | 16600 | 18800 |
| n (Patient) | 54 | 95 | 72 | 77 | 78 | 71 |

| | sCr only | | | | | |
|---|---|---|---|---|---|---|
| | Persistence Period Duration (hr) | | | | | |
| | 24 | | 48 | | 72 | |
| | Non-persistent Cohort | Persistent Cohort | Non-persistent Cohort | Persistent Cohort | Non-persistent Cohort | Persistent Cohort |
| Median | 576 | 983 | 624 | 983 | 611 | 1070 |
| Average | 1570 | 3510 | 1680 | 3820 | 1590 | 4090 |
| Stdev | 3770 | 5550 | 3640 | 5890 | 3510 | 6060 |
| p (t-test) | | 0.022 | | 0.0090 | | 0.0022 |
| Min | 30.5 | 20.6 | 21.1 | 20.6 | 21.1 | 20.6 |
| Max | 18800 | 18800 | 18800 | 18800 | 18800 | 18800 |
| n (Patient) | 56 | 93 | 72 | 77 | 78 | 71 |

TABLE 17.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | UO only | | | | | |
|---|---|---|---|---|---|---|
| | Persistence Period Duration (hr) | | | | | |
| | 24 | | 48 | | 72 | |
| | Non-persistent Cohort | Persistent Cohort | Non-persistent Cohort | Persistent Cohort | Non-persistent Cohort | Persistent Cohort |
| Median | 638 | 1120 | 679 | 1210 | 717 | 1300 |
| Average | 2200 | 4040 | 2160 | 4420 | 2110 | 4780 |
| Stdev | 4370 | 6090 | 4260 | 6400 | 4190 | 6630 |
| p (t-test) | | 0.037 | | 0.013 | | 0.0046 |
| Min | 20.6 | 172 | 20.6 | 194 | 20.6 | 194 |
| Max | 18800 | 18800 | 18800 | 18800 | 18800 | 18800 |
| n (Patient) | 100 | 48 | 106 | 42 | 110 | 38 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.68 | 0.64 | 0.65 | 0.66 | 0.63 | 0.67 | 0.69 | 0.66 | 0.68 |
| SE | 0.044 | 0.045 | 0.050 | 0.045 | 0.045 | 0.052 | 0.044 | 0.045 | 0.053 |
| p Value | 4.1E−5 | 0.0015 | 0.0022 | 4.9E−4 | 0.0039 | 0.0012 | 1.6E−5 | 2.4E−4 | 9.5E−4 |
| nCohort Non-persistent | 54 | 56 | 100 | 72 | 72 | 106 | 78 | 78 | 110 |
| nCohort Persistent | 95 | 93 | 48 | 77 | 77 | 42 | 71 | 71 | 38 |
| Cutoff Quartile 2 | 401 | 401 | 410 | 401 | 401 | 410 | 401 | 401 | 410 |
| Sensitivity | 80% | 78% | 88% | 81% | 79% | 88% | 85% | 83% | 89% |
| Specificity | 33% | 30% | 31% | 31% | 29% | 30% | 33% | 32% | 30% |
| Cutoff Quartile 3 | 794 | 794 | 801 | 794 | 794 | 801 | 794 | 794 | 801 |
| Sensitivity | 60% | 58% | 67% | 60% | 58% | 69% | 62% | 61% | 68% |
| Specificity | 67% | 62% | 58% | 60% | 58% | 58% | 60% | 59% | 56% |
| Cutoff Quartile 4 | 1830 | 1830 | 1840 | 1830 | 1830 | 1840 | 1830 | 1830 | 1840 |
| Sensitivity | 35% | 34% | 31% | 38% | 36% | 33% | 39% | 38% | 37% |
| Specificity | 91% | 89% | 78% | 88% | 86% | 78% | 87% | 86% | 79% |
| OR Quartile 2 | 2.00 | 1.59 | 3.14 | 1.82 | 1.57 | 3.20 | 2.73 | 2.32 | 3.64 |
| p Value | 0.073 | 0.23 | 0.019 | 0.12 | 0.24 | 0.026 | 0.014 | 0.035 | 0.023 |
| Lower limit of 95% CI | 0.938 | 0.748 | 1.21 | 0.855 | 0.742 | 1.15 | 1.23 | 1.06 | 1.20 |
| Upper limit of 95% CI | 4.26 | 3.38 | 8.17 | 3.87 | 3.32 | 8.89 | 6.05 | 5.07 | 11.1 |
| OR Quartile 3 | 3.00 | 2.31 | 2.76 | 2.20 | 1.97 | 3.02 | 2.47 | 2.21 | 2.80 |
| p Value | 0.0021 | 0.016 | 0.0057 | 0.018 | 0.042 | 0.0043 | 0.0072 | 0.018 | 0.0098 |
| Lower limit of 95% CI | 1.49 | 1.17 | 1.34 | 1.14 | 1.03 | 1.42 | 1.28 | 1.15 | 1.28 |
| Upper limit of 95% CI | 6.04 | 4.55 | 5.67 | 4.24 | 3.78 | 6.46 | 4.78 | 4.25 | 6.11 |
| OR Quartile 4 | 5.22 | 4.37 | 1.61 | 4.23 | 3.54 | 1.80 | 4.43 | 3.74 | 2.21 |
| p Value | 0.0014 | 0.0023 | 0.23 | 7.3E−4 | 0.0023 | 0.14 | 3.6E−4 | 0.0012 | 0.054 |
| Lower limit of 95% CI | 1.90 | 1.69 | 0.744 | 1.83 | 1.57 | 0.818 | 1.96 | 1.68 | 0.988 |
| Upper limit of 95% CI | 14.4 | 11.3 | 3.49 | 9.77 | 7.99 | 3.98 | 10.0 | 8.30 | 4.93 |

TABLE 17.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

sCr or UO

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| Median | 547 | 1070 | 611 | 1070 | 592 | 1070 |
| Average | 1250 | 3660 | 1420 | 4060 | 1360 | 4350 |
| Stdev | 3020 | 5710 | 3010 | 6120 | 2910 | 6280 |
| p (t-test) | | 0.0046 | | 0.0012 | | 2.2E−4 |
| Min | 30.5 | 20.6 | 21.1 | 20.6 | 21.1 | 20.6 |
| Max | 16600 | 18800 | 16600 | 18800 | 16600 | 18800 |
| n (Patient) | 54 | 95 | 72 | 77 | 78 | 71 | sCr only

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| Median | 576 | 983 | 624 | 983 | 611 | 1070 |
| Average | 1570 | 3510 | 1680 | 3820 | 1590 | 4090 |
| Stdev | 3770 | 5550 | 3640 | 5890 | 3510 | 6060 |
| p (t-test) | | 0.022 | | 0.0090 | | 0.0022 |
| Min | 30.5 | 20.6 | 21.1 | 20.6 | 21.1 | 20.6 |
| Max | 18800 | 18800 | 18800 | 18800 | 18800 | 18800 |
| n (Patient) | 56 | 93 | 72 | 77 | 78 | 71 |

UO only

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| Median | 638 | 1070 | 718 | 1070 | 729 | 1180 |
| Average | 2240 | 3900 | 2210 | 4160 | 2160 | 4460 |
| Stdev | 4400 | 6010 | 4310 | 6260 | 4240 | 6480 |
| p (t-test) | | 0.057 | | 0.030 | | 0.012 |
| Min | 20.6 | 172 | 20.6 | 194 | 20.6 | 194 |
| Max | 18800 | 18800 | 18800 | 18800 | 18800 | 18800 |
| n (Patient) | 98 | 50 | 103 | 45 | 107 | 41 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.68 | 0.64 | 0.64 | 0.66 | 0.63 | 0.64 | 0.69 | 0.66 | 0.65 |
| SE | 0.044 | 0.045 | 0.049 | 0.045 | 0.045 | 0.051 | 0.044 | 0.045 | 0.053 |
| p Value | 4.1E−5 | 0.0015 | 0.0052 | 4.9E−4 | 0.0039 | 0.0056 | 1.6E−5 | 2.4E−4 | 0.0051 |
| nCohort Non-persistent | 54 | 56 | 98 | 72 | 72 | 103 | 78 | 78 | 107 |
| nCohort Persistent | 95 | 93 | 50 | 77 | 77 | 45 | 71 | 71 | 41 |
| Cutoff Quartile 2 | 401 | 401 | 410 | 401 | 401 | 410 | 401 | 401 | 410 |
| Sensitivity | 80% | 78% | 86% | 81% | 79% | 87% | 85% | 83% | 88% |
| Specificity | 33% | 30% | 31% | 31% | 29% | 30% | 33% | 32% | 30% |
| Cutoff Quartile 3 | 794 | 794 | 801 | 794 | 794 | 801 | 794 | 794 | 801 |
| Sensitivity | 60% | 58% | 64% | 60% | 58% | 64% | 62% | 61% | 63% |
| Specificity | 67% | 62% | 57% | 60% | 58% | 56% | 60% | 59% | 55% |
| Cutoff Quartile 4 | 1830 | 1830 | 1840 | 1830 | 1830 | 1840 | 1830 | 1830 | 1840 |
| Sensitivity | 35% | 34% | 30% | 38% | 36% | 31% | 39% | 38% | 34% |
| Specificity | 91% | 89% | 78% | 88% | 86% | 78% | 87% | 86% | 79% |
| OR Quartile 2 | 2.00 | 1.59 | 2.71 | 1.82 | 1.57 | 2.80 | 2.73 | 2.32 | 3.07 |
| p Value | 0.073 | 0.23 | 0.031 | 0.12 | 0.24 | 0.035 | 0.014 | 0.035 | 0.032 |
| Lower limit of 95% CI | 0.938 | 0.748 | 1.09 | 0.855 | 0.742 | 1.07 | 1.23 | 1.06 | 1.10 |

TABLE 17.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 4.26 | 3.38 | 6.71 | 3.87 | 3.32 | 7.29 | 6.05 | 5.07 | 8.54 |
| OR Quartile 3 | 3.00 | 2.31 | 2.37 | 2.20 | 1.97 | 2.34 | 2.47 | 2.21 | 2.13 |
| p Value | 0.0021 | 0.016 | 0.016 | 0.018 | 0.042 | 0.022 | 0.0072 | 0.018 | 0.045 |
| Lower limit of 95% CI | 1.49 | 1.17 | 1.17 | 1.14 | 1.03 | 1.13 | 1.28 | 1.15 | 1.02 |
| Upper limit of 95% CI | 6.04 | 4.55 | 4.79 | 4.24 | 3.78 | 4.82 | 4.78 | 4.25 | 4.47 |
| OR Quartile 4 | 5.22 | 4.37 | 1.48 | 4.23 | 3.54 | 1.57 | 4.43 | 3.74 | 1.89 |
| p Value | 0.0014 | 0.0023 | 0.32 | 7.3E−4 | 0.0023 | 0.26 | 3.6E−4 | 0.0012 | 0.11 |
| Lower limit of 95% CI | 1.90 | 1.69 | 0.686 | 1.83 | 1.57 | 0.718 | 1.96 | 1.68 | 0.857 |
| Upper limit of 95% CI | 14.4 | 11.3 | 3.19 | 9.77 | 7.99 | 3.44 | 10.0 | 8.30 | 4.19 |

TABLE 17.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | Persistence Period Duration (hr) | | | | | |
| | 24 | | 48 | | 72 | |
| | Non-persistent Cohort | Persistent Cohort | Non-persistent Cohort | Persistent Cohort | Non-persistent Cohort | Persistent Cohort |
| Median | 547 | 1070 | 601 | 1070 | 592 | 1070 |
| Average | 1250 | 3600 | 1280 | 4080 | 1240 | 4310 |
| Stdev | 3080 | 5660 | 2760 | 6100 | 2670 | 6230 |
| p (t-test) | | 0.0060 | | 5.8E−4 | | 1.5E−4 |
| Min | 30.5 | 20.6 | 21.1 | 20.6 | 21.1 | 20.6 |
| Max | 16600 | 18800 | 16600 | 18800 | 16600 | 18800 |
| n (Patient) | 52 | 97 | 69 | 80 | 74 | 75 |

| | sCr only | | | | | |
|---|---|---|---|---|---|---|
| | Persistence Period Duration (hr) | | | | | |
| | 24 | | 48 | | 72 | |
| | Non-persistent Cohort | Persistent Cohort | Non-persistent Cohort | Persistent Cohort | Non-persistent Cohort | Persistent Cohort |
| Median | 569 | 1020 | 611 | 1070 | 592 | 1070 |
| Average | 1560 | 3500 | 1510 | 3910 | 1440 | 4180 |
| Stdev | 3810 | 5520 | 3440 | 5900 | 3320 | 6060 |
| p (t-test) | | 0.023 | | 0.0034 | | 7.7E−4 |
| Min | 30.5 | 20.6 | 21.1 | 20.6 | 21.1 | 20.6 |
| Max | 18800 | 18800 | 18800 | 18800 | 18800 | 18800 |
| n (Patient) | 55 | 94 | 70 | 79 | 76 | 73 |

| | UO only | | | | | |
|---|---|---|---|---|---|---|
| | Persistence Period Duration (hr) | | | | | |
| | 24 | | 48 | | 72 | |
| | Non-persistent Cohort | Persistent Cohort | Non-persistent Cohort | Persistent Cohort | Non-persistent Cohort | Persistent Cohort |
| Median | 630 | 1070 | 642 | 1070 | 680 | 1200 |
| Average | 2140 | 4010 | 2140 | 4120 | 2100 | 4340 |
| Stdev | 4320 | 6020 | 4270 | 6170 | 4210 | 6310 |
| p (t-test) | | 0.031 | | 0.024 | | 0.012 |
| Min | 20.6 | 172 | 20.6 | 172 | 20.6 | 172 |
| Max | 18800 | 18800 | 18800 | 18800 | 18800 | 18800 |
| n (Patient) | 96 | 52 | 99 | 49 | 102 | 46 |

TABLE 17.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.68 | 0.65 | 0.65 | 0.66 | 0.65 | 0.64 | 0.68 | 0.68 | 0.65 |
| SE | 0.044 | 0.045 | 0.048 | 0.044 | 0.045 | 0.050 | 0.044 | 0.044 | 0.050 |
| p Value | 5.2E−5 | 6.9E−4 | 0.0018 | 3.1E−4 | 8.1E−4 | 0.0040 | 3.8E−5 | 3.2E−5 | 0.0023 |
| nCohort Non-persistent | 52 | 55 | 96 | 69 | 70 | 99 | 74 | 76 | 102 |
| nCohort Persistent | 97 | 94 | 52 | 80 | 79 | 49 | 75 | 73 | 46 |
| Cutoff Quartile 2 | 401 | 401 | 410 | 401 | 401 | 410 | 401 | 401 | 410 |
| Sensitivity | 79% | 79% | 87% | 80% | 80% | 86% | 83% | 84% | 87% |
| Specificity | 33% | 31% | 31% | 30% | 30% | 30% | 32% | 33% | 30% |
| Cutoff Quartile 3 | 794 | 794 | 801 | 794 | 794 | 801 | 794 | 794 | 801 |
| Sensitivity | 60% | 59% | 65% | 60% | 59% | 65% | 61% | 62% | 65% |
| Specificity | 67% | 64% | 58% | 61% | 60% | 58% | 61% | 61% | 57% |
| Cutoff Quartile 4 | 1830 | 1830 | 1840 | 1830 | 1830 | 1840 | 1830 | 1830 | 1840 |
| Sensitivity | 35% | 35% | 31% | 38% | 38% | 31% | 39% | 40% | 33% |
| Specificity | 92% | 91% | 78% | 88% | 89% | 78% | 88% | 88% | 78% |
| OR Quartile 2 | 1.87 | 1.66 | 2.92 | 1.75 | 1.69 | 2.61 | 2.29 | 2.49 | 2.91 |
| p Value | 0.11 | 0.19 | 0.020 | 0.14 | 0.17 | 0.038 | 0.035 | 0.022 | 0.029 |
| Lower limit of 95% CI | 0.874 | 0.777 | 1.18 | 0.826 | 0.797 | 1.05 | 1.06 | 1.14 | 1.12 |
| Upper limit of 95% CI | 4.00 | 3.52 | 7.23 | 3.71 | 3.57 | 6.47 | 4.95 | 5.45 | 7.57 |
| OR Quartile 3 | 3.06 | 2.47 | 2.64 | 2.33 | 2.20 | 2.55 | 2.46 | 2.46 | 2.47 |
| p Value | 0.0019 | 0.0098 | 0.0065 | 0.012 | 0.018 | 0.0097 | 0.0074 | 0.0073 | 0.014 |
| Lower limit of 95% CI | 1.51 | 1.24 | 1.31 | 1.21 | 1.14 | 1.26 | 1.27 | 1.28 | 1.20 |
| Upper limit of 95% CI | 6.21 | 4.90 | 5.33 | 4.51 | 4.25 | 5.20 | 4.76 | 4.76 | 5.09 |
| OR Quartile 4 | 6.48 | 5.41 | 1.59 | 4.58 | 4.74 | 1.54 | 4.55 | 4.91 | 1.76 |
| p Value | 8.9E−4 | 0.0011 | 0.23 | 5.7E−4 | 4.2E−4 | 0.27 | 3.9E−4 | 2.0E−4 | 0.15 |
| Lower limit of 95% CI | 2.15 | 1.97 | 0.741 | 1.93 | 2.00 | 0.715 | 1.97 | 2.12 | 0.810 |
| Upper limit of 95% CI | 19.5 | 14.9 | 3.40 | 10.9 | 11.3 | 3.34 | 10.5 | 11.4 | 3.82 |

Example 18. Use of Insulin-Like Growth Factor-Binding Protein 4 for Evaluating Renal Status in Patients Admitted to the ICU: Persistent at RIFLE F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 4 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is failure (F) where the persistence period can start from the time of sample collection to 24, 48, 72, 96 or 168 hours after sample collection. "Non-persistent" indicates those patients who are not persistent at failure (F) and whose minimum RIFLE stage during a period of 24, 48 or 72 hours is non-injury (RIFLE 0), risk of injury (R), or injury (I) where the persistence period can start from the time of sample collection to 24, 48, 72, 96 or 168 hours after sample collection. If a patient dies after failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 18.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | Persistence Period Duration (hr) | | | | | |
| | 24 | | 48 | | 72 | |
| | Non-persistent Cohort | Persistent Cohort | Non-persistent Cohort | Persistent Cohort | Non-persistent Cohort | Persistent Cohort |
| Median | 0.0669 | 1.14 | 0.0851 | 1.75 | 0.0895 | 1.36 |
| Average | 4.30 | 14.0 | 4.43 | 15.5 | 5.82 | 13.2 |
| Stdev | 16.9 | 21.1 | 16.5 | 22.2 | 18.3 | 20.0 |
| p (t-test) | | 0.0028 | | 0.0011 | | 0.040 |
| Min | 0.000212 | 0.000212 | 0.000212 | 0.000212 | 0.000212 | 0.000212 |
| Max | 120 | 73.0 | 120 | 73.0 | 120 | 61.5 |
| n (Patient) | 98 | 51 | 106 | 43 | 113 | 36 |

| | sCr only | | | | | |
|---|---|---|---|---|---|---|
| | Persistence Period Duration (hr) | | | | | |
| | 24 | | 48 | | 72 | |
| | Non-persistent Cohort | Persistent Cohort | Non-persistent Cohort | Persistent Cohort | Non-persistent Cohort | Persistent Cohort |
| Median | 0.0851 | 1.13 | 0.0851 | 1.75 | 0.118 | 1.36 |
| Average | 4.35 | 13.7 | 4.36 | 15.6 | 5.81 | 12.9 |
| Stdev | 17.0 | 21.0 | 16.5 | 22.1 | 18.5 | 19.6 |
| p (t-test) | | 0.0037 | | 8.2E-4 | | 0.046 |
| Min | 0.000212 | 0.000212 | 0.000212 | 0.000212 | 0.000212 | 0.000212 |
| Max | 120 | 73.0 | 120 | 73.0 | 120 | 61.5 |
| n (Patient) | 97 | 52 | 106 | 43 | 111 | 38 |

| | UO only | | | | | |
|---|---|---|---|---|---|---|
| | Persistence Period | | | | | |
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.146 | 1.03 | 0.126 | 1.14 | 0.126 | 1.14 |
| Average | 6.99 | 12.6 | 6.94 | 13.3 | 6.94 | 13.3 |
| Stdev | 19.0 | 18.8 | 18.9 | 19.1 | 18.9 | 19.1 |
| p (t-test) | | 0.24 | | 0.20 | | 0.20 |
| Min | 0.000212 | 0.000339 | 0.000212 | 0.000339 | 0.000212 | 0.000339 |
| Max | 120 | 50.9 | 120 | 50.9 | 120 | 50.9 |
| n (Patient) | 130 | 18 | 131 | 17 | 131 | 17 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.68 | 0.67 | 0.66 | 0.69 | 0.68 | 0.67 | 0.65 | 0.63 | 0.67 |
| SE | 0.048 | 0.048 | 0.074 | 0.050 | 0.051 | 0.075 | 0.055 | 0.054 | 0.075 |
| p Value | 1.9E-4 | 5.2E-4 | 0.033 | 1.4E-4 | 3.0E-4 | 0.027 | 0.0063 | 0.013 | 0.027 |
| nCohort Non-persistent | 98 | 97 | 130 | 106 | 106 | 131 | 113 | 111 | 131 |
| nCohort Persistent | 51 | 52 | 18 | 43 | 43 | 17 | 36 | 38 | 17 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 88% | 87% | 100% | 86% | 84% | 100% | 86% | 82% | 100% |
| Specificity | 22% | 22% | 21% | 21% | 20% | 21% | 20% | 19% | 21% |
| Cutoff Quartile 3 | 0.170 | 0.170 | 0.205 | 0.170 | 0.170 | 0.205 | 0.170 | 0.170 | 0.205 |
| Sensitivity | 63% | 62% | 61% | 67% | 67% | 65% | 64% | 63% | 65% |
| Specificity | 56% | 56% | 52% | 57% | 57% | 52% | 54% | 54% | 52% |
| Cutoff Quartile 4 | 2.99 | 2.99 | 3.01 | 2.99 | 2.99 | 3.01 | 2.99 | 2.99 | 3.01 |
| Sensitivity | 43% | 42% | 39% | 47% | 47% | 41% | 42% | 42% | 41% |
| Specificity | 84% | 84% | 77% | 83% | 83% | 77% | 80% | 80% | 77% |
| OR Quartile 2 | 2.17 | 1.78 | 9.83 | 1.62 | 1.27 | 9.21 | 1.58 | 1.03 | 9.21 |
| p Value | 0.12 | 0.23 | 0.11 | 0.34 | 0.62 | 0.13 | 0.39 | 0.95 | 0.13 |
| Lower limit of 95% CI | 0.819 | 0.700 | 0.574 | 0.605 | 0.496 | 0.537 | 0.555 | 0.401 | 0.537 |

TABLE 18.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 5.76 | 4.51 | 168 | 4.31 | 3.25 | 158 | 4.53 | 2.67 | 158 |
| OR Quartile 3 | 2.15 | 2.01 | 1.67 | 2.70 | 2.70 | 1.98 | 2.08 | 2.02 | 1.98 |
| p Value | 0.030 | 0.047 | 0.32 | 0.0089 | 0.0089 | 0.20 | 0.065 | 0.070 | 0.20 |
| Lower limit of 95% CI | 1.08 | 1.01 | 0.610 | 1.28 | 1.28 | 0.691 | 0.957 | 0.946 | 0.691 |
| Upper limit of 95% CI | 4.31 | 4.00 | 4.58 | 5.69 | 5.69 | 5.67 | 4.50 | 4.30 | 5.67 |
| OR Quartile 4 | 3.89 | 3.71 | 2.12 | 4.25 | 4.25 | 2.36 | 2.80 | 2.94 | 2.36 |
| p Value | 5.5E−4 | 8.2E−4 | 0.15 | 3.0E−4 | 3.0E−4 | 0.11 | 0.012 | 0.0078 | 0.11 |
| Lower limit of 95% CI | 1.80 | 1.72 | 0.756 | 1.94 | 1.94 | 0.826 | 1.25 | 1.33 | 0.826 |
| Upper limit of 95% CI | 8.40 | 8.00 | 5.95 | 9.32 | 9.32 | 6.72 | 6.25 | 6.52 | 6.72 |

TABLE 18.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

sCr or UO

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.0328 | 1.17 | 0.0328 | 1.58 | 0.0851 | 1.17 |
| Average | 4.50 | 12.5 | 4.55 | 13.5 | 6.01 | 11.4 |
| Stdev | 17.5 | 20.2 | 17.2 | 20.9 | 18.9 | 18.6 |
| p (t-test) | | 0.011 | | 0.0058 | | 0.11 |
| Min | 0.000212 | 0.000212 | 0.000212 | 0.000212 | 0.000212 | 0.000212 |
| Max | 120 | 73.0 | 120 | 73.0 | 120 | 61.5 |
| n (Patient) | 91 | 58 | 98 | 51 | 105 | 44 | sCr only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.0487 | 1.13 | 0.0328 | 1.67 | 0.0851 | 1.13 |
| Average | 4.51 | 12.5 | 4.57 | 13.3 | 6.10 | 11.0 |
| Stdev | 17.5 | 20.2 | 17.2 | 20.7 | 19.1 | 18.3 |
| p (t-test) | | 0.012 | | 0.0070 | | 0.15 |
| Min | 0.000212 | 0.000212 | 0.000212 | 0.000212 | 0.000212 | 0.000212 |
| Max | 120 | 73.0 | 120 | 73.0 | 120 | 61.5 |
| n (Patient) | 91 | 58 | 97 | 52 | 103 | 46 |

UO only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.126 | 1.13 | 0.126 | 1.13 | 0.126 | 1.13 |
| Average | 7.28 | 9.57 | 7.22 | 9.96 | 7.22 | 9.96 |
| Stdev | 19.5 | 16.6 | 19.4 | 16.9 | 19.4 | 16.9 |
| p (t-test) | | 0.58 | | 0.52 | | 0.52 |
| Min | 0.000212 | 0.000339 | 0.000212 | 0.000339 | 0.000212 | 0.000339 |
| Max | 120 | 50.9 | 120 | 50.9 | 120 | 50.9 |
| n (Patient) | 123 | 25 | 124 | 24 | 124 | 24 |

TABLE 18.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period | | | | | | | | |
|---|---|---|---|---|---|---|---|---|---|
| | 24 | | | 48 | | | 72 | | |
| Duration (hr) | sCr or UO | sCr only | UO only | sCr or UO | sCr only | UO only | sCr or UO | sCr only | UO only |
| AUC | 0.69 | 0.67 | 0.65 | 0.70 | 0.69 | 0.65 | 0.66 | 0.64 | 0.65 |
| SE | 0.046 | 0.046 | 0.064 | 0.047 | 0.047 | 0.065 | 0.051 | 0.051 | 0.065 |
| p Value | 4.2E-5 | 2.0E-4 | 0.021 | 1.6E-5 | 4.1E-5 | 0.018 | 0.0012 | 0.0049 | 0.018 |
| nCohort Non-persistent | 91 | 91 | 123 | 98 | 97 | 124 | 105 | 103 | 124 |
| nCohort Persistent | 58 | 58 | 25 | 51 | 52 | 24 | 44 | 46 | 24 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 90% | 88% | 100% | 88% | 87% | 100% | 89% | 85% | 100% |
| Specificity | 24% | 23% | 22% | 22% | 22% | 22% | 22% | 20% | 22% |
| Cutoff Quartile 3 | 0.170 | 0.170 | 0.205 | 0.170 | 0.170 | 0.205 | 0.170 | 0.170 | 0.205 |
| Sensitivity | 62% | 60% | 60% | 67% | 65% | 62% | 64% | 61% | 62% |
| Specificity | 57% | 56% | 52% | 58% | 58% | 52% | 55% | 54% | 52% |
| Cutoff Quartile 4 | 2.99 | 2.99 | 3.01 | 2.99 | 2.99 | 3.01 | 2.99 | 2.99 | 3.01 |
| Sensitivity | 41% | 41% | 36% | 43% | 44% | 38% | 41% | 41% | 38% |
| Specificity | 85% | 85% | 77% | 84% | 85% | 77% | 81% | 82% | 77% |
| OR Quartile 2 | 2.76 | 2.19 | 14.5 | 2.17 | 1.78 | 13.8 | 2.19 | 1.43 | 13.8 |
| p Value | 0.040 | 0.099 | 0.064 | 0.12 | 0.23 | 0.069 | 0.14 | 0.46 | 0.069 |
| Lower limit of 95% CI | 1.05 | 0.864 | 0.857 | 0.819 | 0.700 | 0.814 | 0.774 | 0.559 | 0.814 |
| Upper limit of 95% CI | 7.30 | 5.53 | 246 | 5.76 | 4.51 | 235 | 6.19 | 3.64 | 235 |
| OR Quartile 3 | 2.18 | 1.94 | 1.63 | 2.78 | 2.58 | 1.84 | 2.16 | 1.85 | 1.84 |
| p Value | 0.023 | 0.052 | 0.28 | 0.0046 | 0.0079 | 0.18 | 0.037 | 0.088 | 0.18 |
| Lower limit of 95% CI | 1.11 | 0.993 | 0.678 | 1.37 | 1.28 | 0.748 | 1.05 | 0.913 | 0.748 |
| Upper limit of 95% CI | 4.28 | 3.79 | 3.90 | 5.64 | 5.19 | 4.51 | 4.46 | 3.76 | 4.51 |
| OR Quartile 4 | 3.88 | 3.88 | 1.91 | 3.89 | 4.34 | 2.06 | 2.94 | 3.11 | 2.06 |
| p Value | 5.8E-4 | 5.8E-4 | 0.17 | 5.5E-4 | 2.1E-4 | 0.13 | 0.0063 | 0.0038 | 0.13 |
| Lower limit of 95% CI | 1.79 | 1.79 | 0.761 | 1.80 | 2.00 | 0.814 | 1.36 | 1.44 | 0.814 |
| Upper limit of 95% CI | 8.41 | 8.41 | 4.78 | 8.40 | 9.42 | 5.20 | 6.38 | 6.72 | 5.20 |

TABLE 18.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | Persistence Period | | | | | |
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.0328 | 1.21 | 0.0328 | 1.46 | 0.0407 | 1.21 |
| Average | 4.49 | 11.9 | 4.29 | 12.7 | 5.99 | 10.7 |
| Stdev | 17.9 | 19.6 | 17.5 | 20.0 | 19.3 | 17.9 |
| p (t-test) | | 0.018 | | 0.0077 | | 0.15 |
| Min | 0.000212 | 0.000212 | 0.000212 | 0.000212 | 0.000212 | 0.000212 |
| Max | 120 | 73.0 | 120 | 73.0 | 120 | 61.5 |
| n (Patient) | 86 | 63 | 90 | 59 | 98 | 51 |

TABLE 18.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

sCr only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.0328 | 1.17 | 0.0328 | 1.46 | 0.0851 | 1.13 |
| Average | 4.55 | 11.7 | 4.31 | 12.7 | 6.06 | 10.5 |
| Stdev | 18.0 | 19.5 | 17.5 | 20.0 | 19.4 | 17.8 |
| p (t-test) | | 0.022 | | 0.0080 | | 0.17 |
| Min | 0.000212 | 0.000212 | 0.000212 | 0.000212 | 0.000212 | 0.000212 |
| Max | 120 | 73.0 | 120 | 73.0 | 120 | 61.5 |
| n (Patient) | 85 | 64 | 90 | 59 | 97 | 52 |

UO only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.122 | 1.13 | 0.126 | 1.14 | 0.126 | 1.14 |
| Average | 7.21 | 9.31 | 7.15 | 9.61 | 7.15 | 9.61 |
| Stdev | 19.8 | 15.9 | 19.7 | 16.1 | 19.7 | 16.1 |
| p (t-test) | | 0.58 | | 0.52 | | 0.52 |
| Min | 0.000212 | 0.000312 | 0.000212 | 0.000312 | 0.000212 | 0.000312 |
| Max | 120 | 50.9 | 120 | 50.9 | 120 | 50.9 |
| n (Patient) | 116 | 32 | 117 | 31 | 117 | 31 |

| | Persistence Period | | | | | | | | |
|---|---|---|---|---|---|---|---|---|---|
| | 24 | | | 48 | | | 72 | | |
| Duration (hr) | sCr or UO | sCr only | UO only | sCr or UO | sCr only | UO only | sCr or UO | sCr only | UO only |
| AUC | 0.69 | 0.68 | 0.64 | 0.71 | 0.70 | 0.65 | 0.66 | 0.64 | 0.65 |
| SE | 0.045 | 0.045 | 0.058 | 0.044 | 0.045 | 0.059 | 0.048 | 0.049 | 0.059 |
| p Value | 3.0E-5 | 9.1E-5 | 0.014 | 1.7E-6 | 1.2E-5 | 0.012 | 6.5E-4 | 0.0048 | 0.012 |
| nCohort Non-persistent | 86 | 85 | 116 | 90 | 90 | 117 | 98 | 97 | 117 |
| nCohort Persistent | 63 | 64 | 32 | 59 | 59 | 31 | 51 | 52 | 31 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 89% | 88% | 97% | 88% | 86% | 97% | 88% | 85% | 97% |
| Specificity | 24% | 24% | 22% | 23% | 22% | 22% | 22% | 21% | 22% |
| Cutoff Quartile 3 | 0.170 | 0.170 | 0.205 | 0.170 | 0.170 | 0.205 | 0.170 | 0.170 | 0.205 |
| Sensitivity | 62% | 61% | 59% | 66% | 64% | 61% | 63% | 60% | 61% |
| Specificity | 58% | 58% | 53% | 60% | 59% | 53% | 56% | 55% | 53% |
| Cutoff Quartile 4 | 2.99 | 2.99 | 3.01 | 2.99 | 2.99 | 3.01 | 2.99 | 2.99 | 3.01 |
| Sensitivity | 40% | 39% | 34% | 42% | 42% | 35% | 39% | 38% | 35% |
| Specificity | 85% | 85% | 78% | 86% | 86% | 78% | 82% | 81% | 78% |
| OR Quartile 2 | 2.58 | 2.15 | 8.96 | 2.26 | 1.82 | 8.57 | 2.17 | 1.43 | 8.57 |
| p Value | 0.045 | 0.093 | 0.035 | 0.085 | 0.19 | 0.039 | 0.12 | 0.44 | 0.039 |
| Lower limit of 95% CI | 1.02 | 0.881 | 1.17 | 0.894 | 0.744 | 1.12 | 0.819 | 0.581 | 1.12 |
| Upper limit of 95% CI | 6.53 | 5.27 | 68.8 | 5.72 | 4.46 | 65.9 | 5.76 | 3.51 | 65.9 |
| OR Quartile 3 | 2.26 | 2.12 | 1.62 | 2.92 | 2.59 | 1.78 | 2.15 | 1.78 | 1.78 |
| p Value | 0.016 | 0.026 | 0.23 | 0.0021 | 0.0059 | 0.16 | 0.030 | 0.099 | 0.16 |
| Lower limit of 95% CI | 1.16 | 1.10 | 0.733 | 1.48 | 1.32 | 0.795 | 1.08 | 0.898 | 0.795 |
| Upper limit of 95% CI | 4.39 | 4.11 | 3.59 | 5.80 | 5.11 | 4.01 | 4.31 | 3.52 | 4.01 |
| OR Quartile 4 | 3.69 | 3.55 | 1.81 | 4.36 | 4.36 | 1.92 | 2.87 | 2.74 | 1.92 |
| p Value | 9.7E-4 | 0.0014 | 0.17 | 2.3E-4 | 2.3E-4 | 0.13 | 0.0066 | 0.0091 | 0.13 |
| Lower limit of 95% CI | 1.70 | 1.64 | 0.775 | 1.99 | 1.99 | 0.819 | 1.34 | 1.29 | 0.819 |
| Upper limit of 95% CI | 8.03 | 7.71 | 4.24 | 9.52 | 9.52 | 4.53 | 6.13 | 5.85 | 4.53 |

TABLE 18.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

sCr or UO

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.0328 | 1.28 | 0.0328 | 1.46 | 0.0407 | 1.21 |
| Average | 4.40 | 11.9 | 4.29 | 12.7 | 5.35 | 11.7 |
| Stdev | 18.0 | 19.4 | 17.5 | 20.0 | 18.2 | 19.6 |
| p (t-test) | | 0.016 | | 0.0077 | | 0.049 |
| Min | 0.000212 | 0.000212 | 0.000212 | 0.000212 | 0.000212 | 0.000212 |
| Max | 120 | 73.0 | 120 | 73.0 | 120 | 73.0 |
| n (Patient) | 85 | 64 | 90 | 59 | 96 | 53 | sCr only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.0328 | 1.17 | 0.0328 | 1.40 | 0.0487 | 1.17 |
| Average | 4.55 | 11.7 | 4.34 | 12.5 | 5.41 | 11.5 |
| Stdev | 18.0 | 19.5 | 17.6 | 19.9 | 18.3 | 19.5 |
| p (t-test) | | 0.022 | | 0.0097 | | 0.059 |
| Min | 0.000212 | 0.000212 | 0.000212 | 0.000212 | 0.000212 | 0.000212 |
| Max | 120 | 73.0 | 120 | 73.0 | 120 | 73.0 |
| n (Patient) | 85 | 64 | 89 | 60 | 95 | 54 |

UO only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.0873 | 1.13 | 0.104 | 1.13 | 0.104 | 1.13 |
| Average | 6.98 | 9.79 | 6.97 | 9.98 | 6.97 | 9.98 |
| Stdev | 19.9 | 16.1 | 19.7 | 16.4 | 19.7 | 16.4 |
| p (t-test) | | 0.44 | | 0.42 | | 0.42 |
| Min | 0.000212 | 0.000312 | 0.000212 | 0.000312 | 0.000212 | 0.000312 |
| Max | 120 | 50.9 | 120 | 50.9 | 120 | 50.9 |
| n (Patient) | 112 | 36 | 114 | 34 | 114 | 34 |

| | Persistence Period | | | | | | | | |
|---|---|---|---|---|---|---|---|---|---|
| | 24 | | | 48 | | | 72 | | |
| Duration (hr) | sCr or UO | sCr only | UO only | sCr or UO | sCr only | UO only | sCr or UO | sCr only | UO only |
| AUC | 0.70 | 0.68 | 0.66 | 0.71 | 0.70 | 0.66 | 0.67 | 0.65 | 0.66 |
| SE | 0.044 | 0.045 | 0.055 | 0.044 | 0.045 | 0.056 | 0.048 | 0.048 | 0.056 |
| p Value | 9.7E−6 | 9.1E−5 | 0.0029 | 1.7E−6 | 6.6E−6 | 0.0049 | 4.8E−4 | 0.0012 | 0.0049 |
| nCohort Non-persistent | 85 | 85 | 112 | 90 | 89 | 114 | 96 | 95 | 114 |
| nCohort Persistent | 64 | 64 | 36 | 59 | 60 | 34 | 53 | 54 | 34 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 89% | 88% | 97% | 88% | 87% | 97% | 87% | 85% | 97% |
| Specificity | 25% | 24% | 23% | 23% | 22% | 23% | 22% | 21% | 23% |
| Cutoff Quartile 3 | 0.170 | 0.170 | 0.205 | 0.170 | 0.170 | 0.205 | 0.170 | 0.170 | 0.205 |
| Sensitivity | 62% | 61% | 61% | 66% | 65% | 62% | 62% | 61% | 62% |
| Specificity | 59% | 58% | 54% | 60% | 60% | 54% | 56% | 56% | 54% |
| Cutoff Quartile 4 | 2.99 | 2.99 | 3.01 | 2.99 | 2.99 | 3.01 | 2.99 | 2.99 | 3.01 |
| Sensitivity | 41% | 39% | 36% | 42% | 42% | 35% | 40% | 39% | 35% |
| Specificity | 86% | 85% | 79% | 86% | 85% | 78% | 82% | 82% | 78% |
| OR Quartile 2 | 2.67 | 2.15 | 10.6 | 2.26 | 1.88 | 9.75 | 1.84 | 1.53 | 9.75 |
| p Value | 0.038 | 0.093 | 0.023 | 0.085 | 0.17 | 0.028 | 0.20 | 0.35 | 0.028 |
| Lower limit of 95% CI | 1.06 | 0.881 | 1.38 | 0.894 | 0.769 | 1.27 | 0.725 | 0.624 | 1.27 |

TABLE 18.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 6.75 | 5.27 | 81.0 | 5.72 | 4.61 | 74.8 | 4.67 | 3.77 | 74.8 |
| OR Quartile 3 | 2.38 | 2.12 | 1.81 | 2.92 | 2.73 | 1.86 | 2.12 | 1.98 | 1.86 |
| p Value | 0.011 | 0.026 | 0.13 | 0.0021 | 0.0037 | 0.12 | 0.032 | 0.049 | 0.12 |
| Lower limit of 95% CI | 1.22 | 1.10 | 0.843 | 1.48 | 1.39 | 0.849 | 1.07 | 1.00 | 0.849 |
| Upper limit of 95% CI | 4.63 | 4.11 | 3.90 | 5.80 | 5.39 | 4.07 | 4.21 | 3.92 | 4.07 |
| OR Quartile 4 | 4.16 | 3.55 | 2.07 | 4.36 | 4.18 | 1.94 | 3.05 | 2.92 | 1.94 |
| p Value | 3.9E−4 | 0.0014 | 0.080 | 2.3E−4 | 3.3E−4 | 0.12 | 0.0040 | 0.0056 | 0.12 |
| Lower limit of 95% CI | 1.89 | 1.64 | 0.916 | 1.99 | 1.91 | 0.845 | 1.43 | 1.37 | 0.845 |
| Upper limit of 95% CI | 9.16 | 7.71 | 4.69 | 9.52 | 9.12 | 4.46 | 6.52 | 6.23 | 4.46 |

TABLE 18.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

sCr or UO

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.0328 | 1.35 | 0.0169 | 1.58 | 0.0328 | 1.28 |
| Average | 2.93 | 13.3 | 2.79 | 14.2 | 5.25 | 11.5 |
| Stdev | 12.9 | 23.2 | 12.6 | 23.7 | 18.5 | 19.2 |
| p (t-test) | | 7.0E−4 | | 2.2E−4 | | 0.049 |
| Min | 0.000212 | 0.000212 | 0.000212 | 0.000212 | 0.000212 | 0.000212 |
| Max | 110 | 120 | 110 | 120 | 120 | 73.0 |
| n (Patient) | 82 | 67 | 86 | 63 | 93 | 56 | sCr only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.0328 | 1.28 | 0.0328 | 1.52 | 0.0328 | 1.28 |
| Average | 3.05 | 13.4 | 2.91 | 14.2 | 4.09 | 13.5 |
| Stdev | 12.9 | 23.4 | 12.6 | 23.9 | 14.1 | 24.0 |
| p (t-test) | | 8.1E−4 | | 2.5E−4 | | 0.0031 |
| Min | 0.000212 | 0.000212 | 0.000212 | 0.000212 | 0.000212 | 0.000212 |
| Max | 110 | 120 | 110 | 120 | 110 | 120 |
| n (Patient) | 83 | 66 | 87 | 62 | 93 | 56 |

UO only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.0851 | 1.14 | 0.0873 | 1.17 | 0.0873 | 1.17 |
| Average | 6.64 | 10.7 | 6.58 | 11.0 | 6.58 | 11.0 |
| Stdev | 19.6 | 16.9 | 19.5 | 17.0 | 19.5 | 17.0 |
| p (t-test) | | 0.26 | | 0.22 | | 0.22 |
| Min | 0.000212 | 0.000312 | 0.000212 | 0.000312 | 0.000212 | 0.000312 |
| Max | 120 | 50.9 | 120 | 50.9 | 120 | 50.9 |
| n (Patient) | 111 | 37 | 112 | 36 | 112 | 36 |

TABLE 18.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period | | | | | | | | |
|---|---|---|---|---|---|---|---|---|---|
| | 24 | | | 48 | | | 72 | | |
| Duration (hr) | sCr or UO | sCr only | UO only | sCr or UO | sCr only | UO only | sCr or UO | sCr only | UO only |
| AUC | 0.71 | 0.70 | 0.68 | 0.73 | 0.72 | 0.68 | 0.67 | 0.68 | 0.68 |
| SE | 0.043 | 0.044 | 0.054 | 0.043 | 0.043 | 0.054 | 0.047 | 0.047 | 0.054 |
| p Value | 1.6E−6 | 5.9E−6 | 0.0011 | 5.4E−8 | 2.5E−7 | 8.7E−4 | 2.2E−4 | 1.4E−4 | 8.7E−4 |
| nCohort Non-persistent | 82 | 83 | 111 | 86 | 87 | 112 | 93 | 93 | 112 |
| nCohort Persistent | 67 | 66 | 37 | 63 | 62 | 36 | 56 | 56 | 36 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 88% | 88% | 97% | 87% | 87% | 97% | 86% | 86% | 97% |
| Specificity | 24% | 24% | 23% | 23% | 23% | 23% | 22% | 22% | 23% |
| Cutoff Quartile 3 | 0.170 | 0.170 | 0.205 | 0.170 | 0.170 | 0.205 | 0.170 | 0.170 | 0.205 |
| Sensitivity | 63% | 62% | 62% | 67% | 66% | 64% | 62% | 62% | 64% |
| Specificity | 60% | 59% | 54% | 62% | 61% | 54% | 57% | 57% | 54% |
| Cutoff Quartile 4 | 2.99 | 2.99 | 3.01 | 2.99 | 2.99 | 3.01 | 2.99 | 2.99 | 3.01 |
| Sensitivity | 42% | 41% | 38% | 44% | 44% | 39% | 41% | 41% | 39% |
| Specificity | 88% | 87% | 79% | 88% | 87% | 79% | 84% | 84% | 79% |
| OR Quartile 2 | 2.38 | 2.30 | 11.0 | 2.08 | 2.01 | 10.6 | 1.64 | 1.64 | 10.6 |
| p Value | 0.057 | 0.068 | 0.021 | 0.11 | 0.12 | 0.023 | 0.28 | 0.28 | 0.023 |
| Lower limit of 95% CI | 0.973 | 0.941 | 1.44 | 0.852 | 0.823 | 1.38 | 0.670 | 0.670 | 1.38 |
| Upper limit of 95% CI | 5.82 | 5.63 | 84.3 | 5.10 | 4.93 | 81.0 | 4.03 | 4.03 | 81.0 |
| OR Quartile 3 | 2.49 | 2.36 | 1.93 | 3.21 | 3.04 | 2.12 | 2.21 | 2.21 | 2.12 |
| p Value | 0.0069 | 0.011 | 0.090 | 7.8E−4 | 0.0013 | 0.058 | 0.022 | 0.022 | 0.058 |
| Lower limit of 95% CI | 1.29 | 1.22 | 0.902 | 1.63 | 1.54 | 0.975 | 1.12 | 1.12 | 0.975 |
| Upper limit of 95% CI | 4.84 | 4.58 | 4.14 | 6.34 | 6.01 | 4.59 | 4.36 | 4.36 | 4.59 |
| OR Quartile 4 | 5.17 | 4.53 | 2.33 | 6.08 | 5.33 | 2.46 | 3.62 | 3.62 | 2.46 |
| p Value | 8.7E−5 | 2.2E−4 | 0.040 | 1.8E−5 | 4.9E−5 | 0.030 | 0.0010 | 0.0010 | 0.030 |
| Lower limit of 95% CI | 2.28 | 2.03 | 1.04 | 2.66 | 2.38 | 1.09 | 1.68 | 1.68 | 1.09 |
| Upper limit of 95% CI | 11.7 | 10.1 | 5.22 | 13.9 | 11.9 | 5.55 | 7.81 | 7.81 | 5.55 |

Example 19. Use of Insulin-Like Growth Factor-Binding Protein 4 for Evaluating Renal Status in Patients Admitted to the ICU: Persistent at RIFLE I or F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 4 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is injury (I) or failure (F) where the persistence period can start from the time of sample collection to 24, 48, 72, 96 or 168 hours after sample collection. "Non-persistent" indicates those patients who are not persistent at injury (I) or failure (F) and whose minimum RIFLE stage during a period of 24, 48 or 72 hours is non-injury (RIFLE 0) or risk of injury (R) where the persistence period can start from the time of sample collection to 24, 48, 72, 96 or 168 hours after sample collection. If a patient dies after injury (I) or failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 19.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

sCr or UO

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.000473 | 0.899 | 0.0669 | 0.866 | 0.0328 | 1.13 |
| Average | 2.51 | 10.6 | 3.39 | 12.3 | 3.11 | 14.1 |
| Stdev | 14.9 | 20.4 | 13.3 | 22.8 | 12.6 | 24.1 |
| p (t-test) | | 0.011 | | 0.0039 | | 4.0E−4 |
| Min | 0.000212 | 0.000212 | 0.000212 | 0.000212 | 0.000212 | 0.000212 |
| Max | 110 | 120 | 110 | 120 | 110 | 120 |
| n (Patient) | 55 | 94 | 78 | 71 | 88 | 61 | sCr only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.000473 | 0.899 | 0.0407 | 0.872 | 0.0328 | 1.40 |
| Average | 2.65 | 10.7 | 3.38 | 12.0 | 2.97 | 14.5 |
| Stdev | 14.7 | 20.6 | 13.5 | 22.6 | 12.5 | 24.2 |
| p (t-test) | | 0.011 | | 0.0049 | | 2.0E−4 |
| Min | 0.000212 | 0.000212 | 0.000212 | 0.000212 | 0.000212 | 0.000212 |
| Max | 110 | 120 | 110 | 120 | 110 | 120 |
| n (Patient) | 57 | 92 | 76 | 73 | 89 | 60 |

UO only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.146 | 0.869 | 0.126 | 0.927 | 0.126 | 1.35 |
| Average | 7.17 | 9.31 | 6.99 | 10.7 | 6.77 | 12.5 |
| Stdev | 19.9 | 15.6 | 19.4 | 16.9 | 19.1 | 17.7 |
| p (t-test) | | 0.57 | | 0.36 | | 0.18 |
| Min | 0.000212 | 0.000286 | 0.000212 | 0.000286 | 0.000212 | 0.000301 |
| Max | 120 | 50.9 | 120 | 50.9 | 120 | 50.9 |
| n (Patient) | 114 | 34 | 121 | 27 | 125 | 23 |

| | Persistence Period | | | | | | | | |
|---|---|---|---|---|---|---|---|---|---|
| | 24 | | | 48 | | | 72 | | |
| Duration (hr) | sCr or UO | sCr only | UO only | sCr or UO | sCr only | UO only | sCr or UO | sCr only | UO only |
| AUC | 0.74 | 0.73 | 0.59 | 0.64 | 0.65 | 0.62 | 0.68 | 0.69 | 0.67 |
| SE | 0.040 | 0.041 | 0.057 | 0.045 | 0.045 | 0.062 | 0.046 | 0.045 | 0.066 |
| p Value | 5.1E−9 | 2.8E−8 | 0.12 | 0.0022 | 0.0012 | 0.055 | 1.1E−4 | 2.4E−5 | 0.0084 |
| nCohort Non-persistent | 55 | 57 | 114 | 78 | 76 | 121 | 88 | 89 | 125 |
| nCohort Persistent | 94 | 92 | 34 | 71 | 73 | 27 | 61 | 60 | 23 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 86% | 86% | 85% | 85% | 84% | 89% | 85% | 83% | 96% |
| Specificity | 27% | 26% | 19% | 22% | 21% | 20% | 22% | 20% | 21% |
| Cutoff Quartile 3 | 0.170 | 0.170 | 0.205 | 0.170 | 0.170 | 0.205 | 0.170 | 0.170 | 0.205 |
| Sensitivity | 63% | 63% | 56% | 58% | 59% | 59% | 62% | 67% | 65% |
| Specificity | 71% | 70% | 52% | 56% | 58% | 52% | 58% | 61% | 53% |
| Cutoff Quartile 4 | 2.99 | 2.99 | 3.01 | 2.99 | 2.99 | 3.01 | 2.99 | 2.99 | 3.01 |
| Sensitivity | 38% | 38% | 35% | 37% | 37% | 37% | 39% | 43% | 43% |
| Specificity | 96% | 95% | 78% | 85% | 86% | 78% | 84% | 87% | 78% |
| OR Quartile 2 | 2.34 | 2.17 | 1.39 | 1.52 | 1.36 | 1.98 | 1.59 | 1.27 | 5.78 |
| p Value | 0.046 | 0.068 | 0.54 | 0.33 | 0.47 | 0.30 | 0.30 | 0.59 | 0.094 |
| Lower limit of 95% CI | 1.02 | 0.945 | 0.482 | 0.658 | 0.592 | 0.550 | 0.666 | 0.540 | 0.744 |

TABLE 19.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 5.38 | 4.99 | 3.99 | 3.51 | 3.11 | 7.12 | 3.80 | 2.98 | 44.9 |
| OR Quartile 3 | 4.11 | 4.01 | 1.36 | 1.77 | 1.97 | 1.58 | 2.28 | 3.09 | 2.10 |
| p Value | 1.1E−4 | 1.2E−4 | 0.44 | 0.085 | 0.041 | 0.29 | 0.016 | 0.0013 | 0.12 |
| Lower limit of 95% CI | 2.01 | 1.98 | 0.629 | 0.924 | 1.03 | 0.678 | 1.17 | 1.56 | 0.830 |
| Upper limit of 95% CI | 8.41 | 8.15 | 2.94 | 3.39 | 3.78 | 3.68 | 4.45 | 6.12 | 5.30 |
| OR Quartile 4 | 16.4 | 11.1 | 1.94 | 3.18 | 3.47 | 2.05 | 3.43 | 4.91 | 2.79 |
| p Value | 1.9E−4 | 1.4E−4 | 0.12 | 0.0038 | 0.0022 | 0.11 | 0.0017 | 8.7E−5 | 0.030 |
| Lower limit of 95% CI | 3.78 | 3.21 | 0.845 | 1.45 | 1.56 | 0.840 | 1.59 | 2.22 | 1.10 |
| Upper limit of 95% CI | 71.7 | 38.1 | 4.46 | 6.95 | 7.69 | 4.99 | 7.39 | 10.9 | 7.06 |

TABLE 19.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

sCr or UO

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.000472 | 0.927 | 0.0328 | 1.03 | 0.000747 | 1.35 |
| Average | 2.53 | 10.5 | 3.29 | 11.8 | 2.98 | 13.3 |
| Stdev | 15.0 | 20.3 | 13.7 | 22.2 | 13.0 | 23.2 |
| p (t-test) | 0.013 | | 0.0059 | | 8.0E−4 | |
| Min | 0.000212 | 0.000212 | 0.000212 | 0.000212 | 0.000212 | 0.000212 |
| Max | 110 | 120 | 110 | 120 | 110 | 120 |
| n (Patient) | 54 | 95 | 73 | 76 | 82 | 67 | sCr only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.000473 | 0.927 | 0.0328 | 0.899 | 0.0169 | 1.35 |
| Average | 2.66 | 10.6 | 3.46 | 11.6 | 3.09 | 13.1 |
| Stdev | 14.8 | 20.5 | 13.8 | 22.2 | 13.0 | 23.2 |
| p (t-test) | 0.013 | | 0.0082 | | 0.0011 | |
| Min | 0.000212 | 0.000212 | 0.000212 | 0.000212 | 0.000212 | 0.000212 |
| Max | 110 | 120 | 110 | 120 | 110 | 120 |
| n (Patient) | 56 | 93 | 73 | 76 | 82 | 67 |

UO only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.118 | 1.03 | 0.118 | 1.14 | 0.118 | 1.35 |
| Average | 7.08 | 9.15 | 6.89 | 10.2 | 6.66 | 11.5 |
| Stdev | 20.4 | 15.1 | 19.8 | 16.1 | 19.5 | 16.7 |
| p (t-test) | 0.55 | | 0.37 | | 0.21 | |
| Min | 0.000212 | 0.000286 | 0.000212 | 0.000286 | 0.000212 | 0.000301 |
| Max | 120 | 50.9 | 120 | 50.9 | 120 | 50.9 |
| n (Patient) | 106 | 42 | 113 | 35 | 117 | 31 |

TABLE 19.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period | | | | | | | | |
|---|---|---|---|---|---|---|---|---|---|
| | 24 | | | 48 | | | 72 | | |
| Duration (hr) | sCr or UO | sCr only | UO only | sCr or UO | sCr only | UO only | sCr or UO | sCr only | UO only |
| AUC | 0.74 | 0.73 | 0.63 | 0.67 | 0.65 | 0.65 | 0.71 | 0.70 | 0.70 |
| SE | 0.040 | 0.040 | 0.053 | 0.044 | 0.045 | 0.056 | 0.043 | 0.043 | 0.057 |
| p Value | 1.0E-9 | 6.8E-9 | 0.017 | 8.6E-5 | 6.0E-4 | 0.0059 | 6.9E-7 | 3.3E-6 | 5.7E-4 |
| nCohort Non-persistent | 54 | 56 | 106 | 73 | 73 | 113 | 82 | 82 | 117 |
| nCohort Persistent | 95 | 93 | 42 | 76 | 76 | 35 | 67 | 67 | 31 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 86% | 86% | 88% | 86% | 84% | 91% | 87% | 85% | 97% |
| Specificity | 28% | 27% | 21% | 23% | 22% | 21% | 23% | 22% | 22% |
| Cutoff Quartile 3 | 0.170 | 0.170 | 0.205 | 0.170 | 0.170 | 0.205 | 0.170 | 0.170 | 0.205 |
| Sensitivity | 63% | 63% | 60% | 61% | 59% | 63% | 66% | 66% | 68% |
| Specificity | 72% | 71% | 54% | 60% | 59% | 54% | 62% | 62% | 55% |
| Cutoff Quartile 4 | 2.99 | 2.99 | 3.01 | 2.99 | 2.99 | 3.01 | 2.99 | 2.99 | 3.01 |
| Sensitivity | 38% | 38% | 38% | 37% | 36% | 40% | 40% | 40% | 45% |
| Specificity | 96% | 95% | 80% | 86% | 85% | 80% | 87% | 87% | 80% |
| OR Quartile 2 | 2.43 | 2.25 | 1.94 | 1.79 | 1.50 | 2.88 | 1.94 | 1.60 | 8.57 |
| p Value | 0.037 | 0.056 | 0.21 | 0.17 | 0.34 | 0.10 | 0.13 | 0.28 | 0.039 |
| Lower limit of 95% CI | 1.05 | 0.979 | 0.681 | 0.776 | 0.653 | 0.811 | 0.815 | 0.684 | 1.12 |
| Upper limit of 95% CI | 5.59 | 5.18 | 5.51 | 4.15 | 3.43 | 10.2 | 4.64 | 3.76 | 65.9 |
| OR Quartile 3 | 4.46 | 4.34 | 1.71 | 2.33 | 2.08 | 1.99 | 3.15 | 3.15 | 2.54 |
| p Value | 5.6E-5 | 6.0E-5 | 0.15 | 0.012 | 0.028 | 0.085 | 8.5E-4 | 8.5E-4 | 0.029 |
| Lower limit of 95% CI | 2.15 | 2.12 | 0.829 | 1.21 | 1.08 | 0.911 | 1.60 | 1.60 | 1.10 |
| Upper limit of 95% CI | 9.22 | 8.89 | 3.53 | 4.49 | 4.00 | 4.33 | 6.17 | 6.17 | 5.85 |
| OR Quartile 4 | 15.9 | 10.7 | 2.49 | 3.68 | 3.11 | 2.61 | 4.36 | 4.36 | 3.37 |
| p Value | 2.3E-4 | 1.8E-4 | 0.023 | 0.0017 | 0.0052 | 0.021 | 3.2E-4 | 3.2E-4 | 0.0047 |
| Lower limit of 95% CI | 3.64 | 3.10 | 1.14 | 1.63 | 1.40 | 1.15 | 1.96 | 1.96 | 1.45 |
| Upper limit of 95% CI | 69.1 | 36.7 | 5.46 | 8.29 | 6.88 | 5.90 | 9.71 | 9.71 | 7.81 |

TABLE 19.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | Persistence Period | | | | | |
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.000472 | 0.927 | 0.0328 | 0.927 | 0.000747 | 1.21 |
| Average | 2.53 | 10.5 | 3.32 | 11.6 | 3.07 | 12.6 |
| Stdev | 15.0 | 20.3 | 13.8 | 22.0 | 13.3 | 22.7 |
| p (t-test) | | 0.013 | | 0.0070 | | 0.0019 |
| Min | 0.000212 | 0.000212 | 0.000212 | 0.000212 | 0.000212 | 0.000212 |
| Max | 110 | 120 | 110 | 120 | 110 | 120 |
| n (Patient) | 54 | 95 | 72 | 77 | 78 | 71 |

TABLE 19.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

sCr only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.000473 | 0.927 | 0.0328 | 0.872 | 0.0169 | 1.14 |
| Average | 2.66 | 10.6 | 3.50 | 11.5 | 3.24 | 12.4 |
| Stdev | 14.8 | 20.5 | 13.8 | 22.1 | 13.3 | 22.8 |
| p (t-test) | | 0.013 | | 0.0098 | | 0.0028 |
| Min | 0.000212 | 0.000212 | 0.000212 | 0.000212 | 0.000212 | 0.000212 |
| Max | 110 | 120 | 110 | 120 | 110 | 120 |
| n (Patient) | 56 | 93 | 72 | 77 | 78 | 71 |

UO only

| | Persistence Period | | | | | |
|---|---|---|---|---|---|---|
| | 24 | | 48 | | 72 | |
| Duration (hr) | Non-persistent Cohort | Persistent Cohort | Non-persistent Cohort | Persistent Cohort | Non-persistent Cohort | Persistent Cohort |
| Median | 0.122 | 0.899 | 0.104 | 1.13 | 0.104 | 1.28 |
| Average | 7.45 | 8.12 | 7.12 | 9.05 | 6.87 | 9.97 |
| Stdev | 20.9 | 14.4 | 20.4 | 15.1 | 20.0 | 15.6 |
| p (t-test) | | 0.84 | | 0.58 | | 0.39 |
| Min | 0.000212 | 0.000212 | 0.000212 | 0.000212 | 0.000212 | 0.000212 |
| Max | 120 | 50.9 | 120 | 50.9 | 120 | 50.9 |
| n (Patient) | 100 | 48 | 106 | 42 | 110 | 38 |

| | Persistence Period | | | | | | | | |
|---|---|---|---|---|---|---|---|---|---|
| | 24 | | | 48 | | | 72 | | |
| Duration (hr) | sCr or UO | sCr only | UO only | sCr or UO | sCr only | UO only | sCr or UO | sCr only | UO only |
| AUC | 0.74 | 0.73 | 0.59 | 0.68 | 0.66 | 0.63 | 0.71 | 0.69 | 0.66 |
| SE | 0.040 | 0.040 | 0.051 | 0.044 | 0.044 | 0.053 | 0.043 | 0.044 | 0.054 |
| p Value | 1.0E−9 | 6.8E−9 | 0.062 | 5.7E−5 | 4.2E−4 | 0.017 | 1.5E−6 | 1.9E−5 | 0.0031 |
| nCohort Non-persistent | 54 | 56 | 100 | 72 | 72 | 106 | 78 | 78 | 110 |
| nCohort Persistent | 95 | 93 | 48 | 77 | 77 | 42 | 71 | 71 | 38 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 86% | 86% | 85% | 86% | 84% | 88% | 86% | 85% | 92% |
| Specificity | 28% | 27% | 20% | 24% | 22% | 21% | 23% | 22% | 22% |
| Cutoff Quartile 3 | 0.170 | 0.170 | 0.205 | 0.170 | 0.170 | 0.205 | 0.170 | 0.170 | 0.205 |
| Sensitivity | 63% | 63% | 56% | 61% | 60% | 60% | 65% | 63% | 63% |
| Specificity | 72% | 71% | 53% | 61% | 60% | 54% | 63% | 62% | 55% |
| Cutoff Quartile 4 | 2.99 | 2.99 | 3.01 | 2.99 | 2.99 | 3.01 | 2.99 | 2.99 | 3.01 |
| Sensitivity | 38% | 38% | 35% | 36% | 35% | 38% | 39% | 38% | 42% |
| Specificity | 96% | 95% | 80% | 86% | 85% | 80% | 87% | 86% | 81% |
| OR Quartile 2 | 2.43 | 2.25 | 1.46 | 1.85 | 1.55 | 1.94 | 1.83 | 1.52 | 3.26 |
| p Value | 0.037 | 0.056 | 0.43 | 0.15 | 0.30 | 0.21 | 0.16 | 0.33 | 0.067 |
| Lower limit of 95% CI | 1.05 | 0.979 | 0.572 | 0.802 | 0.675 | 0.681 | 0.781 | 0.658 | 0.921 |
| Upper limit of 95% CI | 5.59 | 5.18 | 3.75 | 4.29 | 3.55 | 5.51 | 4.29 | 3.51 | 11.5 |
| OR Quartile 3 | 4.46 | 4.34 | 1.45 | 2.46 | 2.20 | 1.71 | 3.11 | 2.77 | 2.06 |
| p Value | 5.6E−5 | 6.0E−5 | 0.29 | 0.0074 | 0.018 | 0.15 | 9.0E−4 | 0.0027 | 0.062 |
| Lower limit of 95% CI | 2.15 | 2.12 | 0.725 | 1.27 | 1.14 | 0.829 | 1.59 | 1.43 | 0.963 |
| Upper limit of 95% CI | 9.22 | 8.89 | 2.90 | 4.76 | 4.24 | 3.53 | 6.07 | 5.38 | 4.39 |
| OR Quartile 4 | 15.9 | 10.7 | 2.19 | 3.54 | 2.99 | 2.49 | 4.43 | 3.74 | 3.08 |
| p Value | 2.3E−4 | 1.8E−4 | 0.045 | 0.0023 | 0.0068 | 0.023 | 3.6E−4 | 0.0012 | 0.0058 |
| Lower limit of 95% CI | 3.64 | 3.10 | 1.02 | 1.57 | 1.35 | 1.14 | 1.96 | 1.68 | 1.38 |
| Upper limit of 95% CI | 69.1 | 36.7 | 4.73 | 7.99 | 6.63 | 5.46 | 10.0 | 8.30 | 6.86 |

TABLE 19.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

sCr or UO

| | 24 | | 48 | | 72 | |
| --- | --- | --- | --- | --- | --- | --- |
| Persistence Period Duration (hr) | Non-persistent Cohort | Persistent Cohort | Non-persistent Cohort | Persistent Cohort | Non-persistent Cohort | Persistent Cohort |
| Median | 0.000472 | 0.927 | 0.0328 | 0.927 | 0.000747 | 1.21 |
| Average | 2.53 | 10.5 | 3.32 | 11.6 | 3.07 | 12.6 |
| Stdev | 15.0 | 20.3 | 13.8 | 22.0 | 13.3 | 22.7 |
| p (t-test) | | 0.013 | | 0.0070 | | 0.0019 |
| Min | 0.000212 | 0.000212 | 0.000212 | 0.000212 | 0.000212 | 0.000212 |
| Max | 110 | 120 | 110 | 120 | 110 | 120 |
| n (Patient) | 54 | 95 | 72 | 77 | 78 | 71 | sCr only

| | 24 | | 48 | | 72 | |
| --- | --- | --- | --- | --- | --- | --- |
| Persistence Period Duration (hr) | Non-persistent Cohort | Persistent Cohort | Non-persistent Cohort | Persistent Cohort | Non-persistent Cohort | Persistent Cohort |
| Median | 0.000473 | 0.927 | 0.0328 | 0.872 | 0.0169 | 1.14 |
| Average | 2.66 | 10.6 | 3.50 | 11.5 | 3.24 | 12.4 |
| Stdev | 14.8 | 20.5 | 13.8 | 22.1 | 13.3 | 22.8 |
| p (t-test) | | 0.013 | | 0.0098 | | 0.0028 |
| Min | 0.000212 | 0.000212 | 0.000212 | 0.000212 | 0.000212 | 0.000212 |
| Max | 110 | 120 | 110 | 120 | 110 | 120 |
| n (Patient) | 56 | 93 | 72 | 77 | 78 | 71 |

UO only

| | 24 | | 48 | | 72 | |
| --- | --- | --- | --- | --- | --- | --- |
| Persistence Period Duration (hr) | Non-persistent Cohort | Persistent Cohort | Non-persistent Cohort | Persistent Cohort | Non-persistent Cohort | Persistent Cohort |
| Median | 0.142 | 0.869 | 0.0895 | 0.927 | 0.0895 | 1.14 |
| Average | 7.60 | 7.79 | 7.32 | 8.47 | 7.05 | 9.27 |
| Stdev | 21.1 | 14.2 | 20.6 | 14.7 | 20.3 | 15.2 |
| p (t-test) | | 0.95 | | 0.74 | | 0.53 |
| Min | 0.000212 | 0.000212 | 0.000212 | 0.000212 | 0.000212 | 0.000212 |
| Max | 120 | 50.9 | 120 | 50.9 | 120 | 50.9 |
| n (Patient) | 98 | 50 | 103 | 45 | 107 | 41 |

| Persistence Period | 24 | | | 48 | | | 72 | | |
| --- | --- | --- | --- | --- | --- | --- | --- | --- | --- |
| Duration (hr) | sCr or UO | sCr only | UO only | sCr or UO | sCr only | UO only | sCr or UO | sCr only | UO only |
| AUC | 0.74 | 0.73 | 0.58 | 0.68 | 0.66 | 0.61 | 0.71 | 0.69 | 0.64 |
| SE | 0.040 | 0.040 | 0.050 | 0.044 | 0.044 | 0.052 | 0.043 | 0.044 | 0.053 |
| p Value | 1.0E−9 | 6.8E−9 | 0.10 | 5.7E−5 | 4.2E−4 | 0.028 | 1.5E−6 | 1.9E−5 | 0.0063 |
| nCohort Non-persistent | 54 | 56 | 98 | 72 | 72 | 103 | 78 | 78 | 107 |
| nCohort Persistent | 95 | 93 | 50 | 77 | 77 | 45 | 71 | 71 | 41 |
| Cutoff Quartile 2 | 0.000339 | 0.000339 | 0.000339 | 0.000339 | 0.000339 | 0.000339 | 0.000339 | 0.000339 | 0.000339 |
| Sensitivity | 86% | 86% | 84% | 86% | 84% | 87% | 86% | 85% | 90% |
| Specificity | 28% | 27% | 19% | 24% | 22% | 20% | 23% | 22% | 21% |
| Cutoff Quartile 3 | 0.170 | 0.170 | 0.205 | 0.170 | 0.170 | 0.205 | 0.170 | 0.170 | 0.205 |
| Sensitivity | 63% | 63% | 54% | 61% | 60% | 58% | 65% | 63% | 61% |
| Specificity | 72% | 71% | 52% | 61% | 60% | 53% | 63% | 62% | 54% |
| Cutoff Quartile 4 | 2.99 | 2.99 | 3.01 | 2.99 | 2.99 | 3.01 | 2.99 | 2.99 | 3.01 |
| Sensitivity | 38% | 38% | 34% | 36% | 35% | 36% | 39% | 38% | 39% |
| Specificity | 96% | 95% | 80% | 86% | 85% | 80% | 87% | 86% | 80% |
| OR Quartile 2 | 2.43 | 2.25 | 1.26 | 1.85 | 1.55 | 1.66 | 1.83 | 1.52 | 2.53 |
| p Value | 0.037 | 0.056 | 0.61 | 0.15 | 0.30 | 0.31 | 0.16 | 0.33 | 0.11 |
| Lower limit of 95% CI | 1.05 | 0.979 | 0.510 | 0.802 | 0.675 | 0.622 | 0.781 | 0.658 | 0.818 |
| Upper limit of 95% CI | 5.59 | 5.18 | 3.13 | 4.29 | 3.55 | 4.45 | 4.29 | 3.51 | 7.84 |
| OR Quartile 3 | 4.46 | 4.34 | 1.27 | 2.46 | 2.20 | 1.57 | 3.11 | 2.77 | 1.85 |
| p Value | 5.6E−5 | 6.0E−5 | 0.49 | 0.0074 | 0.018 | 0.21 | 9.0E−4 | 0.0027 | 0.10 |
| Lower limit of 95% CI | 2.15 | 2.12 | 0.643 | 1.27 | 1.14 | 0.773 | 1.59 | 1.43 | 0.888 |

TABLE 19.4-continued

Comparison of marker levels and the area under the ROC curve
(AUC) in urine samples for the "persistent" and "non-persistent" cohorts where
persistence starts within 96 hours after sample collection and renal status is assessed by
serum creatinine (sCr) only, urine output (UO) only, or serum creatinine or urine output
RIFLE criteria.

| | | | | | | | | | |
|---|---|---|---|---|---|---|---|---|---|
| Upper limit of 95% CI | 9.22 | 8.89 | 2.52 | 4.76 | 4.24 | 3.18 | 6.07 | 5.38 | 3.85 |
| OR Quartile 4 | 15.9 | 10.7 | 2.01 | 3.54 | 2.99 | 2.15 | 4.43 | 3.74 | 2.62 |
| p Value | 2.3E−4 | 1.8E−4 | 0.073 | 0.0023 | 0.0068 | 0.053 | 3.6E−4 | 0.0012 | 0.017 |
| Lower limit of 95% CI | 3.64 | 3.10 | 0.936 | 1.57 | 1.35 | 0.991 | 1.96 | 1.68 | 1.19 |
| Upper limit of 95% CI | 69.1 | 36.7 | 4.31 | 7.99 | 6.63 | 4.68 | 10.0 | 8.30 | 5.77 |

TABLE 19.5

Comparison of marker levels and the area under the ROC curve
(AUC) in urine samples for the "persistent" and "non-persistent" cohorts where
persistence starts within 168 hours after sample collection and renal status is assessed by
serum creatinine (sCr) only, urine output (UO) only, or serum creatinine or urine output
RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 0.000472 | 0.927 | 0.0328 | 0.899 | 0.0169 | 1.14 |
| Average | 2.38 | 10.4 | 3.27 | 11.4 | 3.06 | 12.1 |
| Stdev | 15.2 | 20.2 | 14.0 | 21.7 | 13.6 | 22.2 |
| p (t-test) | | 0.013 | | 0.0089 | | 0.0032 |
| Min | 0.000212 | 0.000212 | 0.000212 | 0.000212 | 0.000212 | 0.000212 |
| Max | 110 | 120 | 110 | 120 | 110 | 120 |
| n (Patient) | 52 | 97 | 69 | 80 | 74 | 75 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 0.000473 | 1.03 | 0.0328 | 0.927 | 0.000747 | 1.21 |
| Average | 2.48 | 10.6 | 3.22 | 11.5 | 2.98 | 12.4 |
| Stdev | 14.9 | 20.4 | 13.9 | 21.8 | 13.4 | 22.4 |
| p (t-test) | | 0.011 | | 0.0073 | | 0.0020 |
| Min | 0.000212 | 0.000212 | 0.000212 | 0.000212 | 0.000212 | 0.000212 |
| Max | 110 | 120 | 110 | 120 | 110 | 120 |
| n (Patient) | 55 | 94 | 70 | 79 | 76 | 73 |

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 0.104 | 0.899 | 0.0895 | 0.927 | 0.0873 | 1.13 |
| Average | 7.15 | 8.61 | 7.02 | 8.96 | 6.82 | 9.54 |
| Stdev | 21.0 | 14.8 | 20.7 | 15.2 | 20.4 | 15.5 |
| p (t-test) | | 0.66 | | 0.56 | | 0.42 |
| Min | 0.000212 | 0.000212 | 0.000212 | 0.000212 | 0.000212 | 0.000212 |
| Max | 120 | 50.9 | 120 | 50.9 | 120 | 50.9 |
| n (Patient) | 96 | 52 | 99 | 49 | 102 | 46 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.75 | 0.75 | 0.60 | 0.67 | 0.68 | 0.62 | 0.70 | 0.71 | 0.65 |
| SE | 0.040 | 0.040 | 0.050 | 0.044 | 0.044 | 0.050 | 0.043 | 0.043 | 0.050 |
| p Value | 4.5E−10 | 5.2E−10 | 0.036 | 7.9E−5 | 5.1E−5 | 0.015 | 4.9E−6 | 1.4E−6 | 0.0026 |
| nCohort Non-persistent | 52 | 55 | 96 | 69 | 70 | 99 | 74 | 76 | 102 |

TABLE 19.5-continued

Comparison of marker levels and the area under the ROC curve
(AUC) in urine samples for the "persistent" and "non-persistent" cohorts where
persistence starts within 168 hours after sample collection and renal status is assessed by
serum creatinine (sCr) only, urine output (UO) only, or serum creatinine or urine output
RIFLE criteria.

| nCohort Persistent | 97 | 94 | 52 | 80 | 79 | 49 | 75 | 73 | 46 |
|---|---|---|---|---|---|---|---|---|---|
| Cutoff Quartile 2 | 0.000339 | 0.000339 | 0.000339 | 0.000339 | 0.000339 | 0.000339 | 0.000339 | 0.000339 | 0.000339 |
| Sensitivity | 86% | 86% | 85% | 85% | 85% | 88% | 85% | 85% | 91% |
| Specificity | 27% | 27% | 20% | 23% | 23% | 21% | 23% | 22% | 23% |
| Cutoff Quartile 3 | 0.170 | 0.170 | 0.205 | 0.170 | 0.170 | 0.205 | 0.170 | 0.170 | 0.205 |
| Sensitivity | 63% | 64% | 56% | 60% | 61% | 57% | 63% | 64% | 61% |
| Specificity | 73% | 73% | 53% | 61% | 61% | 54% | 62% | 63% | 55% |
| Cutoff Quartile 4 | 2.99 | 2.99 | 3.01 | 2.99 | 2.99 | 3.01 | 2.99 | 2.99 | 3.01 |
| Sensitivity | 38% | 38% | 37% | 36% | 37% | 37% | 39% | 40% | 39% |
| Specificity | 98% | 96% | 81% | 87% | 87% | 81% | 88% | 88% | 81% |
| OR Quartile 2 | 2.18 | 2.34 | 1.36 | 1.71 | 1.65 | 1.93 | 1.74 | 1.62 | 3.06 |
| p Value | 0.066 | 0.046 | 0.51 | 0.20 | 0.23 | 0.19 | 0.20 | 0.26 | 0.052 |
| Lower limit of 95% CI | 0.948 | 1.02 | 0.549 | 0.746 | 0.721 | 0.724 | 0.750 | 0.702 | 0.992 |
| Upper limit of 95% CI | 5.03 | 5.38 | 3.36 | 3.92 | 3.79 | 5.14 | 4.01 | 3.75 | 9.42 |
| OR Quartile 3 | 4.60 | 4.71 | 1.43 | 2.33 | 2.47 | 1.54 | 2.76 | 3.10 | 1.89 |
| p Value | 5.1E−5 | 3.0E−5 | 0.30 | 0.012 | 0.0074 | 0.22 | 0.0027 | 9.1E−4 | 0.078 |
| Lower limit of 95% CI | 2.20 | 2.27 | 0.725 | 1.21 | 1.27 | 0.771 | 1.42 | 1.59 | 0.932 |
| Upper limit of 95% CI | 9.62 | 9.74 | 2.82 | 4.51 | 4.77 | 3.06 | 5.35 | 6.05 | 3.85 |
| OR Quartile 4 | 31.4 | 16.4 | 2.49 | 3.79 | 3.93 | 2.44 | 4.55 | 4.91 | 2.81 |
| p Value | 8.3E−4 | 1.9E−4 | 0.019 | 0.0018 | 0.0013 | 0.022 | 3.9E−4 | 2.0E−4 | 0.0089 |
| Lower limit of 95% CI | 4.17 | 3.78 | 1.16 | 1.64 | 1.70 | 1.14 | 1.97 | 2.12 | 1.30 |
| Upper limit of 95% CI | 237 | 71.7 | 5.35 | 8.74 | 9.07 | 5.26 | 10.5 | 11.4 | 6.09 |

Example 20. Use of Insulin-Like Growth Factor-Binding Protein 6 for Evaluating Renal Status in Patients Admitted to the ICU: Persistent at RIFLE F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 6 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is failure (F) where the persistence period can start from the time of sample collection to 24, 48, 72, 96 or 168 hours after sample collection. "Non-persistent" indicates those patients who are not persistent at failure (F) and whose minimum RIFLE stage during a period of 24, 48 or 72 hours is non-injury (RIFLE 0), risk of injury (R), or injury (I) where the persistence period can start from the time of sample collection to 24, 48, 72, 96 or 168 hours after sample collection. If a patient dies after failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 20.1

Comparison of marker levels and the area under the ROC curve
(AUC) in urine samples for the "persistent" and "non-persistent" cohorts where
persistence starts within 24 hours after sample collection and renal status is assessed by
serum creatinine (sCr) only, urine output (UO) only, or serum creatinine or urine output
RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 44.2 | 171 | 48.9 | 221 | 58.3 | 196 |
| Average | 163 | 507 | 168 | 559 | 197 | 542 |
| Stdev | 336 | 743 | 330 | 792 | 370 | 827 |
| p (t-test) | | 1.5E−4 | | 3.5E−5 | | 6.3E−4 |
| Min | 0.259 | 3.12 | 0.259 | 3.12 | 0.259 | 3.12 |

TABLE 20.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | |
|---|---|---|---|---|---|---|
| Max | 2160 | 3600 | 2160 | 3600 | 2160 | 3600 |
| n (Patient) | 98 | 51 | 106 | 43 | 113 | 36 | sCr only

| | 24 | | 48 | | 72 | |
|---|---|---|---|---|---|---|
| Persistence Period Duration (hr) | Non-persistent Cohort | Persistent Cohort | Non-persistent Cohort | Persistent Cohort | Non-persistent Cohort | Persistent Cohort |
| Median | 47.5 | 149 | 54.2 | 305 | 58.8 | 196 |
| Average | 164 | 497 | 166 | 562 | 198 | 521 |
| Stdev | 337 | 738 | 330 | 791 | 372 | 810 |
| p (t-test) | | 2.3E−4 | | 2.8E−5 | | 0.0011 |
| Min | 0.259 | 3.12 | 0.259 | 3.12 | 0.259 | 3.12 |
| Max | 2160 | 3600 | 2160 | 3600 | 2160 | 3600 |
| n (Patient) | 97 | 52 | 106 | 43 | 111 | 38 |

UO only

| | 24 | | 48 | | 72 | |
|---|---|---|---|---|---|---|
| Persistence Period Duration (hr) | Non-persistent Cohort | Persistent Cohort | Non-persistent Cohort | Persistent Cohort | Non-persistent Cohort | Persistent Cohort |
| Median | 62.9 | 263 | 63.7 | 305 | 63.7 | 305 |
| Average | 245 | 556 | 244 | 582 | 244 | 582 |
| Stdev | 482 | 799 | 481 | 815 | 481 | 815 |
| p (t-test) | | 0.021 | | 0.014 | | 0.014 |
| Min | 0.259 | 12.3 | 0.259 | 12.3 | 0.259 | 12.3 |
| Max | 3600 | 3210 | 3600 | 3210 | 3600 | 3210 |
| n (Patient) | 130 | 18 | 131 | 17 | 131 | 17 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.72 | 0.71 | 0.72 | 0.73 | 0.72 | 0.73 | 0.70 | 0.68 | 0.73 |
| SE | 0.046 | 0.046 | 0.071 | 0.048 | 0.049 | 0.073 | 0.053 | 0.053 | 0.073 |
| p Value | 9.8E−7 | 4.3E−6 | 0.0018 | 2.3E−6 | 5.2E−6 | 0.0017 | 1.6E−4 | 4.8E−4 | 0.0017 |
| nCohort Non-persistent | 98 | 97 | 130 | 106 | 106 | 131 | 113 | 111 | 131 |
| nCohort Persistent | 51 | 52 | 18 | 43 | 43 | 17 | 36 | 38 | 17 |
| Cutoff Quartile 2 | 17.2 | 17.2 | 17.6 | 17.2 | 17.2 | 17.6 | 17.2 | 17.2 | 17.6 |
| Sensitivity | 88% | 87% | 94% | 88% | 86% | 94% | 86% | 84% | 94% |
| Specificity | 32% | 31% | 28% | 30% | 29% | 27% | 28% | 28% | 27% |
| Cutoff Quartile 3 | 78.3 | 78.3 | 80.9 | 78.3 | 78.3 | 80.9 | 78.3 | 78.3 | 80.9 |
| Sensitivity | 71% | 69% | 83% | 72% | 70% | 82% | 72% | 68% | 82% |
| Specificity | 60% | 60% | 55% | 58% | 58% | 54% | 57% | 56% | 54% |
| Cutoff Quartile 4 | 331 | 331 | 331 | 331 | 331 | 331 | 331 | 331 | 331 |
| Sensitivity | 45% | 44% | 44% | 47% | 49% | 47% | 44% | 45% | 47% |
| Specificity | 85% | 85% | 78% | 83% | 84% | 78% | 81% | 81% | 78% |
| OR Quartile 2 | 3.47 | 2.88 | 6.51 | 3.29 | 2.55 | 6.06 | 2.45 | 2.07 | 6.06 |
| p Value | 0.010 | 0.022 | 0.074 | 0.022 | 0.056 | 0.086 | 0.088 | 0.14 | 0.086 |
| Lower limit of 95% CI | 1.34 | 1.16 | 0.836 | 1.18 | 0.977 | 0.776 | 0.875 | 0.787 | 0.776 |
| Upper limit of 95% CI | 8.99 | 7.12 | 50.7 | 9.12 | 6.65 | 47.4 | 6.86 | 5.43 | 47.4 |
| OR Quartile 3 | 3.63 | 3.35 | 6.02 | 3.64 | 3.13 | 5.52 | 3.40 | 2.74 | 5.52 |
| p Value | 5.0E−4 | 9.3E−4 | 0.0063 | 0.0010 | 0.0031 | 0.0096 | 0.0034 | 0.011 | 0.0096 |
| Lower limit of 95% CI | 1.76 | 1.64 | 1.66 | 1.68 | 1.47 | 1.51 | 1.50 | 1.26 | 1.51 |
| Upper limit of 95% CI | 7.50 | 6.84 | 21.8 | 7.86 | 6.66 | 20.1 | 7.70 | 5.98 | 20.1 |
| OR Quartile 4 | 4.55 | 4.34 | 2.79 | 4.25 | 5.00 | 3.13 | 3.31 | 3.47 | 3.13 |
| p Value | 1.4E−4 | 2.1E−4 | 0.048 | 3.0E−4 | 6.8E−5 | 0.031 | 0.0036 | 0.0022 | 0.031 |
| Lower limit of 95% CI | 2.09 | 2.00 | 1.01 | 1.94 | 2.26 | 1.11 | 1.48 | 1.56 | 1.11 |
| Upper limit of 95% CI | 9.90 | 9.42 | 7.71 | 9.32 | 11.0 | 8.83 | 7.41 | 7.69 | 8.83 |

TABLE 20.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 39.7 | 144 | 39.3 | 171 | 47.5 | 144 |
| Average | 164 | 463 | 163 | 506 | 197 | 479 |
| Stdev | 347 | 707 | 338 | 741 | 379 | 764 |
| p (t-test) | | 7.8E−4 | | 1.6E−4 | | 0.0031 |
| Min | 0.259 | 0.723 | 0.259 | 3.12 | 0.259 | 3.12 |
| Max | 2160 | 3600 | 2160 | 3600 | 2160 | 3600 |
| n (Patient) | 91 | 58 | 98 | 51 | 105 | 44 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 40.8 | 144 | 39.7 | 196 | 50.3 | 144 |
| Average | 165 | 462 | 162 | 501 | 198 | 465 |
| Stdev | 347 | 708 | 339 | 735 | 382 | 750 |
| p (t-test) | | 8.4E−4 | | 1.7E−4 | | 0.0045 |
| Min | 0.259 | 0.723 | 0.259 | 3.12 | 0.259 | 3.12 |
| Max | 2160 | 3600 | 2160 | 3600 | 2160 | 3600 |
| n (Patient) | 91 | 58 | 97 | 52 | 103 | 46 |

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 59.0 | 119 | 59.4 | 123 | 59.4 | 123 |
| Average | 249 | 446 | 248 | 460 | 248 | 460 |
| Stdev | 493 | 707 | 491 | 718 | 491 | 718 |
| p (t-test) | | 0.095 | | 0.077 | | 0.077 |
| Min | 0.259 | 5.59 | 0.259 | 5.59 | 0.259 | 5.59 |
| Max | 3600 | 3210 | 3600 | 3210 | 3600 | 3210 |
| n (Patient) | 123 | 25 | 124 | 24 | 124 | 24 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.71 | 0.70 | 0.67 | 0.73 | 0.73 | 0.68 | 0.70 | 0.69 | 0.68 |
| SE | 0.045 | 0.045 | 0.063 | 0.045 | 0.045 | 0.064 | 0.050 | 0.049 | 0.064 |
| p Value | 2.7E−6 | 8.9E−6 | 0.0057 | 2.8E−7 | 4.5E−7 | 0.0061 | 6.8E−5 | 1.5E−4 | 0.0061 |
| nCohort Non-persistent | 91 | 91 | 123 | 98 | 97 | 124 | 105 | 103 | 124 |
| nCohort Persistent | 58 | 58 | 25 | 51 | 52 | 24 | 44 | 46 | 24 |
| Cutoff Quartile 2 | 17.2 | 17.2 | 17.6 | 17.2 | 17.2 | 17.6 | 17.2 | 17.2 | 17.6 |
| Sensitivity | 86% | 84% | 92% | 88% | 87% | 92% | 86% | 85% | 92% |
| Specificity | 32% | 31% | 28% | 32% | 31% | 28% | 30% | 29% | 28% |
| Cutoff Quartile 3 | 78.3 | 78.3 | 80.9 | 78.3 | 78.3 | 80.9 | 78.3 | 78.3 | 80.9 |
| Sensitivity | 69% | 69% | 76% | 73% | 73% | 75% | 73% | 72% | 75% |
| Specificity | 62% | 62% | 55% | 61% | 62% | 55% | 59% | 59% | 55% |
| Cutoff Quartile 4 | 331 | 331 | 331 | 331 | 331 | 331 | 331 | 331 | 331 |
| Sensitivity | 41% | 41% | 36% | 43% | 44% | 38% | 41% | 41% | 38% |
| Specificity | 85% | 85% | 77% | 84% | 85% | 77% | 81% | 82% | 77% |
| OR Quartile 2 | 2.92 | 2.42 | 4.57 | 3.47 | 2.88 | 4.33 | 2.65 | 2.29 | 4.33 |
| p Value | 0.015 | 0.039 | 0.047 | 0.010 | 0.022 | 0.056 | 0.046 | 0.074 | 0.056 |
| Lower limit of 95% CI | 1.23 | 1.05 | 1.02 | 1.34 | 1.16 | 0.966 | 1.02 | 0.922 | 0.966 |
| Upper limit of 95% CI | 6.96 | 5.60 | 20.4 | 8.99 | 7.12 | 19.4 | 6.91 | 5.69 | 19.4 |
| OR Quartile 3 | 3.56 | 3.56 | 3.92 | 4.17 | 4.40 | 3.64 | 3.84 | 3.69 | 3.64 |
| p Value | 3.7E−4 | 3.7E−4 | 0.0066 | 1.5E−4 | 8.1E−5 | 0.010 | 6.0E−4 | 6.8E−4 | 0.010 |
| Lower limit of 95% CI | 1.77 | 1.77 | 1.46 | 2.00 | 2.11 | 1.35 | 1.78 | 1.74 | 1.35 |
| Upper limit of 95% CI | 7.15 | 7.15 | 10.5 | 8.72 | 9.20 | 9.80 | 8.30 | 7.83 | 9.80 |
| OR Quartile 4 | 3.88 | 3.88 | 1.91 | 3.89 | 4.34 | 2.06 | 2.94 | 3.11 | 2.06 |
| p Value | 5.8E−4 | 5.8E−4 | 0.17 | 5.5E−4 | 2.1E−4 | 0.13 | 0.0063 | 0.0038 | 0.13 |

TABLE 20.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 1.79 | 1.79 | 0.761 | 1.80 | 2.00 | 0.814 | 1.36 | 1.44 | 0.814 |
| Upper limit of 95% CI | 8.41 | 8.41 | 4.78 | 8.40 | 9.42 | 5.20 | 6.38 | 6.72 | 5.20 |

TABLE 20.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 39.3 | 119 | 38.5 | 161 | 47.4 | 119 |
| Average | 167 | 436 | 161 | 463 | 190 | 455 |
| Stdev | 355 | 685 | 348 | 700 | 366 | 737 |
| p (t-test) | | 0.0021 | | 6.4E−4 | | 0.0038 |
| Min | 0.259 | 0.723 | 0.259 | 3.12 | 0.259 | 3.12 |
| Max | 2160 | 3600 | 2160 | 3600 | 2160 | 3600 |
| n (Patient) | 86 | 63 | 90 | 59 | 98 | 51 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 39.7 | 119 | 38.5 | 161 | 47.5 | 118 |
| Average | 168 | 430 | 161 | 463 | 191 | 447 |
| Stdev | 357 | 682 | 348 | 701 | 368 | 732 |
| p (t-test) | | 0.0029 | | 6.6E−4 | | 0.0052 |
| Min | 0.259 | 0.723 | 0.259 | 3.12 | 0.259 | 3.12 |
| Max | 2160 | 3600 | 2160 | 3600 | 2160 | 3600 |
| n (Patient) | 85 | 64 | 90 | 59 | 97 | 52 |

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 59.4 | 113 | 59.7 | 117 | 59.7 | 117 |
| Average | 244 | 422 | 243 | 432 | 243 | 432 |
| Stdev | 490 | 672 | 488 | 680 | 488 | 680 |
| p (t-test) | | 0.097 | | 0.081 | | 0.081 |
| Min | 0.259 | 5.59 | 0.259 | 5.59 | 0.259 | 5.59 |
| Max | 3600 | 3210 | 3600 | 3210 | 3600 | 3210 |
| n (Patient) | 116 | 32 | 117 | 31 | 117 | 31 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.70 | 0.69 | 0.65 | 0.73 | 0.72 | 0.65 | 0.69 | 0.68 | 0.65 |
| SE | 0.044 | 0.044 | 0.058 | 0.044 | 0.044 | 0.058 | 0.048 | 0.048 | 0.058 |
| p Value | 4.7E−6 | 1.6E−5 | 0.0080 | 2.0E−7 | 4.1E−7 | 0.0089 | 9.9E−5 | 2.3E−4 | 0.0089 |
| nCohort Non-persistent | 86 | 85 | 116 | 90 | 90 | 117 | 98 | 97 | 117 |
| nCohort Persistent | 63 | 64 | 32 | 59 | 59 | 31 | 51 | 52 | 31 |
| Cutoff Quartile 2 | 17.2 | 17.2 | 17.6 | 17.2 | 17.2 | 17.6 | 17.2 | 17.2 | 17.6 |
| Sensitivity | 87% | 86% | 94% | 90% | 88% | 94% | 88% | 87% | 94% |
| Specificity | 34% | 33% | 30% | 34% | 33% | 30% | 32% | 31% | 30% |
| Cutoff Quartile 3 | 78.3 | 78.3 | 80.9 | 78.3 | 78.3 | 80.9 | 78.3 | 78.3 | 80.9 |
| Sensitivity | 67% | 66% | 69% | 69% | 69% | 68% | 69% | 67% | 68% |
| Specificity | 62% | 61% | 55% | 62% | 62% | 55% | 59% | 59% | 55% |

TABLE 20.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Cutoff Quartile 4 | 331 | 331 | 331 | 331 | 331 | 331 | 331 | 331 | 331 |
| Sensitivity | 40% | 39% | 34% | 42% | 42% | 35% | 39% | 38% | 35% |
| Specificity | 85% | 85% | 78% | 86% | 86% | 78% | 82% | 81% | 78% |
| OR Quartile 2 | 3.50 | 3.00 | 6.48 | 4.64 | 3.71 | 6.19 | 3.47 | 2.88 | 6.19 |
| p Value | 0.0046 | 0.010 | 0.014 | 0.0015 | 0.0044 | 0.016 | 0.010 | 0.022 | 0.016 |
| Lower limit of 95% CI | 1.47 | 1.30 | 1.47 | 1.80 | 1.51 | 1.40 | 1.34 | 1.16 | 1.40 |
| Upper limit of 95% CI | 8.32 | 6.94 | 28.6 | 12.0 | 9.16 | 27.4 | 8.99 | 7.12 | 27.4 |
| OR Quartile 3 | 3.21 | 3.01 | 2.71 | 3.75 | 3.75 | 2.54 | 3.17 | 2.93 | 2.54 |
| p Value | 7.8E-4 | 0.0014 | 0.019 | 2.1E-4 | 2.1E-4 | 0.029 | 0.0016 | 0.0028 | 0.029 |
| Lower limit of 95% CI | 1.63 | 1.53 | 1.18 | 1.86 | 1.86 | 1.10 | 1.55 | 1.45 | 1.10 |
| Upper limit of 95% CI | 6.34 | 5.91 | 6.22 | 7.55 | 7.55 | 5.85 | 6.49 | 5.95 | 5.85 |
| OR Quartile 4 | 3.69 | 3.55 | 1.81 | 4.36 | 4.36 | 1.92 | 2.87 | 2.74 | 1.92 |
| p Value | 9.7E-4 | 0.0014 | 0.17 | 2.3E-4 | 2.3E-4 | 0.13 | 0.0066 | 0.0091 | 0.13 |
| Lower limit of 95% CI | 1.70 | 1.64 | 0.775 | 1.99 | 1.99 | 0.819 | 1.34 | 1.29 | 0.819 |
| Upper limit of 95% CI | 8.03 | 7.71 | 4.24 | 9.52 | 9.52 | 4.53 | 6.13 | 5.85 | 4.53 |

TABLE 20.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 39.0 | 123 | 38.5 | 161 | 44.2 | 119 |
| Average | 162 | 438 | 161 | 463 | 182 | 460 |
| Stdev | 355 | 680 | 348 | 700 | 358 | 730 |
| p (t-test) | | 0.0017 | | 6.4E-4 | | 0.0022 |
| Min | 0.259 | 0.723 | 0.259 | 3.12 | 0.259 | 3.12 |
| Max | 2160 | 3600 | 2160 | 3600 | 2160 | 3600 |
| n (Patient) | 85 | 64 | 90 | 59 | 96 | 53 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 39.7 | 119 | 39.0 | 144 | 47.5 | 118 |
| Average | 168 | 430 | 163 | 455 | 184 | 451 |
| Stdev | 357 | 682 | 350 | 697 | 359 | 726 |
| p (t-test) | | 0.0029 | | 9.2E-4 | | 0.0031 |
| Min | 0.259 | 0.723 | 0.259 | 3.12 | 0.259 | 3.12 |
| Max | 2160 | 3600 | 2160 | 3600 | 2160 | 3600 |
| n (Patient) | 85 | 64 | 89 | 60 | 95 | 54 |

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 58.5 | 118 | 58.9 | 118 | 58.9 | 118 |
| Average | 214 | 497 | 216 | 507 | 216 | 507 |
| Stdev | 382 | 829 | 380 | 851 | 380 | 851 |
| p (t-test) | | 0.0056 | | 0.0051 | | 0.0051 |
| Min | 0.259 | 5.59 | 0.259 | 5.59 | 0.259 | 5.59 |
| Max | 2160 | 3600 | 2160 | 3600 | 2160 | 3600 |
| n (Patient) | 112 | 36 | 114 | 34 | 114 | 34 |

TABLE 20.4-continued

Comparison of marker levels and the area under the ROC curve
(AUC) in urine samples for the "persistent" and "non-persistent" cohorts where
persistence starts within 96 hours after sample collection and renal status is assessed by
serum creatinine (sCr) only, urine output (UO) only, or serum creatinine or urine output
RIFLE criteria.

| Persistence Period | 24 | | | 48 | | | 72 | | |
| --- | --- | --- | --- | --- | --- | --- | --- | --- | --- |
| Duration (hr) | sCr or UO | sCr only | UO only | sCr or UO | sCr only | UO only | sCr or UO | sCr only | UO only |
| AUC | 0.71 | 0.69 | 0.68 | 0.73 | 0.72 | 0.67 | 0.69 | 0.68 | 0.67 |
| SE | 0.043 | 0.044 | 0.054 | 0.044 | 0.044 | 0.056 | 0.047 | 0.047 | 0.056 |
| p Value | 1.2E−6 | 1.6E−5 | 0.0010 | 2.0E−7 | 9.3E−7 | 0.0026 | 4.2E−5 | 1.3E−4 | 0.0026 |
| nCohort Non-persistent | 85 | 85 | 112 | 90 | 89 | 114 | 96 | 95 | 114 |
| nCohort Persistent | 64 | 64 | 36 | 59 | 60 | 34 | 53 | 54 | 34 |
| Cutoff Quartile 2 | 17.2 | 17.2 | 17.6 | 17.2 | 17.2 | 17.6 | 17.2 | 17.2 | 17.6 |
| Sensitivity | 88% | 86% | 94% | 90% | 88% | 94% | 89% | 87% | 94% |
| Specificity | 34% | 33% | 31% | 34% | 34% | 31% | 32% | 32% | 31% |
| Cutoff Quartile 3 | 78.3 | 78.3 | 80.9 | 78.3 | 78.3 | 80.9 | 78.3 | 78.3 | 80.9 |
| Sensitivity | 67% | 66% | 69% | 69% | 68% | 68% | 68% | 67% | 68% |
| Specificity | 62% | 61% | 56% | 62% | 62% | 55% | 59% | 59% | 55% |
| Cutoff Quartile 4 | 331 | 331 | 331 | 331 | 331 | 331 | 331 | 331 | 331 |
| Sensitivity | 41% | 39% | 36% | 42% | 42% | 35% | 40% | 39% | 35% |
| Specificity | 86% | 85% | 79% | 86% | 85% | 78% | 82% | 82% | 78% |
| OR Quartile 2 | 3.62 | 3.00 | 7.73 | 4.64 | 3.85 | 7.09 | 3.74 | 3.10 | 7.09 |
| p Value | 0.0036 | 0.010 | 0.0068 | 0.0015 | 0.0034 | 0.0096 | 0.0066 | 0.014 | 0.0096 |
| Lower limit of 95% CI | 1.52 | 1.30 | 1.76 | 1.80 | 1.56 | 1.61 | 1.44 | 1.25 | 1.61 |
| Upper limit of 95% CI | 8.62 | 6.94 | 34.0 | 12.0 | 9.49 | 31.2 | 9.67 | 7.65 | 31.2 |
| OR Quartile 3 | 3.39 | 3.01 | 2.92 | 3.75 | 3.49 | 2.58 | 3.10 | 2.87 | 2.58 |
| p Value | 4.5E−4 | 0.0014 | 0.0087 | 2.1E−4 | 4.0E−4 | 0.021 | 0.0017 | 0.0031 | 0.021 |
| Lower limit of 95% CI | 1.72 | 1.53 | 1.31 | 1.86 | 1.75 | 1.15 | 1.53 | 1.43 | 1.15 |
| Upper limit of 95% CI | 6.71 | 5.91 | 6.51 | 7.55 | 6.97 | 5.79 | 6.27 | 5.77 | 5.79 |
| OR Quartile 4 | 4.16 | 3.55 | 2.07 | 4.36 | 4.18 | 1.94 | 3.05 | 2.92 | 1.94 |
| p Value | 3.9E−4 | 0.0014 | 0.080 | 2.3E−4 | 3.3E−4 | 0.12 | 0.0040 | 0.0056 | 0.12 |
| Lower limit of 95% CI | 1.89 | 1.64 | 0.916 | 1.99 | 1.91 | 0.845 | 1.43 | 1.37 | 0.845 |
| Upper limit of 95% CI | 9.16 | 7.71 | 4.69 | 9.52 | 9.12 | 4.46 | 6.52 | 6.23 | 4.46 |

TABLE 20.5

Comparison of marker levels and the area under the ROC curve
(AUC) in urine samples for the "persistent" and "non-persistent" cohorts where
persistence starts within 168 hours after sample collection and renal status is assessed by
serum creatinine (sCr) only, urine output (UO) only, or serum creatinine or urine output
RIFLE criteria.

| | sCr or UO | | | | | |
| --- | --- | --- | --- | --- | --- | --- |
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 37.9 | 126 | 37.5 | 171 | 40.8 | 123 |
| Average | 141 | 451 | 137 | 477 | 178 | 451 |
| Stdev | 309 | 688 | 302 | 702 | 361 | 713 |
| p (t-test) | | 3.6E−4 | | 9.3E−5 | | 0.0023 |
| Min | 0.259 | 0.723 | 0.259 | 3.12 | 0.259 | 3.12 |
| Max | 2160 | 3600 | 2160 | 3600 | 2160 | 3600 |
| n (Patient) | 82 | 67 | 86 | 63 | 93 | 56 |

| | sCr only | | | | | |
| --- | --- | --- | --- | --- | --- | --- |
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 39.0 | 123 | 38.1 | 166 | 40.8 | 123 |
| Average | 146 | 450 | 141 | 476 | 164 | 474 |
| Stdev | 310 | 693 | 303 | 707 | 319 | 736 |
| p (t-test) | | 4.8E−4 | | 1.3E−4 | | 5.1E−4 |
| Min | 0.259 | 0.723 | 0.259 | 3.12 | 0.259 | 3.12 |
| Max | 2160 | 3600 | 2160 | 3600 | 2160 | 3600 |
| n (Patient) | 83 | 66 | 87 | 62 | 93 | 56 |

TABLE 20.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 58.3 | 119 | 58.5 | 123 | 58.5 | 123 |
| Average | 201 | 528 | 200 | 539 | 200 | 539 |
| Stdev | 358 | 839 | 357 | 848 | 357 | 848 |
| p (t-test) | | 0.0012 | | 8.2E−4 | | 8.2E−4 |
| Min | 0.259 | 5.59 | 0.259 | 5.59 | 0.259 | 5.59 |
| Max | 2160 | 3600 | 2160 | 3600 | 2160 | 3600 |
| n (Patient) | 111 | 37 | 112 | 36 | 112 | 36 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.72 | 0.71 | 0.69 | 0.74 | 0.73 | 0.69 | 0.70 | 0.70 | 0.69 |
| SE | 0.043 | 0.043 | 0.053 | 0.042 | 0.043 | 0.054 | 0.046 | 0.046 | 0.054 |
| p Value | 2.5E−7 | 1.1E−6 | 3.1E−4 | 6.8E−9 | 4.0E−8 | 3.6E−4 | 2.1E−5 | 1.4E−5 | 3.6E−4 |
| nCohort Non-persistent | 82 | 83 | 111 | 86 | 87 | 112 | 93 | 93 | 112 |
| nCohort Persistent | 67 | 66 | 37 | 63 | 62 | 36 | 56 | 56 | 36 |
| Cutoff Quartile 2 | 17.2 | 17.2 | 17.6 | 17.2 | 17.2 | 17.6 | 17.2 | 17.2 | 17.6 |
| Sensitivity | 87% | 86% | 95% | 89% | 89% | 94% | 88% | 88% | 94% |
| Specificity | 34% | 34% | 32% | 35% | 34% | 31% | 32% | 32% | 31% |
| Cutoff Quartile 3 | 78.3 | 78.3 | 80.9 | 78.3 | 78.3 | 80.9 | 78.3 | 78.3 | 80.9 |
| Sensitivity | 67% | 67% | 70% | 70% | 69% | 69% | 68% | 68% | 69% |
| Specificity | 63% | 63% | 57% | 64% | 63% | 56% | 60% | 60% | 56% |
| Cutoff Quartile 4 | 331 | 331 | 331 | 331 | 331 | 331 | 331 | 331 | 331 |
| Sensitivity | 42% | 41% | 38% | 44% | 44% | 39% | 41% | 41% | 39% |
| Specificity | 88% | 87% | 79% | 88% | 87% | 79% | 84% | 84% | 79% |
| OR Quartile 2 | 3.34 | 3.22 | 8.06 | 4.29 | 4.14 | 7.73 | 3.33 | 3.33 | 7.73 |
| p Value | 0.0048 | 0.0061 | 0.0057 | 0.0016 | 0.0020 | 0.0068 | 0.0090 | 0.0090 | 0.0068 |
| Lower limit of 95% CI | 1.45 | 1.40 | 1.83 | 1.74 | 1.68 | 1.76 | 1.35 | 1.35 | 1.76 |
| Upper limit of 95% CI | 7.72 | 7.45 | 35.4 | 10.6 | 10.2 | 34.0 | 8.23 | 8.23 | 34.0 |
| OR Quartile 3 | 3.55 | 3.35 | 3.10 | 4.11 | 3.89 | 2.92 | 3.20 | 3.20 | 2.92 |
| p Value | 2.6E−4 | 4.7E−4 | 0.0055 | 6.8E−5 | 1.2E−4 | 0.0087 | 0.0011 | 0.0011 | 0.0087 |
| Lower limit of 95% CI | 1.80 | 1.70 | 1.40 | 2.05 | 1.94 | 1.31 | 1.59 | 1.59 | 1.31 |
| Upper limit of 95% CI | 7.00 | 6.61 | 6.90 | 8.23 | 7.79 | 6.51 | 6.42 | 6.42 | 6.51 |
| OR Quartile 4 | 5.17 | 4.53 | 2.33 | 6.08 | 5.33 | 2.46 | 3.62 | 3.62 | 2.46 |
| p Value | 8.7E−5 | 2.2E−4 | 0.040 | 1.8E−5 | 4.9E−5 | 0.030 | 0.0010 | 0.0010 | 0.030 |
| Lower limit of 95% CI | 2.28 | 2.03 | 1.04 | 2.66 | 2.38 | 1.09 | 1.68 | 1.68 | 1.09 |
| Upper limit of 95% CI | 11.7 | 10.1 | 5.22 | 13.9 | 11.9 | 5.55 | 7.81 | 7.81 | 5.55 |

Example 21. Use of Insulin-Like Growth Factor-Binding Protein 6 for Evaluating Renal Status in Patients Admitted to the ICU: Persistent at RIFLE I or F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Insulin-like growth factor-binding protein 6 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is injury (I) or failure (F) where the persistence period can start from the time of sample collection to 24, 48, 72, 96 or 168 hours after sample collection. "Non-persistent" indicates those patients who are not persistent at injury (I) or failure (F) and whose minimum RIFLE stage during a period of 24, 48 or 72 hours is non-injury (RIFLE 0) or risk of injury (R) where the persistence period can start from the time of sample collection to 24, 48, 72, 96 or 168 hours after sample collection. If a patient dies after injury (I) or failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 21.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 22.2 | 118 | 37.9 | 117 | 39.3 | 171 |
| Average | 114 | 378 | 149 | 425 | 141 | 482 |
| Stdev | 312 | 612 | 315 | 676 | 299 | 713 |
| p (t-test) | | 0.0033 | | 0.0015 | | 9.5E−5 |
| Min | 0.259 | 0.723 | 0.259 | 0.723 | 0.259 | 0.723 |
| Max | 2160 | 3600 | 2160 | 3600 | 2160 | 3600 |
| n (Patient) | 55 | 94 | 78 | 71 | 88 | 61 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 30.9 | 110 | 35.3 | 117 | 39.0 | 180 |
| Average | 124 | 378 | 153 | 413 | 146 | 480 |
| Stdev | 311 | 618 | 322 | 669 | 305 | 717 |
| p (t-test) | | 0.0045 | | 0.0028 | | 1.4E−4 |
| Min | 0.259 | 0.723 | 0.259 | 0.723 | 0.259 | 0.723 |
| Max | 2160 | 3600 | 2160 | 3600 | 2160 | 3600 |
| n (Patient) | 57 | 92 | 76 | 73 | 89 | 60 |

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 59.4 | 138 | 63.7 | 190 | 63.7 | 243 |
| Average | 242 | 417 | 241 | 469 | 236 | 535 |
| Stdev | 495 | 649 | 483 | 713 | 476 | 755 |
| p (t-test) | | 0.097 | | 0.045 | | 0.014 |
| Min | 0.259 | 2.91 | 0.259 | 7.04 | 0.259 | 7.04 |
| Max | 3600 | 3210 | 3600 | 3210 | 3600 | 3210 |
| n (Patient) | 114 | 34 | 121 | 27 | 125 | 23 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.74 | 0.71 | 0.66 | 0.69 | 0.69 | 0.67 | 0.72 | 0.72 | 0.70 |
| SE | 0.040 | 0.042 | 0.056 | 0.044 | 0.043 | 0.061 | 0.044 | 0.044 | 0.065 |
| p Value | 7.5E−10 | 3.7E−7 | 0.0032 | 1.6E−5 | 1.5E−5 | 0.0046 | 4.7E−7 | 4.3E−7 | 0.0021 |
| nCohort Non-persistent | 55 | 57 | 114 | 78 | 76 | 121 | 88 | 89 | 125 |
| nCohort Persistent | 94 | 92 | 34 | 71 | 73 | 27 | 61 | 60 | 23 |
| Cutoff Quartile 2 | 17.2 | 17.2 | 17.6 | 17.2 | 17.2 | 17.6 | 17.2 | 17.2 | 17.6 |
| Sensitivity | 85% | 84% | 91% | 85% | 85% | 93% | 85% | 85% | 91% |
| Specificity | 42% | 39% | 30% | 33% | 34% | 29% | 32% | 31% | 28% |
| Cutoff Quartile 3 | 78.3 | 78.3 | 80.9 | 78.3 | 78.3 | 80.9 | 78.3 | 78.3 | 80.9 |
| Sensitivity | 65% | 63% | 68% | 63% | 63% | 70% | 69% | 68% | 74% |
| Specificity | 75% | 70% | 55% | 62% | 62% | 55% | 62% | 62% | 54% |
| Cutoff Quartile 4 | 331 | 331 | 331 | 331 | 331 | 331 | 331 | 331 | 331 |
| Sensitivity | 36% | 36% | 35% | 38% | 37% | 37% | 43% | 43% | 43% |
| Specificity | 93% | 91% | 78% | 86% | 86% | 78% | 86% | 87% | 78% |
| OR Quartile 2 | 4.11 | 3.23 | 4.39 | 2.73 | 2.93 | 5.09 | 2.70 | 2.60 | 4.08 |
| p Value | 3.9E−4 | 0.0028 | 0.020 | 0.014 | 0.0082 | 0.033 | 0.020 | 0.025 | 0.066 |
| Lower limit of 95% CI | 1.88 | 1.50 | 1.26 | 1.23 | 1.32 | 1.14 | 1.17 | 1.13 | 0.909 |
| Upper limit of 95% CI | 8.97 | 6.96 | 15.3 | 6.05 | 6.51 | 22.6 | 6.23 | 6.01 | 18.3 |
| OR Quartile 3 | 5.41 | 4.01 | 2.58 | 2.77 | 2.76 | 2.85 | 3.68 | 3.49 | 3.38 |
| p Value | 7.7E−6 | 1.2E−4 | 0.021 | 0.0027 | 0.0027 | 0.023 | 2.2E−4 | 4.0E−4 | 0.016 |
| Lower limit of 95% CI | 2.58 | 1.98 | 1.15 | 1.43 | 1.42 | 1.16 | 1.84 | 1.75 | 1.25 |
| Upper limit of 95% CI | 11.3 | 8.15 | 5.79 | 5.38 | 5.36 | 7.01 | 7.37 | 6.97 | 9.14 |
| OR Quartile 4 | 7.22 | 5.82 | 1.94 | 3.74 | 3.47 | 2.05 | 4.70 | 4.91 | 2.79 |
| p Value | 4.3E−4 | 6.5E−4 | 0.12 | 0.0012 | 0.0022 | 0.11 | 1.3E−4 | 8.7E−5 | 0.030 |

TABLE 21.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 2.40 | 2.11 | 0.845 | 1.68 | 1.56 | 0.840 | 2.13 | 2.22 | 1.10 |
| Upper limit of 95% CI | 21.7 | 16.0 | 4.46 | 8.30 | 7.69 | 4.99 | 10.4 | 10.9 | 7.06 |

TABLE 21.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 21.6 | 117 | 33.8 | 118 | 37.5 | 161 |
| Average | 115 | 375 | 148 | 408 | 140 | 453 |
| Stdev | 315 | 610 | 324 | 657 | 308 | 687 |
| p (t-test) | | 0.0041 | | 0.0027 | | 3.0E−4 |
| Min | 0.259 | 0.723 | 0.259 | 0.723 | 0.259 | 0.723 |
| Max | 2160 | 3600 | 2160 | 3600 | 2160 | 3600 |
| n (Patient) | 54 | 95 | 73 | 76 | 82 | 67 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 28.9 | 109 | 36.8 | 114 | 37.5 | 161 |
| Average | 125 | 374 | 155 | 401 | 142 | 450 |
| Stdev | 314 | 616 | 327 | 659 | 311 | 688 |
| p (t-test) | | 0.0057 | | 0.0046 | | 4.0E−4 |
| Min | 0.259 | 0.723 | 0.259 | 0.723 | 0.259 | 0.723 |
| Max | 2160 | 3600 | 2160 | 3600 | 2160 | 3600 |
| n (Patient) | 56 | 93 | 73 | 76 | 82 | 67 |

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 58.2 | 124 | 58.8 | 126 | 58.8 | 221 |
| Average | 213 | 457 | 213 | 505 | 209 | 559 |
| Stdev | 390 | 775 | 382 | 837 | 376 | 876 |
| p (t-test) | | 0.013 | | 0.0046 | | 0.0011 |
| Min | 0.259 | 2.91 | 0.259 | 5.59 | 0.259 | 5.59 |
| Max | 2160 | 3600 | 2160 | 3600 | 2160 | 3600 |
| n (Patient) | 106 | 42 | 113 | 35 | 117 | 31 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.74 | 0.71 | 0.67 | 0.70 | 0.68 | 0.68 | 0.73 | 0.72 | 0.70 |
| SE | 0.040 | 0.042 | 0.051 | 0.043 | 0.044 | 0.055 | 0.042 | 0.042 | 0.057 |
| p Value | 1.4E−9 | 6.2E−7 | 6.9E−4 | 2.9E−6 | 3.5E−5 | 0.0012 | 7.0E−8 | 1.9E−7 | 6.0E−4 |
| nCohort Non-persistent | 54 | 56 | 106 | 73 | 73 | 113 | 82 | 82 | 117 |
| nCohort Persistent | 95 | 93 | 42 | 76 | 76 | 35 | 67 | 67 | 31 |
| Cutoff Quartile 2 | 17.2 | 17.2 | 17.6 | 17.2 | 17.2 | 17.6 | 17.2 | 17.2 | 17.6 |
| Sensitivity | 85% | 84% | 90% | 86% | 84% | 91% | 87% | 85% | 90% |
| Specificity | 43% | 39% | 31% | 36% | 34% | 30% | 34% | 33% | 29% |
| Cutoff Quartile 3 | 78.3 | 78.3 | 80.9 | 78.3 | 78.3 | 80.9 | 78.3 | 78.3 | 80.9 |
| Sensitivity | 64% | 62% | 69% | 63% | 62% | 71% | 69% | 69% | 74% |
| Specificity | 74% | 70% | 58% | 63% | 62% | 57% | 65% | 65% | 56% |

TABLE 21.2-continued

Comparison of marker levels and the area under the ROC curve
(AUC) in urine samples for the "persistent" and "non-persistent" cohorts where
persistence starts within 48 hours after sample collection and renal status is assessed by
serum creatinine (sCr) only, urine output (UO) only, or serum creatinine or urine output
RIFLE criteria.

| Cutoff Quartile 4 | 331 | 331 | 331 | 331 | 331 | 331 | 331 | 331 | 331 |
|---|---|---|---|---|---|---|---|---|---|
| Sensitivity | 36% | 35% | 36% | 37% | 36% | 37% | 40% | 40% | 42% |
| Specificity | 93% | 91% | 79% | 86% | 85% | 79% | 87% | 87% | 79% |
| OR Quartile 2 | 4.29 | 3.36 | 4.29 | 3.27 | 2.78 | 4.59 | 3.34 | 2.80 | 3.82 |
| p Value | 2.6E−4 | 0.0020 | 0.010 | 0.0037 | 0.011 | 0.017 | 0.0048 | 0.013 | 0.036 |
| Lower limit of 95% CI | 1.96 | 1.56 | 1.42 | 1.47 | 1.27 | 1.32 | 1.45 | 1.24 | 1.09 |
| Upper limit of 95% CI | 9.39 | 7.27 | 13.0 | 7.27 | 6.08 | 16.0 | 7.72 | 6.32 | 13.4 |
| OR Quartile 3 | 5.13 | 3.80 | 3.02 | 2.92 | 2.60 | 3.27 | 4.00 | 4.00 | 3.72 |
| p Value | 1.5E−5 | 2.2E−4 | 0.0043 | 0.0016 | 0.0045 | 0.0048 | 7.5E−5 | 7.5E−5 | 0.0036 |
| Lower limit of 95% CI | 2.45 | 1.87 | 1.42 | 1.50 | 1.35 | 1.43 | 2.01 | 2.01 | 1.54 |
| Upper limit of 95% CI | 10.7 | 7.71 | 6.46 | 5.68 | 5.04 | 7.43 | 7.95 | 7.95 | 9.00 |
| OR Quartile 4 | 6.97 | 5.61 | 2.12 | 3.68 | 3.11 | 2.19 | 4.36 | 4.36 | 2.80 |
| p Value | 5.5E−4 | 8.4E−4 | 0.061 | 0.0017 | 0.0052 | 0.061 | 3.2E−4 | 3.2E−4 | 0.017 |
| Lower limit of 95% CI | 2.32 | 2.04 | 0.966 | 1.63 | 1.40 | 0.965 | 1.96 | 1.96 | 1.20 |
| Upper limit of 95% CI | 21.0 | 15.4 | 4.66 | 8.29 | 6.88 | 4.98 | 9.71 | 9.71 | 6.50 |

TABLE 21.3

Comparison of marker levels and the area under the ROC curve
(AUC) in urine samples for the "persistent" and "non-persistent" cohorts where
persistence starts within 72 hours after sample collection and renal status is assessed by
serum creatinine (sCr) only, urine output (UO) only, or serum creatinine or urine output
RIFLE criteria.

sCr or UO

| Persistence Period Duration (hr) | 24 | | 48 | | 72 | |
|---|---|---|---|---|---|---|
| | Non-persistent Cohort | Persistent Cohort | Non-persistent Cohort | Persistent Cohort | Non-persistent Cohort | Persistent Cohort |
| Median | 21.6 | 117 | 33.4 | 117 | 35.3 | 126 |
| Average | 115 | 375 | 148 | 404 | 140 | 435 |
| Stdev | 315 | 610 | 327 | 654 | 315 | 672 |
| p (t-test) | | 0.0041 | | 0.0033 | | 6.8E−4 |
| Min | 0.259 | 0.723 | 0.259 | 0.723 | 0.259 | 0.723 |
| Max | 2160 | 3600 | 2160 | 3600 | 2160 | 3600 |
| n (Patient) | 54 | 95 | 72 | 77 | 78 | 71 | sCr only

| Persistence Period Duration (hr) | 24 | | 48 | | 72 | |
|---|---|---|---|---|---|---|
| | Non-persistent Cohort | Persistent Cohort | Non-persistent Cohort | Persistent Cohort | Non-persistent Cohort | Persistent Cohort |
| Median | 28.9 | 109 | 35.3 | 111 | 37.5 | 119 |
| Average | 125 | 374 | 156 | 397 | 147 | 427 |
| Stdev | 314 | 616 | 329 | 655 | 318 | 674 |
| p (t-test) | | 0.0057 | | 0.0055 | | 0.0012 |
| Min | 0.259 | 0.723 | 0.259 | 0.723 | 0.259 | 0.723 |
| Max | 2160 | 3600 | 2160 | 3600 | 2160 | 3600 |
| n (Patient) | 56 | 93 | 72 | 77 | 78 | 71 |

UO only

| Persistence Period Duration (hr) | 24 | | 48 | | 72 | |
|---|---|---|---|---|---|---|
| | Non-persistent Cohort | Persistent Cohort | Non-persistent Cohort | Persistent Cohort | Non-persistent Cohort | Persistent Cohort |
| Median | 58.5 | 118 | 58.9 | 118 | 58.9 | 123 |
| Average | 221 | 411 | 217 | 448 | 212 | 485 |
| Stdev | 400 | 735 | 391 | 778 | 384 | 809 |
| p (t-test) | | 0.043 | | 0.018 | | 0.0065 |
| Min | 0.259 | 2.91 | 0.259 | 3.55 | 0.259 | 3.55 |
| Max | 2160 | 3600 | 2160 | 3600 | 2160 | 3600 |
| n (Patient) | 100 | 48 | 106 | 42 | 110 | 38 |

TABLE 21.3-continued

Comparison of marker levels and the area under the ROC curve
(AUC) in urine samples for the "persistent" and "non-persistent" cohorts where
persistence starts within 72 hours after sample collection and renal status is assessed by
serum creatinine (sCr) only, urine output (UO) only, or serum creatinine or urine output
RIFLE criteria.

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.74 | 0.71 | 0.64 | 0.70 | 0.68 | 0.65 | 0.73 | 0.71 | 0.66 |
| SE | 0.040 | 0.042 | 0.050 | 0.042 | 0.043 | 0.052 | 0.042 | 0.043 | 0.054 |
| p Value | 1.4E−9 | 6.2E−7 | 0.0042 | 2.1E−6 | 2.6E−5 | 0.0038 | 6.0E−8 | 1.3E−6 | 0.0026 |
| nCohort Non-persistent | 54 | 56 | 100 | 72 | 72 | 106 | 78 | 78 | 110 |
| nCohort Persistent | 95 | 93 | 48 | 77 | 77 | 42 | 71 | 71 | 38 |
| Cutoff Quartile 2 | 17.2 | 17.2 | 17.6 | 17.2 | 17.2 | 17.6 | 17.2 | 17.2 | 17.6 |
| Sensitivity | 85% | 84% | 90% | 86% | 84% | 90% | 87% | 86% | 89% |
| Specificity | 43% | 39% | 32% | 36% | 35% | 31% | 36% | 35% | 30% |
| Cutoff Quartile 3 | 78.3 | 78.3 | 80.9 | 78.3 | 78.3 | 80.9 | 78.3 | 78.3 | 80.9 |
| Sensitivity | 64% | 62% | 65% | 64% | 62% | 67% | 68% | 66% | 68% |
| Specificity | 74% | 70% | 57% | 64% | 62% | 57% | 65% | 64% | 56% |
| Cutoff Quartile 4 | 331 | 331 | 331 | 331 | 331 | 331 | 331 | 331 | 331 |
| Sensitivity | 36% | 35% | 31% | 36% | 35% | 33% | 39% | 38% | 37% |
| Specificity | 93% | 91% | 78% | 86% | 85% | 78% | 87% | 86% | 79% |
| OR Quartile 2 | 4.29 | 3.36 | 4.05 | 3.39 | 2.88 | 4.29 | 3.86 | 3.23 | 3.64 |
| p Value | 2.6E−4 | 0.0020 | 0.0071 | 0.0027 | 0.0082 | 0.010 | 0.0016 | 0.0048 | 0.023 |
| Lower limit of 95% CI | 1.96 | 1.56 | 1.46 | 1.53 | 1.32 | 1.42 | 1.67 | 1.43 | 1.20 |
| Upper limit of 95% CI | 9.39 | 7.27 | 11.2 | 7.54 | 6.31 | 13.0 | 8.92 | 7.30 | 11.1 |
| OR Quartile 3 | 5.13 | 3.80 | 2.42 | 3.10 | 2.76 | 2.61 | 3.94 | 3.50 | 2.80 |
| p Value | 1.5E−5 | 2.2E−4 | 0.015 | 9.2E−4 | 0.0027 | 0.012 | 8.0E−5 | 2.8E−4 | 0.0098 |
| Lower limit of 95% CI | 2.45 | 1.87 | 1.19 | 1.59 | 1.42 | 1.24 | 1.99 | 1.78 | 1.28 |
| Upper limit of 95% CI | 10.7 | 7.71 | 4.93 | 6.04 | 5.36 | 5.51 | 7.79 | 6.87 | 6.11 |
| OR Quartile 4 | 6.97 | 5.61 | 1.61 | 3.54 | 2.99 | 1.80 | 4.43 | 3.74 | 2.21 |
| p Value | 5.5E−4 | 8.4E−4 | 0.23 | 0.0023 | 0.0068 | 0.14 | 3.6E−4 | 0.0012 | 0.054 |
| Lower limit of 95% CI | 2.32 | 2.04 | 0.744 | 1.57 | 1.35 | 0.818 | 1.96 | 1.68 | 0.988 |
| Upper limit of 95% CI | 21.0 | 15.4 | 3.49 | 7.99 | 6.63 | 3.98 | 10.0 | 8.30 | 4.93 |

TABLE 21.4

Comparison of marker levels and the area under the ROC curve
(AUC) in urine samples for the "persistent" and "non-persistent" cohorts where
persistence starts within 96 hours after sample collection and renal status is assessed by
serum creatinine (sCr) only, urine output (UO) only, or serum creatinine or urine output
RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 21.6 | 117 | 33.4 | 117 | 35.3 | 126 |
| Average | 115 | 375 | 148 | 404 | 140 | 435 |
| Stdev | 315 | 610 | 327 | 654 | 315 | 672 |
| p (t-test) | | 0.0041 | | 0.0033 | | 6.8E−4 |
| Min | 0.259 | 0.723 | 0.259 | 0.723 | 0.259 | 0.723 |
| Max | 2160 | 3600 | 2160 | 3600 | 2160 | 3600 |
| n (Patient) | 54 | 95 | 72 | 77 | 78 | 71 |

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 28.9 | 109 | 35.3 | 111 | 37.5 | 119 |
| Average | 125 | 374 | 156 | 397 | 147 | 427 |
| Stdev | 314 | 616 | 329 | 655 | 318 | 674 |
| p (t-test) | | 0.0057 | | 0.0055 | | 0.0012 |
| Min | 0.259 | 0.723 | 0.259 | 0.723 | 0.259 | 0.723 |
| Max | 2160 | 3600 | 2160 | 3600 | 2160 | 3600 |
| n (Patient) | 56 | 93 | 72 | 77 | 78 | 71 |

TABLE 21.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 58.5 | 118 | 58.8 | 117 | 58.8 | 119 |
| Average | 223 | 399 | 220 | 424 | 216 | 457 |
| Stdev | 403 | 723 | 396 | 756 | 389 | 785 |
| p (t-test) | | 0.060 | | 0.033 | | 0.014 |
| Min | 0.259 | 2.91 | 0.259 | 3.55 | 0.259 | 3.55 |
| Max | 2160 | 3600 | 2160 | 3600 | 2160 | 3600 |
| n (Patient) | 98 | 50 | 103 | 45 | 107 | 41 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.74 | 0.71 | 0.64 | 0.70 | 0.68 | 0.65 | 0.73 | 0.71 | 0.66 |
| SE | 0.040 | 0.042 | 0.049 | 0.042 | 0.043 | 0.051 | 0.042 | 0.043 | 0.052 |
| p Value | 1.4E−9 | 6.2E−7 | 0.0040 | 2.1E−6 | 2.6E−5 | 0.0041 | 6.0E−8 | 1.3E−6 | 0.0030 |
| nCohort Non-persistent | 54 | 56 | 98 | 72 | 72 | 103 | 78 | 78 | 107 |
| nCohort Persistent | 95 | 93 | 50 | 77 | 77 | 45 | 71 | 71 | 41 |
| Cutoff Quartile 2 | 17.2 | 17.2 | 17.6 | 17.2 | 17.2 | 17.6 | 17.2 | 17.2 | 17.6 |
| Sensitivity | 85% | 84% | 90% | 86% | 84% | 91% | 87% | 86% | 90% |
| Specificity | 43% | 39% | 33% | 36% | 35% | 32% | 36% | 35% | 31% |
| Cutoff Quartile 3 | 78.3 | 78.3 | 80.9 | 78.3 | 78.3 | 80.9 | 78.3 | 78.3 | 80.9 |
| Sensitivity | 64% | 62% | 64% | 64% | 62% | 64% | 68% | 66% | 66% |
| Specificity | 74% | 70% | 57% | 64% | 62% | 56% | 65% | 64% | 56% |
| Cutoff Quartile 4 | 331 | 331 | 331 | 331 | 331 | 331 | 331 | 331 | 331 |
| Sensitivity | 36% | 35% | 30% | 36% | 35% | 31% | 39% | 38% | 34% |
| Specificity | 93% | 91% | 78% | 86% | 85% | 78% | 87% | 86% | 79% |
| OR Quartile 2 | 4.29 | 3.36 | 4.36 | 3.39 | 2.88 | 4.83 | 3.86 | 3.23 | 4.12 |
| p Value | 2.6E−4 | 0.0020 | 0.0045 | 0.0027 | 0.0082 | 0.0053 | 0.0016 | 0.0048 | 0.012 |
| Lower limit of 95% CI | 1.96 | 1.56 | 1.58 | 1.53 | 1.32 | 1.60 | 1.67 | 1.43 | 1.36 |
| Upper limit of 95% CI | 9.39 | 7.27 | 12.1 | 7.54 | 6.31 | 14.6 | 8.92 | 7.30 | 12.5 |
| OR Quartile 3 | 5.13 | 3.80 | 2.37 | 3.10 | 2.76 | 2.34 | 3.94 | 3.50 | 2.46 |
| p Value | 1.5E−5 | 2.2E−4 | 0.016 | 9.2E−4 | 0.0027 | 0.022 | 8.0E−5 | 2.8E−4 | 0.019 |
| Lower limit of 95% CI | 2.45 | 1.87 | 1.17 | 1.59 | 1.42 | 1.13 | 1.99 | 1.78 | 1.16 |
| Upper limit of 95% CI | 10.7 | 7.71 | 4.79 | 6.04 | 5.36 | 4.82 | 7.79 | 6.87 | 5.21 |
| OR Quartile 4 | 6.97 | 5.61 | 1.48 | 3.54 | 2.99 | 1.57 | 4.43 | 3.74 | 1.89 |
| p Value | 5.5E−4 | 8.4E−4 | 0.32 | 0.0023 | 0.0068 | 0.26 | 3.6E−4 | 0.0012 | 0.11 |
| Lower limit of 95% CI | 2.32 | 2.04 | 0.686 | 1.57 | 1.35 | 0.718 | 1.96 | 1.68 | 0.857 |
| Upper limit of 95% CI | 21.0 | 15.4 | 3.19 | 7.99 | 6.63 | 3.44 | 10.0 | 8.30 | 4.19 |

TABLE 21.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | sCr or UO | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 21.6 | 117 | 32.9 | 118 | 35.3 | 126 |
| Average | 107 | 374 | 147 | 396 | 141 | 419 |
| Stdev | 311 | 605 | 332 | 643 | 322 | 658 |
| p (t-test) | | 0.0034 | | 0.0044 | | 0.0014 |
| Min | 0.259 | 0.723 | 0.259 | 0.723 | 0.259 | 0.723 |
| Max | 2160 | 3600 | 2160 | 3600 | 2160 | 3600 |
| n (Patient) | 52 | 97 | 69 | 80 | 74 | 75 |

TABLE 21.5-continued

Comparison of marker levels and the area under the ROC curve
(AUC) in urine samples for the "persistent" and "non-persistent" cohorts where
persistence starts within 168 hours after sample collection and renal status is assessed by
serum creatinine (sCr) only, urine output (UO) only, or serum creatinine or urine output
RIFLE criteria.

| | sCr only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 26.8 | 110 | 33.4 | 117 | 35.3 | 126 |
| Average | 115 | 377 | 145 | 400 | 137 | 430 |
| Stdev | 307 | 614 | 327 | 647 | 315 | 665 |
| p (t-test) | | 0.0037 | | 0.0034 | | 7.3E−4 |
| Min | 0.259 | 0.723 | 0.259 | 0.723 | 0.259 | 0.723 |
| Max | 2160 | 3600 | 2160 | 3600 | 2160 | 3600 |
| n (Patient) | 55 | 94 | 70 | 79 | 76 | 73 |

| | UO only | | | | | |
|---|---|---|---|---|---|---|
| | 24 | | 48 | | 72 | |
| Persistence Period Duration (hr) | Non-persistent Cohort | Persistent Cohort | Non-persistent Cohort | Persistent Cohort | Non-persistent Cohort | Persistent Cohort |
| Median | 54.3 | 121 | 58.3 | 119 | 54.3 | 138 |
| Average | 207 | 422 | 207 | 434 | 203 | 459 |
| Stdev | 380 | 729 | 376 | 749 | 371 | 767 |
| p (t-test) | | 0.019 | | 0.015 | | 0.0070 |
| Min | 0.259 | 2.91 | 0.259 | 2.91 | 0.259 | 2.91 |
| Max | 2160 | 3600 | 2160 | 3600 | 2160 | 3600 |
| n (Patient) | 96 | 52 | 99 | 49 | 102 | 46 |

| Persistence Period | 24 | | | 48 | | | 72 | | |
|---|---|---|---|---|---|---|---|---|---|
| Duration (hr) | sCr or UO | sCr only | UO only | sCr or UO | sCr only | UO only | sCr or UO | sCr only | UO only |
| AUC | 0.75 | 0.72 | 0.66 | 0.70 | 0.70 | 0.65 | 0.72 | 0.72 | 0.67 |
| SE | 0.040 | 0.041 | 0.048 | 0.042 | 0.042 | 0.049 | 0.042 | 0.042 | 0.050 |
| p Value | 4.5E−10 | 7.2E−8 | 8.4E−4 | 1.2E−6 | 2.2E−6 | 0.0018 | 2.3E−7 | 6.8E−8 | 8.9E−4 |
| nCohort Non-persistent | 52 | 55 | 96 | 69 | 70 | 99 | 74 | 76 | 102 |
| nCohort Persistent | 97 | 94 | 52 | 80 | 79 | 49 | 75 | 73 | 46 |
| Cutoff Quartile 2 | 17.2 | 17.2 | 17.6 | 17.2 | 17.2 | 17.6 | 17.2 | 17.2 | 17.6 |
| Sensitivity | 85% | 84% | 90% | 85% | 85% | 90% | 85% | 86% | 89% |
| Specificity | 42% | 40% | 33% | 36% | 36% | 32% | 35% | 36% | 31% |
| Cutoff Quartile 3 | 78.3 | 78.3 | 80.9 | 78.3 | 78.3 | 80.9 | 78.3 | 78.3 | 80.9 |
| Sensitivity | 64% | 63% | 65% | 64% | 63% | 65% | 67% | 67% | 67% |
| Specificity | 75% | 71% | 58% | 65% | 64% | 58% | 66% | 66% | 58% |
| Cutoff Quartile 4 | 331 | 331 | 331 | 331 | 331 | 331 | 331 | 331 | 331 |
| Sensitivity | 36% | 36% | 33% | 36% | 37% | 33% | 39% | 40% | 35% |
| Specificity | 94% | 93% | 79% | 87% | 87% | 79% | 88% | 88% | 79% |
| OR Quartile 2 | 4.01 | 3.51 | 4.70 | 3.22 | 3.10 | 4.20 | 3.15 | 3.47 | 3.75 |
| p Value | 4.7E−4 | 0.0014 | 0.0028 | 0.0035 | 0.0047 | 0.0056 | 0.0048 | 0.0028 | 0.011 |
| Lower limit of 95% CI | 1.84 | 1.62 | 1.70 | 1.47 | 1.41 | 1.52 | 1.42 | 1.54 | 1.35 |
| Upper limit of 95% CI | 8.73 | 7.60 | 13.0 | 7.07 | 6.80 | 11.6 | 7.00 | 7.85 | 10.4 |
| OR Quartile 3 | 5.31 | 4.11 | 2.64 | 3.30 | 3.10 | 2.55 | 3.92 | 3.93 | 2.84 |
| p Value | 1.3E−5 | 1.1E−4 | 0.0065 | 5.1E−4 | 9.2E−4 | 0.0097 | 8.3E−5 | 8.2E−5 | 0.0052 |
| Lower limit of 95% CI | 2.50 | 2.01 | 1.31 | 1.68 | 1.59 | 1.26 | 1.99 | 1.99 | 1.37 |
| Upper limit of 95% CI | 11.3 | 8.41 | 5.33 | 6.46 | 6.06 | 5.20 | 7.74 | 7.75 | 5.89 |
| OR Quartile 4 | 9.22 | 7.22 | 1.85 | 3.79 | 3.93 | 1.80 | 4.55 | 4.91 | 2.06 |
| p Value | 4.3E−4 | 4.3E−4 | 0.11 | 0.0018 | 0.0013 | 0.13 | 3.9E−4 | 2.0E−4 | 0.068 |
| Lower limit of 95% CI | 2.68 | 2.40 | 0.863 | 1.64 | 1.70 | 0.836 | 1.97 | 2.12 | 0.949 |
| Upper limit of 95% CI | 31.8 | 21.7 | 3.95 | 8.74 | 9.07 | 3.88 | 10.5 | 11.4 | 4.46 |

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A method comprising:
   (a) obtaining a body fluid sample from a subject having a persistent RIFLE I acute kidney injury or a persistent RIFLE F acute kidney injury; and
   (b) detecting a level of one or more of insulin-like growth factor-binding protein 2, insulin-like growth factor-binding protein 3, insulin-like growth factor-binding protein 4, and insulin-like growth factor-binding protein 6 in the sample,
   wherein the persistent RIFLE I acute kidney injury is an acute kidney injury for a period of 48 hours or more at a minimum RIFLE stage of RIFLE stage I, and wherein the persistent RIFLE F acute kidney injury is an acute kidney injury for a period of 48 hours or more at a minimum RIFLE stage of RIFLE stage F.

2. The method of claim 1, wherein the sample has an elevated level of the one or more of insulin-like growth factor-binding protein 2, insulin-like growth factor-binding protein 3, insulin-like growth factor-binding protein 4, and insulin-like growth factor-binding protein 6 as compared to a predetermined threshold level.

3. The method of claim 1, wherein the detecting comprises contacting all or a portion of the sample with a binding reagent which binds to the one or more of insulin-like growth factor-binding protein 2, insulin-like growth factor-binding protein 3, insulin-like growth factor-binding protein 4, and insulin-like growth factor-binding protein 6, and generating an assay result indicative of binding of the one or more of insulin-like growth factor-binding protein 2, insulin-like growth factor-binding protein 3, insulin-like growth factor-binding protein 4, and insulin-like growth factor-binding protein 6.

4. The method of claim 3, wherein the assay result is a measured concentration of the one or more of insulin-like growth factor-binding protein 2, insulin-like growth factor-binding protein 3, insulin-like growth factor-binding protein 4, and insulin-like growth factor-binding protein 6.

5. The method of claim 4, wherein the assay result is a composite of a plurality of assay results.

6. The method of claim 3, wherein the binding reagent is an antibody.

7. The method of claim 1, further comprising treating the subject for the persistent RIFLE I acute kidney injury or the persistent RIFLE F acute kidney injury.

8. The method of claim 1, further comprising administering renal replacement therapy to the subject having the persistent RIFLE I acute kidney injury or the persistent RIFLE F acute kidney injury.

9. The method of claim 8, wherein the renal replacement therapy comprises one or more of hemodialysis, peritoneal dialysis, hemofiltration, and renal transplantation.

10. The method of claim 1, wherein the subject has the persistent RIFLE F acute kidney injury.

11. The method of claim 1, wherein the subject has the persistent RIFLE I acute kidney injury.

12. The method of claim 1, wherein the body fluid sample is a urine sample.

13. A method of treating acute kidney injury comprising:
(a) obtaining a urine sample from a subject;
(b) detecting a level of one or more of insulin-like growth factor-binding protein 2, insulin-like growth factor-binding protein 3, insulin-like growth factor-binding protein 4, and insulin-like growth factor-binding protein 6 in the urine sample;
(c) determining that the subject is at increased risk of future persistence of a RIFLE I acute kidney injury or future persistence of a RIFLE F acute kidney injury based on the level of one or more of insulin-like growth factor-binding protein 2, insulin-like growth factor-binding protein 3, insulin-like growth factor-binding protein 4, and insulin-like growth factor-binding protein 6 in the urine sample, and
(d) administering renal replacement therapy to the subject at the increased risk of future persistence of the RIFLE I acute kidney injury or future persistence of the RIFLE F acute kidney injury.

14. The method of claim 13, wherein the renal replacement therapy comprises one or more of hemodialysis, peritoneal dialysis, hemofiltration, and renal transplantation.

15. The method of claim 13, wherein the subject is determined to have an increased likelihood of the future persistence of the RIFLE I acute kidney injury or the future persistence of the RIFLE F acute kidney injury for 72 hours after the time the urine sample is obtained from the subject.

16. The method of claim 13, wherein the future persistence comprises a persistence period that starts 72 hours after the sample is obtained.

* * * * *

```
                                SEQUENCE LISTING

<160> NUMBER OF SEQ ID NOS: 5

<210> SEQ ID NO 1
<211> LENGTH: 291
<212> TYPE: PRT
<213> ORGANISM: Homo sapiens
<220> FEATURE:
<221> NAME/KEY: misc_feature
<223> OTHER INFORMATION: Insulin-like growth factor-binding protein 3
      precursor

<400> SEQUENCE: 1

Met Gln Arg Ala Arg Pro Thr Leu Trp Ala Ala Ala Leu Thr Leu Leu
1               5                   10                  15

Val Leu Leu Arg Gly Pro Pro Val Ala Arg Ala Gly Ala Ser Ser Ala
            20                  25                  30

Gly Leu Gly Pro Val Val Arg Cys Glu Pro Cys Asp Ala Arg Ala Leu
        35                  40                  45

Ala Gln Cys Ala Pro Pro Pro Ala Val Cys Ala Glu Leu Val Arg Glu
    50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
                85                  90                  95

Ser Pro Asp Glu Ala Arg Pro Leu Gln Ala Leu Leu Asp Gly Arg Gly
            100                 105                 110

Leu Cys Val Asn Ala Ser Ala Val Ser Arg Leu Arg Ala Tyr Leu Leu
        115                 120                 125

Pro Ala Pro Pro Ala Pro Gly Asn Ala Ser Glu Ser Glu Glu Asp Arg
    130                 135                 140

Ser Ala Gly Ser Val Glu Ser Pro Ser Val Ser Ser Thr His Arg Val
145                 150                 155                 160

Ser Asp Pro Lys Phe His Pro Leu His Ser Lys Ile Ile Ile Ile Lys
                165                 170                 175

Lys Gly His Ala Lys Asp Ser Gln Arg Tyr Lys Val Asp Tyr Glu Ser
            180                 185                 190

Gln Ser Thr Asp Thr Gln Asn Phe Ser Ser Glu Ser Lys Arg Glu Thr
        195                 200                 205

Glu Tyr Gly Pro Cys Arg Arg Glu Met Glu Asp Thr Leu Asn His Leu
    210                 215                 220

Lys Phe Leu Asn Val Leu Ser Pro Arg Gly Val His Ile Pro Asn Cys
225                 230                 235                 240

Asp Lys Lys Gly Phe Tyr Lys Lys Lys Gln Cys Arg Pro Ser Lys Gly
                245                 250                 255
```

```
Arg Lys Arg Gly Phe Cys Trp Cys Val Asp Lys Tyr Gly Gln Pro Leu
        260                 265                 270

Pro Gly Tyr Thr Thr Lys Gly Lys Glu Asp Val His Cys Tyr Ser Met
            275                 280                 285

Gln Ser Lys
    290

<210> SEQ ID NO 2
<211> LENGTH: 7
<212> TYPE: PRT
<213> ORGANISM: Homo sapiens
<220> FEATURE:
<221> NAME/KEY: misc_feature
<223> OTHER INFORMATION: domain identified in Insulin-like growth
      factor-binding protein 3 in isoform 2

<400> SEQUENCE: 2

Gly Glu Pro Pro Ala Pro Gly
1               5

<210> SEQ ID NO 3
<211> LENGTH: 325
<212> TYPE: PRT
<213> ORGANISM: Homo sapiens
<220> FEATURE:
<221> NAME/KEY: misc_feature
<223> OTHER INFORMATION: Insulin-like growth factor-binding protein 2
      precursor

<400> SEQUENCE: 3

Met Leu Pro Arg Val Gly Cys Pro Ala Leu Pro Leu Pro Pro Pro Pro
1               5                   10                  15

Leu Leu Pro Leu Leu Leu Leu Leu Leu Gly Ala Ser Gly Gly Gly Gly
            20                  25                  30

Gly Ala Arg Ala Glu Val Leu Phe Arg Cys Pro Pro Cys Thr Pro Glu
        35                  40                  45

Arg Leu Ala Ala Cys Gly Pro Pro Val Ala Pro Pro Ala Ala Val Ala
    50                  55                  60

Ala Ala Val Ala Gly Gly Ala Arg Met Pro Cys Ala Glu Leu Val Arg
65                  70                  75                  80

Glu Pro Gly Cys Gly Cys Cys Ser Val Cys Ala Arg Leu Glu Gly Glu
                85                  90                  95

Ala Cys Gly Val Tyr Thr Pro Arg Cys Gly Gln Gly Leu Arg Cys Tyr
            100                 105                 110

Pro His Pro Gly Ser Glu Leu Pro Leu Gln Ala Leu Val Met Gly Glu
        115                 120                 125

Gly Thr Cys Glu Lys Arg Arg Asp Ala Glu Tyr Gly Ala Ser Pro Glu
    130                 135                 140

Gln Val Ala Asp Asn Gly Asp Asp His Ser Glu Gly Leu Val Glu
145                 150                 155                 160

Asn His Val Asp Ser Thr Met Asn Met Leu Gly Gly Gly Gly Ser Ala
                165                 170                 175

Gly Arg Lys Pro Leu Lys Ser Gly Met Lys Glu Leu Ala Val Phe Arg
            180                 185                 190

Glu Lys Val Thr Glu Gln His Arg Gln Met Gly Lys Gly Gly Lys His
        195                 200                 205

His Leu Gly Leu Glu Glu Pro Lys Lys Leu Arg Pro Pro Pro Ala Arg
    210                 215                 220
```

Thr Pro Cys Gln Gln Glu Leu Asp Gln Val Leu Glu Arg Ile Ser Thr
225                 230                 235                 240

Met Arg Leu Pro Asp Glu Arg Gly Pro Leu Glu His Leu Tyr Ser Leu
            245                 250                 255

His Ile Pro Asn Cys Asp Lys His Gly Leu Tyr Asn Leu Lys Gln Cys
            260                 265                 270

Lys Met Ser Leu Asn Gly Gln Arg Gly Glu Cys Trp Cys Val Asn Pro
        275                 280                 285

Asn Thr Gly Lys Leu Ile Gln Gly Ala Pro Thr Ile Arg Gly Asp Pro
        290                 295                 300

Glu Cys His Leu Phe Tyr Asn Glu Gln Gln Glu Ala Arg Gly Val His
305                 310                 315                 320

Thr Gln Arg Met Gln
                325

<210> SEQ ID NO 4
<211> LENGTH: 258
<212> TYPE: PRT
<213> ORGANISM: Homo sapiens
<220> FEATURE:
<221> NAME/KEY: misc_feature
<223> OTHER INFORMATION: Insulin-like growth factor-binding protein 4
      precursor

<400> SEQUENCE: 4

Met Leu Pro Leu Cys Leu Val Ala Ala Leu Leu Ala Ala Gly Pro
1               5                   10                  15

Gly Pro Ser Leu Gly Asp Glu Ala Ile His Cys Pro Pro Cys Ser Glu
            20                  25                  30

Glu Lys Leu Ala Arg Cys Arg Pro Pro Val Gly Cys Glu Glu Leu Val
        35                  40                  45

Arg Glu Pro Gly Cys Gly Cys Cys Ala Thr Cys Ala Leu Gly Leu Gly
    50                  55                  60

Met Pro Cys Gly Val Tyr Thr Pro Arg Cys Gly Ser Gly Leu Arg Cys
65                  70                  75                  80

Tyr Pro Pro Arg Gly Val Glu Lys Pro Leu His Thr Leu Met His Gly
                85                  90                  95

Gln Gly Val Cys Met Glu Leu Ala Glu Ile Glu Ala Ile Gln Glu Ser
            100                 105                 110

Leu Gln Pro Ser Asp Lys Asp Glu Gly Asp His Pro Asn Asn Ser Phe
        115                 120                 125

Ser Pro Cys Ser Ala His Asp Arg Arg Cys Leu Gln Lys His Phe Ala
    130                 135                 140

Lys Ile Arg Asp Arg Ser Thr Ser Gly Gly Lys Met Lys Val Asn Gly
145                 150                 155                 160

Ala Pro Arg Glu Asp Ala Arg Pro Val Pro Gln Gly Ser Cys Gln Ser
                165                 170                 175

Glu Leu His Arg Ala Leu Glu Arg Leu Ala Ala Ser Gln Ser Arg Thr
            180                 185                 190

His Glu Asp Leu Tyr Ile Ile Pro Ile Pro Asn Cys Asp Arg Asn Gly
        195                 200                 205

Asn Phe His Pro Lys Gln Cys His Pro Ala Leu Asp Gly Gln Arg Gly
    210                 215                 220

Lys Cys Trp Cys Val Asp Arg Lys Thr Gly Val Lys Leu Pro Gly Gly
225                 230                 235                 240

Leu Glu Pro Lys Gly Glu Leu Asp Cys His Gln Leu Ala Asp Ser Phe

```
                   245                 250                 255
Arg Glu

<210> SEQ ID NO 5
<211> LENGTH: 240
<212> TYPE: PRT
<213> ORGANISM: Homo sapiens
<220> FEATURE:
<221> NAME/KEY: misc_feature
<223> OTHER INFORMATION: Insulin-like growth factor-binding protein 6
      precursor

<400> SEQUENCE: 5

Met Thr Pro His Arg Leu Leu Pro Pro Leu Leu Leu Leu Ala Leu
1               5                   10                  15

Leu Leu Ala Ala Ser Pro Gly Gly Ala Leu Ala Arg Cys Pro Gly Cys
                20                  25                  30

Gly Gln Gly Val Gln Ala Gly Cys Pro Gly Gly Cys Val Glu Glu Glu
            35                  40                  45

Asp Gly Gly Ser Pro Ala Glu Gly Cys Ala Glu Ala Glu Gly Cys Leu
    50                  55                  60

Arg Arg Glu Gly Gln Glu Cys Gly Val Tyr Thr Pro Asn Cys Ala Pro
65                  70                  75                  80

Gly Leu Gln Cys His Pro Pro Lys Asp Asp Glu Ala Pro Leu Arg Ala
                85                  90                  95

Leu Leu Leu Gly Arg Gly Arg Cys Leu Pro Ala Arg Ala Pro Ala Val
            100                 105                 110

Ala Glu Glu Asn Pro Lys Glu Ser Lys Pro Gln Ala Gly Thr Ala Arg
            115                 120                 125

Pro Gln Asp Val Asn Arg Arg Asp Gln Gln Arg Asn Pro Gly Thr Ser
130                 135                 140

Thr Thr Pro Ser Gln Pro Asn Ser Ala Gly Val Gln Asp Thr Glu Met
145                 150                 155                 160

Gly Pro Cys Arg Arg His Leu Asp Ser Val Leu Gln Gln Leu Gln Thr
                165                 170                 175

Glu Val Tyr Arg Gly Ala Gln Thr Leu Tyr Val Pro Asn Cys Asp His
            180                 185                 190

Arg Gly Phe Tyr Arg Lys Arg Gln Cys Arg Ser Ser Gln Gly Gln Arg
            195                 200                 205

Arg Gly Pro Cys Trp Cys Val Asp Arg Met Gly Lys Ser Leu Pro Gly
            210                 215                 220

Ser Pro Asp Gly Asn Gly Ser Ser Ser Cys Pro Thr Gly Ser Ser Gly
225                 230                 235                 240
```